US009765074B2

(12) United States Patent
Pasternak et al.

(10) Patent No.: US 9,765,074 B2

(45) Date of Patent: Sep. 19, 2017

(54) INHIBITORS OF THE RENAL OUTER MEDULLARY POTASSIUM CHANNEL

(71) Applicant: Merck Sharp & Dohme Corp., Rahway, NJ (US)

(72) Inventors: Alexander Pasternak, Princeton, NJ (US); Fa-Xiang Ding, Staten Island, NY (US); Shuzhi Dong, Plainsboro, NJ (US); Dipshikha Biswas, Woodbridge, NJ (US); Haifeng Tang, Metuchen, NJ (US); Jinlong Jiang, Scotch Plains, NJ (US); Cangming Yang, Highland Park, NJ (US); Xin Gu, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/774,390

(22) PCT Filed: Mar. 10, 2014

(86) PCT No.: PCT/US2014/022332

§ 371 (c)(1),
(2) Date: Sep. 10, 2015

(87) PCT Pub. No.: WO2014/150132

PCT Pub. Date: Sep. 25, 2014

(65) Prior Publication Data

US 2016/0024091 A1 Jan. 28, 2016

Related U.S. Application Data

(60) Provisional application No. 61/787,510, filed on Mar. 15, 2013.

(51) Int. Cl.

| | |
|---|---|
| ***A61K 31/24*** | (2006.01) |
| ***C07D 471/10*** | (2006.01) |
| ***A61K 31/401*** | (2006.01) |
| ***C07D 471/20*** | (2006.01) |
| ***A61K 31/403*** | (2006.01) |
| ***A61K 31/405*** | (2006.01) |
| ***A61K 31/407*** | (2006.01) |
| ***A61K 31/41*** | (2006.01) |
| ***A61K 31/417*** | (2006.01) |
| ***A61K 31/4178*** | (2006.01) |
| ***A61K 31/4184*** | (2006.01) |

(Continued)

(52) U.S. Cl.

CPC ............ *C07D 471/10* (2013.01); *A61K 31/24* (2013.01); *A61K 31/401* (2013.01); *A61K 31/403* (2013.01); *A61K 31/405* (2013.01); *A61K 31/407* (2013.01); *A61K 31/41* (2013.01); *A61K 31/417* (2013.01); *A61K 31/4178* (2013.01); *A61K 31/4184* (2013.01); *A61K 31/435* (2013.01); *A61K 31/444* (2013.01); *A61K 31/4422* (2013.01); *A61K 31/472* (2013.01); *A61K 31/497* (2013.01); *A61K 31/4965* (2013.01); *A61K 31/4995* (2013.01); *A61K 31/501* (2013.01); *A61K 31/506* (2013.01); *A61K 31/519* (2013.01); *A61K 31/5386* (2013.01); *A61K 31/55* (2013.01); *A61K 31/551* (2013.01); *A61K 31/554* (2013.01); *A61K 31/585* (2013.01); *A61K 31/675* (2013.01); *A61K 45/06* (2013.01); *C07D 471/20* (2013.01); *C07D 498/20* (2013.01)

(58) Field of Classification Search

CPC ............................ C07D 471/10; A61K 31/438

USPC ............................................................ 546/15

See application file for complete search history.

(56) References Cited

U.S. PATENT DOCUMENTS 2,988,551 A 6/1961 Morren
3,435,002 A 3/1969 Holub (Continued)

FOREIGN PATENT DOCUMENTS

EP 0099148 B1 2/1988
EP 0175376 B1 4/1991

(Continued)

OTHER PUBLICATIONS

ACCF/AHA Practice Guideline, 2009 Focused update incorporated into the ACC/AHA 2005 guidelines . . . , Circulation, 2009, e391-e436, 119.

(Continued)

*Primary Examiner* — Rita Desai

(74) *Attorney, Agent, or Firm* — Baerbel R. Brown; Catherine D. Fitch

(57) ABSTRACT

The present invention provides compounds of Formula I

I

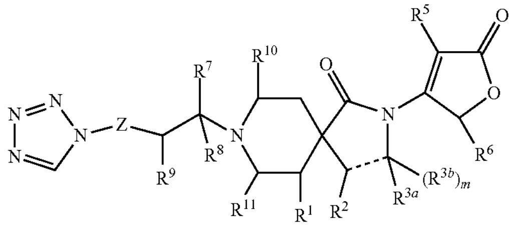

and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and chronic kidney disease and conditions associated with excessive salt and water retention.

14 Claims, No Drawings

(51) Int. Cl.

| | |
|---|---|
| ***A61K 31/4422*** | (2006.01) |
| ***A61K 31/472*** | (2006.01) |
| ***A61K 31/4965*** | (2006.01) |
| ***A61K 31/519*** | (2006.01) |
| ***A61K 31/55*** | (2006.01) |
| ***A61K 31/551*** | (2006.01) |
| ***A61K 31/554*** | (2006.01) |
| ***A61K 31/585*** | (2006.01) |
| ***A61K 31/675*** | (2006.01) |
| ***A61K 31/435*** | (2006.01) |
| ***A61K 31/444*** | (2006.01) |
| ***A61K 31/497*** | (2006.01) |
| ***A61K 31/4995*** | (2006.01) |
| ***A61K 31/501*** | (2006.01) |
| ***A61K 31/506*** | (2006.01) |
| ***A61K 31/5386*** | (2006.01) |
| ***A61K 45/06*** | (2006.01) |
| ***C07D 498/20*** | (2006.01) |

(56) References Cited

U.S. PATENT DOCUMENTS

| | | | |
|---|---|---|---|
| 3,632,608 | A | 1/1972 | Holub |
| 3,749,722 | A | 7/1973 | Holub |
| 4,579,863 | A | 4/1986 | Horwell et al. |
| 4,806,536 | A | 2/1989 | Cross et al. |
| 4,992,547 | A | 2/1991 | Berner et al. |
| 5,145,885 | A | 9/1992 | Berner et al. |
| 5,215,989 | A | 6/1993 | Baldwin et al. |
| 5,614,526 | A | 3/1997 | Godel et al. |
| 5,736,546 | A | 4/1998 | Kawashima et al. |
| 6,258,813 | B1 | 7/2001 | Arlt et al. |
| 6,787,543 | B2 | 9/2004 | Take et al. |
| 8,673,920 | B2 | 3/2014 | Pasternak et al. |
| 8,952,166 | B2 | 2/2015 | Ding et al. |
| 2004/0110793 | A1 | 6/2004 | Lloyd et al. |
| 2004/0204404 | A1 | 10/2004 | Zelle et al. |
| 2005/0215526 | A1 | 9/2005 | Hulme et al. |
| 2005/0267121 | A1 | 12/2005 | Li et al. |
| 2006/0183739 | A1 | 8/2006 | Tsaklakidis et al. |
| 2006/0183742 | A1 | 8/2006 | Mederski et al. |
| 2006/0211692 | A1 | 9/2006 | Mederski et al. |
| 2007/0004750 | A1 | 1/2007 | Lorsbach et al. |
| 2007/0072865 | A1 | 3/2007 | Fukatsu et al. |
| 2007/0093472 | A1 | 4/2007 | Mederski et al. |
| 2007/0275990 | A1 | 11/2007 | Ohmoto et al. |
| 2008/0003214 | A1 | 1/2008 | Cezanne et al. |
| 2008/0090794 | A1 | 4/2008 | Dinsmore et al. |
| 2010/0286123 | A1 | 11/2010 | Pasternak et al. |

FOREIGN PATENT DOCUMENTS

| | | | |
|---|---|---|---|
| EP | 1094063 | A1 | 4/2001 |
| EP | 1939175 | A1 | 7/2009 |
| FR | 2673182 | | 8/1992 |
| FR | 2673182 | A1 | 8/1992 |
| GB | 949088 | A | 2/1964 |
| GB | 1575310 | A | 9/1980 |
| GB | 2116967 | | 7/1986 |
| JP | 10203986 | | 8/1998 |
| WO | 9744329 | | 11/1997 |
| WO | 0051611 | A1 | 9/2000 |
| WO | 0232874 | | 4/2002 |
| WO | 0204314 | A1 | 6/2002 |
| WO | 0250061 | A1 | 6/2002 |
| WO | 2004020422 | A1 | 3/2004 |
| WO | 2004037817 | A1 | 5/2004 |
| WO | 2004046110 | | 6/2004 |
| WO | 2005037843 | | 4/2005 |
| WO | 2005044797 | | 5/2005 |
| WO | 2006034341 | A2 | 3/2006 |
| WO | 2006034769 | A1 | 4/2006 |
| WO | 2006098342 | A1 | 9/2006 |
| WO | 2006129199 | A1 | 12/2006 |
| WO | 2007075629 | A2 | 7/2007 |
| WO | 2008147864 | | 12/2008 |
| WO | 2008147864 | A2 | 12/2008 |
| WO | 2009149508 | | 11/2009 |
| WO | 2010129379 | A1 | 11/2010 |
| WO | 2012058116 | A1 | 5/2012 |
| WO | 2012058134 | A1 | 5/2012 |
| WO | 2013028474 | A1 | 2/2013 |
| WO | 2013039802 | A1 | 3/2013 |
| WO | 2013062892 | A1 | 5/2013 |
| WO | 2013062900 | A1 | 5/2013 |
| WO | 2013066714 | A1 | 5/2013 |
| WO | 2013066717 | A1 | 5/2013 |
| WO | 2013066718 | A2 | 5/2013 |
| WO | 2013090271 | A1 | 6/2013 |
| WO | 2014018764 | A1 | 1/2014 |
| WO | 2014085210 | A1 | 6/2014 |
| WO | 2014099633 | A2 | 6/2014 |
| WO | 2014126944 | A2 | 8/2014 |
| WO | 2015017305 | A1 | 2/2015 |
| WO | 2015065866 | A1 | 5/2015 |
| WO | 2015095097 | A2 | 6/2015 |
| WO | 2015100147 | A1 | 7/2015 |
| WO | 2015105736 | A1 | 7/2015 |

OTHER PUBLICATIONS

Baltzly, R., The preparation of N-mono-substituted and unsymmetrically disubstituted piperazines, J. Am. Chemoc., 1994, 263-266, 66.

Bhave, G., Small-molecule modulators of inward rectifier K+ channels: recent advances and future possibilities, Future Med Chem, 2010, 757-774, 2(5).

Bhave,G., Development of a selective small-molecule inhibitor Kir1.1, the renal outer medullary potassium channel, Mol. Pharmacol., 2011, 42-50, 79.

Brater et al., Diuretic Therapy, Drug Therapy, 1998, 387-395, 339.

Brewster et al., Antihypertensive 1,4-bis (2-indol-3-ylethyl)piperazines, Chimie Ther., 1973, 169-172 (English trans.), 2.

Cerkvenik-Flajs V, Determination of residues of azaperone in the kidneys by liquid chromatography with fluorescence, Anal. Chim. Acta., 2007, 374-382, 586.

Chemical Abstracts (2004), Abstract No. 697771-49-6, “1,3-Isobenzofurandione 5-[[4-[(5-chloro-2-methoxyphenyl)sulfonyl]-1- . . . ”.

Cheymol et al., Increase in the effects of epinephrine and acetylcholine . . . , Comptes Rendus des seances de la Societe de Biologie, 1951, 496-499 (English trans.), 145.

Dorwald, Side reactions in Organic Synthesis: A Guide to Successful Synthesis Design, 2005, Chapter 1.

Fallen, K., The Kir channel immunoglobuling domain is essential for Kir1.1 (ROMK) thermodynamic stability, trafficing and gating, Channels, 2009, 57-66, 3.

Felker et al, Diuretic strategies in patients with acute decompensated heart failure, New Eng. J. Med., 2011, 797-805, 364.

Frank, Managing hypertension using combination therapy, Am. Fam. Physician, 2008, 1279-1286, 77.

Fritch et al., Design, syntheses, and SAR of 2,8-diazaspiro[4.5]decanones at T-type calcium channel antagonists, Bioorganic & Medicinal Chemistry Letters, 2010, 6375-6378, 20.

International Search Report for PCT/US2014/022332 mailed Jun. 17, 2014; 6 pages.

Kulkarni, YD, Possible antifertility agents, part III. Synthesis of 4-(substituted aminomethyl)-5,6,7-trimethoxyphthalid . . . (abstract)), Biol. Mem., 1987, 141-144, 13.

Lanyi et al., Piperazine-Derivatives II, Res. Lab. of Chinoin-Fabrik Chemisch-Pharma. Prod., 1968, 1431-1435 (English trans.), 18.

Lewis, L. M., High-throughput screening reveals a small-molecule inhibitor of the Renal Outer Medullary Potassium Channel and Kir7.1, Mol. Pharncol., 2009, 1094-1103, 76.

(56) References Cited

OTHER PUBLICATIONS

Lutz, R. E., Antimalarials. Some Piperazine Derivatives, J. Org. Chem., 1947, 771-775, 12, BO.
Miyake et al., Synthesis of 1-substituted isochroman . . . , Takeda Res. Lab., 1982, 24-40 (English trans.), 41.
Sica, D. A., Diuretic use in renal disease, Nature, 2012, 100-109, 8.
Zejc et al., Piperazine derivative of dimethylxanthines, Polish J. Pharmacol. & Pharm., 1975, 311-316 (English trans.), 27.

INHIBITORS OF THE RENAL OUTER MEDULLARY POTASSIUM CHANNEL

CROSS REFERENCE TO RELATED APPLICATIONS

This application is a U.S. National Phase application under 35 U.S.C. §371 of PCT Application No. PCT/US14/022332 filed Mar. 10, 2014, which claims priority from U.S. Provisional Application Ser. No. 61/787,510, filed Mar. 15, 2013.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population,* Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir*7.1, Mol Pharmacol, 2009, 76(5): p. 1094-1103. The compound VU591 was later reported in Bhave, G. et al., *Development of a Selective Small-Molecule Inhibitor of Kir*1.1*, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

VU590

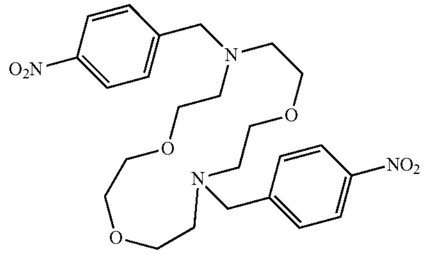

VU591

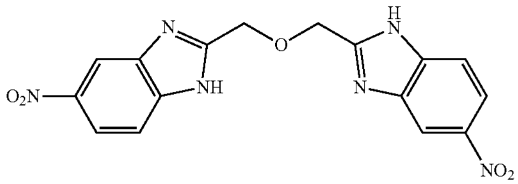

Patent application publication number WO2010/129379, published Nov. 11, 2010 having common representative Merck Sharp & Dohme Corp., (also published as US2010/0286123 on same date), describes ROMK inhibitors having the generic formula:

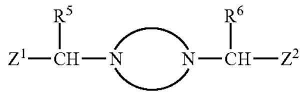

and, e.g., an embodiment

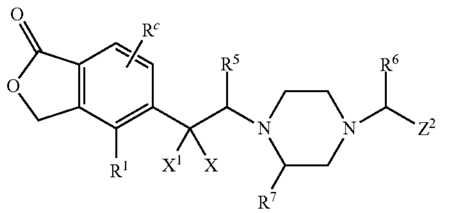

wherein $R^5$ and $R^6$ are independently —H, —$C_{1-6}$ alkyl, —$C_{3-6}$ cycloalkyl, —$CF_3$, —$CHF_2$, —$CH_2F$ or —$CH_2OH$; X is —H, —OH, —$OCl_{1-3}$alkyl, —F, oxo, $NH_2$ or —$CH_3$; and $X^1$ is —H or —$CH_3$.

Patent application publication number WO2012/058134, published May 3, 2012, having common representative Merck Sharp & Dohme Corp., describes ROMK inhibitors having the generic formula:

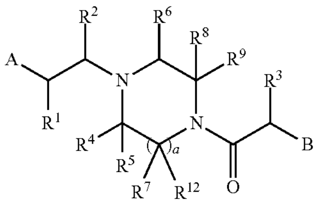

wherein A and B are mono and/or bicyclic aromatic groups; $R^2$ is —H, —$C_{1-6}$ alkyl, —$C_{3-6}$ cycloalkyl, $CF_3$, —$CH_2OH$, or —$CO_2R$, or $R^2$ can be joined to $R^1$ or $R^{10a}$ to form a ring; $R^3$ is —H, —$C_{1-6}$ alkyl, —$C_{3-6}$ cycloalkyl, —OH, —F, —$OC_{1-3}$ alkyl, or —$CH_2OH$, or $R^3$ can be joined to Rift to form a ring.

Patent application publication number WO2012/058116, published May 3, 2012, having common representative Merck Sharp & Dohme Corp., describes ROMK inhibitors having the generic formula:

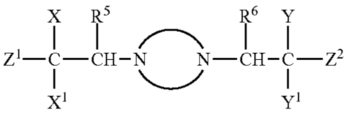

and, e.g., an embodiment

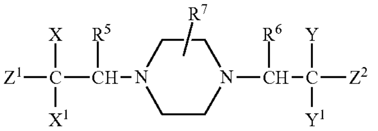

wherein $R^5$ and $R^6$ are independently —H, —$C_{1-6}$ alkyl or —C(O)$OC_{1-3}$alkyl; and X, $X^1$, Y and $Y^1$ are independently —H or —$C_{1-6}$alkyl; or $Y^1$ can be joined together with $Z^2$ to form a fused ring system.

However, continuing discovery of selective small molecule inhibitors of ROMK is still needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I

I

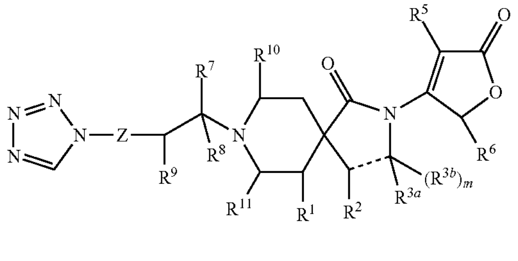

and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention is directed to compounds having structural Formula I:

I

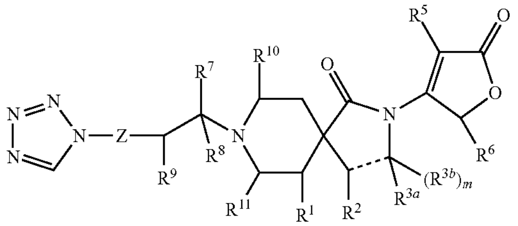

or a pharmaceutically acceptable salt thereof wherein:

Z is

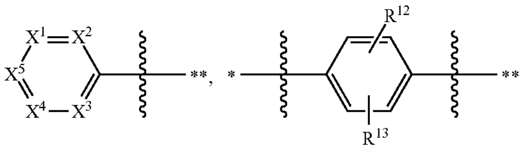

or

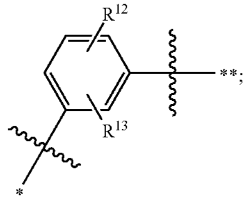

$X^1$, $X^2$ and $X^3$ are each independently selected from $C(R^4)$ or N;

one of $X^4$ and $X^5$ is *—C and the other is $C(R^4)$ or N;

provided that at least one and at most two of $X^1$, $X^2$, $X^3$, $X^4$ and $X^5$ is N;

Each $R^4$ is independently —H, halo (particularly —F or —CO, —CN, —$C_{3-6}$cycloalkyl, —C(O)O$C_{1-4}$alkyl, —O$C_{1-4}$alkyl, or —$C_{1-4}$alkyl optionally substituted with —OH or 1-3 of —F;

wherein * indicates the point of attachment to the N-tetrazolyl ring and ** indicates the point of attachment to —CH($R^9$)—;

$R^1$ is —H, halo particularly —F, —OH, or —O$C_{1-3}$alkyl particularly —$OCH_3$;

m is an integer selected from zero ($R^{3b}$ is absent) and 1 ($R^{3b}$ is present);

$R^2$ is —H, ═O (oxo), —OH, —$C_{1-3}$alkyl or —O$C_{1-3}$alkyl;

$R^{3a}$ is —H, —$C_{3-4}$cycloalkyl or —$C_{1-3}$alkyl optionally substituted with —$OCH_3$ or 1 to 3 of —F;

$R^{3b}$ is —H or —$C_{1-3}$alkyl, or $R^{3b}$ is absent when the dashed bond is a double bond;

or $R^{3a}$ and $R^{3b}$ are joined together with the carbon to which they are both attached to form cyclopropyl or cyclobutyl;

$R^5$ is —H, halo, —$C_{3-6}$ cycloalkyl or —$C_{1-3}$alkyl optionally substituted with —O—$C_{1-3}$alkyl;

$R^6$ is —H or —$C_{1-3}$alkyl;

$R^7$ is —H or —$C_{1-3}$alkyl optionally substituted with —OH, —$OCH_3$ or 1 to 3 of —F;

$R^8$ is —H or —$C_{1-3}$alkyl;

or $R^7$ and $R^8$ are joined together with the carbon to which they are both attached to form —$C_{3-4}$cycloalkyl;

$R^9$ is —H, —F, —OH, —$C_{1-3}$alkyl, —O$C_{1-3}$alkyl or —$CH_2OH$;

$R^{10}$ is —H, —$C_{1-3}$alkyl optionally substituted with —OH, —$OCH_3$, or 1 to 3 of —F;

$R^{11}$ is —H, —$C_{1-3}$alkyl optionally substituted with —OH, —$OCH_3$, or 1 to 3 of —F; or $R^{10}$ and $R^{11}$ are joined together to represent —$CH_2$—$CH_2$—, —$CH_2$—N($CH_3$)—$CH_2$— or —$CH_2OCH_2$—;

$R^{12}$ and $R^{13}$ are each independently —H, halo (particularly —F or —Cl), —CN, —$C_{3-6}$cycloalkyl, —C(O)O$C_{1-4}$ alkyl, —O$C_{1-4}$alkyl, or —$C_{1-4}$alkyl optionally substituted with or —OH or 1-3 of —F; and the dashed bond (" - - - ") represents a single or double bond provided that:

(i) when m is 1, then the dashed bond is a single bond; and (ii) when m is zero and $R^2$ is not ═O, then the dashed bond is a double bond.

In an and embodiment of this invention are compounds of Formula I having structural Formula II and the pharmaceutically acceptable salts thereof:

II

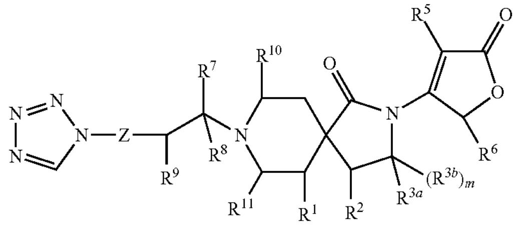

wherein each of the variables Z, $R^1$, $R^2$, $R^{3a}$, $R^{3b}$, $R^5$, $R^6$, $R^7$, $R^8$, $R^9$, $R^{10}$, $R^{11}$, and all other variables therein are as defined in Formula I.

In an embodiment of this invention are compounds of Formula I having structural Formula III and the pharmaceutically acceptable salts thereof:

III

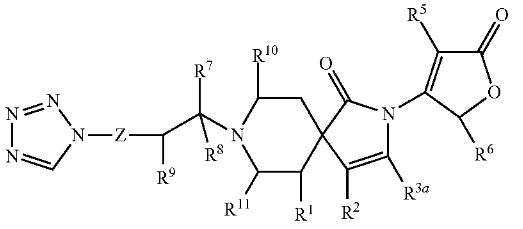

wherein each of the variables Z, $R^1$, $R^2$, $R^{3a}$, $R^5$, $R^6$, $R^7$, $R^8$, $R^9$, $R^{10}$, $R^{11}$, and all other variables therein are as defined in Formula I.

In an embodiment of this invention are compounds of Formula I, II or III wherein Z is:

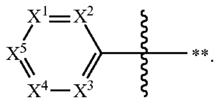

In a class of this embodiment, Z is

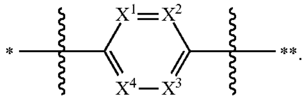

In another class of this embodiment Z is

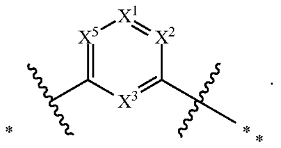

In another embodiment are compounds having structural Formula I, II or III wherein Z is:

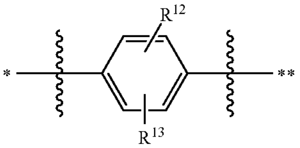

or

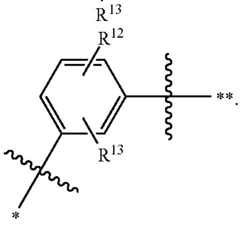

In an embodiment of this invention are compounds of Formula I having structural Formula IV and the pharmaceutically acceptable salts thereof:

IV

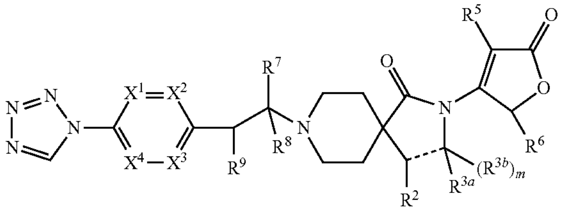

wherein each of the variables $X^1$, $X^2$, $X^3$, $X^4$, $R^2$, $R^{3a}$, $R^{3b}$, $R^5$, $R^6$, $R^7$, $R^8$, $R^9$, and all other variables therein are as defined in Formula I.

In another embodiment of this invention are compounds of Formula IV or a pharmaceutically acceptable salt thereof wherein:

$X^1$, $X^2$, $X^3$ and $X^4$ are each independently selected from $C(R^4)$ or N;

provided that at least one and at most two of $X^1$, $X^2$, $X^3$ and $X^4$ is N;

and each $R^4$ is independently —H or —$C_{1-4}$alkyl optionally substituted with 1-3 of —F;

$R^2$ is —H, =O, —OH, —$C_{1-3}$alkyl or —$OC_{1-3}$alkyl;

$R^{3a}$ is —H, —$C_{3-4}$cycloalkyl or —$C_{1-3}$alkyl optionally substituted with —$OCH_3$ or 1 to 3 of —F;

$R^{3b}$ is —H or —$C_{1-3}$alkyl, or $R^{3b}$ is absent when the dashed bond is a double bond;

$R^5$ is —H or —$CH_3$;

$R^6$ is —H or —$CH_3$;

$R^7$ is —H, —$CH_3$ or —$CH_2OH$;

$R^8$ is —H or —$CH_3$;

$R^9$ is —H, —F, —OH, —$C_{1-3}$alkyl, —$OC_{1-3}$alkyl; and the dashed bond (" - - - ") represents a single or double bond provided that:

(i) when m is 1, then the dashed bond is a single bond; and (ii) when m is zero and $R^2$ is not =O, then the dashed bond is a double bond.

In an embodiment of this invention are compounds of Formula I, II or III, wherein $R^1$ is H, —$CH_3$ or F, and more particularly it is —H.

In an embodiment of this invention are compounds of Formula I, II or III or IV, wherein $R^2$ is —H, —OH, =O, —$CH_3$ or —$OCH_3$, and more particularly it is —H.

In an embodiment of this invention are compounds of Formula I, II, III or IV, wherein $R^{3a}$ is —H, —$C_{1-3}$alkyl, cyclopropyl, and more particularly it is —H or —$CH_3$.

In an embodiment of this invention are compounds of Formula I, II or IV wherein $R^{3b}$ is —H or —$C_{1-3}$alkyl, and more particularly it is —H, or $R^{3b}$ is absent when the dashed bond is a double bond.

In an embodiment of this invention are compounds of Formula I, II, III or IV wherein each $R^4$ is independently —H, —F, —Cl, —$C(O)OCH_3$, —$C_{3-4}$cycloalkyl particularly cyclopropyl, —$OCH_3$, or —$C_{1-3}$alkyl optionally substituted with —OH or 1-3 of —F, and particularly each $R^4$ is —H or —$C_{1-3}$alkyl. In a class of this embodiment are compounds of Formula I, II, III or IV wherein at least one $R^4$ is —H.

In an embodiment of this invention are compounds of Formula I, II, III or IV wherein $R^5$ is —H, halo particularly —F or —Cl, or —$C_{1-3}$alkyl, and more particularly it is —H or —$CH_3$.

In an embodiment of this invention are compounds of Formula I, II, III or IV wherein $R^6$ is —H or —$CH_3$, and more particularly it is —H.

In an embodiment of this invention are compounds of Formula I, II, III or IV wherein $R^7$ is —H, —$CH_3$ or —$CH_2OH$, and more particularly it is —H or —$CH_3$.

In an embodiment of this invention are compounds of Formula I, II, III or IV wherein $R^8$ is —H or —$CH_3$, more preferably it is —H.

In an embodiment of this invention are compounds of Formula I, II, III or IV wherein $R^9$—H, —F, —OH, —$C_{1-3}$alkyl, —$OC_{1-3}$alkyl, and particularly it is —H or —OH.

In an embodiment of this invention are compounds of Formula I, II or III, wherein $R^{10}$ is —H, —$CH_2OH$, —$CH_2OCH_3$, or —$C_{1-3}$alkyl optionally substituted with 1 to 3 of —F.

In an embodiment of this invention are compounds of Formula I, II or III, wherein $R^{11}$ is —H, —$CH_2OH$, —$CH_2OCH_3$, or —$C_{1-3}$alkyl optionally substituted with 1 to 3 of —F.

In an embodiment of this invention are compounds of Formula I, II or III, wherein $R^{12}$ and $R^{13}$ are each independently —H, —F, —Cl, —$CF_3$, —$C_{1-3}$alkyl or —$OC_{1-3}$alkyl.

In another embodiment of this invention are compounds of Formula I, II, III or IV wherein each variable, when present in a Formula, is as follows: $R^1$ is —H; $R^2$ is —H; $R^{3a}$ is —H or —$C_{1-3}$alkyl; $R^{3b}$ is —H or $R^{3b}$ is absent and the dashed bond is a double bond; $R^4$ is —H or —$CH_3$ at each occurrence; $R^5$ is —H or —$CH_3$; $R^6$ is —H or —$CH_3$; $R^7$ is —H or —$CH_3$ optionally substituted with —OH, —$OCH_3$ or 1 to 3 of —F; $R^8$ is —H or —$CH_3$; $R^9$ is —H, —F, —OH, —$CH_3$, —O—$CH_3$, and particularly it is —H or —OH; $R^{10}$ is —H; and $R^{11}$ is —H.

All structural Formulas, embodiments and classes thereof described herein include the pharmaceutically acceptable salts of the compounds defined therein.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me). "Cycloalkyl" is a cyclized alkyl ring having the indicated number of carbon atoms. Examples of cycloalkyl include cyclopropyl, cyclobutyl, cyclopentyl and cyclohexyl.

"Halo" means —F, —Cl, —Br, or —I. Fluoro or chloro are preferred.

Unless expressly depicted or described otherwise, variables depicted in a structural formula with a "floating" bond, such as $R^{12}$ and $R^{13}$, are permitted on any available carbon atom in the ring to which the variable is attached.

Reference to the compounds of Formula I herein encompasses the compounds of Formulas I, II, III and IV and all embodiments and classes thereof. Reference to the compounds of this invention as those of a specific formula or embodiment, e.g., Formula I, II, III, or IV or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof Reference to the compounds of Formula I herein encompasses the compounds of Formulas I, II, III and IV and all embodiments and classes thereof. Reference to the compounds of this invention as those of a specific formula or embodiment, e.g., Formula I, II, III, or IV or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding pharmaceutically acceptable salts. Thus, the compounds of Formula I which contain acidic groups can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —$COO^-$ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of claim 1 in a therapeutically effective amount to a patient in need of diueresis, natriuresis or both. The inhibition of ROMK by the compounds of Formula I can be examined, for example, in the Thallium Flux Assay described below. Moreover, this invention also relates to the use of the compounds of Formula I or salts thereof to validate in vitro assays, for example but not limited to the Thallium Flux Assay described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascitis, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 μM or less, preferably 1 μM or less, and more preferably 0.25 μM or less, in the Thallium Flux Assay, described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. The "R" substituents in the Schemes correspond to the substituents defined in Formula I at the same positions on the structures. The ring

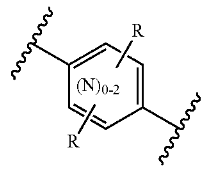

is intended to represent Z as defined in Formula I and encompasses the six-carbon phen-di-yl ring or the ring having one or two nitrogens replacing one or two of the carbons.

Compound 1.3, which is substituted at the benzylic position with an OH group, can be prepared following the sequence detailed in Scheme 1. Coupling of epoxide 1.1 to spirocyclic amines 1.2 at elevated temperatures leads to the formation of alcohols 1.3 (Nomura, Y. et al. Chemical & Pharmaceutical Bulletin, 1995, 43(2), 241-6). The reaction can be carried out with conventional heating, or by heating using a microwave apparatus. A number of solvents can be used in this reaction, for example, ethanol and 2-propanol. Spirocyclic amines may be free bases, or they may be salts, in which case a base such as triethylamine or N;N-diisopropylethylamine may be added. Note that when enantiomerically pure chiral epoxides are employed (such as (R)-1.1 in Scheme 1) epoxide opening occurs with retention of stereochemistry in the benzylic position and individual isomer (R)-1.3 may be obtained (and if the (S)-epoxide is employed the alcohol produced will have the opposite stereochemistry to that shown). Alternatively, chiral HPLC separation of enantiomers or diastereomers of 1.3 may be performed to provide single enantiomers or diastereomers.

SCHEME 1

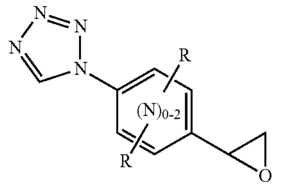

+

1.1

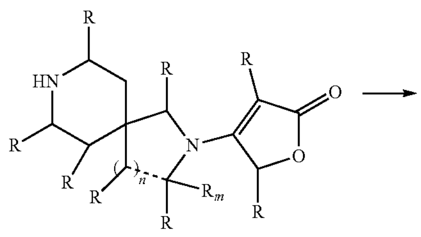

1.2

-continued

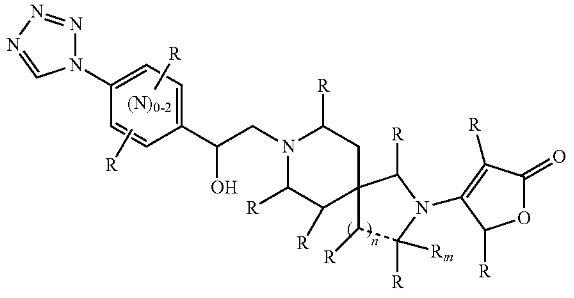

1.3

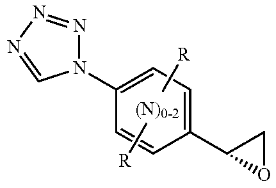

+

(R)-1.1

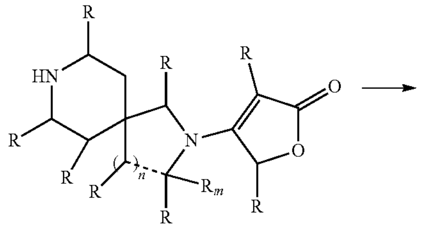

1.2

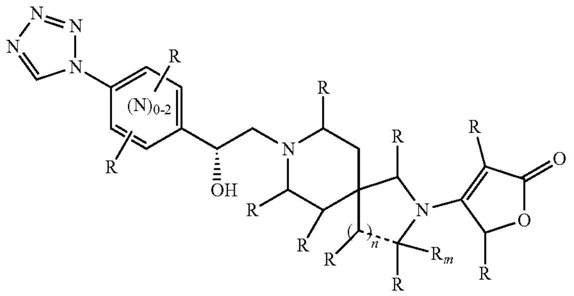

(R)-1.3

Compounds of formula 2.4 can be prepared by the sequence detailed in Scheme 2. Alhehydes or ketones 2.1 may be used in reductive alkylation reactions of spirocyclic amines 2.2 to afford ROMK inhibitors of the formula 2.4 by using various reductive amination conditions (for example using sodium cyanoborohydride, sodium triacetoxy borohydride, or titanium tetra-isopropoxide, followed by sodium borohydride or sodium cyanoborohydride). Alternatively, compounds of formula 2.4 can also be prepared by addition of amine 2.2 to an olefin of type 2.3 in the presence of a catalyst $Rh(COD)_2BF_4$/DPEPhos. Under this condition, the olefins of type 2.3 may be required to be activated by a nitrogen atom or other electron-withdrawing group at the position ortho to the double bond on the aromatic ring.

SCHEME 2

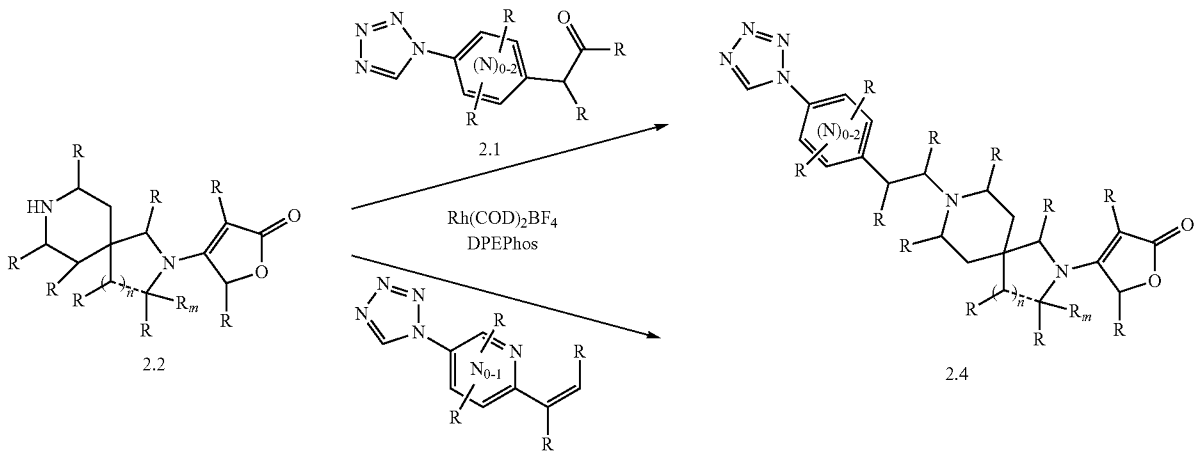

2.1 2.2 2.3 2.4

Preparation of tetrazole-epoxide intermediates of type 3.5 may start from halo-substituted aniline 3.1 (Scheme 3, X=halo). Thus, formation of the tetrazole ring can be accomplished by stirring $CF_3CO_2TMS$, $N_3TMS$ and $CH(OEt)_3$ in ethyl acetate or $NaN_3$ and $CH(OEt)_3$ in acetic acid at room temperature. The epoxide ring in intermediate 3.5 can be built by treatment of 3.2 (where X is chloride, bromide, iodide, or trifluoromethane sulfonate) with potassium vinyl trifluoroborate (Molander, G.; Luciana, A. Journal of Organic Chemistry, 2005, 70(10), 3950-3956) under palladium catalyzed coupling conditions followed by epoxidation of the formed styrene with NBS/NaOH. Alternatively, other methods for formation of styrene may be employed, for example, using vinylstannane reagents and palladium catalysis, and other methods for epoxidation of the styrene may use, for rexample, mCPBA. The racemic epoxides of formula 3.5 can be resolved under chiral HPLC chromatography conditions to afford its Enantiomers®-3.5 and (S)-3.5, which can be used in place of 1.1 according to Scheme 1.

SCHEME 3

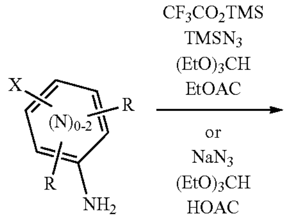

3.1

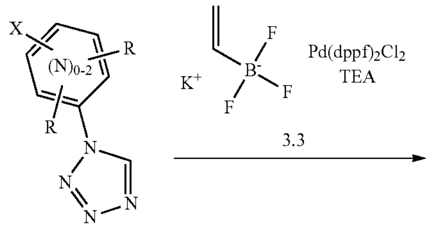

3.2 3.3

-continued

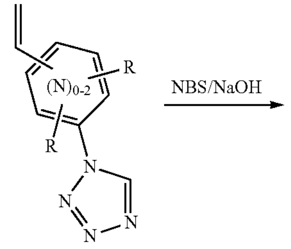

3.4

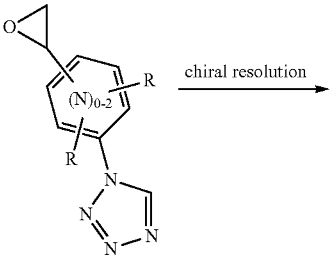

3.5

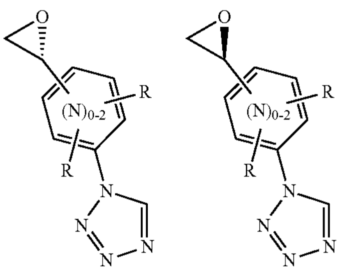

3.5A 3.5B

Enantiopure epoxides (R)-3.5 or (S)-3.5 can also be prepared as shown in Scheme 4. Treatment of 4.1 (where X is bromide, iodide, or trifluoromethane sulfonate) with commercially available vinyl butylether 4.2 under palladium catalyzed conditions with a suitable ligand (for example $Pd(OAc)_2$, DPPP) can provide the enol ethers 4.3. Enol ethers may also be prepared using other methods known in the art. Treatment of the resulting enol ethers with NBS or other similar reagents affords the corresponding bromomethyl ketones 4.4. These can be subjected to a variety of asymmetric ketone reduction conditions, for example with an enzyme that can affect such a transformation with high enantioselectivity. Subsequent treatment with a base such as triethylamine leads to cyclization, affording the enantioenriched epoxides (R)-4.5A or (S)-4.5B (depending upon the asymmetric reducing agent).

SCHEME 4

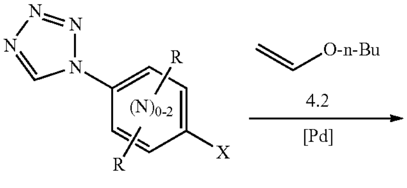

4.1

-continued

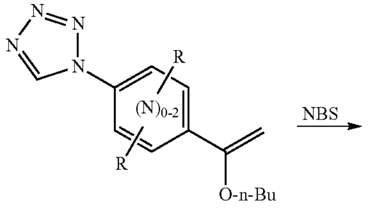

4.3

-continued

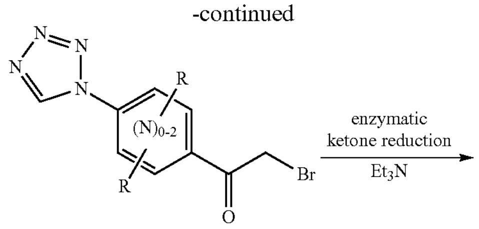

4.4

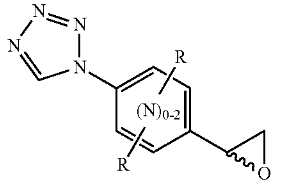

(R)- or (S)-4.5

Aldehydes 5.3 and 5.5 can be prepared in numerous ways, with two approaches described in Scheme 5. Aldehyde 5.3 can be prepared by hydrogenation of intermediate epoxides 5.1 followed by oxidation with Dess-Martin periodinane. Aldehydes 5.5 with alkoxy substitution at the benzylic position may be synthesized by PTSA-catalyzed addition of alcohols to the epoxide, and subsequent oxidation of the alcohols 5.4 to aldehydes 5.5.

SCHEME 5

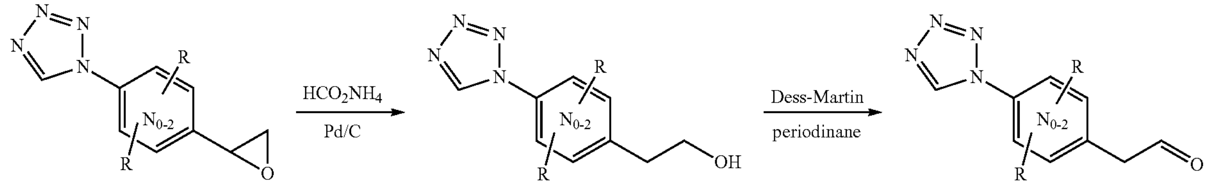

5.1 5.2 5.3

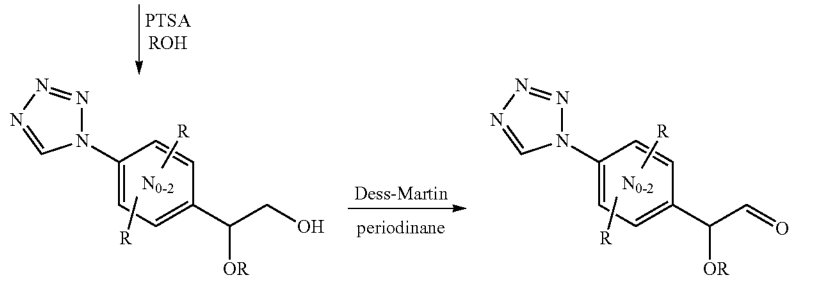

5.4 5.5

Spirocyclic amidofuranones 6.4 can be prepared as described in Scheme 6. Spirocyclic amino lactams 6.1 may be coupled to furanone triflates or bromides 6.2 using a palladium catalyst and ligand, for example palladium acetate and 4,5-Bis(diphenylphosphino)-9,9-dimethylxanthene. Some spirocyclic amino lactams 6.1 described herein are commercially available; others can be prepared as described in the experimental section below. 4-Bromofuran-2(5H)-one is commercially available; other furanones can be prepared as described in the examples below. Intermediates 6.3 are converted to spirocyclic amidofuranones 6.4 by removal of the protective group. For example, tert-butoxycarbonyl can be removed with TFA or HCl.

SCHEME 6

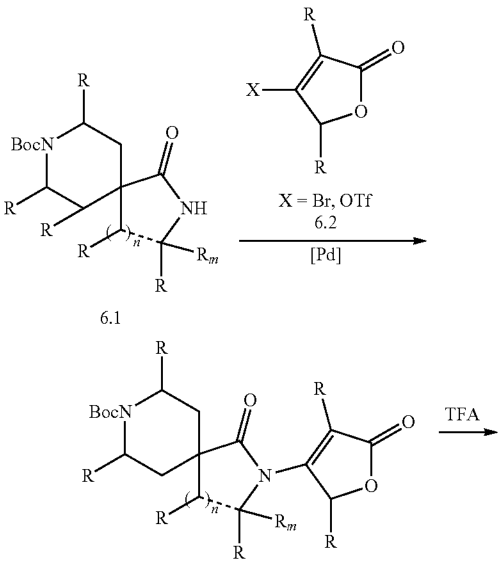

6.1

6.2

6.3

-continued

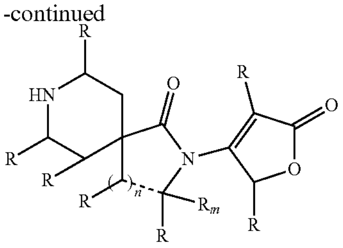

6.4

Spirocyclic amino lactams 7.4, can be prepared in numerous ways, including those described in Scheme 7. Commercially available aminoesters 7.1 can be alkylated with bromoacetonitrile 7.2 using a base such as lithium diisopropylamide to afford nitrile intermediates 7.3. Reduction, for example using platinum oxide and hydrogen, or Raney Nickel, produces lactams 7.4. Alternatively, aminoesters may be alkylated with allyl halides 7.5 using a base such as lithium diisopropylamide to furnish allyl intermediates 7.6. Oxidative cleavage, employing, for example, osmium tetroxide and sodium periodate provides ketones or aldehydes 7.7. Reductive amination with tandem lactam cyclization to 7.4 can be accomplished in several ways, including by treatment with ammonium acetate and sodium cyanoborohydride in a solvent such as methanol, as shown.

SCHEME 7

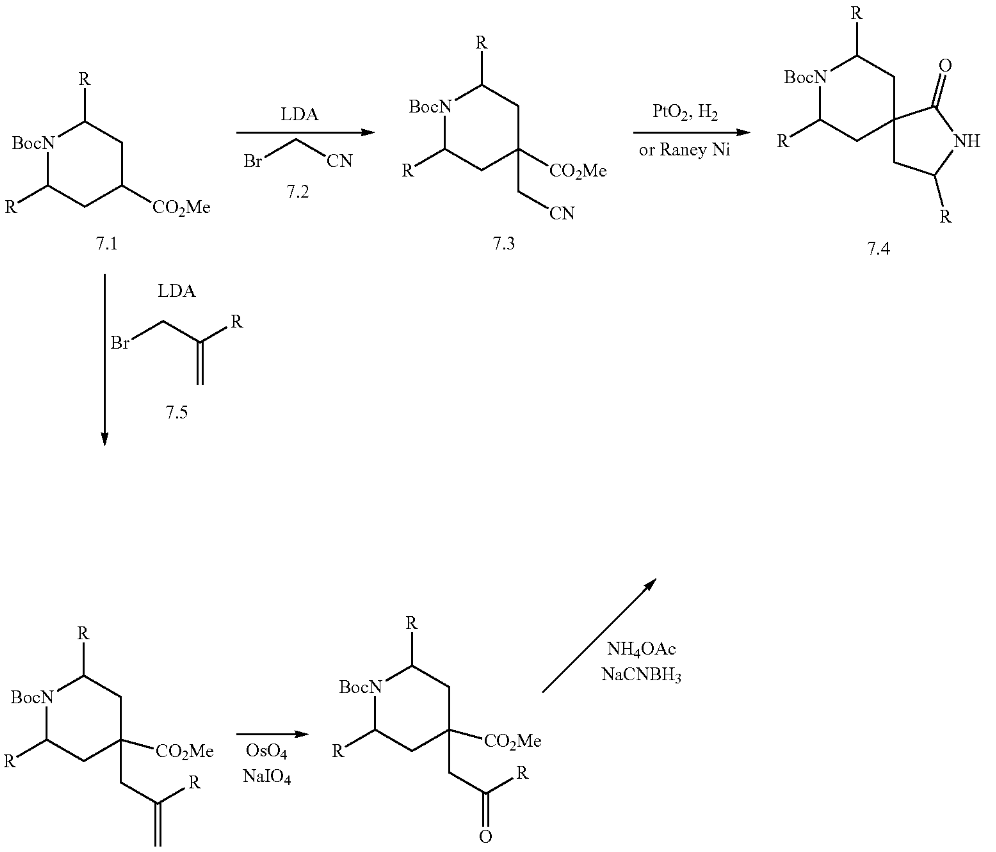

7.1

7.2

7.3

7.4

7.5

7.6

7.7

Spirocyclic amino lactams 8.7 with hydroxy on the five-membered ring can be prepared as described in Scheme 8. Commercially available aminoesters 8.1 can be alkylated with aldehydes 8.2 using a base such as lithium diisopropylamide to afford alcohols 8.3. Both BOC groups in 8.3 can be removed with TFA in DCM. This can be followed by ring-closure with potassium carbonate in methanol and subsequent adding the BOC group back to the basic amine group to give intermediates 8.4. Coupling of lactams 8.4 with furanone triflates or bromides 8.5 using a palladium catalyst and ligand gives 8.6, followed by chiral separation and BOC-deprotection with TFA in DCM to provide the spiral furanones (S)-8.7 and (R)-8.7.

SCHEME 8

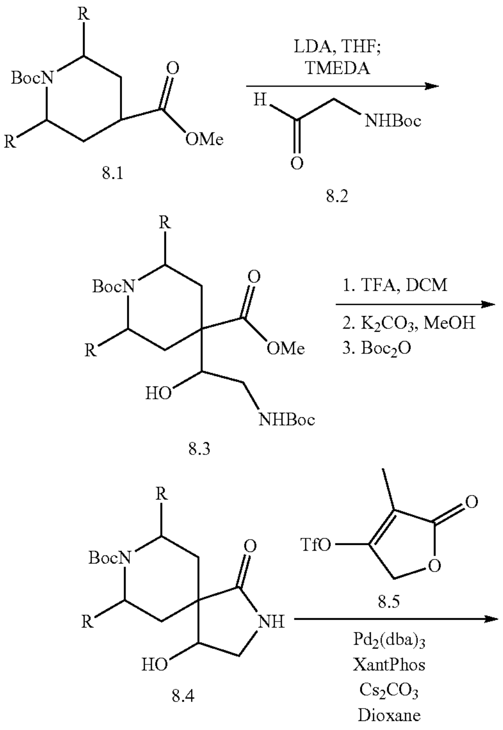

8.1
8.2
8.3
8.4
8.5

-continued

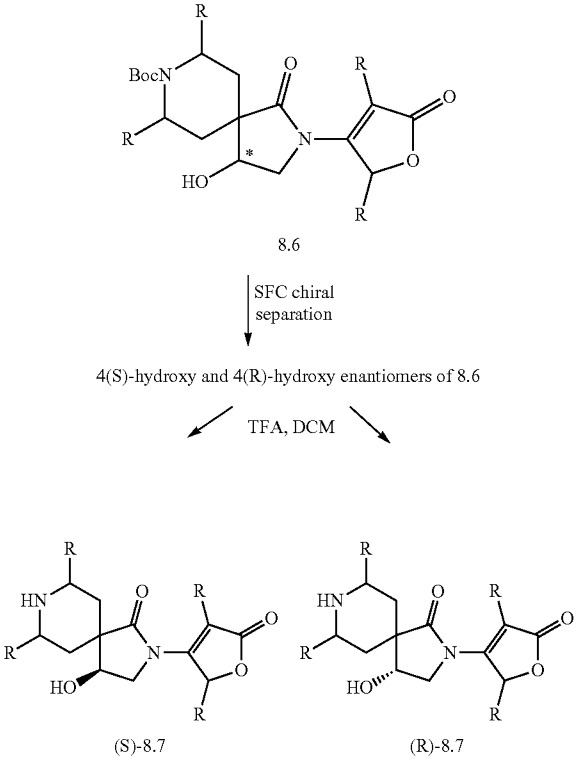

8.6
(S)-8.7
(R)-8.7

Spirocyclic amino lactams (S)-9.2 and (R)-9.2 with alkoxy on the five-membered ring can be prepared by alkylation of spirocyclic amino lactams (S)-8.6 and (R)-8.6 using $Ag_2O$ as a base. Spirocyclic amino lactams (S)-9.3 and (R)-9.3 with fluorine on the five-membered ring may be prepared by treatment of (S)-8.6 and (R)-8.6 with XtalFluor and TEA.2HF at −78° C. Treatment of (S)-8.6 and (R)-8.6 with XtalFluor at 0° C. using DBU as a base affords spirocyclic amino lactams 9.1 with a double bond on the five-membered ring.

SCHEME 9

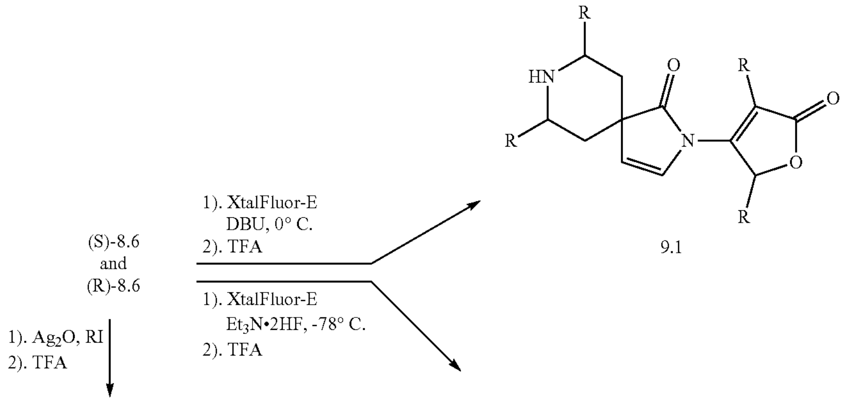

(S)-8.6
and
(R)-8.6
9.1

-continued

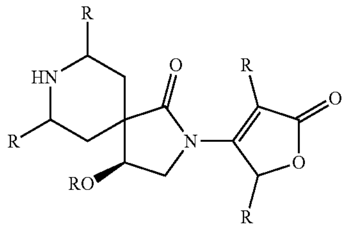

(S)-9.2

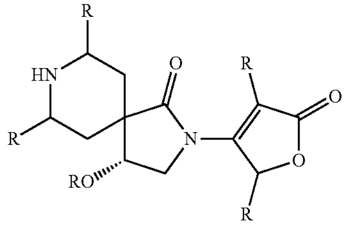

(R)-9.2

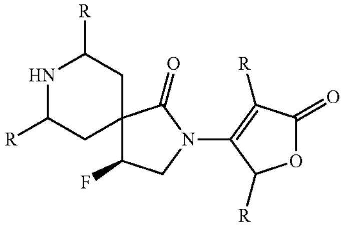

(S)-9.3

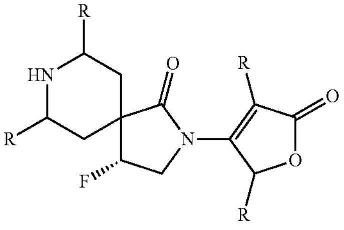

(R)9.3

Scheme 10 shows preparation of spirocyclic furanone intermediates 10.6 and 10.7. Commercially available aminoesters 10.1 can be alkylated with bromoacetonitrile using a base such as KHMDS to afford nitrile intermediates 10.2. Reduction, for example using platinum oxide and hydrogen, produces aminoalcohols 10.3, which are cyclized with ammonia in methanol to give lactams 10.4. Coupling of lactams 10.4 with furanone triflates or bromides using a palladium catalyst and ligand followed by column separation generates intermediates trans-isomers 10.5A and cis-isomers 10.5B. The spiral furanones of type 10.6A and 10.6B can be obtained by removal the benzyl (Bn) group via hydrogenation of 10.5A and 10.5B

SCHEME 10

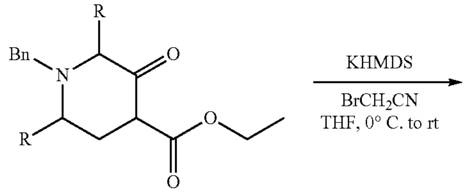

10.1

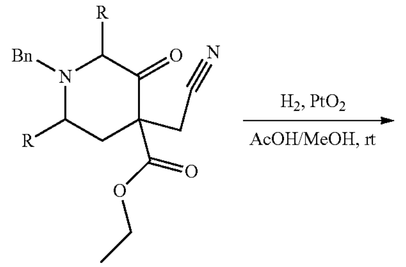

10.2

-continued

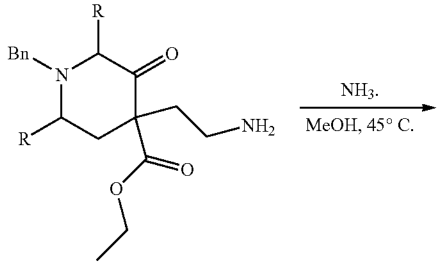

10.3

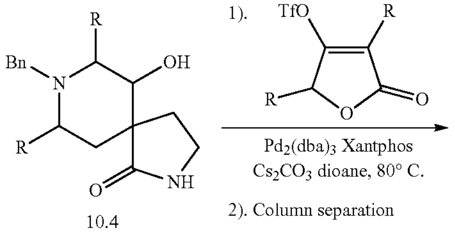

10.4

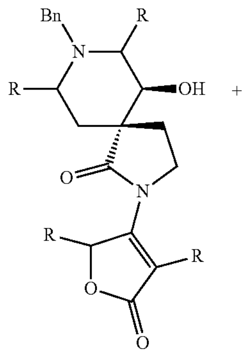

10.5A
trans, racemic
fast eluted

-continued

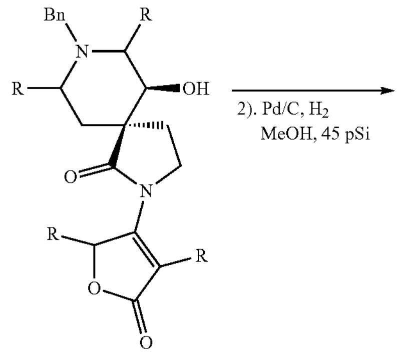

10.5B
cis, racemic
slow eluted

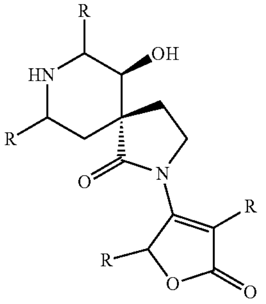

+

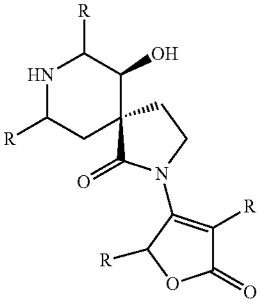

10.6
trans, racemic
isomer A 10.7
cis, racemic
isomer B

As shown in Scheme 11, the benzyl-protection group in cis racemic alcohols 10.5B is replaced by a BOC group. The BOC-protected compounds of type 11.1 can then be transformed to trans-racemic fluorides 11.2 which are separated by chiral column and subsequently deprotected with TFA in DCM to give intermediates of type 11.3.

SCHEME 11

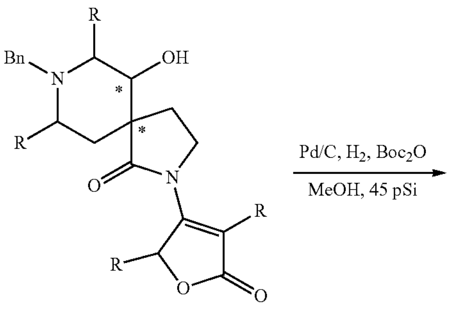

10.5B
cis spiral, racemic

-continued

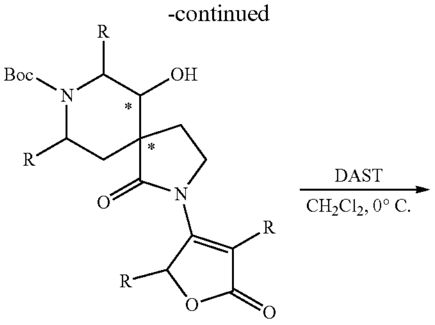

11.1
cis spiral, racemic

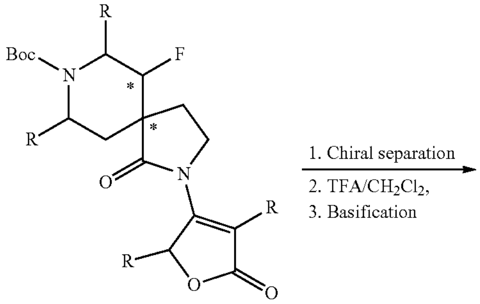

11.2
trans spiral, racemic

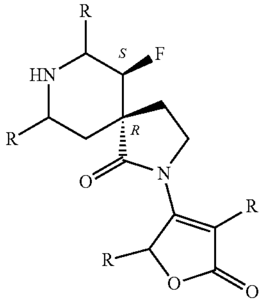

(trans 5R,6S)-11.3

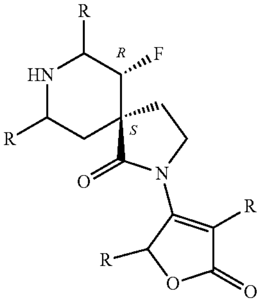

(trans 5S,6R)-11.3

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

The subject compounds may be prepared by modification of the procedures disclosed in the Examples as appropriate. Starting materials are commercially available or made by known procedures or as illustrated Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60E-254, layer thickness 0.25 mm or liquid chromatography-mass spectrometry (LC-MS).

Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 μm. The flow rate was 1 mL/min, and the injection volume was 10 μL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage.

Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual $CH_3OH$ peak or TMS was used as internal reference in $CD_3OD$ solutions. Coupling constants (J) were reported in hertz (Hz).

Chiral analytical chromatography was usually performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid (SFC) conditions. Alternatively, chiral preparative chromatography was by supercritical fluid (SFC) conditions using one of Chiralpak AS, Chiralpak AD-H, Chiralcel OD-H, Chiralpak IC, or Chiralcel OJ-H columns (250×21.2 mm) (Daicel Chemical Industries, Ltd.). Where retention times (or order of elution) are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used. Concentration of solutions was generally carried out on a rotary evaporator under reduced pressure Crystallization or recrystallization techniques are intended to describe a purification procedure that was used, but do not imply that the resulting product obtained from the procedure is crystalline.

Abbreviations and acronyms that may be used herein include: —C(O)$CH_3$ (Ac); —OC(O)$CH_3$ (OAc); acetic acid (AcOH; HOAc); 1-chloroethylchloroformate (ACE-C1); 2,2'-bis(diphenylphosphino)-1,1'-binaphthyl (BINAP); benzyl (Bn); t-butyloxycarbonyl (Boc or BOC); di-t-butyl dicarbonate ($(BOC)_2O$, $Boc_2O$); benzyloxycarbonyl (Cbz); Cyclopentyl methyl ether (CPME); Carbonyldiimidazole (CDI); Diethylaminosulfur trifluoride (DAST); dibenzylideneacetone (dba); 1,8-Diazabicyclo[5.4.0]undec-7-ene (DBU); 1,2-dichloroethane (DCE); dichloromethane (DCM); diethyl amine (DEA); dimethoxyethane (DME); Diisobutylaluminium hydride (DIBAL-H); N,N-diisopropylethylamine (DIEA, DIPEA, Hunig's base); dioxane is 1,4-dioxane; di-isopropylamine (DIPA); 1,1'-bis(diphenylphosphino)ferrocene (dppf, DPPF); Dess-Martin Periodinane (DMP; 1,1,1-Triacetoxy-1,1-dihydro-1,2-benziodoxol-3(1H)-one); dimethylsulfide (DMS); dimethylsulfoxide (DMSO); N;N-dimethylformamide (DMF); 4-dimethylaminopyridine (DMAP); dimethylacetamide (DMA; DMAC); 1,3-Bis(diphenylphosphino)propane (DPPP); (Oxydi-2,1-phenylene)bis(diphenylphosphine) (DPEPhos); ethyl acetate (EtOAc or EA); diethyl ether (ether or $Et_2O$); 1-ethyl-3-(3-dimethylaminopropyl)carbodiimide (EDC, EDAC or EDCI); 2-(7-Aza-1H-benzotriazole-1-yl)-1,1,3,3-tetramethyluronium hexafluorophosphate (HATU); hexane (Hex); hexamethylphosphoramide (HMPA); 1-Hydroxybenzotriazole hydrate (HOBt); isopropanol (IPA); isopropyl acetate (IPAc); Potassium bis(trimethylsilyl)amide (KHMDS); lithium aluminum hydride (LAH); lithium diisopropylamide (LDA); 3-chloroperoxybenzoic acid (mCPBA); methanol (MeOH); $CH_3SO_2$— (mesyl or Ms); methane sulfonyl chloride or mesyl chloride (MsCl); methanesulfonic acid (MsOH); methyl tert-butyl ether (MTBE); nicotinamide adenine dinucleotide phosphate (NADP); N-bromo succinimide (NBS); N-chlorosuccinimide (NCS); N-iodosuccinimide (NIS); N-methylmorpholine-N-oxide (NMO); N-methyl morpholine (NMP); sodium hexamethyldisilazide (NaHMDS); sodium triacetoxyborohydride ($NaBH(OAc)_3$); Pyridinium chlorochromate (PCC); phenyl (Ph); petroleum ether (PE or petrol ether); tetrakis(triphenylphosphine)palladium ($Pd(PPh_3)_4$); tris(dibenzylidineacetone)dipalladium ($Pd_2(dba)_3$); Pd(dppf)C12 or $PdCl_2$(dppf) is 1,1'-Bis(diphenylphosphino)ferrocene]dichloropalladium (II) which may be complexed with $CH_2$C12; tetra-n-butylammonium fluoride (TBAF); tert-butyldimethylsilyl chloride (TBS-Cl); triethylamine (TEA); trifluoroacetic acid (TFA); —$SO_2CF_3$ (TO; trifluoromethanesulfonic acid (triflic acid, TfOH); trifluoromethanesulfonic anhydride (triflic anhydride, $(Tf)_2O$); 2-tetrahydrofuran (THF); N,N,N',N'-Tetramethylethylenediamine (TMEDA); p-toluenesulfonic acid (TsOH or PTSA); Dicyclohexylphosphino-2',4',6'-triisopropylbiphenyl (X-Phos); Diethylaminodifluorosulfinium tetrafluoroborate (XtalFluor-E®); 4,5-Bis(diphenylphosphino)-9,9-dimethylxanthene (Xantphos). Additional abbreviations and acronyms are: racemic or racemate (rac.); starting material (SM); round-bottom flask (RB or RBF); aqueous (aq); saturated aqueous (sat'd); saturated aqueous sodium chloride solution (brine); medium pressure liquid chromatography (MPLC); high pressure liquid chromatography (HPLC); preparative HPLC (prep-HPLC); flash chromatography (FC); liquid chromatography (LC); supercritical fluid chromatography (SFC); thin layer chromatography (TLC); preparative TLC (prep-TLC); mass spectrum (ms or MS); liquid chromatography-mass spectrometry (LC-MS, LCMS or LC/MS); column volume (CV); room temperature (rt, r.t. or RT); hour(s) (h or hr); minute(s) (min); retention time ($R_t$); gram(s) (g); milligram(s) (mg);

milliliter(s) (mL); microliter(s) (μL); millimole (mmol); volume:volume (V/V). CELITE® is a trademark name for diatomaceous earth, and SOLKA FLOC® is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In many of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate. Any Intermediates described below may be referred to herein by their number preceded by "I-." For illustration, in the example titled "Intermediate 2," the racemic parent title compound would be referred to as Intermediate 2 (or 1-2), and the separated stereoisomers are noted as Intermediates 2A and 2B (or I-2A and I-2B). In some examples, compounds having a chiral center were derived synthetically from a single isomer intermediate; e.g., Example 2 was made using stereoisomer I-1B. Except for a defined chiral center in a parent isomer mixture, absolute stereochemistry (R or 5) of each of the separated isomers was not determined, unless specifically described otherwise. An asterisk (*) may be used in a chemical structure drawing that indicates the location of a chiral center.

INTERMEDIATE 1

1A

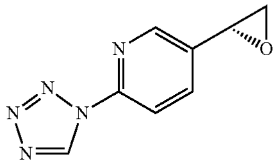

1B

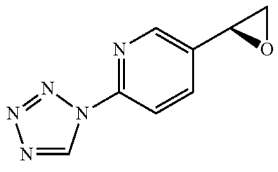

(S)-5-(Oxiran-2-yl)-2-(1H-tetrazol-1-yl)pyridine (1A) and

(R)-5-(Oxiran-2-yl)-2-(1H-tetrazol-1-yl)pyridine (1B)

Step A: 5-Bromo-2-(1H-tetrazol-1-yl)pyridine

To a solution of 5-bromopyridin-2-amine (5.0 g, 28.9 mmol) in acetic acid (40 ml, 699 mmol) was added (diethoxymethoxy) ethane (7.70 ml, 46.2 mmol), followed by sodium azide (2.82 g, 43.3 mmol). The mixture was heated at 80° C. for 1 h, cooled to room temperature and diluted with water. Precipitate was collected by filtration and dried under high vacuum to provide the title compound.

Step B: 5-Ethenyl-2-(1H-tetrazol-1-yl)pyridine

To a stirring solution of 5-bromo-2-(1H-tetrazol-1-yl) pyridine (1.0 g, 4.42 mmol), in EtOH (70 mL) was added bis[(diphenylphosphino)ferrocene]dichloropalladium(II), complex with dichloromethane (0.361 g, 0.442 mmol), potassium vinyl trifluoroborate (1.18 g, 8.85 mmol, 2 equiv.), triethylamine (1.23 mL, 8.85 mmol, 2 equiv), and water (0.5 mL). The reaction mixture was heated at reflux (90° C., oil bath) under $N_2$. Upon completion (1-2 h) as determined by reverse phase HPLC-MS and TLC (eluent: 10% ethyl acetate in hexane), the mixture was cooled to room temperature, and then diluted with water. The organic layer was separated, and the aqueous layer was extracted with EtOAc. The combined organic layers were washed with brine, dried over $MgSO_4$, and concentrated. The crude material was chromatographed over a column of $SiO_2$ (0-20% EtOAc in hexane as eluent). Evaporation of the solvent yielded the title compound. LCMS $[M+1]^+$=174.0.

Step C: 5-(Oxiran-2-yl)-2-(1H-tetrazol-1-yl)pyridine (1)

To a solution of 5-ethenyl-2-(1H-tetrazol-1-yl)pyridine (0.664 g, 3.83 mmol) in a 2:1 ratio of $H_2O$:t-BuOH (30 mL) was added N-bromosuccinimide (0.751 g, 4.22 mmol) in portions over 5 min. The mixture was heated at 40° C. for 1 h, cooled to 5° C., made basic with sodium hydroxide aqueous solution (0.46 g in 5 mL of $H_2O$, 11.50 mmol), stirred for another 1 h at the same temperature, and poured into $H_2O$ (10 mL). The product precipitated out. The solid was collected by filtration, washed with water, and dried in vacuo. $^1H$ NMR (500 MHz, DMSO-$d_6$), δ 10.17 (s, 1H), 8.60 (d, J=1.4 Hz, 1H), 8.04-7.99 (m, 2H), 4.14 (dd, J=2.7 Hz, J=2.8 Hz, 1H), 3.23 (t, J=4.6 Hz, 1H), 3.02 (dd, J=25 Hz, 1H); LCMS $[M+1]^+$=190. Further chiral separation (AD-H 30×250 mm, 50% MeOH/$CO_2$, 70 mL/min, 100 bar, 46 mg in MeOH/DCM) afforded faster eluted 1A (5)-5-(oxiran-2-yl)-2-1H-tetrazol-1-yl)pyridine and slower eluted 1B (R)-5-(oxiran-2-yl)-2-(1H-tetrazol-1-yl)pyridine

INTERMEDIATE 2

2A

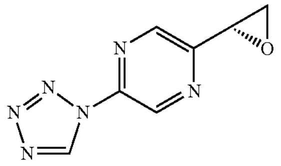

-continued

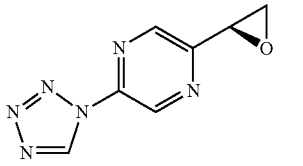

2B (S)-2-(Oxiran-2-yl)-5-(1H-tetrazol-1-yl)pyrazine (2A) and (R)-2-(Oxiran-2-yl)-5-(1H-tetrazol-1-yl)pyrazine (2B)

Step A: 2-Bromo-5-(1H-tetrazol-1-yl)pyrazine

To a solution of 5-bromopyrazin-2-amine (10.75 g, 57.5 mmol) in ethyl acetate (150 ml) was added trimethylsilyl 2,2,2-trifluoroacetate (16.88 ml, 98 mmol). After the mixture was stirred for 5 min, triethoxymethane (17.21 ml, 103 mmol) was added. The resulting mixture was stirred for another five min, and this was followed by addition of azidotrimethylsilane (12.09 ml, 92 mmol). Stirring continued at rt for 2 days, and the mixture was concentrated under reduced pressure. Recrystallization of the residue from ethyl acetate afforded 2-bromo-5-(1H-tetrazol-1-yl)pyrazine. LCMS $[M+2+1]^+$=228.9.

Step B: 2-(1H-Tetrazol-1-yl)-5-vinylpyrazine

A solution of 2-bromo-5-(1H-tetrazol-1-yl)pyrazine (11.2 g, 49.3 mmol), potassium vinyltrifluoroborate (13.22 g, 99.0 mmol), 1,1'-bis(diphenylphosphino)ferrocene-palladium(ii) dichloride dichloromethane complex (2.01 g, 2.47 mmol), and TEA (13.75 ml, 99.0 mmol) in ethanol (150 ml) was heated at reflux at 82° C. for 4 h. The reaction mixture was cooled to rt, and the precipitate was filtered off. The filtrate was concentrated, and the residue was purified by flash chromatography (Biotage, Si, ethyl acetate in hexane: 35 to 45%) affording 2-(1H-tetrazol-1-yl)-5-vinylpyrazine LCMS $[M+1]^+$=175.10. The filter cake was stirred in DCM (50 mL), and the solid was filtered off. The filtrate was concentrated to afford more 2-(1H-tetrazol-1-yl)-5-vinylpyrazine.

Step C: 2-(Oxiran-2-yl)-5-(1H-tetrazol-1-yl)pyrazine

To a suspension of 2-(1H-tetrazol-1-yl)-5-vinylpyrazine (6.7 g, 38.5 mmol) in t-BuOH:water (96 ml: 190 ml) was added N-bromosuccinimide (7.53 g, 42.3 mmol) in portions at rt. The mixture was heated at 50° C. for 1 h, and cooled to 0° C. in an ice bath. NaOH (4.61 g in 30 mL water, 115 mmol) was added dropwise, and the resulting mixture was stirred at the same temperature for 20 min. The product was collected by filtration, washed with water, dried under vacuum to give 2-(1H-tetrazol-1-yl)-5-vinylpyrazine LCMS $[M+1]^+$=191.07. Chiral separation (AD-H 30×250 mm, 50% MeOH/$CO_2$, 70 mL/min, 100 bar, MeOH/DCM) afforded faster eluted isomer 2A (S)-2-(oxiran-2-yl)-5-(1H-tetrazol-1-yl)pyrazine and slower eluted isomer 2B (R)-2-(oxiran-2-yl)-5-(1H-tetrazol-1-yl)pyrazine. LCMS $[M+1]^+$=191.1.

The following epoxide intermediates in Table 1 were prepared employing a similar synthetic method as that described for Intermediates 1 or 2. Column 2 shows the structure of the starting material followed by the method used (either I-1 for the procedure described for Intermediate 1, or 1-2 for the procedure described for Intermediate 2).

TABLE 1

Epoxides prepared using the method described for I-1 or I-2

| Intermediate No. | Column 2 | Structure and name | Structure and name | LC-MS $[M + 1]^+$ |
|---|---|---|---|---|
| 3 | 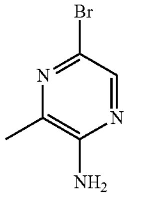 Method: I-2 | 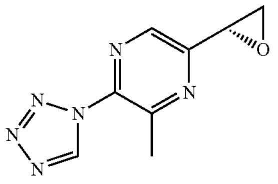 Fast eluted 3A (S)-3-methyl-5-(oxiran-2-yl)-2-(1H-tetrazol-1-yl)pyrazine | 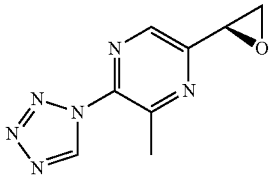 Slow eluted 3B (R)-3-methyl-5-(oxiran-2-yl)-2-(1H-tetrazol-1-yl)pyrazine | 205 |
| 4 | 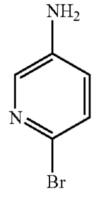 Method: I-1 | 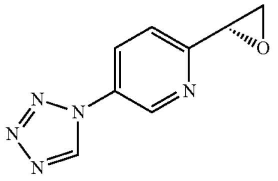 Fast eluted 4A (S)-2-(oxiran-2-yl)-5-(1H-tetrazol-1-yl)pyridine | 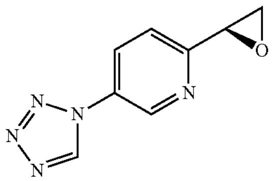 Slow eluted 4B (R)-2-(oxiran-2-yl)-5-(1H-tetrazol-1-yl)pyridine | 190.10 |

TABLE 1-continued

Epoxides prepared using the method described for I-1 or I-2

| Intermediate No. | Column 2 | Structure and name | Structure and name | LC-MS $[M + 1]^+$ |
|---|---|---|---|---|
| 5 | 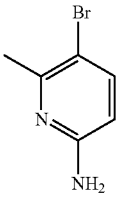<br>Method: I-1 | 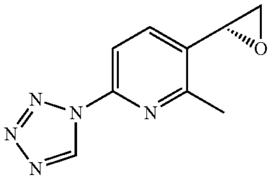<br>Fast eluted 5A<br>(S)-2-methyl-3-(oxiran-2-yl)-6-(1H-tetrazol-1-yl)pyridine | 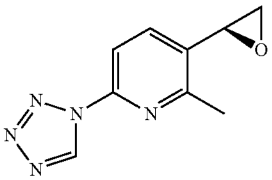<br>Slow eluted 5B<br>(R)-2-methyl-3-(oxiran-2-yl)-6-(1H-tetrazol-1-yl)pyridine | 188.10<br>$([M + 1 - 28]^+)$ |
| 6 | 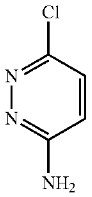<br>Method: I-2 | 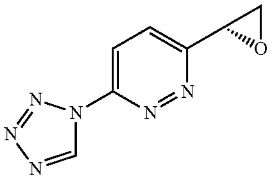<br>Fast eluted 6A<br>(S)-3-(oxiran-2-yl)-6-(1H-tetrazol-1-yl)pyridazine | 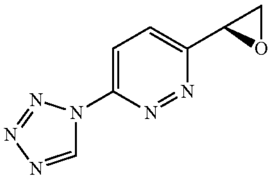<br>Slow eluted 6B<br>(R)-3-(oxiran-2-yl)-6-(1H-tetrazol-1-yl)pyridazine | 191.16 |
| 7 | 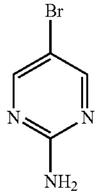<br>Method: I-2 | 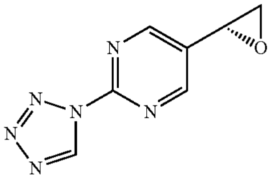<br>Fast eluted 7A<br>(S)-5-(oxiran-2-yl)-2-(1H-tetrazol-1-yl)pyrimidine | 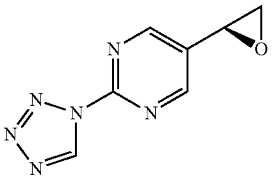<br>Slow eluted 7B<br>(R)-5-(oxiran-2-yl)-2-(1H-tetrazol-1-yl)pyrimidine | 191.07 |
| 8 | 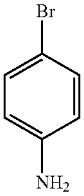<br>Method: I-2 | 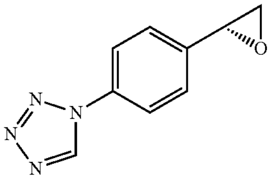<br>Fast eluted 8A<br>(S)-1-(4-(oxiran-2-yl)phenyl)-1H-tetrazole | 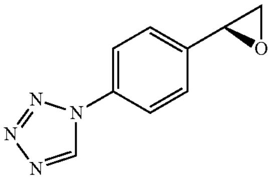<br>Slow eluted 8B<br>(R)-1-(4-(oxiran-2-yl)phenyl)-1H-tetrazole | 189.13 |
| 9 | 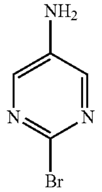<br>Method: I-2 | 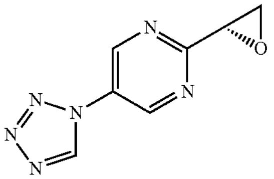<br>Fast eluted 9A<br>(S)-2-(oxiran-2-yl)-5-(1H-tetrazol-1-yl)pyrimidine | 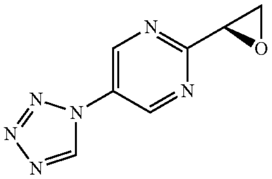<br>Slow eluted 9B<br>(R)-2-(oxiran-2-yl)-5-(1H-tetrazol-1-yl)pyrimidine | 191.12 |

TABLE 1-continued

Epoxides prepared using the method described for I-1 or I-2

| Intermediate No. | Column 2 | Structure and name | Structure and name | LC-MS $[M + 1]^+$ |
|---|---|---|---|---|
| 10 | 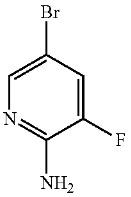 Method: I-2 | 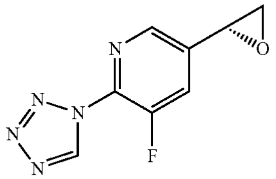 Fast eluted 10A (S)-3-fluoro-5-(oxiran-2-yl)-2-(1H-tetrazol-1-yl)pyridine | 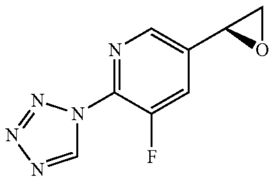 Slow eluted 10B (R)-3-fluoro-5-(oxiran-2-yl)-2-(1H-tetrazol-1-yl)pyridine | 208.12 |
| 11 | 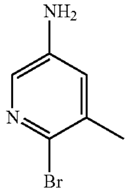 Method: I-2 | 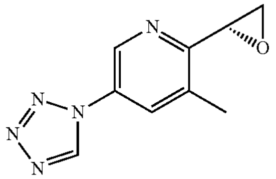 Fast eluted 11A (S)-3-methyl-2-(oxiran-2-yl)-5-(1H-tetrazol-1-yl)pyridine | 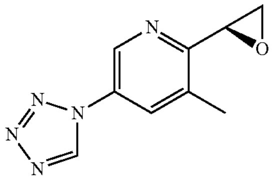 Slow eluted 11B (R)-3-methyl-2-(oxiran-2-yl)-5-(1H-tetrazol-1-yl)pyridine | 204.12 |
| 12 | 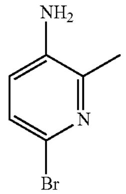 Method: I-2 | 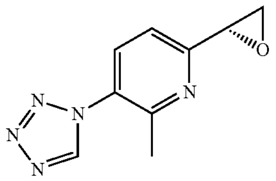 Fast eluted 12A (S)-2-methyl-6-(oxiran-2-yl)-3-(1H-tetrazol-1-yl)pyridine | 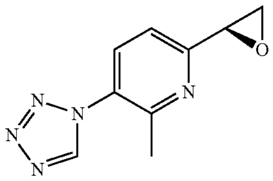 Slow eluted 12B (R)-2-methyl-6-(oxiran-2-yl)-3-(1H-tetrazol-1-yl)pyridine | 204.10 |
| 13 | 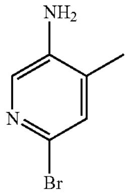 Method: I-2 | 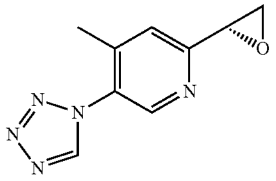 Fast eluted 13A (S)-4-methyl-2-(oxiran-2-yl)-5-(1H-tetrazol-1-yl)pyridine | 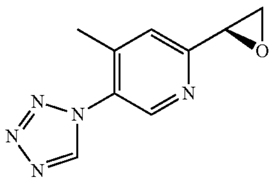 Slow eluted 13B (R)-4-methyl-2-(oxiran-2-yl)-5-(1H-tetrazol-1-yl)pyridine | 204.11 |
| 14 | 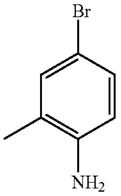 Method: I-2 | 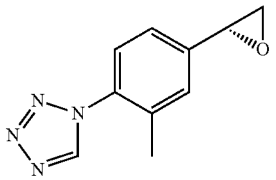 Fast eluted 14A (S)-1-(2-methyl-4-(oxiran-2-yl)phenyl)-1H-tetrazole | 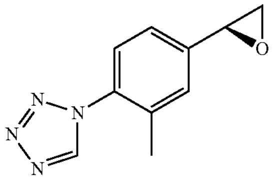 Slow eluted 14B (R)-1-(2-methyl-4-(oxiran-2-yl)phenyl)-1H-tetrazole | 203.3 |

TABLE 1-continued

| Epoxides prepared using the method described for I-1 or I-2 | | | | |
|---|---|---|---|---|
| Intermediate No. | Column 2 | Structure and name | Structure and name | LC-MS [M + 1]$^+$ |
| 15 | 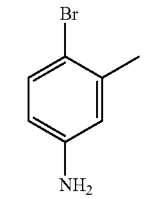 Method: I-2 | 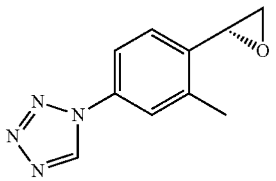 Fast eluted 15A (S)-1-(3-methyl-4-(oxiran-2-yl)phenyl)-1H-tetrazole | 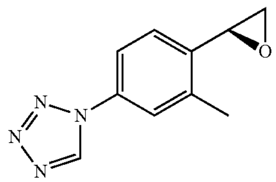 Slow eluted 15B (R)-1-(3-methyl-4-(oxiran-2-yl)phenyl)-1H-tetrazole | 203.1 |
| 16 | 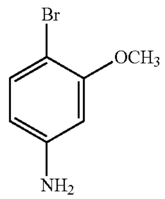 Method: I-2 | 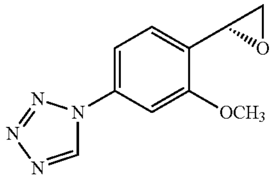 Fast eluted 16A (S)-1-(3-methoxy-4-(oxiran-2-yl)phenyl)-1H-tetrazole | 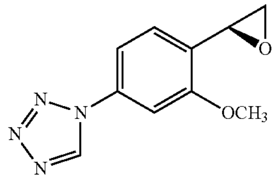 Slow eluted 16B (R)-1-(3-methoxy-4-(oxiran-2-yl)phenyl)-1H-tetrazole | 219.3 |
| 17 | 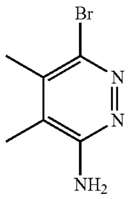 Method: I-2 | 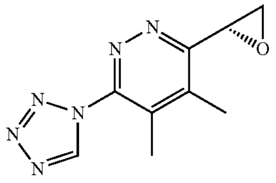 Fast eluted 17A (S)-4,5-dimethyl-3-(oxiran-2-yl)-6-(1H-tetrazol-1-yl)pyridazine | 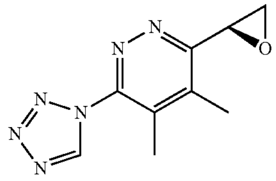 Slow eluted 17B (R)-4,5-dimethyl-3-(oxiran-2-yl)-6-(1H-tetrazol-1-yl)pyridazine | 219.2 |
| 18 | 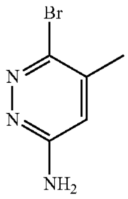 Method: I-2 | 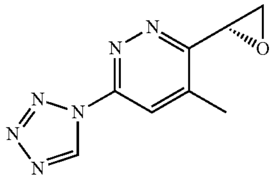 Fast eluted 18A (S)-4-methyl-3-(oxiran-2-yl)-6-(1H-tetrazol-1-yl)pyridazine | 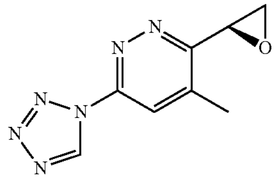 Slow eluted 18B (R)-4-methyl-3-(oxiran-2-yl)-6-(1H-tetrazol-1-yl)pyridazine | 205.3 |
| 19 | 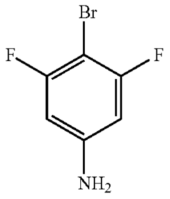 Method: I-2 | 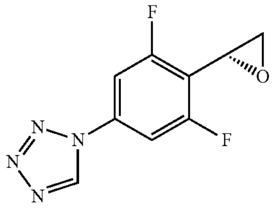 Fast eluted 19A (S)-1-(3,5-difluoro-4-(oxidant-2-yl)phenyl)-1H-tetrazole | 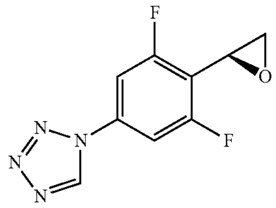 Slow eluted 19B (R)-1-(3,5-difluoro-4-(oxidant-2-yl)phenyl)-1H-tetrazole | 225.3 |

TABLE 1-continued

Epoxides prepared using the method described for I-1 or I-2

| Intermediate No. | Column 2 | Structure and name | Structure and name | LC-MS [M + 1]$^+$ |
| --- | --- | --- | --- | --- |
| 20 | 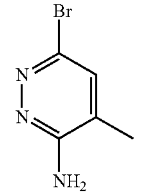 Method: I-2 | 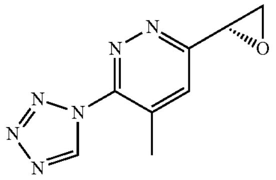 Fast eluted 20A (S)-4-methyl-6-(oxiran-2-yl)-3-(1H-tetrazol-1-yl)pyridazine | 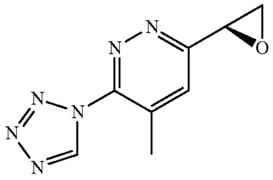 Slow eluted 20B (R)-4-methyl-6-(oxiran-2-yl)-3-(1H-tetrazol-1-yl)pyridazine | 205.4 |
| 21 | 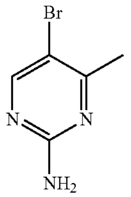 Method: I-2 | 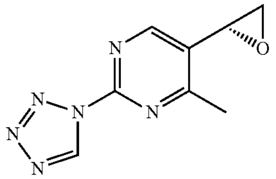 Fast eluted 21A (S)-4-methyl-5-(oxiran-2-yl)-2-(1H-tetrazol-1-yl)pyrimidine | 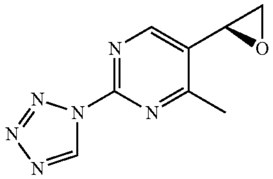 Slow eluted 21B (R)-4-methyl-5-(oxiran-2-yl)-2-(1H-tetrazol-1-yl)pyrimidine | 205.3 |
| 22 | 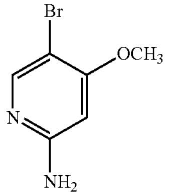 Method: I-2 | 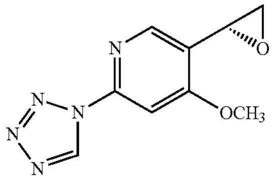 Fast eluted 22A (S)-4-methoxy-5-(oxiran-2-yl)-2-(1H-tetrazol-1-yl)pyridine | 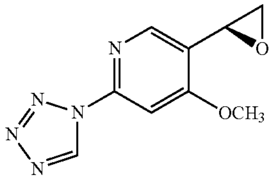 Slow eluted 22B (R)-4-methoxy-5-(oxiran-2-yl)-2-(1H-tetrazol-1-yl)pyridine | 220.2 |
| 23 | 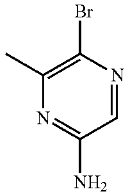 Method: I-2 | 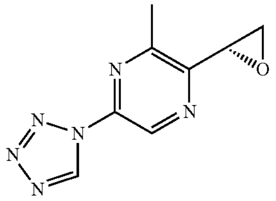 Fast eluted 23A (S)-3-methyl-2-(oxiran-2-yl)-5-(1H-tetrazol-1-yl)pyrazine | 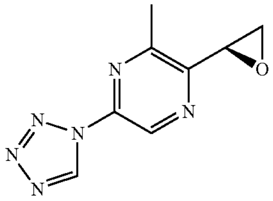 Slow eluted 23B (R)-3-methyl-2-(oxiran-2-yl)-5-(1H-tetrazol-1-yl)pyrazine | 205.3 |
| 24 | 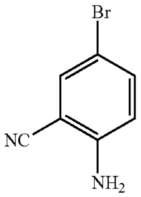 Method: I-2 | 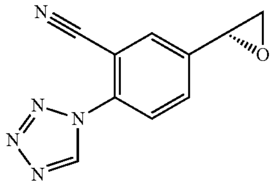 Fast eluted 24A (S)-4-methyl-5-(oxiran-2-yl)-2-(1H-tetrazol-1-yl)benzonitrile | 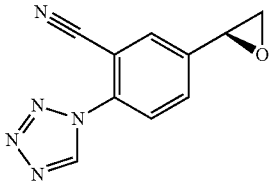 Slow eluted 24B (R)-4-methyl-5-(oxiran-2-yl)-2-(1H-tetrazol-1-yl)benzonitrile | 214.2 |

TABLE 1-continued

| Epoxides prepared using the method described for I-1 or I-2 | | | | |
|---|---|---|---|---|
| Intermediate No. | Column 2 | Structure and name | Structure and name | LC-MS [M + 1]+ |
| 25 | 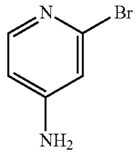 Method: I-2 | 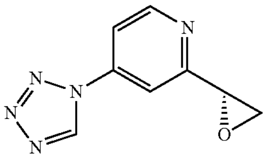 Fast eluted 25A (S)-2-(oxiran-2-yl)-4-(1H-tetrazol-1-yl)pyridine | 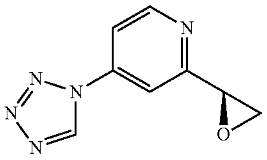 Slow eluted 25B (R)-2-(oxiran-2-yl)-4-(1H-tetrazol-1-yl)pyridine | 190.0 |
| 26 | 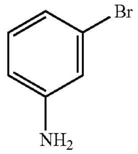 Method: I-2 | 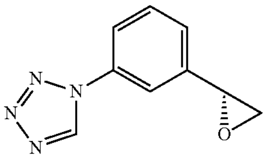 Fast eluted 26A (S)-1-(2-methyl-3-(oxidant-2-yl)phenyl)-1H-tetrazole | 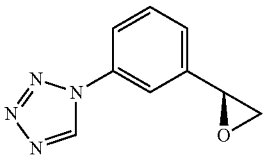 Slow eluted 26B (R)-1-(2-methyl-3-(oxidant-2-yl)phenyl)-1H-tetrazole | 189.1 |
| 27 | 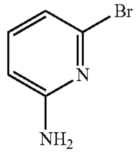 Method: I-2 | 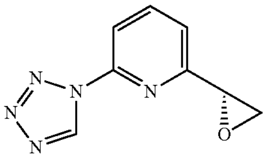 Fast eluted 27A (S)-2-(oxiran-2-yl)-6-(1H-tetrazol-1-yl)pyridine | 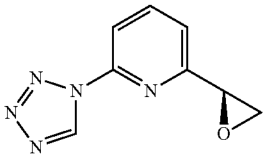 Slow eluted 27B (R)-2-(oxiran-2-yl)-6-(1H-tetrazol-1-yl)pyridine | 190.2 |
| 28 | 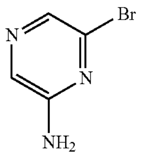 Method: I-2 | 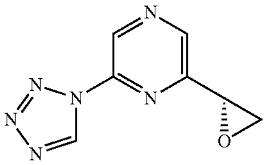 Fast eluted 28A (S)-2-(oxiran-2-yl)-6-(1H-tetrazol-1-yl)pyridine | 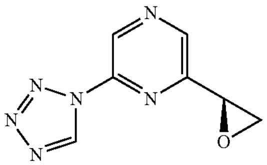 Slow eluted 28B (R)-2-(oxiran-2-yl)-6-(1H-tetrazol-1-yl)pyridine | 191.2 |
| 29 | 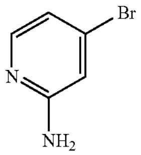 Method: I-2 | 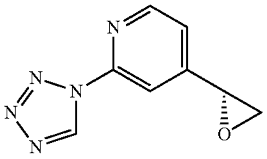 Fast eluted 29A (S)-4-(oxiran-2-yl)-2-(1H-tetrazol-1-yl)pyridine | 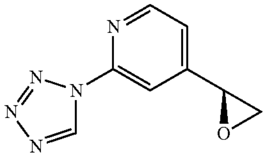 Slow eluted 29B (R)-4-(oxiran-2-yl)-2-(1H-tetrazol-1-yl)pyridine | 190.2 |
| 30 | 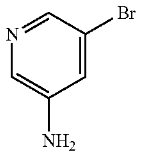 Method: I-2 | 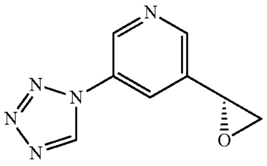 Fast eluted 30A (S)-3-(oxiran-2-yl)-5-(1H-tetrazol-1-yl)pyridine | 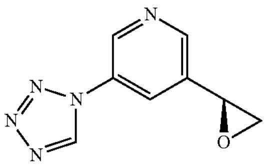 Slow eluted 30B (R)-4-(oxiran-2-yl)-2-(1H-tetrazol-1-yl)pyridine | 190.2 |

TABLE 1-continued

| Epoxides prepared using the method described for I-1 or I-2 | | | | |
|---|---|---|---|---|
| Intermediate No. | Column 2 | Structure and name | Structure and name | LC-MS [M + 1]+ |
| 31 | 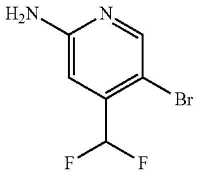 Method: I-2 | 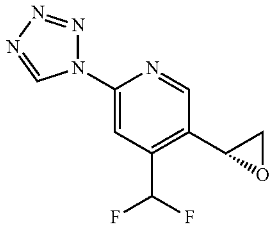 Fast eluted 31A (R)-4-(difluoromethyl)-5-(oxiran-2-yl)-2-(1H-tetrazol-1-yl)pyridine | 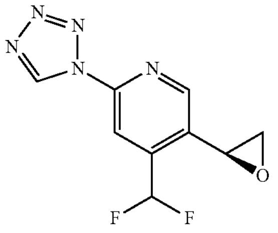 Slow eluted 31B (S)-4-(difluoromethyl)-5-(oxiran-2-yl)-2-(1H-tetrazol-1-yl)pyridine | 240.3 |
| 32 | 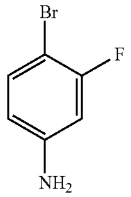 Method: I-2 | 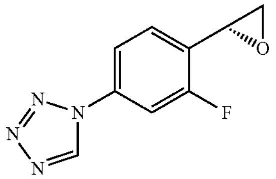 Fast eluted 32A (S)-3-fluoro-2-(oxiran-2-yl)-5-(1H-tetrazol-1-yl)pyridine | 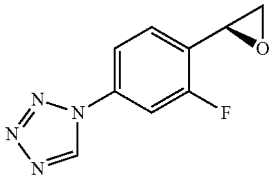 Slow eluted 33B (R)-3-fluoro-2-(oxiran-2-yl)-5-(1H-tetrazol-1-yl)pyridine | 207.3 |
| 33 | 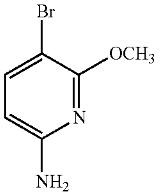 Method: I-2 | 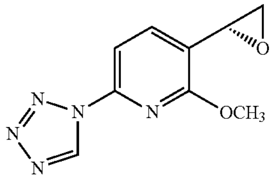 Fast eluted 33A (S)-2-methoxy-3-(oxiran-2-yl)-6-(1H-tetrazol-1-yl)pyridine | 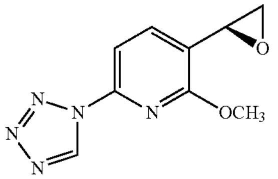 Slow eluted 33B (R)-2-methoxy-3-(oxiran-2-yl)-6-(1H-tetrazol-1-yl)pyridine | 220.5 |
| 34 | 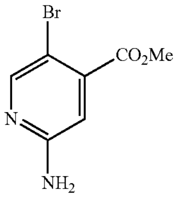 Method I-2 | 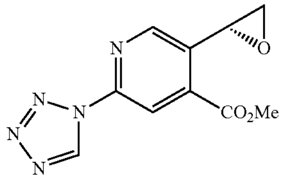 Fast eluted 34A (S)-methyl 5-(oxiran-2-yl)-2-(1H-tetrazol-1-yl)isonicotinate | 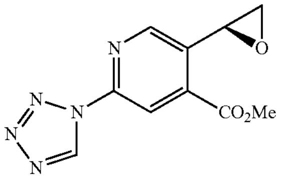 Slow eluted 34B (R)-methyl 5-(oxiran-2-yl)-2-(1H-tetrazol-1-yl)isonicotinate | 248.3 |
| 35 | 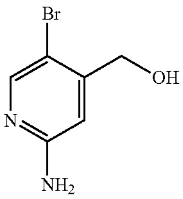 Method: I-2 | 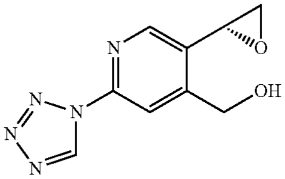 Fast eluted 35A (S)-(5-(oxiran-2-yl)-2-(1H-tetrazol-1-yl)pyridin-4-yl)methanolyl)isonicotinamide | 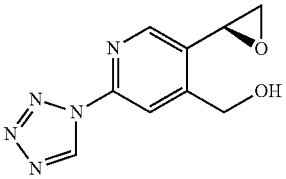 Slow eluted 35B (R)-(5-(oxiran-2-yl)-2-(1H-tetrazol-1-yl)pyridin-4-yl)methanolyl)isonicotinamide | 219.2 |

INTERMEDIATE 36

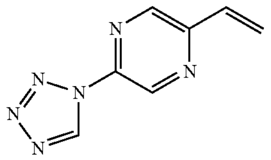

2-(1H-Tetrazol-1-yl)-5-vinylpyrazine

Step A: 2-Bromo-5-(1H-tetrazol-1-yl)pyrazine

To a solution of 5-bromopyrazin-2-amine (10.75 g, 57.5 mmol) in ethyl acetate (150 ml) was added trimethylsilyl 2,2,2-trifluoroacetate (16.88 ml, 98 mmol). The mixture was stirred for 5 min, and triethoxymethane (17.21 ml, 103 mmol) was added. After the resulting mixture was stirred for another five min, azidotrimethylsilane (12.09 ml, 92 mmol) was added. Stirring continued at rt for 2 days, and the mixture was concentrated under reduced pressure. Recrystallization of the residue from ethyl acetate afforded the title compound. LCMS $[M+2+1]^+$=228.9.

Step B: 2-(1H-Tetrazol-1-yl)-5-vinylpyrazine

A solution of 2-bromo-5-(1H-tetrazol-1-yl)pyrazine (11.2 g, 49.3 mmol), potassium vinyltrifluoroborate (13.22 g, 99.0 mmol), 1,1'-bis(diphenylphosphino)ferrocene-palladium(ii) dichloride dichloromethane complex (2.01 g, 2.47 mmol), and TEA (13.75 ml, 99.0 mmol) in ethanol (150 ml) was heated at reflux at 82° C. for 4 h. The reaction mixture was allowed to cool to rt, and the precipitation was filtered off. The filtrate was concentrated, and the residue was purified by flash chromatography (Biotage, Si, ethyl acetate in hexane: 35 to 45%) affording the title compound. The filter cake was stirred in DCM (50 mL), and the solid was filtered off. The filtrate was concentrated to afford more of the title compound. LCMS $[M+1]^+$=175.1.

The following arylvinyl intermediates in Table 2 were prepared employing a similar synthetic method as that described for Intermediate 36 using the noted starting material.

TABLE 2

Arylvinyls prepared according to the method described for INTERMEDIATE 36

| Intermediate No. | Starting material | Structure and name | LC-MS $[M+1]^+$ |
|---|---|---|---|
| 37 | 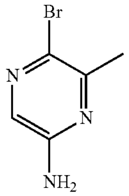 | 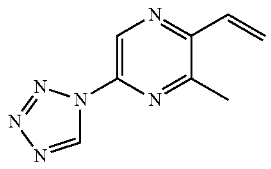 3-methyl-5-(1H-tetrazol-1-yl)-2-vinylpyrazine | 189.3 |
| 38 | 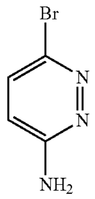 | 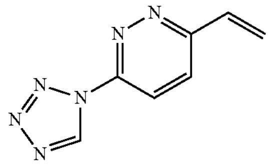 3-(1H-tetrazol-1-yl)-6-vinylpyridazine | 174.2 |
| 39 | 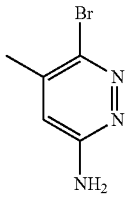 | 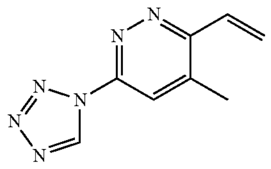 4-methyl-6-(1H-tetrazol-1-yl)-3-vinylpyridazine | 189.0 |
| 40 | 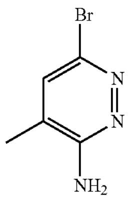 | 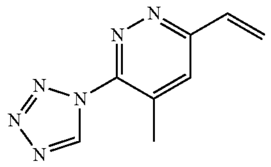 4-methyl-3-(1H-tetrazol-1-yl)-6-vinylpyridazine | 189.1 |

TABLE 2-continued
Arylvinyls prepared according to the method described for INTERMEDIATE 36
| Intermediate No. | Starting material | Structure and name | LC-MS $[M + 1]^+$ |
|---|---|---|---|
| 41 | 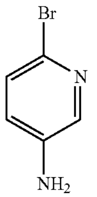 | 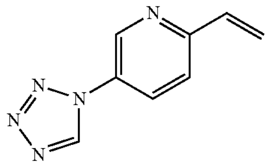 5-(1H-tetrazol-1-yl)-2-vinylpyridine | 174.2 |
| 42 | 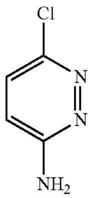 | 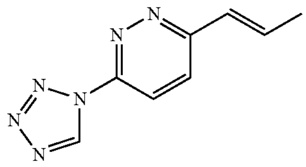 (E)-3-(prop-1-en-1-yl)-6-(1H-tetrazol-1-yl)pyridazine | 189.2 |
| 43 | 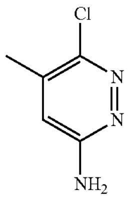 | 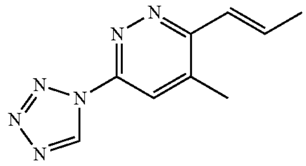 (E)-4-methyl-3-(prop-1-en-1-yl)-6-(1H-tetrazol-1-yl)pyridazine | 203.1 |
| 44 | 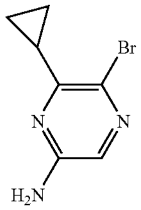 [SMILES: Nc1cnc(Br)c(C2CC2)n1] | 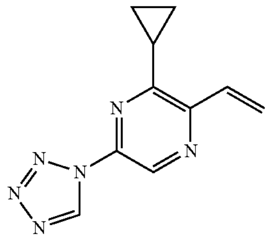 3-cyclopropyl-5-(1H-tetrazol-1-yl)-2-vinylpyrazine | 215.2 |
| 45 | 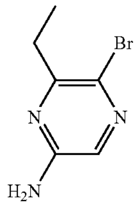 | 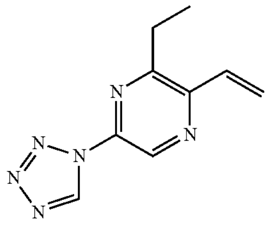 3-ethyl-5-(1H-tetrazol-1-yl)-2-vinylpyrazine | 203.1 |

INTERMEDIATE 46

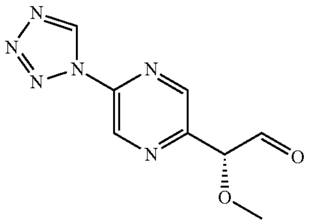 [SMILES: CO[C@@H](C=O)c1cnc(-n2cnnn2)cn1]

(R)-2-(5-(1H-Tetrazol-1-yl)pyrazin-2-yl)-2-methoxyacetaldehyde

Step A: (R)-2-(6-(1H-Tetrazol-1-yl)pyrazin-3-yl)-2-methoxyethanol (R)-3-(oxiran-2-yl)-6-(1H-tetrazol-1-yl)pyridazine (0.96 g, 5.05 mmol) in dry MeOH (50 ml) was heated at 85° C. in the presence of 4-methylbenzenesulfonic acid (0.087 g, 0.505 mmol) overnight. The mixture was cooled to rt, and concentrated. The residue was dissolved in 10 ml DMSO, and was purified by HPLC [5-75% acetonitrile (+0.05% TFA) in $H_2O$ (+0.05% TFA)]. The solvent was removed, and the residue was dissolved in DCM. The DCM solution was washed with $NaHCO_3$, dried over $MgSO_4$ and concentrated to provide the titel compound. LCMS $[M+1-28]^+$=195.0.

Step B: (R)-2-(6-(1H-Tetrazol-1-yl)pyrazin-3-yl)-2-methoxyacetaldehyde

To a solution of (R)-2-(6-(1H-tetrazol-1-yl)pyrazin-3-yl)-2-methoxyethanol (0.4 g, 1.80 mmol) in DCM (30 ml) was added Dess-Martin periodane (0.764 g, 1.80 mmol) at rt. The resulting solution was stirred at rt overnight, and was directly used in the next step. LCMS $[M+1-28]^+$=192.9.

The following aldehyde intermediates in Table 3 were prepared employing a similar synthetic method as that described for 1-46, but using the starting material and solvent in Step A as noted in the table.

TABLE 3

Aldehydes prepared using the method described for I-46

| Intermediate No. | Starting Material | Structure and name | LC-MS $[M + 1 - 28]^+$ |
|---|---|---|---|
| 47 | 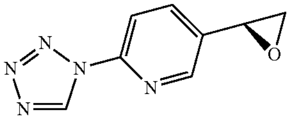 i-PrOH | 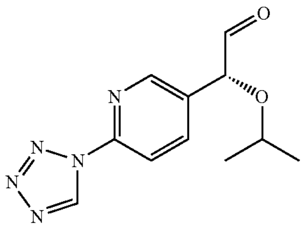 (R)-2-(6-(1H-tetrazol-1-yl)pyridin-3-yl)-2-isopropoxyacetaldehyde | 223.0 |
| 48 | 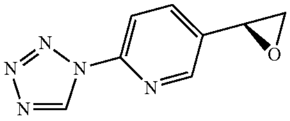 MeOH | 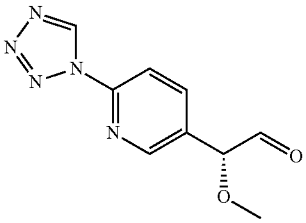 (R)-2-(6-(1H-tetrazol-1-yl)pyridin-3-yl)-2-methoxyacetaldehyde | 192.0 |
| 49 | 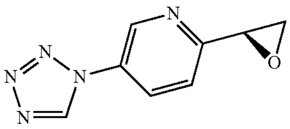 MeOH | 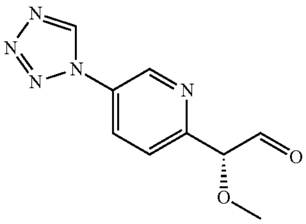 (R)-2-(5-(1H-tetrazol-1-yl)pyridin-2-yl)-2-methoxyacetaldehyde | 192.0 |

INTERMEDIATE 50

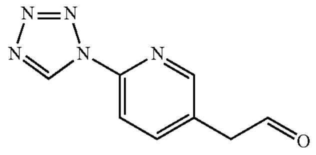 [SMILES: O=CCc1ccc(-n2cnnn2)nc1]

2-(6-(1H-Tetrazol-1-yl)pyridin-3-yl)acetaldehyde

Step A: 2-(6-(1H-Tetrazol-1-yl)pyridin-3-yl)ethanol

To a solution of 5-(oxiran-2-yl)-2-(1H-tetrazol-1-yl)pyridine (500 mg, 2.64 mmol) in ethanol (5. mL) was added 10% Pd/C (101 mg, 0.952 mmol) and $HC(O)ONH_4$ (500 mg, 7.93 mmol). The reaction mixture was vigorously stirred for 1.5 h, then filtered through a pad of silica gel. The filtrate was concentrated to give the title compound. $^1$H NMR (500 MHz, $CDCl_3$) δ 9.54 (s, 1 H), 8.43 (d, J=2.0 Hz, 1 H), 8.02 (d, J=8.3 Hz, 1 H), 7.90 (dd, J=8.3, 2.0 Hz, 1H), 3.91 (t, J=6.3 Hz, 2 H), 2.96 (t, J=6.3 Hz, 2 H).

Step B: 2-(6-(1H-Tetrazol-1-yl)pyridin-3-yl)acetaldehyde

To a solution of 2-(6-(1H-tetrazol-1-yl)pyridin-3-yl)ethanol (100 mg, 0.523 mmol) in DCM (2.6 mL) was added Dess-Martin periodinane (333 mg, 0.785 mmol). The mixture was stirred for 1.5 h, diluted with 10% $Na_2S_2O_3$ and 10% $NaHCO_3$ aqueous, and stirred for 20 min. The aqueous layer was extracted with DCM, and the combined organic layers were washed with brine, dried ($MgSO_4$), and concentrated to give the title compound. LCMS $[M+1]^+$=190.

The following aldehyde intermediates in Table 4 were prepared employing a similar synthetic method as that described for I-50, but using the noted starting material.

TABLE 4

| Aldehydes prepared were prepared employing a similar synthetic method as that described for according to the method described for I-50 | | | |
|---|---|---|---|
| Intermediate No. | Starting material | Structure and name | |
| 51 | 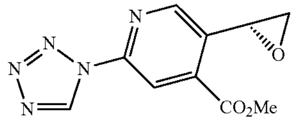 [SMILES: COC(=O)c1cc(-n2cnnn2)ncc1[C@H]1CO1] | 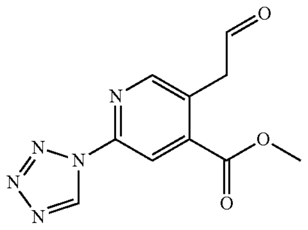 methyl 5-(2-oxoethyl)-2-(1H-tetrazol-1-yl)isonicotinate | LC-MS [M + 1]+ 248.4 |
| 52 | 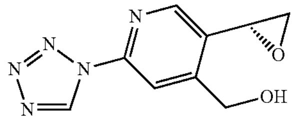 [SMILES: OCc1cc(-n2cnnn2)ncc1[C@H]1CO1] | 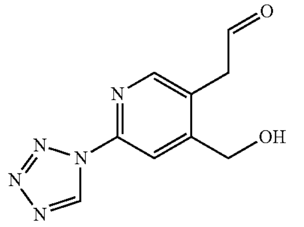 2-(4-(hydroxymethyl)-6-(1H-tetrazol-1-yl)pyridin-3-yl)acetaldehyde | LC-MS [M + 1]+ 220.3 |

INTERMEDIATE 53

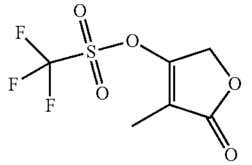

4-Methyl-5-oxo-2,5-dihydrofuran-3-yl trifluoromethanesulfonate

Step A: Ethyl 4-bromo-2-methyl-3-oxobutanoate

To a solution of ethyl 2-methyl-3-oxobutanoate (5.05 g, 35.0 mmol) in water (10 mL) at 0° C. was added bromine (1.805 mL, 35.0 mmol) dropwise over 2 h. The resulting mixture was stirred at room temperature for 16 h, and extracted with ethyl acetate. The organic layer was separated, dried over sodium sulfate, and concentrated in vacuo to give the title compound. $^1$H NMR (500 MHz, $CDCl_3$), δ 4.32-4.27 (m, 2 H), 2.455 (s, 2 H), 1.99 (s, 3 H), 1.337-1.31 (t, 3 H).

Step B: 4-Hydroxy-3-methylfuran-2(5H)-one

A mixture of ethyl 4-bromo-2-methyl-3-oxobutanoate (7.81 g, 35 mmol) and hydrogen bromide (0.040 mL, 48%, 0.35 mmol) was heated at 100° C. for 6 h. The precipitate was collected by filtration, and washed with ethyl acetate to give the title compound. $^1$H NMR (500 MHz, $CDCl_3$), δ 4.60 (s, 2 H), 3.31 (s, 1H), 1.69 (s, 3 H).

Step C: 4-Methyl-5-oxo-2,5-dihydrofuran-3-yl trifluoromethanesulfonate

To a solution of 4-hydroxy-3-methylfuran-2(5H)-one (400 mg, 3.51 mmol) in DCM (10 mL) at −78° C. was added 2,6-lutidine (0.612 mL, 5.26 mmol) and trifluoromethanesulfonic anhydride (0.711 mL, 4.21 mmol) dropwise. The reaction mixture was stirred at −78° C. for 0.5 h, and at rt for 1 h. The mixture was diluted with DCM (100 mL), washed with 1 N hydrogen chloride (3×100 mL) and saturated aqueous sodium bicarbonate, dried over sodium sulfate, and concentrated under reduced pressure to give the title compound. LCMS $[M+1]^+$=247.0.

INTERMEDIATE 54

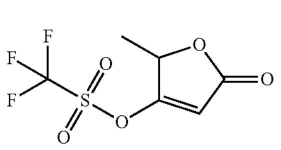

2-Methyl-5-oxo-2,5-dihydrofuran-3-yl trifluoromethanesulfonate

Step A: Ethyl 4-bromo-3-oxopentanoate

To a solution of ethyl 3-oxopentanoate (5.0 g, 34.7 mmol) in chloroform (27 mL) at 0° C. was added bromine (1.787 ml, 34.7 mmol) in chloroform (10 mL) dropwise. The resulting solution was stirred at rt for 16h, washed with water, dried over sodium sulphate, and concentrated to give the title compound. $^1$HNMR (500 MHz, $CDCl_3$), δ4.670-4.630 (dd, J=6.7 Hz, 1H), 4.251-4.208 (dd, J=7.2 Hz, 2H), 3.883-3.851 (d, J=16 Hz, 1H), 3.687-3.655 (d, J=16 Hz, 1H), 1.804-1.791 (d, J=6.8 Hz, 3H), 1.323-1.295 (m, J=7.2 Hz, 3H).

Step B: 4-Hydroxy-5-methylfuran-2(5H)-one

Ethyl 4-bromo-3-oxopentanoate (7.49 g, 33.6 mmol) was treated with potassium hydroxide (5.03 g, 90 mmol) in water (36 mL) at 0° C. The resulting mixture was vigorously stirred at 0° C. for 4 h, and extracted with methylene chloride (2×100 mL). The aqueous was acidified to pH<1 with 6 N hydrogen chloride, and extracted with methylene chloride (3×100 mL). The combined organic layers were dried over sodium sulphate, and concentrated to give the title compound. $^1$HNMR (500 MHz, $CDCl_3$), δ5.064 (s, 1 H), 4.949-4.878 (m, 1 H), 3.251-3.239 (m, 1 H), 1.566-1.547 (m, 3 H).

Step C: 2-Methyl-5-oxo-2,5-dihydrofuran-3-yl trifluoromethanesulfonate

To a solution of 4-hydroxy-5-methylfuran-2(5H)-one in methylene chloride (10 mL) at −78° C. was added 2,6-lutidine (−0.612 mL, 5.26 mmol) and triflic anhydride (0.711 mL, 4.21 mmol) dropwise. The reaction temperature was maintained at −78° C. for 0.5 h and at rt for 1 h. The mixture was washed with hydrogen chloride (1 N, 3×100 mL), then diluted sodium bicarbonate, and then dried over sodium sulfate to give the title compound. LC/MS $[M+1]^+$=247.0.

INTERMEDIATE 55

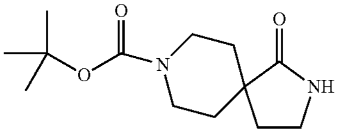 [SMILES: CC(C)(C)OC(=O)N1CCC2(CCNC2=O)CC1]

tert-Butyl 1-oxo-2,8-diazaspiro[4.5]decane-8-carboxylate

Step A: Methyl piperidine-4-carboxylate

To a solution of piperidine-4-carboxylic acid (1000 g, 7.75 mol) in MeOH (8000 mL) was added $SOCl_2$ (1000 mL) at 0° C. The mixture was stirred at rt for 18 h and concentrated to give the title compound. $^1$H-NMR (400 MHz, $CD_3OD$) δ 3.74 (s, 3 H), 3.43-3.35 (m, 2 H), 3.12-3.06 (m, 2 H), 2.81-2.74 (m, 1 H), 2.20-2.15 (m, 2H), 1.95-1.85 (m, 2H).

Step B: 1-tert-Butyl 4-methyl piperidine-1,4-dicarboxylate

To a solution of methyl piperidine-4-carboxylate (1400 g, 7.75 mol) in DCM (8000 mL) was added $NaHCO_3$ (1953 g, 23.21 mol) and $Boc_2O$ (2030 g, 9.3 mol) dropwise at 0° C. The mixture was stirred at rt for 18 h, and was filtered. The filtrate was concentrated in vacuo to give the title compound. $^1$H-NMR (400 MHz, $CDCl_3$) δ 4.100-3.90 (m, 2 H), 3.68 (s, 3 H), 2.85-2.79 (m, 2 H), 2.47-2.41 (m, 1 H), 1.88-1.80 (m, 2 H), 1.66-1.52 (m, 2H), 1.47 (s, 9 H).

Step C: 1-tert-Butyl 4-methyl 4-(cyanomethyl)piperidine-1,4-dicarboxylate

LDA [prepared from n-BuLi (2.5 M, 420 mL) and diisopropylamine (128 g, 1.07 mol) in THF (300 mL)] was added dropwise to a solution of 1-tert-butyl 4-methyl piperidine-1,4-dicarboxylate (185 g, 761.3 mmol) in THF (1200 mL) at −70° C. under $N_2$. The mixture was stirred at −70° C. for 1.5 h, and to this mixture was added a solution of bromoacetonitrile (128 g, 1.12 mol) in THF (300 mL) at −70° C. Stirring continued at −70° C. for 1 h and at 20° C. for 18 h. The resulting mixture was quenched with $H_2O$. The organic layer was separated, and the aqueous layer was extracted with EtOAc (500 mL×3). The combined organic extracts were dried over $Na_2SO_4$ and concentrated. The residue was purified by silica gel chromatography eluted with PE/EA (5:1) to give the title compound. $^1$H-NMR (400 MHz, $CDCl_3$) δ 3.90-3.75 (m, 5 H), 3.12-3.00 (m, 2 H), 2.61-2.56 (m, 2 H), 2.19-2.1 (m, 2 H), 1.59-1.50 (m, 2 H), 1.40 (s, 9 H).

Step D: tert-Butyl 1-oxo-2,8-diazaspiro[4.5]decane-8-carboxylate

To a solution of 1-tert-butyl 4-methyl 4-(cyanomethyl) piperidine-1,4-dicarboxylate (350 g, 1.2 mol) in MeOH (6000 mL) were added $NH_3.H_2O$ (400 mL) and Raney-Ni (300 g) at rt. The mixture was stirred under 2 MPa of hydrogen at 50° C. for 18 h, and filtered. The filtrate was concentrated. The crude product was washed with EtOAc to give the title compound. $^1$H-NMR (400 MHz, $CDCl_3$) δ 6.30

(s, 1 H), 4.08-3.92 (m, 2 H), 3.38-3.30 (m, 2 H), 3.01-2.91 (m, 2 H), 2.10-2.00 (m, 2 H), 1.88-1.78 (m, 2 H), 1.49-1.32 (m, 11 H).

INTERMEDIATE 56

I-56

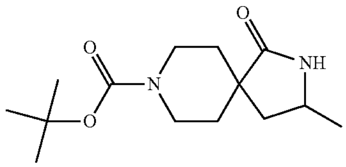

I-56A

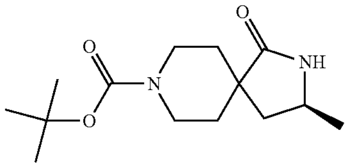

I-56B

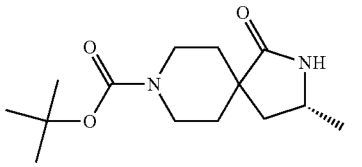

tert-Butyl 3-methyl-1-oxo-2,8-diazaspiro[4.5]decane-8-carboxylate (racemic, I-56)

(5)-tert-Butyl 3-methyl-1-oxo-2,8-diazaspiro[4.5]decane-8-carboxylate (I-56A); and (R)-tert-Butyl 3-methyl-1-oxo-2,8-diazaspiro[4.5]decane-8-carboxylate (I-56B)

Step A: 1-tert-Butyl 4-methyl 4-(2-methylallyl)piperidine-1,4-dicarboxylate

A solution of N-boc-piperidine-4-carboxylic acid methyl ester (2 g, 8.22 mmol) in THF (40 ml) was cooled to −78° C. Under nitrogen, to this solution was added LDA (6.17 ml, 12.33 mmol, 2.0 m in THF) dropwise. The reaction mixture was stirred at −78° C. for 30 minutes, and a solution of 3-bromo-2-methylpropene (1.6 g, 11.85 mmol) in THF (2 ml) was added. After the mixture was stirred for 1 h at the same temperature, the reaction was quenched with saturated ammonium chloride aqueous (5 ml). The mixture was allowed to warm up to rt, extracted with EtOAc (50 ml×2). The combined organic layers were washed with brine (30 ml), dried over anhydrous sodium sulfate and filtered. The filtrate was concentrated and the crude product was purified by column chromatography eluting with 0-30% ethyl acetate/hexane to give the title compound. LCMS $[M-56+1]^+$=242.2.

Step B: 1-tert-Butyl 4-methyl 4-(2-oxopropyl)piperidine-1,4-dicarboxylate

To a solution of 1-tert-butyl 4-methyl 4-(2-methylallyl) piperidine-1,4-dicarboxylate (2.2 g, 7.40 mmol) in dioxane/water (60 ml, 1/1) under nitrogen was added osmium tetroxide (0.038 g, 0.148 mmol) and sodium periodate (2.88 g, 13.46 mmol). The mixture was stirred at rt for 3 h. The mixture was then diluted with dichloromethane (50 ml), washed with 20% $Na_2S_2O_3$ (20 ml). The organic layers were combined and washed with brine (20 ml), dried over anhydrous sodium sulfate, and filtered. The filtrates were concentrated and the residue was purified by column chromatography eluting with 0-60% ethyl acetate in hexane to afford the title compound. LCMS $[M+23]^+$=322.2.

Step C: tert-Butyl 3-methyl-1-oxo-2,8-diazaspiro[4.5]decane-8-carboxylate (I-56)

To a solution of 1-tert-Butyl 4-methyl 4-(2-oxopropyl) piperidine-1,4-dicarboxylate (1.15 g, 3.84 mmol) in methanol (25 ml) was added ammonium acetate (3.85 g, 49.9 mmol), sodium cyanoborohydride (0.681 g, 10.83 mmol) and magnesium sulfate (2.54 g, 21.13 mmol). The mixture was heated at 80° C. in a sealed tube for 12 hours, cooled to rt, and filtered through a pad of CELITE. The filter cake was washed with methanol. The combined filtrates were then concentrated, and the residue was purified by column chromatography eluting with 0-10% methanol in ethyl acetate to afford the title compound. LCMS $[M+23]^+$=291.2.

Step D: I-56A and I-56B tert-Butyl 3-methyl-1-oxo-2,8-diazaspiro[4.5]decane-8-carboxylate was subjected to SFC chiral separation. The enantiomers I-56A and I-56B were resolved on a Chiralcel IA column eluting with 30% MeOH:MeCN (2:1)/$CO_2$ (100 bar, 35° C.).

INTERMEDIATE 57

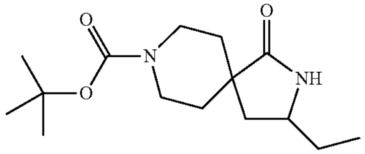 [SMILES: CCC1CC2(CCN(C(=O)OC(C)(C)C)CC2)C(=O)N1]

tert-Butyl 3-ethyl-1-oxo-2,8-diazaspiro[4.5]decane-8-carboxylate (racemic)

Step A: 1-tert-Butyl 4-ethyl 4-(2-bromoallyl)piperidine-1,4-dicarboxylate

To a solution of 1-tert-butyl 4-ethyl piperidine-1,4-dicarboxylate (9.56 ml, 38.9 mmol) in THF (200 ml) were added dropwise lithium diisopropylamide (29.1 ml, 58.3 mmol) at −78° C. This was followed by stirring at the same temperature for 50 min. 2,3-Dibromoprop-1-ene (5.47 ml, 56.0 mmol) in THF (10 ml) was then added to the reaction mixture slowly. The resulting mixture was stirred at −78° C. for 1.5 h, quenched with $NH_4Cl$ solution (15 ml) and warmed to rt.

The aqueous layer was extracted with EtOAc (30 ml×3). The combined organics were washed with brine (30 ml), dried over $MgSO_4$ and concentrated to get the crude product which was purified by silica gel column chromatography (RediSep 220 g Gold column) using (0-30)% EtOAc/Hexanes as mobile phase to give the title compound.

Step B: 1-tert-Butyl 4-ethyl 4-(2-methylenebutyl)piperidine-1,4-dicarboxylate

To a solution of 1-tert-butyl 4-ethyl 4-(2-bromoallyl) piperidine-1,4-dicarboxylate (5.0 g, 13.29 mmol) in THF (80 ml) in a sealed tube were added BINAP (3.31 g, 5.32 mmol), diethylzinc (15.95 ml, 15.95 mmol) and $Pd(OAc)_2$ (0.597 g, 2.66 mmol). The resulting mixture was degassed and heated for 16 hours at 100° C., and concentrated under reduced pressure. The crude product was purified by silica gel column chromatography (RediSep 220 g Gold column) using (0-30)% EtOAc/Hexanes as mobile phase to give the title compound.

Step C: 1-tert-Butyl 4-ethyl 4-(2-oxobutyl)piperidine-1,4-dicarboxylate

To a solution of 1-tert-butyl 4-ethyl 4-(2-methylenebutyl) piperidine-1,4-dicarboxylate (1.0 g, 3.07 mmol) in acetone (20 ml) and water (20 ml) was added potassium tetrahydroxydioxidoosmium (0.041 g, 0.111 mmol). The mixture was stirred for 10 min. Solid sodium periodate (2.62 g, 12.26 mmol) was added in 4 portions during 1 hour while the reaction temperature was maintained below 40° C. using an ice-bath. The resulting mixture was stirred for 1 hour at room temperature. After 2 h LCMS showed incomplete reaction. Another 0.036 eq. of potassium tetrahydroxydioxidoosmium (0.041 g, 0.111 mmol) was added to the mixture, and the mixture was stirred at rt for another 2 h. The suspension was filtered and, the filtrate was concentrated to remove acetone. The aqueous layer was extracted with DCM (15 ml×3). The combined organic layers were washed with 10% $Na_2S_2O_3$ solution (20 ml×2), dried over anhydrous $Na_2SO_4$, and concentrated to get the crude product which was purified by silica gel column chromatography (80 g RediSep Gold column) using (0-35)% EtOAc/Hexanes as mobile phase to give the title compound.

Step D: tert-Butyl 3-ethyl-1-oxo-2,8-diazaspiro[4.5] decane-8-carboxylate

To a stirred solution of 1-tert-butyl 4-ethyl 4-(2-oxobutyl) piperidine-1,4-dicarboxylate (0.78 g, 2.382 mmol) in ethanol (24 ml) in a sealed tube were added ammonium acetate (2.387 g, 31.0 mmol), sodium cyanoborohydride (0.422 g, 6.72 mmol) and magnesium sulfate (1.577 g, 13.10 mmol). The resulting mixture was heated for 16 hours at 80° C., and filtered over CELITE to remove $MgSO_4$. The filtrate was concentrated. The residue was redissolved in DCM (20 ml) and the solution was washed with saturated $NaHCO_3$ (10 ml), water (10 ml) and brine (10 ml). The organic layer was dried over anhydrous $MgSO_4$ concentrated. The crude product was purified by silica gel column chromatography (40 g RediSep Gold column) using (0-10)% MeOH/EtOAc to give the title compound. LCMS $[M+1]^+$=282.1

INTERMEDIATE 58

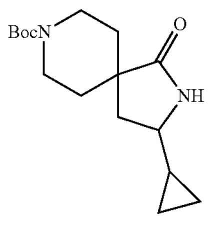 [SMILES: CC(C)(C)OC(=O)N1CCC2(CC1)CC(C1CC1)NC2=O]

tert-Butyl 3-cyclopropyl-1-oxo-2,8-diazaspiro[4.5] decane-8-carboxylate (racemic)

tert-butyl 3-cyclopropyl-1-oxo-2,8-diazaspiro[4.5]decane-8-carboxylate was synthesized from potassium cyclopropyltrifluoroborate following essentially the same procedure described above for I-57.

INTERMEDIATE 59

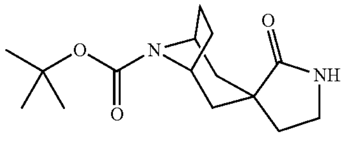 [SMILES: CC(C)(C)OC(=O)N1C2CCC1CC1(CCNC1=O)C2]

(1R,3r,5S)-tert-Butyl 2'-oxo-8-azaspiro[bicyclo [3.2.1]octane-3,3'-pyrrolidine]-8-carboxylate Step A: (1R,3s,5S)-8-tert-butyl 3-methyl 8-azabicyclo[3.2.1]octane-3,8-dicarboxylate To a solution of (1R,3s,5S)-8-(tert-butoxycarbonyl)-8-azabicyclo[3.2.1]octane-3-carboxylic acid (5.0 g, 19.58 mmol) in a solvent mixture of dry MeOH (60 ml) and DCM (60.0 ml) was added (trimethylsilyl)diazomethane (19.58 ml, 39.2 mmol). The mixture was stirred for 0.5 hr, and AcOH (5 ml) was added. Volatiles were removed under reduced pressure. The residue was dissolved in EtOAc, and the solution was washed with saturated $NaHCO_3$ and brine, and dried over MgSO4. The solvent was removed to give a solid which was used in the next step without further purification. LCMS $[M+1-56]^+$=214.1

Step B: (1R,3r,5S)-8-tert-Butyl 3-methyl 3-(cyanomethyl)-8-azabicyclo[3.2.1]octane-3,8-dicarboxylate To a solution of (1R,3r,5S)-8-tert-butyl 3-methyl 8-azabicyclo[3.2.1]octane-3,8-dicarboxylate (5 g, 18.56 mmol) in THF (100 ml) was added LDA (13.92 ml, 27.8 mmol) at −78° C. The mixture was stirred at the same temperature for 30 min, then to this mixture was added bromoacetonitrile (1.940 ml, 27.8 mmol) in THF (15 ml) by injection. The resulting mixture was stirred at −78° C. for 15 min, quenched with saturated $KHSO_4$ at −78° C., warmed up to rt and diluted with ether (100 ml). The organic layer was separated, and the aqueous layer was extracted with ether (50 ml). The combined organic layers were washed with brine, dried ($MgSO_4$), and concentrated. The residue was purified by column (silica gel 120 g, EtOAc-Hexane-O-50% gradient, then 50% EtOAc. $^1$H-NMR (500 MHz, $CDCl_3$): δ ppm 4.18 (1 H, m), 4.27 (1 H, m), 3.83 (3 H, s), 2.58 (2 H, m), 2.43 (2 H, m), 1.55-1.95 (6 H, m), 1.50 (9 H, s). LCMS $[M+1-100]^+$=209.2.

Step C: (1R,3r,5S)-8-tert-Butyl 3-methyl 3-(2-aminoethyl)-8-azabicyclo[3.2.1]octane-3,8-dicarboxylate To a solution of (1R,3r,5S)-8-tert-butyl 3-methyl 3-(cyanomethyl)-8-azabicyclo[3.2.1]octane-3,8-dicarboxylate (4.0 g, 12.97 mmol) in ethanol (20 ml) and AcOH (20 ml) was added platinum(IV) oxide (0.295 g, 1.297 mmol). The mixture was hydrogenated on a shaker (45 psi hydrogen) at rt for 24 hr. The catalyst was filtered off through a CELITE pad, and the filtrate was concentrated. The crude material was used in the next step without further purification. LCMS $[M+1]^+$=313.20; $[M+1-56]^+$=257.1.

Step D: (1R,3r,5S)-tert-Butyl 2'-oxo-8-azaspiro[bicyclo[3.2.1]octane-3,3'-pyrrolidine]-8-carboxylate A mixture of (1R,3r,5S)-8-tert-butyl 3-methyl 3-(2-aminoethyl)-8-azabicyclo[3.2.1]octane-3,8-dicarboxylate (4.2 g, 13.44 mmol) and potassium carbonate (9.29 g, 67.2 mmol) in MeOH (50 ml) was heated at 60° C. for 1 hr. The resulting mixture was concentrated, and diluted with DCM (50 ml). The suspension was filtered through a silica gel pad. The filtrate was concentrated to give the title compound. $^1$H-NMR (500 MHz, $CDCl_3$): δ ppm 5.95 (1 H, bs), 4.30 (1 H, m), 4.20 (1 H, m), 3.26 (2 H, t, J=7.0 Hz), 1.75-2.15 (6 H, m), 1.47 (9 H, s). LCMS $[M+1]^+$=281.15; $[M+1-56]^+$=225.1.

INTERMEDIATE 60

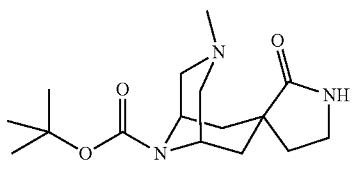 [SMILES: CN1CC2CC3(CCNC3=O)CC(C1)N2C(=O)OC(C)(C)C]

(1R,3's,5S)-tert-Butyl 3-methyl-2'-oxo-3,9-diazaspiro[bicyclo[3.3.1]nonane-7,3'-pyrrolidine]-9-carboxylate Step A: (1R,5S)-tert-Butyl 3-methyl-7-(((trifluoromethyl)sulfonyl)oxy)-3,9-diazabicyclo[3.3.1]non-6-ene-9-carboxylate To a solution of (1R,5S)-tert-butyl 3-methyl-7-oxo-3,9-diazabicyclo[3.3.1]nonane-9-carboxylate (10 g, 39.3 mmol) in tetrahydrofuran (100 mL) was added diisopropyllithium solution (23.59 mL, 47.2 mmol) at −78° C. dropwise. The solution was stirred at −78° C. for 0.5 h, and was added a solution of 2-[N,N-bis(trifluoromethanesulfonyl)amino]-5-chloropyridine (18.53 g, 47.2 mmol) in tetrahydrofuran (25 mL). The resulting mixture was stirred at −78° C. for 2 h and at rt for 20 min, quenched with saturated ammonium chloride aqueous, and diluted with ethyl acetate. The organic layer was separated, washed with aqueous saturated sodium bicarbonate, dried over sodium sulfate, and concentrated. The residue was purified on silica gel using ethyl acetate and hexane as eluting solvents to give the title compound. LCMS $[M+1]^+$=386.9.

Step B: (1R,5S)-9-tert-Butyl 7-methyl 3-methyl-3,9-diazabicyclo[3.3.1]non-6-ene-7,9-dicarboxylate To a solution of (1R,5S)-tert-butyl 3-methyl-7-(((trifluoromethyl)sulfonyl)oxy)-3,9-diazabicyclo[3.3.1]non-6-ene-9-carboxylate (14 g, 36.2 mmol) and diisopropylethylamine (9.47 mL, 54.3 mmol) in a solvent mixture of methanol (100 mL) and DMF (100 mL) was added triphenylphosphine (0.95 g, 3.62 mmol) and palladium (II) acetate (0.407 g, 1.812 mmol). The mixture was stirred under carbon monoxide atmosphere (1 atm) for 24, concentrated and partitioned between ethyl acetate and water. The organic layer was washed with brine, dried over sodium sulfate, and concentrated. The residue was purified on silica gel column using ethyl acetate and hexane as eluting solvents to give the title compound. LCMS $[M+1]^+$=297.2.

Step C: (1R,5S)-9-tert-Butyl 7-methyl 3-methyl-3,9-diazabicyclo[3.3.1]nonane-7,9-dicarboxylate To a solution of (1R,5S)-9-tert-butyl 7-methyl 3-methyl-3,9-diazabicyclo[3.3.1]non-6-ene-7,9-dicarboxylate (4.69 g, 15.83 mmol) in methanol (50 mL) was added palladium on carbon (10%, 1.684 g, 1.583 mmol). The mixture was subjected to hydrogenation (40 psi hydrogen) for three days, and filtered through CELITE under nitrogen. The filtrate was concentrated to give the title compound. LCMS $[M+1]^+$=299.1.

Step D: (1R,5S,7s)-9-tert-Butyl 7-methyl 7-(cyanomethyl)-3-methyl-3,9-diazabicyclo[3.3.1]nonane-7,9-dicarboxylate To a solution of diisopropylamine (3.28 mL, 23.02 mmol) in tetrahydrofuran (5 mL) was added n-butyllithium (11.51 mL, 23.02) dropwise at 0° C. The solution was stirred at 0° C. for 0.5 h to form LDA solution. To another flask charged with a solution of (1R,5S)-9-tert-butyl 7-methyl 3-methyl-3,9-diazabicyclo[3.3.1]nonane-7,9-dicarboxylate (4.58 g, 15.35 mmol) in tetrahydrofuran (50 ML) was added at −78° C. the above LDA solution dropwise. The resulting mixture was stirred at −78° C. for 1 h. Bromoacetonitrile (1.54 mL, 22.10 mmol) was added dropwise, and the resulting solution was stirred at −78° C. for another 1h. The reaction was quenched with saturated ammonium chloride aqueous, and the resulting mixture was diluted with ethyl acetate. The organic layer was separated, and the aqueous layer was extracted with ethyl acetate. The combined organic layers were dried over sodium sulfate, and concentrated. The residue was purified on silica gel using methanol and dichloromethane as eluting solvents to give the title compound. LCMS $[M+1]^+$=338.2.

Step E: (1R,5S,7s)-9-tert-Butyl 7-methyl 7-(2-aminoethyl)-3-methyl-3,9-diazabicyclo[3.3.1]nonane-7,9-dicarboxylate To a solution of (1R,5S,7s)-9-tert-butyl 7-methyl 7-(cyanomethyl)-3-methyl-3,9-diazabicyclo[3.3.1]nonane-7,9-dicarboxylate (4.39 g, 13.01 mmol) in methanol (30 mL) was added platinum (IV) oxide (0.207 g, 0.911 mmol). The mixture was hydrogenated at a hydrogen pressure of 40 psi for 16 h, and was filtered through CELITE. The filtrate was concentrated to give the title compound. LCMS $[M+1]^+$=342.2.

Step F: (1R,3's,5S)-tert-Butyl 3-methyl-2'-oxo-3,9-diazaspiro[bicyclo[3.3.1]nonane-7,3'-pyrrolidine]-9-carboxylate To a solution of (1R,5S,7s)-9-tert-butyl 7-methyl 7-(2-aminoethyl)-3-methyl-3,9-diazabicyclo[3.3.1]nonane-7,9-dicarboxylate (4.44 g, 13.0 mmol) in methanol (100 mL) was added potassium carbonate (10.78 g, 78 mmol). The suspension was heated at reflux for 8 h. After cooled to rt, the mixture was filtered, and the filtrate was concentrated. The residue was dissolved in methylene chloride (200 mL), dried over sodium sulfate and concentrated to give the title compound. LCMS $[M+1]^+$=310.2.

INTERMEDIATE 61

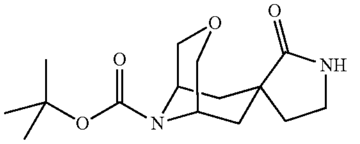 [SMILES: CC(C)(C)OC(=O)N1C2COCC1CC1(CCNC1=O)C2]

(1R,3's,5S)-tert-Butyl 2'-oxo-3-oxa-9-azaspirobicycle[3.3.1]nonane-7,3'-pyrrolidine]-9-carboxylate The title compound was made from (1R,5S)-tert-butyl 7-oxo-3-oxa-9-azabicyclo[3.3.1]nonane-9-carboxylate using essentially the same procedure described for making (1R,3's,5S)-tert-butyl 3-methyl-2'-oxo-3,9-diazaspirobicycle[3.3.1]nonane-7,3'-pyrrolidine]-9-carboxylate (I-60). LCMS $[M+1]^+$=310.26.

INTERMEDIATE 62

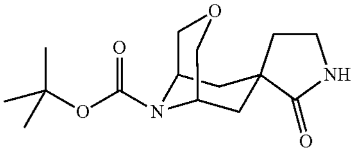 [SMILES: CC(C)(C)OC(=O)N1C2COCC1CC1(CCNC1=O)C2]

(1R,3'r,5S)-tert-Butyl 2'-oxo-3-oxa-9-azaspiro[bicyclo[3.3.1]nonane-7,3'-pyrrolidine]-9-carboxylate Step A: (1R,5S,E)-tert-Butyl 7-(1-cyano-2-methoxy-2-oxoethylidene)-3-oxa-9-azabicyclo[3.3.1]nonane-9-carboxylate A solution of methyl 2-cyanoacetate (4.39 ml, 49.7 mmol), (1R,5S)-tert-butyl 7-oxo-3-oxa-9-azabicyclo[3.3.1]nonane-9-carboxylate (8 g, 33.2 mmol), ammonium acetate (3.83 g, 49.7 mmol), and acetic acid (7.59 ml, 133 mmol) in toluene (100 ml) was heated at 150° C. overnight with a Dean-Stark trap to remove water generated from the reaction. The mixture was concentrated, and the residue was dissolved in ethyl acetate (200 mL). The organic layer was washed with aqueous saturated sodium bicarbonate, dried over sodium sulfate, and concentrated. The crude product was purified on silica gel column using ethyl acetate/hexane as eluting solvents to give the title compound. LCMS $[M+1-100]^+$=223.0.

Step B: (1R,5S,7s)-tert-Butyl 7-(1-cyano-2-methoxy-2-oxoethyl)-7-vinyl-3-oxa-9-azabicyclo[3.3.1]nonane-9-carboxylate To a suspension of (1R,5S,E)-tert-butyl 7-(1-cyano-2-methoxy-2-oxoethylidene)-3-oxa-9-azabicyclo[3.3.1]nonane-9-carboxylate (10.82 g, 33.6 mmol) and copper(I) iodide (6.39 g, 33.6 mmol) in tetrahydrofuran at 0° C. was slowly added vinylmagnesium bromide (50.3 ml, 50.3 mmol) over 2h. The mixture was stirred at 0° C. for 0.5 h and at rt for 2h. The reaction was quenched with saturated ammonium chloride aqueous (300 mL). The organic layer was separated, and the aqueous layer was extracted with ethyl acetate three times. The combined organic layers were dried over sodium sulfate, and concentrated. The crude material was purified on silica gel using ethyl acetate/hexane as eluting solvents to give the title compound. LCMS $[M+23]^+$=372.9.

Step C: 2-((1R,5S,7s)-9-(tert-Butoxycarbonyl)-7-vinyl-3-oxa-9-azabicyclo[3.3.1]nonan-7-yl)-2-cyanoacetic acid To a solution of (1R,5S,7s)-tert-butyl 7-(1-cyano-2-methoxy-2-oxoethyl)-7-vinyl-3-oxa-9-azabicyclo[3.3.1]nonane-9-carboxylate (1.3 g, 3.71 mmol) in a solvent mixture of tetrahydrofuran (10 ml), methanol (3 ml) and water (3 ml) was added lithium hydroxide (18.55 ml, 18.55 mmol). The solution was stirred at rt for 2h. After volatiles were removed, the alkaline phase was acidified at 0° C. with 1N HCl to about pH=4. The mixture was then extracted with 30% isopropanol/methylene chloride (3×100 mL). The combined organic layers were dried over sodium sulfate, and concentrated to give the title compound. LCMS $[M+1-100]^+$=237.0.

Step D: (1R,5S,7r)-tert-Butyl 7-(cyanomethyl)-7-vinyl-3-oxa-9-azabicyclo[3.3.1]nonane-9-carboxylate A solution of 2-((1R,5S,7s)-9-(tert-butoxycarbonyl)-7-vinyl-3-oxa-9-azabicyclo[3.3.1]nonan-7-yl)-2-cyanoacetic acid (1.1 g, 3.27 mmol) in DMF (10 ml) was heated at 130° C. for 20 min. After cooled down to rt, the reaction mixture was partitioned between ethyl acetate (200 mL) and brine. The organic layer was separated, dried over sodium sulfate, and concentrated. The crude material was purified on a silica gel column using ethyl acetate/hexane as eluting solvents to give the title compound. LCMS $[M+1-100]^+$=193.0.

Step E: (1R,5S,7r)-tert-Butyl 7-(cyanomethyl)-7-formyl-3-oxa-9-azabicyclo[3.3.1]nonane-9-carboxylate To a solution of (1R,5S,7r)-tert-butyl 7-(cyanomethyl)-7-vinyl-3-oxa-9-azabicyclo[3.3.1]nonane-9-carboxylate (0.66 g, 2.257 mmol) in dioxane (10 ml) and water (3 ml) was added sodium periodate (1.931 g, 9.03 mmol) and osmium tetroxide (0.035 ml, 0.113 mmol). After the mixture was stirred at rt overnight, thiosulfate (2 g) was added. The resulting mixture was stirred at rt for 0.5h and filtered. The filtrate was partitioned between methylene chloride and saturated sodium bicarbonate. The organic layer was separated, and the alkaline phase was extracted with methylene chloride (3×100 mL). The combined organic layers were dried over sodium sulfate, and concentrated to give the title compound. LCMS $[M+1-100]^+$=195.0.

Step F: (1R,5S,7r)-9-(tert-Butoxycarbonyl)-7-(cyanomethyl)-3-oxa-9-azabicyclo[3.3.1]nonane-7-carboxylic acid To a solution of (1R,5S,7r)-tert-butyl 7-(cyanomethyl)-7-formyl-3-oxa-9-azabicyclo[3.3.1]nonane-9-carboxylate (613 mg, 2.083 mmol) in tert-BuOH (10 ml) and water (5 ml) was added sodium dihydrogen phosphate (750 mg, 6.25 mmol) and 2-methyl-2-butene (1.098 ml, 10.41 mmol). The solution was cooled to 0° C., and sodium chlorite (565 mg, 6.25 mmol) was added in portions. The reaction solution was stirred at 0° C. for 1h. This was followed by addition of additional sodium dihydrogen phosphate (750 mg, 6.25 mmol), 2-methyl-2-butene (1.098 ml, 10.41 mmol) and sodium chlorite (565 mg, 6.25 mmol). Stirring continued at 0° C. for 2 h. The reaction was quenched with 1 N HCl to about pH=4. The mixture was diluted with water (100 mL), and extracted with methylene chloride (3×100 mL). The combined organic layers were dried over sodium sulfate, and concentrated to give the title compound. LCMS $[M+23]^+$=333.0.

Step G: (1R,5S,7r)-9-tert-Butyl 7-methyl 7-(cyanomethyl)-3-oxa-9-azabicyclo[3.3.1]nonane-7,9-dicarboxylate To a solution of (1R,5S,7r)-9-(tert-butoxycarbonyl)-7-(cyanomethyl)-3-oxa-9-azabicyclo[3.3.1]nonane-7-carboxylic acid (646 mg, 2.082 mmol) in methanol (10 ml) was added TMS-diazomethane (5.20 ml, 10.41 mmol) dropwise until no bubble generation. The reaction was quenched with acetic acid (a few drops). The mixture was concentrated to give the title compound. LCMS $[M+23]^+$=346.9.

Step H: (1R,5S,7r)-9-tert-Butyl 7-methyl 7-(2-aminoethyl)-3-oxa-9-azabicyclo[3.3.1]nonane-7,9-dicarboxylate A mixture of (1R,5S,7r)-9-tert-butyl 7-methyl 7-(cyanomethyl)-3-oxa-9-azabicyclo[3.3.1]nonane-7,9-dicarboxylate (0.58 g, 1.788 mmol) and platinum(IV) oxide (0.082 g, 0.358 mmol) in methanol (10 ml) and acetic acid (10 ml) was hydrogenated (45 Psi hydrogen) over weekend, and filtered through CELITE under nitrogen. The filtrate was concentrated to give the title compound. LCMS $[M+1]^+$=329.0.

Step I: (1R,3'r,5S)-tert-Butyl 2'-oxo-3-oxa-9-azaspiro[bicyclo[3.3.1]nonane-7,3'-pyrrolidine]-9-carboxylate A mixture of (1R,5S,7r)-9-tert-butyl 7-methyl 7-(2-aminoethyl)-3-oxa-9-azabicyclo[3.3.1]nonane-7,9-dicarboxylate (0.59 g, 1.797 mmol) and potassium carbonate (1.490 g, 10.78 mmol) in methanol (50 ml) was heated at reflux for 4h. The mixture was concentrated, and the residue was partitioned between methylene chloride and water. The organic layer was separated, and the aqueous phase was extracted with methylene three times. The combined organic layers were dried over sodium sulfate, and concentrated to give the title compound. LCMS $[M+23]^+$=319.0.

Step J: (1R,3'r,5S)-tert-Butyl 1'-(4-methyl-5-oxo-2,5-dihydrofuran-3-yl)-2'-oxo-3-oxa-9-azaspiro[bicyclo[3.3.1]nonane-7,3'-pyrrolidine]-9-carboxylate To a mixture of (1R,3'r,5S)-tert-butyl 2'-oxo-3-oxa-9-azaspiro[bicyclo[3.3.1]nonane-7,3'-pyrrolidine]-9-carboxylate (0.42 g, 1.417 mmol) and 4-methyl-5-oxo-2,5-dihydrofuran-3-yl trifluoromethanesulfonate (I-53) (0.454 g, 1.842 mmol) in toluene (15 ml) was added potassium carbonate (0.588 g, 4.25 mmol), Xantphos (0.328 g, 0.567 mmol), water (0.077 ml, 4.25 mmol), and palladium (II) acetate (0.064 g, 0.283 mmol) under $N_2$. The mixture was heated at 70° C. overnight, and filtered. The filtrate was concentrated under reduced pressure, and the residue was purified on silica gel column using ethyl acetate/hexane to give the title compound. LCMS $[M+23]^+$=393.2.

Step K: (1R,3'r,5S)-1'-(4-Methyl-5-oxo-2,5-dihydrofuran-3-yl)-3-oxa-9-azaspiro[bicycle[3.3.1]-nonane-7,3'-pyrrolidin]-2'-one To a solution of (1R,3'r,5S)-tert-butyl 1'-(4-methyl-5-oxo-2,5-dihydrofuran-3-yl)-2'-oxo-3-oxa-9-azaspiro[bicyclo[3.3.1]nonane-7,3'-pyrrolidine]-9-carboxylate (0.22 g, 0.561 mmol) in methylene chloride (4 ml) was added trifluroroacetic acid (4 ml, 51.9 mmol). The solution was stirred at rt for 2h, and concentrated. The residue was basified to a free amine on Bond Elut SCX ion exchange column washed with methanol followed by 1N ammonia in methanol to give the title compound. LCMS $[M+1]^+$=293.2.

INTERMEDIATE 63

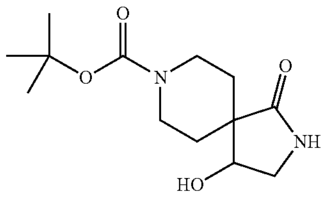 [SMILES: CC(C)(C)OC(=O)N1CCC2(CC1)C(=O)NCC2O]

tert-Butyl 4-hydroxy-1-oxo-2,8-diazaspiro[4.5]decane-8-carboxylate (racemic)

Step A: 1-tert-Butyl 4-methyl 4-(2-((tert-butoxycarbonyl)amino)-1-hydroxyethyl)piperidine-1,4-dicarboxylate To a solution of LDA [prepared in situ from n-butyllithium (20 mL, 49.3 mmol) and diisopropylamine (5.16 mg, 51.0 mmol) in THF (40 mL) at 0° C.] was added dropwise 1-tert-butyl 4-methyl piperidine-1,4-dicarboxylate (4.00 g, 16.4 mmol) in TMEDA (15 mL, 99 mmol) via a syringe pump at −78° C. for 10 min. The mixture was stirred at the same temperature for 30 min. tert-Butyl(2-oxoethyl)carbamate (8.11 g, 51.0 mmol) in THF (20 mL) was added slowly by syringe pump for 15 min. The mixture was stirred at −78° C. for 30 min, quenched with saturated $NH_4Cl$ aqueous at −78° C., warmed up to rt and diluted with EtOAc (200 mL). The organic layer was separated, and the aqueous layer was extracted with EtOAc (100 mL). The combined organic layers were washed with brine, dried ($MgSO_4$), and concentrated. The residue was purified by column chromatography (80 g, silica gel, MeOH/DCM, gradient 0-10%, monitor at 210 nM) to afford the title compound. LCMS $[M+1]^+$=403.

Step B: tert-Butyl 4-hydroxy-1-oxo-2,8-diazaspiro[4.5]decane-8-carboxylate

To a solution of 1-tert-butyl 4-methyl 4-(2-((tert-butoxycarbonyl)amino)-1-hydroxyethyl)piperidine-1,4-dicarboxylate (4000 mg, 9.94 mmol) in DCM (100 mL) was added TFA (23 mL, 298 mmol) at 0° C. The solution was stirred for 2 h, concentrated and dried in vacuo briefly to remove excess TFA. The residue was dissolved in MeOH (100 mL).

To the solution was added potassium carbonate (13.7 g, 99 mmol). The reaction mixture was heated at 60° C. for 2 h, and cooled to rt. Saturated aqueous $NaHCO_3$ (50 mL) followed by $(Boc)_2O$ (6.51 g, 29.8 mmol) was added. The resulting mixture was stirred overnight, then extracted with DCM, dried over $MgSO_4$, and concentrated to give the crude product, which was purified by column chromatography (0-20% MeOH/DCM, monitor at 210 nM) to afford the title compound. LCMS $[M+1]^+$=271.

INTERMEDIATE 64

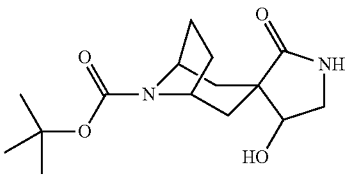 [SMILES: CC(C)(C)OC(=O)N1C2CCC1CC1(C2)C(=O)NCC1O]

(1R,3r,5S)-tert-Butyl 4'-hydroxy-2'-oxo-8-azaspiro [bicyclo[3.2.1]octane-3,3'-pyrrolidine]-8-carboxylate (racemic)

The title compound was synthesized following the procedure as for tert-butyl 4-hydroxy-1-oxo-2,8-diazaspiro[4.5] decane-8-carboxylate (I-63) but starting from (1R,3s,5S)-8-tert-butyl 3-methyl 8-azabicyclo[3.2.1]octane-3,8-dicarboxylate (I-59, Step A). LCMS $[M+1]^+$=297.5.

INTERMEDIATE 65

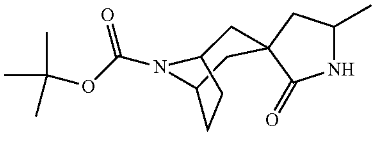 [SMILES: CC1CC2(CC3CCC(C2)N3C(=O)OC(C)(C)C)C(=O)N1]

(1R,3r,5S)-tert-Butyl 5'-methyl-2'-oxo-8-azaspiro [bicyclo[3.2.1]octane-3,3'-pyrrolidine]-8-carboxylate (racemic)

Step A: (1R,3r,5S)-8-tert-Butyl 3-methyl 8-azabicyclo[3.2.1]octane-3,8-dicarboxylate To a solution of (1R,3r,5S)-8-(tert-butoxycarbonyl)-8-azabicyclo[3.2.1]octane-3-carboxylic acid (10 g, 39.2 mmol) and methanol (4.75 mL, 118 mmol) in methylene chloride (200 mL) was added EDC (11.26 g, 58.8 mmol), diisopropylethylamine (13.68 mL, 78 mmol) and DMAP (0.479 g, 3.92 mmol). The solution was stirred at rt for 16 h, washed with potassium bisulfate (1 N, 200 mL), water (200 mL) and aqueous saturated sodium bicarbonate, dried over sodium sulfate, and concentrated to give the title compound. LCMS $[M+1]^+$=270.1.

Step B: (1R,3r,5S)-8-tert-Butyl 3-methyl 3-(2-methylallyl)-8-azabicyclo[3.2.1]octane-3,8-dicarboxylate To a solution of diisopropylamine (5.94 mL, 41.7 mmol) in tetrahydrofuran (5 mL) at 0° C. was added n-butyllithium (16.66 mL, 41.7 mmol) dropwise. The solution was stirred at 0° C. for 0.5h, and was added dropwise to a solution of (1R,3r,5S)-8-tert-butyl 3-methyl 8-azabicyclo[3.2.1]octane-3,8-dicarboxylate (7.48 g, 27.8 mmol) in tetrahydrofuran (90 mL) at −78° C. The resulting mixture was stirred at −78° C. for 1 h, and to this mixture was added 3-Bromo-2-methyl-propene (4.03 mL, 40.0 mmol) dropwise. After stirring at −78° C. for 1.5 h, the reaction was quenched with saturated ammonium acetate aqueous. The reaction mixture was diluted with ethyl acetate, washed with saturated ammonium acetate aqueous twice, dried over sodium sulfate, and concentrated. The residue was purified on a silica gel column using ethyl acetate/hexane as eluting solvents to give the title compound. LCMS $[M+1]^+$=324.3.

Step C: (1R,3r,5S)-8-tert-Butyl 3-methyl 3-(2-oxo-propyl)-8-azabicyclo[3.2.1]octane-3,8-dicarboxylate To a solution of (1R,3r,5S)-8-tert-butyl 3-methyl 3-(2-methylallyl)-8-azabicyclo[3.2.1]octane-3,8-dicarboxylate (7.99 g, 24.7 mmol) in dioxane (100 mL) and water (50 mL) was added sodium periodate (10.57 g, 49.4 mmol) and osmium tetroxide (0.126 g, 0.494 mmol). The mixture was stirred at rt for 18 h, and sodium thiosulfate (1 g) was added. After stirring at rt for 0.5 h, the mixture was filtered, and the filtrate was concentrated. The residue was dissolved in ethyl acetate (300 mL), washed with brine, dried over sodium sulfate, and concentrated. The residue was purified on silica gel using ethyl acetate and hexane as eluting solvents to give the title compound. LCMS $[M+1]^+$=326.2.

Step D: (1R,3r,5S)-tert-Butyl 5'-methyl-2'-oxo-8-azaspiro[bicyclo[3.2.1]octane-3,3'-pyrrolidine]-8-carboxylate To a solution of (1R,3r,5S)-8-tert-butyl 3-methyl 3-(2-oxopropyl)-8-azabicyclo[3.2.1]octane-3,8-dicarboxylate (7.9 g, 24.28 mmol) in methanol (50 mL) were added magnesium sulfate (5.84 g, 48.6 mmol), ammonium acetate (3.74 g, 48.6 mmol) and sodium cyanoborohydride (3.05 g, 48.6 mmol). The mixture was heated at 80° C. in a sealed tube for 18 h. After cooled down to rt, the mixture was filtered, and the filtrate was concentrated. The residue was partitioned between methylene chloride and saturated sodium bicarbonate. The organic layer was separated, and the aqueous layer was extracted with methylene chloride. The combined organic layers were dried over sodium sulfate, and concentrated. The residue was purified on silica gel using ethyl acetate as eluting solvent to give the title compound. LCMS $[M+1]^+$=295.3.

INTERMEDIATE 66

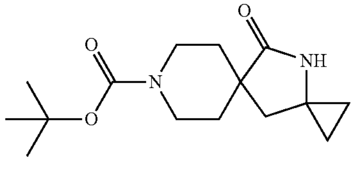 [SMILES: CC(C)(C)OC(=O)N1CCC2(CC1)CC1(CC1)NC2=O]

tert-Butyl 11-oxo-8,12-diazadispiro[2.1.5.2]dodecane-8-carboxylate

Step A: 1-tert-Butyl 4-methyl 4-(cyanomethyl)piperidine-1,4-dicarboxylate

To a stirred solution of 1-tert-butyl 4-methyl piperidine-1,4-dicarboxylate (10.00 g, 41.1 mmol) in THF (130 mL) was added LDA (33.3 mL, 66.6 mmol) dropwise at −78° C. under $N_2$. After the mixture was stirred at −78° C. for 1 h, 2-bromoacetonitrile (5.5 mL, 82.3 mmol) was added. The resulting mixture was stirred at the same temperature for 4 h, at rt for 18 h, and quenched with saturated aqueous $NH_4Cl$ aqueous. The organic solvent was removed in vacuo, and the aqueous layer was extracted with ethyl acetate (100 mL). The extract was dried over anhydrous sodium sulfate, filtered and concentrated. The crude product was purified by flash chromatography (0-15% ethyl acetate in petroleum ether) to give the title compound. LCMS $[M+1]^+$=283.

Step B: tert-Butyl 11-oxo-8,12-diazadispiro[2.1.5.2]dodecane-8-carboxylate

To a solution of 1-tert-butyl 4-methyl 4-(cyanomethyl)piperidine-1,4-dicarboxylate (2.05 g, 7.27) and titanium(IV) isopropoxide (2.38 mL, 2.5 mmol) in THF (40 mL) was added ethylmagnesium bromide (5.3 mL, 16.0 mmol). The mixture was stirred at rt for 1 h, quenched with diluted hydrochloric acid (1 M, 10 mL), and extracted with dichloromethane (100 mL). The combined organic layers were dried over anhydrous sodium sulfate, filtered and concentrated. The crude product was purified by flash chromatography (0-60% ethyl acetate in petroleum ether) to give the title compound. LCMS $[M+1]^+$=281.

INTERMEDIATE 67

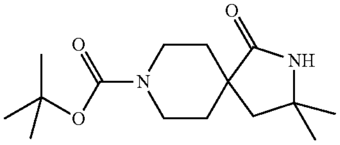 [SMILES: CC1(C)CC2(CCN(C(=O)OC(C)(C)C)CC2)C(=O)N1]

tert-Butyl 3,3-dimethyl-1-oxo-2,8-diazaspiro[4.5]decane-8-carboxylate

To a solution of tert-Butyl 11-oxo-8,12-diazadispiro[2.1.5.2]dodecane-8-carboxylate (I-66) (500 mg, 1.79 mmol) in a mixture of acetic acid/ethyl acetate (v: v=1:1, 10 mL) was added platinum (IV) dioxide (40 mg, 0.179 mmol) under $N_2$. The reaction mixture was stirred under hydrogen (3 atm) at room temperature for 4 h, filtered through a pad of Celite. The filtrate was concentrated to give the title compound. LCMS $[M+1]^+$=283.

INTERMEDIATE 68

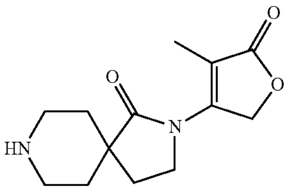

2-(4-Methyl-5-oxo-2,5-dihydrofuran-3-yl)-2,8-diazaspiro[4.5]decan-1-one

Step A: tert-Butyl 2-(4-methyl-5-oxo-2,5-dihydrofuran-3-yl)-1-oxo-2,8-diazaspiro[4.5]decane-8-carboxylate To a mixture of tert-butyl 1-oxo-2,8-diazaspiro[4.5]decane-8-carboxylate (I-55, 80.0 g, 315 mmol) and 4-methyl-5-oxo-2,5-dihydrofuran-3-yl trifluoromethanesulfonate (I-53, 85.2 g, 346 mmol), Xantphos (13.6 g, 23.6 mmol), and $Cs_2CO_3$ (153.7 g, 471.8 mmol) in toluene (1200 mL), was added $Pd_2(dba)_3$ (7.20 g, 7.86 mmol) under $N_2$. The reaction mixture was heated at 90° C. under $N_2$ for 18 h, then filtered through a pad of CELITE. The filtrate was concentrated. The residue was purified via crystallization to give the title compound. $^1H$ NMR (400 MHz, $CDCl_3$) δ 5.23 (s, 2 H), 4.02-3.99 (m, 4 H), 3.06-3.05 (m, 2 H), 2.15-2.11 (m, 2 H), 2.02 (s, 3 H), 1.87-1.81 (m, 2 H), 1.51-1.41 (m, 11 H).

Step B: 2-(4-Methyl-5-oxo-2,5-dihydrofuran-3-yl)-2,8-diazaspiro[4.5]decan-1-one

To a mixture of tert-butyl 2-(4-methyl-5-oxo-2,5-dihydrofuran-3-yl)-1-oxo-2,8-diazaspiro[4.5]decane-8-carboxylate (57.0 g, 163 mmol) in EtOAc (180 mL) was added saturated HCl(gas)/EtOAc (712 mL) at 0° C. The reaction mixture was stirred at room temperature for 3 h, then filtered. The filtrate was concentrated to give the HCl salt. To a mixture of the HCl salt (54.2 g, 189 mmol) in MeOH (550 mL) was added $NaHCO_3$ (31.8 g, 378 mmol) at 0° C. The mixture was stirred at rt for 3 h until the pH=8. The mixture was filtered, and the filtrate was concentrated. The residue was re-dissolved in MeOH, and concentrated until a precipitate appeared. The precipitate was filtered off. The filtrate was concentrated to give 2-(4-methyl-5-oxo-2,5-dihydrofuran-3-yl)-2,8-diazaspiro[4.5]decan-1-one as a free amine. 1H NMR (400 MHz, $CD_3OD$) δ 5.24 (s, 2 H), 4.10-4.07 (m, 2 H), 3.22-3.16 (m, 2 H), 2.93-2.87 (m, 2 H), 2.22-2.19 (m, 2 H), 2.0 (s, 3 H), 1.94-1.87 (m, 2 H), 1.67-1.61 (m, 2 H).

INTERMEDIATE 69

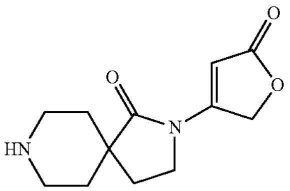

2-(5-Oxo-2,5-dihydrofuran-3-yl)-2,8-diazaspiro[4.5]decan-1-one

Step A: tert-butyl 1-oxo-2-(5-oxo-2,5-dihydrofuran-3-yl)-2,8-diazaspiro[4.5]decane-8-carboxylate A mixture of tert-butyl 1-oxo-2,8-diazaspiro[4.5]decane-8-carboxylate (I-55, 1.83 g, 7.20 mmol), commercially available 4-bromofuran-2(5H)-one (1.41 g, 8.63 mmol), Xantphos (0.416 g, 0.720 mmol), water (0.389 mL, 21.6 mmol), and potassium carbonate (1.99 g, 14.39 mmol) in toluene (50 mL) was added palladium acetate (0.081 g, 0.36 mmol) under $N_2$. The mixture was heated at 65° C. for 16 h, and filtered through CELITE. The filtrate was concentrated. The residue was purified on silica gel column using EtOAc/hexane as eluting solvents to give the title compound. LCMS $[M+1]^+$=337.1.

Step B: 2-(5-Oxo-2,5-dihydrofuran-3-yl)-2,8-diazaspiro[4.5]decan-1-one

To a solution of tert-butyl 1-oxo-2-(5-oxo-2,5-dihydrofuran-3-yl)-2,8-diazaspiro[4.5]decane-8-carboxylate (5.70 g, 16.9 mmol) in methylene chloride (10 mL) was added trifluoroacetic acid (26.1 mL, 339 mmol). The solution was stirred at rt for 1h, and concentrated under reduced pressure. The crude material was basified to a free amine on Bond Elut SCX ion exchange column washed with methanol to remove TFA followed by 1N ammonia in methanol solution to collect the title compound. LCMS $[M+1]^+$=237.0.

TABLE 5

INTERMEDIATES prepared following a similar procedure as for I-68 or I-69

| INTERMEDIATE # | Starting bromide or triflate | Starting intermediate | Structure and name | LC-MS $[M + 1]^+$ |
|---|---|---|---|---|
| 70 | 53 | 59 | 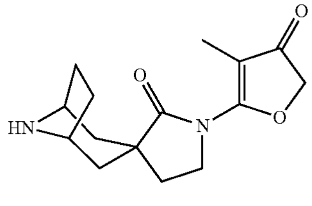 [SMILES: CC1=C(N2CCC3(CC4CCC(C3)N4)C2=O)OCC1=O] (1R,3r,5S)-1'-(4-methyl-5-oxo-2,5-dihydrofuran-3-yl)-8-azaspiro[bicyclo[3.2.1]octane-3,3'-pyrrolidin]-2'-one | 277.1 |
| 71 | 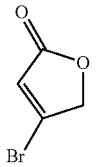 | 59 | 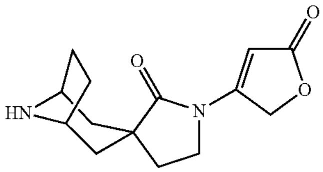 [SMILES: O=C1C=C(N2CCC3(CC4CCC(C3)N4)C2=O)CO1] (1R,3r,5S)-1'-(5-oxo-2,5-dihydrofuran-3-yl)-8-azaspiro[bicyclo[3.2.1]octane-3,3'-pyrrolidin]-2'-one | 263 |
| 72 | 53 | 60 | 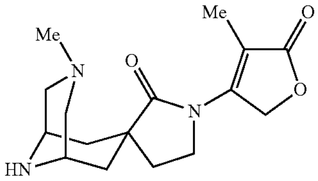 [SMILES: CC1=C(N2CCC3(CC4CN(C)CC(C3)N4)C2=O)COC1=O] (1R,3's,5S)-3-methyl-1'-(4-methyl-5-oxo-2,5-dihydrofuran-3-yl)-3,9-diazaspiro[bicyclo[3.3.1]nonane-7,3'-pyrrolidin]-2'-one | 306 |
| 73A 73B | 53 | 56 | 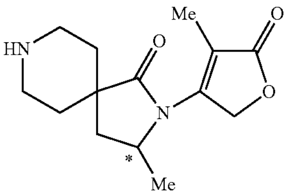 [SMILES: CC1=C(N2C(=O)C3(CCNCC3)CC2C)COC1=O] 3-methyl-2-(4-methyl-5-oxo-2,5-dihydrofuran-3-yl)-2,8-diazaspiro[4.5]decan-1-one (from fast eluted BOC-isomer) 3-methyl-2-(4-methyl-5-oxo-2,5-dihydrofuran-3-yl)-2,8-diazaspiro[4.5]decan-1-one (from slow eluted BOC-isomer) | 265 |

TABLE 5-continued

INTERMEDIATES prepared following a similar procedure as for I-68 or I-69

| INTERMEDIATE # | Starting bromide or triflate | Starting intermediate | Structure and name | LC-MS [M + 1]+ |
|---|---|---|---|---|
| 74A | 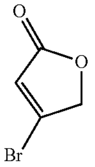 | 56A | 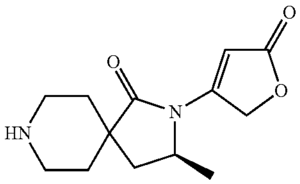 [SMILES: C[C@H]1CC2(CCNCC2)C(=O)N1C1=CC(=O)OC1] (S)-3-methyl-2-(5-oxo-2,5-dihydrofuran-3-yl)-2,8-diazaspiro[4.5]decan-1-one | 251 |
| 74 B | 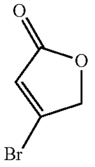 | 56B | 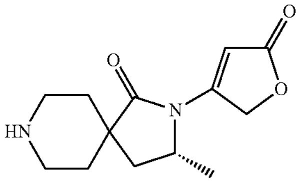 [SMILES: C[C@@H]1CC2(CCNCC2)C(=O)N1C1=CC(=O)OC1] (R)-3-methyl-2-(5-oxo-2,5-dihydrofuran-3-yl)-2,8-diazaspiro[4.5]decan-1-one | 251 |
| 75 | 53 | 61 | 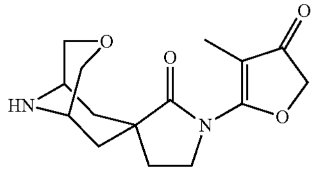 [SMILES: CC1=C(N2CCC3(CC4COCC(C3)N4)C2=O)OCC1=O] (1R,3's,5S)-1'-(4-methyl-5-oxo-2,5-dihydrofuran-3-yl)-3-oxa-9-azaspiro[bicyclo[3.3.1]nonane-7,3'-pyrrolidin]-2'-one | 293 |
| 76 | 53 | 62 | 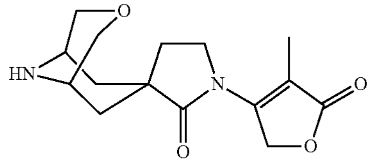 [SMILES: CC1=C(N2CCC3(CC4COCC(C3)N4)C2=O)COC1=O] (1R,3'r,5S)-1'-(4-methyl-5-oxo-2,5-dihydrofuran-3-yl)-3-oxa-9-azaspiro[bicyclo[3.3.1]nonane-7,3'-pyrrolidin]-2'-one | 293 |
| 77 | 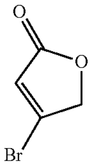 | 67 | 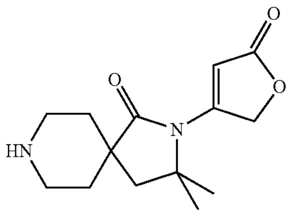 [SMILES: CC1(C)CC2(CCNCC2)C(=O)N1C1=CC(=O)OC1] 3,3-dimethyl-2-(5-oxo-2,5-dihydrofuran-3-yl)-2,8-diazaspiro[4.5]decan-1-one | 265 |
| 78 | 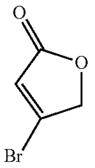 | 57 | 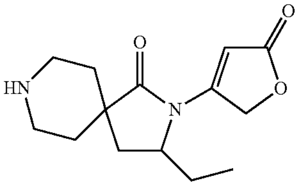 [SMILES: CCC1CC2(CCNCC2)C(=O)N1C1=CC(=O)OC1] 3-ethyl-2-(5-oxo-2,5-dihydrofuran-3-yl)-2,8-diazaspiro[4.5]decan-1-one (racemic) | 265 |

TABLE 5-continued

| INTERMEDIATES prepared following a similar procedure as for I-68 or I-69 | | | | |
|---|---|---|---|---|
| INTERMEDIATE # | Starting bromide or triflate | Starting intermediate | Structure and name | LC-MS $[M+1]^+$ |
| 79 | 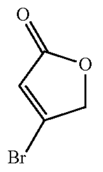 | 58 | 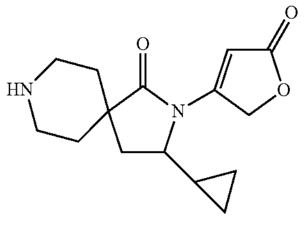 [SMILES: O=C1C=C(N2C(=O)C3(CCNCC3)CC2C2CC2)CO1] 3-cyclopropyl-2-(5-oxo-2,5-dihydrofuran-3-yl)-2,8-diazaspiro[4.5]decan-1-one (racemic) | 277 |
| 80 | 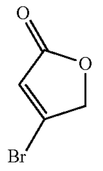 | 66 | 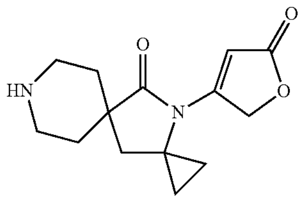 [SMILES: O=C1C=C(N2C(=O)C3(CCNCC3)CC23CC3)CO1] 12-(5-oxo-2,5-dihydro-furan-3-yl)-8,12-diaza-dispiro[2.1.5.2]dodecan-11-one | 263 |
| 81 | 50 | 55 | 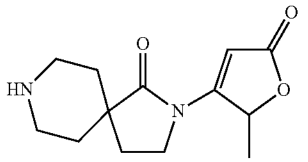 [SMILES: CC1OC(=O)C=C1N1CCC2(CCNCC2)C1=O] 2-(2-methyl-5-oxo-2,5-dihydrofuran-3-yl)-2,8-diazaspiro[4.5]decan-1-one (racemic) | 251 |
| 82 | 50 | 56A | 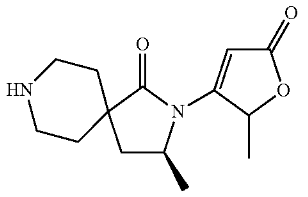 [SMILES: CC1OC(=O)C=C1N1C(=O)C2(CCNCC2)C[C@@H]1C] (3S)-3-methyl-2-(2-methyl-5-oxo-2,5-dihydrofuran-3-yl)-2,8-diazaspiro[4.5]decan-1-one (two isomers) | 265 |
| 83 | 50 | 56B | 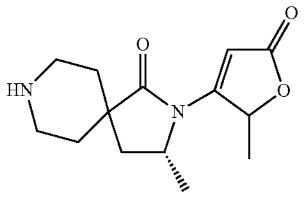 [SMILES: CC1OC(=O)C=C1N1C(=O)C2(CCNCC2)C[C@H]1C] (3R)-3-methyl-2-(2-methyl-5-oxo-2,5-dihydrofuran-3-yl)-2,8-diazaspiro[4.5]decan-1-one (two isomers) | 265 |

INTERMEDIATEs 84A and 84B

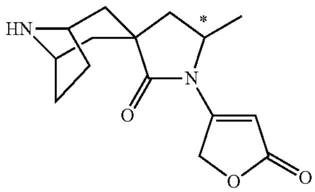 [SMILES: CC1CC2(CC3CCC(C2)N3)C(=O)N1C1=CC(=O)OC1]

(1R,3r,5S,5'S)-5'-Methyl-1'-(5-oxo-2,5-dihydrofuran-3-yl)-8-azaspiro[bicyclo[3.2.1]octane-3,3'-pyrrolidin]-2'-one; and (1R,3r,5S,5'R)-5'-Methyl-1'-(5-oxo-2,5-dihydrofuran-3-yl)-8-azaspiro[bicyclo[3.2.1]octane-3,3'-pyrrolidin]-2'-one Step A: Racemate and 5'S and 5'R enantiomers of (1R,3r,5S)-tert-Butyl 5'-methyl-2'-oxo-1'-(5-oxo-2,5-dihydrofuran-3-yl)-8-azaspiro[bicyclo[3.2.1]octane-3,3'-pyrrolidine]-8-carboxylate To a solution of (1R,3r,5S)-tert-butyl 5'-methyl-2'-oxo-8-azaspiro[bicyclo[3.2.1]octane-3,3'-pyrrolidine]-8-carboxylate (I-65, 2.41 g, 8.19 mmol) in toluene (30 mL) were added 3-bromo-furanone (1.60 g, 9.82 mmol), Xantphos (0.474 g, 0.819 mmol), potassium carbonate (2.263 g, 16.37 mmol), water (0.442 g, 24.56 mmol), and palladium acetate (0.092 g, 0.409 mmol). The mixture was heated at 65° C. for 16h under $N_2$. After cooling down to rt, the mixture was filtered, and the filtrate was concentrated. The residue was purified on a silica gel column using ethyl acetate and hexane as eluting solvents to give the racemate of the title compound. The enantiomers were separated on chiral AS column (30×250 mm) using methanol/acetonitrile/carbon dioxide to give the faster eluted enantiomer I-84A-BOC, LCMS $[M+1]^+$=377.04; and the slower eluted enantiomer I-84B-BOC, LCMS $[M+1]^+$=377.0.

Step B: 5'S and 5'R enantiomers of (1R,3r,5S)-5'-Methyl-1'-(5-oxo-2,5-dihydrofuran-3-yl)-8-azaspiro[bicyclo[3.2.1]octane-3,3'-pyrrolidin]-2'-one To a solution of I-84A-BOC (0.8 g, 2.125 mmol) in methylene chloride (5 mL) was added trifluoroacetic acid (3.27 mL, 42.5 mmol). The resulting solution was stirred at rt for 1h. After the volatiles were removed under reduced pressure, the residue was dissolved in methanol (5 mL) and basified to a free amine on a Bond Elut SCX ion-exchange column washed with methanol followed by 1 N ammonia in methanol to give enantiomer I-84A: LCMS [M+1]'=277.0. Enantiomer I-84B was synthesized from I-84B-BOC following the same procedure as described for I-84A LCMS $[M+1]^+$=277.0. Absolute stereochemistry at *C for each enantiomer was not determined.

INTERMEDIATE 85A and 85B

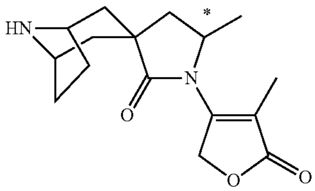

85A (enantiomer A)
85B (enantiomer B)

(1R,3r,5S,5' R)-5'-Methyl-1'-(4-methyl-5-oxo-2,5-dihydrofuran-3-yl)-8-azaspiro[bicyclo[3.2.1]octane-3,3'-pyrrolidin]-2'-one and (1R,3r,5S,5'S)-5'-Methyl-1'-(4-methyl-5-oxo-2,5-dihydrofuran-3-yl)-8-azaspiro[bicyclo[3.2.1]octane-3,3'-pyrrolidin]-2'-one The racemate and 5'S and 5'R enantiomers of the title compound were made employing a similar procedure as described for making I-84A and 84B, but starting with 4-methyl-5-oxo-2,5-dihydrofuran-3-yl trifluoromethanesulfonate (I-53) and (1R,3r,5S)-tert-butyl 5'-methyl-2'-oxo-8-azaspiro[bicyclo[3.2.1]octane-3,3'-pyrrolidine]-8-carboxylate (I-65). Enantiomer 85A: LCMS $[M+1]^+$=291.07). Enantiomer 85B: LCMS $[M+1]^+$=291.07). The designation of "84A' and "84B" is based on synthesis from the faster eluting Boc-intermediate I-85A-BOC or slower eluting I-85B-BOC, respectively. Absolute stereochemistry at *C for each enantiomer was not determined.

INTERMEDIATE 86A and 86B

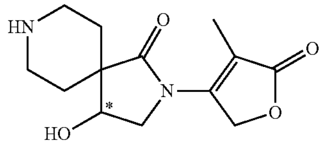

86A (enantiomer A)
86B (enantiomer B)

(4S)-4-Hydroxy-2-(4-methyl-5-oxo-2,5-dihydrofuran-3-yl)-2,8-diazaspiro[4.5]decan-1-one; and (4R)-4-Hydroxy-2-(4-methyl-5-oxo-2,5-dihydrofuran-3-yl)-2,8-diazaspiro[4.5]decan-1-one Step A: tert-Butyl 4-hydroxy-2-(4-methyl-5-oxo-2,5-dihydrofuran-3-yl)-1-oxo-2,8-diazaspiro[4.5]decane-8-carboxylate To a round bottom flask charged tert-butyl 4-hydroxy-1-oxo-2,8-diazaspiro[4.5]decane-8-carboxylate (I-63, 400 mg, 1.48 mmol), 4-methyl-5-oxo-2,5-dihydrofuran-3-yl trifluoromethanesulfonate (546 mg, 2.22 mmol), $Pd_2(dba)_3$ (33.9 mg, 0.037 mmol), Xantphos (64.2 mg, 0.111 mmol), and cesium carbonate (964 mg, 2.96 mmol) was added dioxane (6 mL) under $N_2$. The reaction mixture was heated at 90° C.

overnight, and filtered through CELITE. The filtrate was concentrated to give the crude product, which was purified by column chromatography (0-10% MeOH/DCM) to give the title compound. LCMS $[M+1]^+$=367.

Step B: tert-Butyl 4-hydroxy-2-(4-methyl-5-oxo-2,5-dihydrofuran-3-yl)-1-oxo-2,8-diazaspiro[4.5]decane-8-carboxylate (fast eluted, BOC-enantiomer A; slow eluted, BOC-enantiomer B)

The racemic mixture was separated by SFC-HPLC, using the following conditions: chiralcel OJ, 21×250 mm, 10% MeOH+0.2 DEA, 50 mL/min to afford BOC-enantiomer A: LCMS $[M+1]^+$=367; BOC-enantiomer B: LCMS $[M+1]^+$=367.

Step C: Enantiomer A and Enantiomer B of 4-hydroxy-2-(4-methyl-5-oxo-2,5-dihydrofuran-3-yl)-2,8-diazaspiro[4.5]decan-1-one To a solution of the BOC-enantiomer A (15 mg) in dichloromethane (1 mL) was added trifluoroacetic acid (0.2 mL). The resulting solution was stirred at rt for 1h, and the volatile was removed under reduced pressure. The residue was basified to a free amine on Bond Elut SCX ion exchange column washed with methanol followed by 1 N ammonia/methanol to give Enantiomer A): LCMS $[M+1]^+$=267. Enantiomer B was synthesized from BOC-enantiomer B following essentially the same procedure as described for Enantiomer A: LCMS $[M+1]^+$=267. Absolute stereochemistry at *C for each enantiomer was not determined.

INTERMEDIATE 88A and 88B

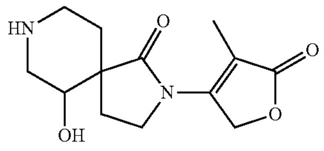

88A (trans, racemic)
88B (cis racemic)

6-Hydroxy-2-(4-methyl-5-oxo-2,5-dihydrofuran-3-yl)-2,8-diazaspiro[4.5]decan-1-one Step A: Ethyl 1-benzyl-4-(cyanomethyl)-3-oxopiperidine-4-carboxylate To a flask charged with ethyl 1-benzyl-3-oxopiperidine-4-carboxylate (1.0 g, 3.8 mmol) and a stir bar was added $K_2CO_3$ (1.06 g, 7.6 mmol), bromoacetonitrile (0.92 g, 7.6 mm, 0°), and acetone (15 mL). The reaction was allowed to stir at RT for 2h, then heated to 45° C. for 3h. The reaction was quenched with saturated $NH_4Cl$ aqueous, extracted with EtOAc, dried over $Na_2SO4$, filtered and concentrated. The crude product was purified by MPLC to furnish the title compound. LCMS $[M+1]^+$=301.

TABLE 6

INTERMEDIATES prepared following a similar procedure as for I-86

| INTERMEDIATE # | Starting bromide or triflate | Starting Intermediate | Structure and name | LC-MS $[M + 1]^+$ |
|---|---|---|---|---|
| 87A | 53 | 64 | 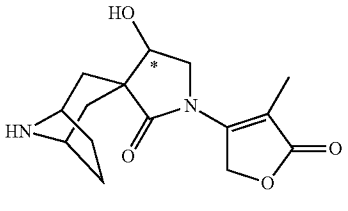 [SMILES: CC1=C(N2CC(O)C3(CC4CCC(C3)N4)C2=O)COC1=O] (1R,3r,5S)-4'-hydroxy-1'-(4-methyl-5-oxo-2,5-dihydrofuran-3-yl)-8-azaspiro[bicyclo[3.2.1]octane-3,3'-pyrrolidin]-2'-one | 293 |
| 87B | 53 | 64 | 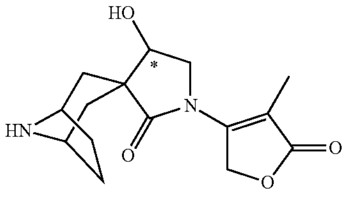 [SMILES: CC1=C(N2CC(O)C3(CC4CCC(C3)N4)C2=O)COC1=O] (1R,3r,5S)-4'-hydroxy-1'-(4-methyl-5-oxo-2,5-dihydrofuran-3-yl)-8-azaspiro[bicyclo[3.2.1]octane-3,3'-pyrrolidin]-2'-one | 293 |

Step B: 8-Benzyl-6-hydroxy-2,8-diazaspiro[4.5]decan-1-one

To a flask charged with ethyl 1-benzyl-4-(cyanomethyl)-3-oxopiperidine-4-carboxylate (900 mg, 3.0 mmol) were added platinum oxide (100 mg, 0.44 mmol), MeOH (20 mL) and acetic acid (20 mL). The mixture was allowed to stir vigorously under an atmosphere of hydrogen for 24 h. The catalyst was removed by filtration through a pad of CELITE, and the filtrate was concentrated under reduced pressure. The residue was dissolved in EtOH (100 mL), and added $K_2CO_3$ (2.1 g, 15 mmol). The mixture was heated at 90° C. for 4 h, cooled to rt, and added DCM (200 mL) to precipitate the solids. The solids were then removed by filtration, and the crude mixture was adsorbed onto silica gel column, and flushed out with DCM and 10% MeOH (mixed with 10% $NH_4OH$). LCM $[M+1]^+$=261.

Step C: 8-Benzyl-6-hydroxy-2-(4-methyl-5-oxo-2,5-dihydrofuran-3-yl)-2,8-diazaspiro[4.5]decan-1-one To a flask charged with 8-Benzyl-6-hydroxy-2,8-diazaspiro[4.5]decan-1-one (520 mg, 2.0 mmol) were added palladium acetate (22 mg, 0.10 mmol), $K_2CO_3$ (550 mg, 4.00 mmol), Xantphos (120 mg, 0.20 mmol), 4-Methyl-5-oxo-2,5-dihydrofuran-3-yl trifluoromethanesulfonate (640 mg, 2.6 mmol), and water (110 mg, 6.0 mmol). The mixture was heated to 60° C. for 2h. The reaction mixture was diluted with EtOAc, washed with water, dried over $Na_2SO_4$, filtered and concentrated to an oil. The oil was loaded onto a silica gel column, and purified by MPLC with hexane and EtOAc. Two spots were separated, and the slow moving spot as the major product (Bn-cis, racemic) LCMS $[M+1]^+$=357.

Step D: 6-Hydroxy-2-(4-methyl-5-oxo-2,5-dihydrofuran-3-yl)-2,8-diazaspiro[4.5]decan-1-one (cis, racemic)

To a solution of 8-benzyl-6-hydroxy-2-(4-methyl-5-oxo-2,5-dihydrofuran-3-yl)-2,8-diazaspiro[4.5]decan-1-one (Bn-cis, racemic, 150 mg, 0.42 mmol) in MeOH (2 mL) was added palladium on carbon (45 mg, 0.42 mmol) and a few drops of HOAc. The mixture was allowed to stir under an atmosphere of hydrogen for 16 hours. The catalyst was filtered off, and the crude material was used without further purification. LCMS $[M+1]^+$=267. 6-Hydroxy-2-(4-methyl-5-oxo-2,5-dihydrofuran-3-yl)-2,8-diazaspiro[4.5]decan-1-one (trans, racemic) was prepared from 8-benzyl-6-hydroxy-2-(4-methyl-5-oxo-2,5-dihydrofuran-3-yl)-2,8-diazaspiro[4.5]decan-1-one (Bn-trans, racemic) following the same procedure.

INTERMEDIATE 89A and 89B

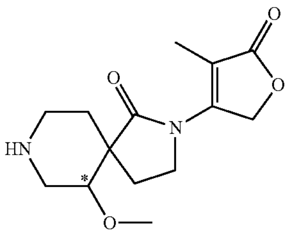

89A (cis, enantiomer A)
89B (cis, enantiomer A)

(5R,6S)-6-methoxy-2-(4-methyl-5-oxo-2,5-dihydrofuran-3-yl)-2,8-diazaspiro[4.5]decan-1-one; 5S,6R)-6-methoxy-2-(4-methyl-5-oxo-2,5-dihydrofuran-3-yl)-2,8-diazaspiro[4.5]decan-1-one Step A: tert-Butyl 6-hydroxy-2-(4-methyl-5-oxo-2,5-dihydrofuran-3-yl)-1-oxo-2,8-diazaspiro[4.5]decane-8-carboxylate (cis)

To a solution of 8-benzyl-6-hydroxy-2-(2-methyl-3-oxocyclopent-1-en-1-yl)-2,8-diazaspiro[4.5]decan-1-one (step c for I-88B, slow eluted, cis) (10 g, 28.2 mmol) and di-tert-butylcarbonate (7.21 ml, 31.0 mmol) in methanol (50 ml) was added palladium on carbon (1.501 g, 1.411 mmol). The resulting mixture was subjected to hydrogenation at 45 Psi at rt over the weekend, and filtered through CELITE under nitrogen. The filtrate was concentrated and the residue was purified on silica gel using ethyl acetate/hexane as eluting solvents to give the title compound. LCMS $[M+1]^+$=367.1.

Step B: tert-Butyl 6-methoxy-2-(4-methyl-5-oxo-2,5-dihydrofuran-3-yl)-1-oxo-2,8-diazaspiro[4.5]decane-8-carboxylate (cis, fast BOC-enatiomer) and tert-butyl 6-methoxy-2-(4-methyl-5-oxo-2,5-dihydrofuran-3-yl)-1-oxo-2,8-diazaspiro[4.5]decane-8-carboxylate (cis, slow BOC-enatiomer)

To a mixture of tert-butyl 6-hydroxy-2-(4-methyl-5-oxo-2,5-dihydrofuran-3-yl)-1-oxo-2,8-diazaspiro[4.5]decane-8-carboxylate (cis) (2 g, 5.46 mmol) and silver oxide (1.391 g, 6.00 mmol) in acetonitrile (50 ml) was added methyl iodide (3.41 ml, 54.6 mmol). The mixture was heated at 60° C. in a sealed tube overnight, cooled to rt, and filtered. The filtrate was concentrated and the residue was purified by silica gel chromatography using ethyl acetate/hexane to give tert-butyl 6-methoxy-2-(4-methyl-5-oxo-2,5-dihydrofuran-3-yl)-1-oxo-2,8-diazaspiro[4.5]decane-8-carboxylate (cis, racemate). LCMS $[M+1]^+$=380.99. The racetmate was further separated on AD chiral column give tert-butyl 6-methoxy-2-(4-methyl-5-oxo-2,5-dihydrofuran-3-yl)-1-oxo-2,8-diazaspiro[4.5]decane-8-carboxylate (cis, fast BOC-enantiomer), and tert-butyl 6-methoxy-2-(4-methyl-5-oxo-2,5-dihydrofuran-3-yl)-1-oxo-2,8-diazaspiro[4.5]decane-8-carboxylate (cis, slow-BOC-enantiomer).

Step C: 6-Methoxy-2-(4-methyl-5-oxo-2,5-dihydrofuran-3-yl)-2,8-diazaspiro[4.5]decan-1-one (cis, enantiomer A)

To the solution of tert-butyl 6-methoxy-2-(4-methyl-5-oxo-2,5-dihydrofuran-3-yl)-1-oxo-2,8-diazaspiro[4.5]decane-8-carboxylate (cis, fast BOC-enantiomer) (2.17 g, 5.70 mmol) in methylene chloride (7 ml) was added trifluoroacetic (7 ml, 91 mmol). The resulting solution was stirred at rt for 2 h, and concentrated. The residue was basified on Bond Elut SCX ion exchange column washed with methanol first, then eluted with 1 N ammonia in methanol to give 6-methoxy-2-(4-methyl-5-oxo-2,5-dihydrofuran-3-yl)-2,8-diazaspiro[4.5]decan-1-one (cis, enantiomer A). LCMS $[M+1]^+$=281.1.

6-Methoxy-2-(4-methyl-5-oxo-2,5-dihydrofuran-3-yl)-2,8-diazaspiro[4.5]decan-1-one (cis, enantiomer B)

To a solution of tert-butyl 6-methoxy-2-(4-methyl-5-oxo-2,5-dihydrofuran-3-yl)-1-oxo-2,8-diazaspiro[4.5]decane-8- carboxylate (cis, slow BOC-enantiomer) (2.17 g, 5.70 mmol) in methylene chloride (7 ml) was added trifluoroacetic (7 ml, 91 mmol). The resulting solution was stirred at rt for 2 h, and concentrated. The residue was basified on Bond Elut SCX ion exchange column washed with methanol first, then eluted with 1 N ammonia in methanol to give 6-methoxy-2-(4-methyl-5-oxo-2,5-dihydrofuran-3-yl)-2,8-diazaspiro[4.5]decan-1-one (cis, enantiomer B). LCMS [M+1$^+$=281.1. Absolute stereochemistry at *C for each enantiomer was not determined.

INTERMEDIATE 90A and 90B

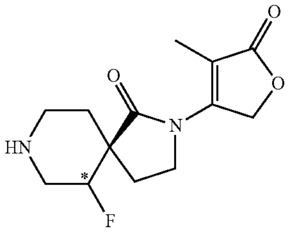

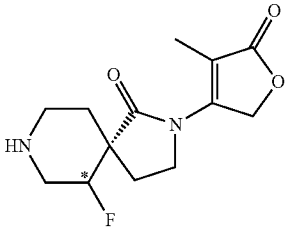

(5R,6S)-6-Fluoro-2-(4-methyl-5-oxo-2,5-dihydrofuran-3-yl)-2,8-diazaspiro[4.5]decan-1-one; (5S,6R)-6-Fluoro-2-(4-methyl-5-oxo-2,5-dihydrofuran-3-yl)-2,8-diazaspiro[4.5]decan-1-one Step A: tert-Butyl 6-fluoro-2-(4-methyl-5-oxo-2,5-dihydrofuran-3-yl)-1-oxo-2,8-diazaspiro[4.5]decane-8-carboxylate (trans, fast BOC-enantiomer) and tert-butyl 6-fluoro-2-(4-methyl-5-oxo-2,5-dihydrofuran-3-yl)-1-oxo-2,8-diazaspiro[4.5]decane-8-carboxylate (trans, slow BOC-enantiomer)

To the solution of tert-butyl 6-hydroxy-2-(4-methyl-5-oxo-2,5-dihydrofuran-3-yl)-1-oxo-2,8-diazaspiro[4.5]decane-8-carboxylate (BOC-analog of 1-88, cis, racemic) (1.84 g, 5.02 mmol) in methylene chloride (100 ml) was added DAST (0.863 ml, 6.53 mmol) dropwise under nitrogen at 0° C. The resulting solution was stirred at 0° C. for 2.5 h, quenched with addition of 200 mL saturated sodium bicarbonate. The organic layer was separated, and the aqueous layer was extracted with methylene chloride two times. The combined organic layers were dried over sodium sulfate, concentrated and the residue was purified on silica gel column using ethyl acetate/hexane as eluting solvents to give tert-butyl 6-fluoro-2-(4-methyl-5-oxo-2,5-dihydrofuran-3-yl)-1-oxo-2,8-diazaspiro[4.5]decane-8-carboxylate (trans, racemic). LCMS [M+1]$^+$=369.19. The racemate was separated on AD to give tert-butyl 6-fluoro-2-(4-methyl-5-oxo-2,5-dihydrofuran-3-yl)-1-oxo-2,8-diazaspiro[4.5]decane-8-carboxylate (trans, fast BOC-enantiomer) and tert-butyl 6-fluoro-2-(4-methyl-5-oxo-2,5-dihydrofuran-3-yl)-1-oxo-2,8-diazaspiro[4.5]decane-8-carboxylate (trans, slow BOC-enantiomer). LCMS [M+1−56]$^+$=313.0.

Step B: 6-Fluoro-2-(4-methyl-5-oxo-2,5-dihydrofuran-3-yl)-2,8-diazaspiro[4.5]decan-1-one (trans, enantiomer 90A)

To a solution of tert-butyl 6-fluoro-2-(4-methyl-5-oxo-2,5-dihydrofuran-3-yl)-1-oxo-2,8-diazaspiro[4.5]decane-8-carboxylate (trans, fast BOC-enantiomer) (0.60 g, 1.629 mmol) in methylene chloride (5 ml) was added trifluoroacetic acid (5 ml, 64.9 mmol). The resulting solution was stirred at rt for 2 h, and concentrated. The residue was basified on Bond Elut SCX ion exchange column washed with MeOH to removing the acid followed by 1 N ammonia in methanol eluting to give 6-fluoro-2-(4-methyl-5-oxo-2,5-dihydrofuran-3-yl)-2,8-diazaspiro[4.5]decan-1-one (trans, enantiomer A). LCMS [M+1]'=269.0.

6-Fluoro-2-(4-methyl-5-oxo-2,5-dihydrofuran-3-yl)-2,8-diazaspiro[4.5]decan-1-one (trans, enantiomer 90B) was synthesized from trans, slow BOC-enantiomer following the same procedure for I-88B. LCMS [M+1]$^+$=269.0. Absolute stereochemistry at *C for each enantiomer was not determined.

INTERMEDIATE 91

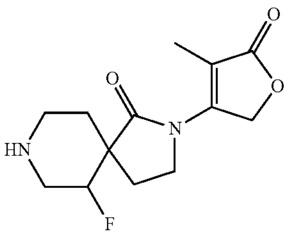 [SMILES: CC1=C(N2CCC3(CCNCC3F)C2=O)COC1=O]

6-Fluoro-2-(4-methyl-5-oxo-2,5-dihydrofuran-3-yl)-2,8-diazaspiro[4.5]decan-1-one (cis, racemic)

6-Fluoro-2-(4-methyl-5-oxo-2,5-dihydrofuran-3-yl)-2,8-diazaspiro[4.5]decan-1-one (cis, racemic) was synthesized from 8-benzyl-6-hydroxy-2-(2-methyl-3-oxocyclopent-1-en-1-yl)-2,8-diazaspiro[4.5]decan-1-one (step C for 1-88, fast eluted, trans) following a similar procedure as for 1-90 without further chiral separation. LCMS [M+1]$^+$=269.0.

INTERMEDIATE 92

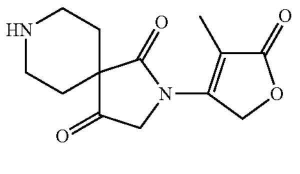 [SMILES: CC1=C(N2CC(=O)C3(CCNCC3)C2=O)COC1=O]

2-(4-Methyl-5-oxo-2,5-dihydrofuran-3-yl)-2,8-diazaspiro[4.5]decane-1,4-dione

Step A: tert-Butyl 2-(4-methyl-5-oxo-2,5-dihydrofuran-3-yl)-1,4-dioxo-2,8-diazaspiro[4.5]decane-8-carboxylate To tert-butyl 4-hydroxy-2-(4-methyl-5-oxo-2,5-dihydrofuran-3-yl)-1-oxo-2,8-diazaspiro[4.5]decane-8-carboxylate (200 mg, 0.546 mmol) in DCM (2.8 mL) was added sodium bicarbonate (68.8 mg, 0.819 mmol) and Dess-Martin periodane (347 mg, 0.819 mmol). The reaction mixture was vigorously stirred for 1.5 h, quenched with 10% $Na_2S_2O_3$, and $NaHCO_3$, and stirred for 20 min. The aqueous layer was extracted with DCM, and the combined organic layers were washed with brine, dried, and concentrated to give the title compound. LCMS $[M+1]^+$=365.

Step B: 2-(4-Methyl-5-oxo-2,5-dihydrofuran-3-yl)-2,8-diazaspiro[4.5]decane-1,4-dione To a solution of tert-butyl 2-(4-methyl-5-oxo-2,5-dihydrofuran-3-yl)-1,4-dioxo-2,8-diazaspiro[4.5]decane-8-carboxylate (150 mg) in dichloromethane (5 mL) was added trifluoroacetic acid (1 mL). The resulting solution was stirred at rt for 1h, and volatile was removed. The residue was basified to a free amine on Bond Elut SCX ion exchange column washed with methanol followed by 1 N ammonia/methanol to give the title compound. LCMS $[M+1]^+$=265.

INTERMEDIATE 93A

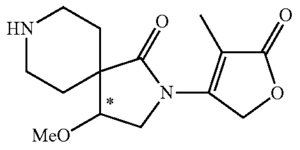

93A (enantiomer A)
93B (enantiomer B)

(4S)-4-Methoxy-2-(4-methyl-5-oxo-2,5-dihydrofuran-3-yl)-2,8-diazaspiro[4.5]decan-1-one (4R)-4-Methoxy-2-(4-methyl-5-oxo-2,5-dihydrofuran-3-yl)-2,8-diazaspiro[4.5]decan-1-one Step A: tert-Butyl 4-methoxy-2-(4-methyl-5-oxo-2,5-dihydrofuran-3-yl)-1-oxo-2,8-diazaspiro[4.5]decane-8-carboxylate To a solution of racemic tert-butyl 4-hydroxy-2-(4-methyl-5-oxo-2,5-dihydrofuran-3-yl)-1-oxo-2,8-diazaspiro[4.5]decane-8-carboxylate (BOC-INTERMEDIATE of Step A for I-86A, 100 mg, 0.273 mmol) in acetonitrile (1 mL) were added iodomethane (171 μL, 2.73 mmol) and silver oxide (69.6 mg, 0.300 mmol). The vial was sealed, wrapped with aluminum foil, and stirred at 58° C. for 15 h. The reaction mixture was filtered through CELITE, concentrated to give the crude product, which was purified by column chromatography (0-10% MeOH/DCM) to afford the title compound. LCMS $[M+1]^+$=381.

Step B: tert-Butyl 4-methoxy-2-(4-methyl-5-oxo-2,5-dihydrofuran-3-yl)-1-oxo-2,8-diazaspiro[4.5]decane-8-carboxylate (fast eluted, BOC-enantiomer A) and tert-butyl 4-methoxy-2-(4-methyl-5-oxo-2,5-dihydrofuran-3-yl)-1-oxo-2,8-diazaspiro[4.5]decane-8-carboxylate (slow eluted, BOC-enantiomer B)

The racemic mixture was separated by SFC-HPLC, using the following conditions: chiralcel AD-H, 2×25 cm, 15% MeOH, 60 mL/min to afford fast eluted isomer: tert-butyl 4-methoxy-2-(4-methyl-5-oxo-2,5-dihydrofuran-3-yl)-1-oxo-2,8-diazaspiro[4.5]decane-8-carboxylate (BOC-enantiomer A, LCMS $[M+1]^+$=381 and slow eluted isomer: tert-butyl 4-methoxy-2-(4-methyl-5-oxo-2,5-dihydrofuran-3-yl)-1-oxo-2,8-diazaspiro[4.5]decane-8-carboxylate (BOC-enantiomer B, LCMS $[M+1]^+$=381).

Step C: 4-Methoxy-2-(4-methyl-5-oxo-2,5-dihydrofuran-3-yl)-2,8-diazaspiro[4.5]decan-1-one (enantiomer A) and 4-methoxy-2-(4-methyl-5-oxo-2,5-dihydrofuran-3-yl)-2,8-diazaspiro[4.5]decan-1-one (enantiomer B)

To a solution of BOC-enantiomer A, tert-butyl 4-methoxy-2-(4-methyl-5-oxo-2,5-dihydrofuran-3-yl)-1-oxo-2,8-diazaspiro[4.5]decane-8-carboxylate (30 mg) in dichloromethane (1 mL) was added trifluoroacetic acid (0.2 mL), and the resulting solution was stirred at rt for 1h. After volatile was removed under reduced pressure, the residue was basified to a free amine on a Bond Elut SCX ion exchange column washed with methanol followed by 1 N ammonia/methanol to give 4-methoxy-2-(4-methyl-5-oxo-2,5-dihydrofuran-3-yl)-2,8-diazaspiro[4.5]decan-1-one (enantiomer A). LCMS $[M+1]^+$=281. 4-Methoxy-2-(4-methyl-5-oxo-2,5-dihydrofuran-3-yl)-2,8-diazaspiro[4.5]decan-1-one (enatiomer B) was synthesized from BOC-enantiomer B following the same procedure as described above. LCMS $[M+1]^+$=281. Absolute stereochemistry at *C for each enantiomer was not determined.

TABLE 7

| INTERMEDIATES prepared following a similar procedure as for I-93 | | | |
|---|---|---|---|
| INTERMEDIATE # | Starting Intermediate | Structure, name and characterization | LCMS $[M + 1]^+$ |
| 94A<br>94B | 64 | 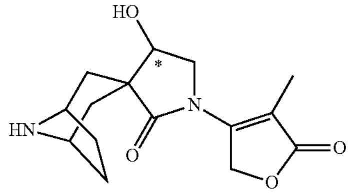 [SMILES: CC1=C(N2CC(O)C3(CC4CCC(C3)N4)C2=O)COC1=O]<br>(1R,3r,5S)-4'-methoxy-1'-(4-methyl-5-oxo-2,5-dihydrofuran-3-yl)-8-azaspiro[bicyclo[3.2.1]octane-3,3'-pyrrolidin]-2'-one; 94A: fast eluting; 94B: slow eluting | 307 for both enantiomers |

INTERMEDIATE 95A and 95B

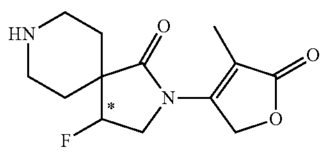

95A (enantiomer A)
95B (enantiomer B)

(4S)-4-Fluoro-2-(4-methyl-5-oxo-2,5-dihydrofuran-3-yl)-2,8-diazaspiro[4.5]decan-1-one (4R)-4-Fluoro-2-(4-methyl-5-oxo-2,5-dihydrofuran-3-yl)-2,8-diazaspiro[4.5]decan-1-one Step A: tert-Butyl 4-fluoro-2-(4-methyl-5-oxo-2,5-dihydrofuran-3-yl)-1-oxo-2,8-diazaspiro[4.5]decane-8-carboxylate To a solution of tert-butyl 4-hydroxy-2-(4-methyl-5-oxo-2,5-dihydrofuran-3-yl)-1-oxo-2,8-diazaspiro[4.5]decane-8-carboxylate (500 mg, 1.365 mmol) in DCM (14 mL) at −78° C. was added triethylamine trihydrofluoride (445 μl, 2.73 mmol), triethylamine (190 μl, 1.36 mmol), and XtalFluor-E (469 mg, 2.05 mmol). The reaction mixture was stirred overnight while warming up to rt, and quenched with aqueous $NaHCO_3$. The organic layer was separated and the aqueous layer was extracted with DCM (30 mL). The combined organic layers were dried ($MgSO_4$) and purified by column chromatography (80 g silica gel ISCO gold column, 0-100% EtOAc/hex) to give tert-butyl 4-fluoro-2-(4-methyl-5-oxo-2,5-dihydrofuran-3-yl)-1-oxo-2,8-diazaspiro[4.5]decane-8-carboxylate. LCMS $[M+1]^+$=369.

Step B: tert-Butyl 4-fluoro-2-(4-methyl-5-oxo-2,5-dihydrofuran-3-yl)-1-oxo-2,8-diazaspiro[4.5]decane-8-carboxylate (fast eluted, BOC-enantiomer A) and tert-butyl 4-fluoro-2-(4-methyl-5-oxo-2,5-dihydrofuran-3-yl)-1-oxo-2,8-diazaspiro[4.5]decane-8-carboxylate (slow eluted, BOC-enantiomer B)

The racemic mixture was separated by SFC-HPLC, using the following conditions: chiralpak AS, 21×250 mm, 20% MeOH+0.2% DEA, 50 mL/min to afford fast eluted isomer: tert-butyl 4-fluoro-2-(4-methyl-5-oxo-2,5-dihydrofuran-3-yl)-1-oxo-2,8-diazaspiro[4.5]decane-8-carboxylate (BOC-enantiomer A, LCMS $[M+1]^+$=369) and slow eluted isomer: tert-butyl 4-fluoro-2-(4-methyl-5-oxo-2,5-dihydrofuran-3-yl)-1-oxo-2,8-diazaspiro[4.5]decane-8-carboxylate (BOC-enantiomer B, LCMS $[M+1]^+$=369.

Step C: 4-Fluoro-2-(4-methyl-5-oxo-2,5-dihydrofuran-3-yl)-2,8-diazaspiro[4.5]decan-1-one (Enantiomer A and Enantiomer B)

To a solution of BOC-enantiomer A tert-butyl 4-fluoro-2-(4-methyl-5-oxo-2,5-dihydrofuran-3-yl)-1-oxo-2,8-diazaspiro[4.5]decane-8-carboxylate and (150 mg) in dichloromethane (5 mL) was added trifluoroacetic acid (1 mL), and the resulting solution was stirred at rt for 1h. After the volatile was removed, the residue was basified to a free amine on a Bond Elut SCX ion exchange column washed with methanol followed by 1 N ammonia/methanol to give Enantiomer A of the title compound: LCMS $[M+1]^+$=269. 4-Fluoro-2-(4-methyl-5-oxo-2,5-dihydrofuran-3-yl)-2,8-diazaspiro[4.5]decan-1-one (enantiomer B) was synthesized from BOC-enantiomer B following the same procedure as described above. LCMS $[M+1]^+$=269. BOC-enantiomer B was used to prepare Enantiomer A of the title compound in a similar fashion. Absolute stereochemistry at *C for each enantiomer was not determined.

INTERMEDIATE 96

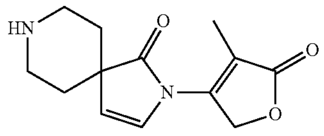 [SMILES: CC1=C(N2C=CC3(CCNCC3)C2=O)COC1=O]

2-(4-methyl-5-oxo-2,5-dihydrofuran-3-yl)-2,8-diazaspiro[4.5]dec-3-en-1-one

Step A: tert-Butyl 2-(4-methyl-5-oxo-2,5-dihydrofuran-3-yl)-1-oxo-2,8-diazaspiro[4.5]dec-3-ene-8-carboxylate To a solution of tert-butyl 4-hydroxy-2-(4-methyl-5-oxo-2,5-dihydrofuran-3-yl)-1-oxo-2,8-diazaspiro[4.5]decane-8-carboxylate (300 mg, 0.819 mmol) in DCM (8.2 mL) at 0° C. were added DBU (370 μl, 2.46 mmol) and XtalFluor-E (562 mg, 2.46 mmol). The mixture was stirred overnight while warming up to rt, and quenched with aqueous $NaHCO_3$. The organic layer was separated, and the aqueous layer was extracted with DCM (30 mL). The combined organic layers were dried ($MgSO_4$), and concentrated. The crude material was purified by column chromatography (0-100% EtOAc/hex) to give the title compound. LCMS $[M+1]^+$=349.

Step B: 2-(4-Methyl-5-oxo-2,5-dihydrofuran-3-yl)-2,8-diazaspiro[4.5]dec-3-en-1-one To a solution of tert-butyl 2-(4-methyl-5-oxo-2,5-dihydrofuran-3-yl)-1-oxo-2,8-diazaspiro[4.5]dec-3-ene-8-carboxylate (150 mg) in dichloromethane (5 mL) was added trifluoroacetic acid (1 mL). The resulting solution was stirred at rt for 1h. After volatiles were removed, the residue was basified to a free amine on a Bond Elut SCX ion exchange column washed with methanol followed by 1 N ammonia/methanol to give the title compound, LCMS $[M+1]^+$=249.

INTERMEDIATE 97

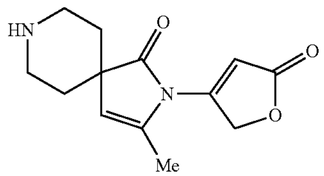 [SMILES: CC1=CC2(CCNCC2)C(=O)N1C1=CC(=O)OC1]

3-Methyl-2-(5-oxo-2,5-dihydrofuran-3-yl)-2,8-diazaspiro[4.5]dec-3-en-1-one

Step A: 1-tert-Butyl 4-methyl 4-(2-((tert-butoxycarbonyl)amino)-1-hydroxypropyl)piperidine-1,4-dicarboxylate To a solution of LDA [prepared by adding n-BuLi (27.7 mL, 55.5 mmol) to diisopropylamine (8.04 mL, 57.3 mmol) in THF (40 mL) at 0° C.] was added 1-tert-butyl 4-methyl piperidine-1,4-dicarboxylate (4.50 g, 18.5 mmol) in TMEDA (16.6 mL, 111 mmol) dropwise via a syringe pump at −78° C. over 20 min. The mixture was stirred at the same temperature for 30 min, and (S)-tert-butyl (1-oxopropan-2-yl)carbamate (9.93 g, 57.3 mmol) in THF (20 mL) was added slowly by the syringe pump over 20 min. The mixture was stirred at −78° C. for 30 min, and quenched with saturated $NH_4Cl$ aqueous at −78° C., warmed up to rt and diluted with EtOAc (200 mL). The organic layer was separated, and the aqueous layer was extracted with EtOAc (100 mL). The combined organic layers were washed with brine, dried ($MgSO_4$), and concentrated. The residue was purified by column chromatography (MeOH/DCM, gradient 0-10%) to afford the title compound. LCMS $[M+1]^+$=417.

Step B: tert-Butyl 4-hydroxy-3-methyl-1-oxo-2,8-diazaspiro[4.5]decane-8-carboxylate To a solution of 1-tert-butyl 4-methyl 4-(2-((tert-butoxycarbonyl)amino)-1-hydroxypropyl)piperidine-1,4-dicarboxylate (8.00 g, 19.2 mmol) in DCM (190 mL) was added TFA (44.4 mL, 576 mmol) at 0° C. The resulting solution was stirred for 2 h, and volatile was removed under reduced pressure. The residue was dried in high vacuum briefly to remove excess TFA, and was re-dissolved in MeOH (190 mL). After the mixture was heated with $K_2CO_3$ (26.5 g, 192 mmol) at 60° C. for 2 h, and cooled to rt, saturated $NaHCO_3$ aqueous (60 mL) and $(Boc)_2O$ (12.6 g, 57.6 mmol) were added. The reaction mixture was stirred overnight at rt. The organic layer was separated, and the aqueous layer was extracted with DCM. The combined organic layers were dried over $MgSO_4$, and concentrated to give the crude product which was purified by column chromatography (0-20% MeOH/DCM) to give the title compound. LCMS $[M+1]^+$=285.

Step C: tert-Butyl 4-hydroxy-3-methyl-1-oxo-2-(5-oxo-2,5-dihydrofuran-3-yl)-2,8-diazaspiro[4.5]decane-8-carboxylate To a round bottom flask charged with tert-butyl 4-hydroxy-3-methyl-1-oxo-2,8-diazaspiro[4.5]decane-8-carboxylate (1000 mg, 3.52 mmol), 4-bromofuran-2(5H)-one (860 mg, 5.28 mmol), $Pd(OAc)_2$ (79 mg, 0.352 mmol), XantPhos (305 mg, 0.528 mmol), and $K_2CO_3$ (972 mg, 7.03 mmol) were added under nitrogen dioxane (14 mL) and water (190 μL, 10.6 mmol) by injection. The mixture was heated at 90° C. overnight, and filtered through CELITE pad. The filtrate was concentrated to give the crude product, which was purified by column chromatography (0-10% MeOH/DCM). Thus obtained material was purified by another column with EtOAc/hex 0-100% to remove color to deliver the title compound. LCMS $[M+1]^+$=367.

Step D: tert-Butyl 4-iodo-3-methyl-1-oxo-2-(5-oxo-2,5-dihydrofuran-3-yl)-2,8-diazaspiro[4.5]decane-8-carboxylate To a solution of tert-butyl 4-hydroxy-3-methyl-1-oxo-2-(5-oxo-2,5-dihydrofuran-3-yl)-2,8-diazaspiro[4.5]decane-8-carboxylate (370 mg, 1.01 mmol) in toluene (20 mL) were added at rt $PPh_3$ (397 mg, 1.515 mmol), imidazole (137 mg, 2.02 mmol), and $I_2$ (384 mg, 1.515 mmol). The mixture was stirred for 10 h at 100° C., and quenched with $NaHCO_3$ aqueous solution. The organic was separated, and the aqueous layer was extracted with DCM. The combined organic layers were dried (MgSO4) and purified by column chromatography (0-100% EtOAc/hex) to give the title compound. LCMS $[M+1-56]^+$=421.

Step E: 4-Iodo-3-methyl-2-(5-oxo-2,5-dihydrofuran-3-yl)-2,8-diazaspiro[4.5]decan-1-one tert-Butyl 4-iodo-3-methyl-1-oxo-2-(5-oxo-2,5-dihydrofuran-3-yl)-2,8-diazaspiro[4.5]decane-8-carboxylate (100 mg, 0.210 mmol) in DCM (1.1 mL) was treated with TFA (485 μL, 6.30 mmol) at 0° C. to give TFA salt after solvent was evaporated. The TFA salt was basified to a free amine on Bond Elut SCX ion exchange column washed with methanol followed by 1 N ammonia/methanol to get the title compound. LCMS $[M+1]^+$=377.

Step F: 3-Methyl-2-(5-oxo-2,5-dihydrofuran-3-yl)-2,8-diazaspiro[4.5]dec-3-en-1-one To a solution of 4-iodo-3-methyl-2-(5-oxo-2,5-dihydrofuran-3-yl)-2,8-diazaspiro[4.5]decan-1-one (180 mg, 0.478 mmol) in THF (4.8 mL) was added 10-ethyl-2,3,4,6,7,8,9,10-octahydropyrimido[1,2-a]azepine (polymer-bound, 1.15 mmol/g, 2.5 g resin) at rt. The reaction mixture was heated on a shaker at 60° C. for 5 h. The resin was filtered off, and washed with MeOH. The filtrate was concentrated under vacuum to give the title compound. LCMS [M+1]'=249.

INTERMEDIATE 98

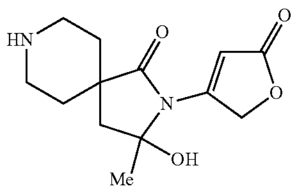 [SMILES: CC1(O)CC2(CCNCC2)C(=O)N1C1=CC(=O)OC1]

3-Hydroxy-3-methyl-2-(5-oxo-2,5-dihydrofuran-3-yl)-2,8-diazaspiro[4.5]decan-1-one (racemic)

Step A: tert-Butyl 3-methyl-1-oxo-2-(5-oxo-2,5-dihydrofuran-3-yl)-2,8-diazaspiro[4.5]dec-3-ene-8-carboxylate (racemic)

To a solution of tert-butyl 4-hydroxy-3-methyl-1-oxo-2-(5-oxo-2,5-dihydrofuran-3-yl)-2,8-diazaspiro[4.5]decane-8-carboxylate (600 mg, 1.64 mmol) in DCM (16 mL) were added DBU (864 μL, 5.73 mmol) and XtalFluor-E (1312 mg, 5.73 mmol) at 0° C. The mixture was stirred for 2 days while warming up to rt, and quenched with aqueous $NaHCO_3$. The organic layer was separated, and the aqueous layer was extracted with DCM (30 mL). The combined organic layers were dried ($MgSO_4$) and concentrated. The crude product was purified by column chromatography (0-100% EtOAc/hex) to give the title compound. LCMS $[M+1]^+$=349.

Step B: 3-Hydroxy-3-methyl-2-(5-oxo-2,5-dihydrofuran-3-yl)-2,8-diazaspiro[4.5]decan-1-one (racemic)

tert-Butyl 3-methyl-1-oxo-2-(5-oxo-2,5-dihydrofuran-3-yl)-2,8-diazaspiro[4.5]dec-3-ene-8-carboxylate (140 mg, 0.402 mmol) in DCM (2.0 mL) was treated with TFA (1.0 mL, 12.06 mmol) at 0° C. to give TFA salt after evaporation of solvents. The TFA salt was basified to a free amine on Bond Elut SCX ion exchange column washed with methanol followed by 1 N ammonia/methanol to get the title compound. LCMS $[M+1]^+$=267.

INTERMEDIATE 99

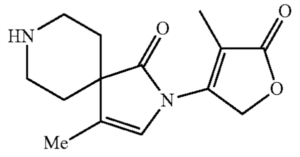 [SMILES: CC1=CN(C2=C(C)C(=O)OC2)C(=O)C12CCNCC2]

4-Methyl-2-(4-methyl-5-oxo-2,5-dihydrofuran-3-yl)-2,8-diazaspiro[4.5]dec-3-en-1-one Step A: tert-Butyl 2-(4-methyl-5-oxo-2,5-dihydrofuran-3-yl)-1,4-dioxo-2,8-diazaspiro[4.5]-decane-8-carboxylate To a solution of tert-butyl 4-hydroxy-2-(4-methyl-5-oxo-2,5-dihydrofuran-3-yl)-1-oxo-2,8-diazaspiro[4.5]decane-8-carboxylate (200 mg, 0.546 mmol) in DCM (2.8 mL) were added sodium bicarbonate (68.8 mg, 0.819 mmol) and Dess-Martin periodinane (347 mg, 0.819 mmol). The reaction mixture was vigorously stirred for 1.5 h, then quenched with 10% $Na_2S_2O_3$ and $NaHCO_3$. After stirred for 20 min, the aqueous layer was extracted with DCM. The combined organic layers were washed with brine, dried, and concentrated to give the title compound. LCMS $[M+1]^+$=365.

Step B: tert-Butyl 2-(4-methyl-5-oxo-2,5-dihydrofuran-3-yl)-1-oxo-4-(((trifluoromethyl)sulfonyl)oxy)-2,8-diazaspiro[4.5]dec-3-ene-8-carboxylate To a flask charged with tert-butyl 2-(4-methyl-5-oxo-2,5-dihydrofuran-3-yl)-1,4-dioxo-2,8-diazaspiro[4.5]decane-8-carboxylate (200 mg, 0.549 mmol) in THF (3 mL) was added NaHMDS (1.10 mL, 1 M in THF, 1.10 mmol) dropwise over 5 min at −78° C. After the solution was stirred for 2 h at the same temperature, N-phenylbis(trifluoromethanesulfonimide) (314 mg, 0.878 mmol) in THF (2 mL) was added dropwise over 5 min. Stirring continued at −78° C. for 2 h, and at rt overnight. The reaction was quenched with saturated aqueous $NH_4Cl$. The organic layer was separated, and the aqueous layer was extracted with EtOAc. The combined organic layers were dried (MgSO4) and concentrated. The crude material was purified by column chromatography (0-10% MeOH/DCM) to afford the title compound. LCMS $[M+1]^+$=497.

Step C: tert-Butyl 4-methyl-2-(4-methyl-5-oxo-2,5-dihydrofuran-3-yl)-1-oxo-2,8-diazaspiro[4.5]dec-3-ene-8-carboxylate To a solution of tert-butyl 2-(4-methyl-5-oxo-2,5-dihydrofuran-3-yl)-1-oxo-4-(((trifluoromethyl)sulfonyl)oxy)-2,8-diazaspiro[4.5]dec-3-ene-8-carboxylate (180 mg, 0.363 mmol) in THF (3.6 mL) were added $Pd(Ph_3P)_4$ (209 mg, 0.181 mmol) and trimethylaluminum (3.6 mL, 7.25 mmol) at 0° C. The reaction mixture was stirred at rt for 2 h, quenched with saturated $NaHCO_3$ aqueous at 0° C. (highly exothermo) and diluted with EtOAc. The organic layer was separated, and the aqueous layer was extracted with EtOAc. The combined organic layers were dried over $Mg_2SO_4$ and concentrated under reduced pressure. The crude material was purified by column chromatography (0-10% MeOH/DCM) to afford the title compound. LCMS $[M+1]^+$=363.

Step D: 4-Methyl-2-(4-methyl-5-oxo-2,5-dihydrofuran-3-yl)-2,8-diazaspiro[4.5]dec-3-en-1-one tert-Butyl 4-methyl-2-(4-methyl-5-oxo-2,5-dihydrofuran-3-yl)-1-oxo-2,8-diazaspiro[4.5]dec-3-ene-8-carboxylate (140 mg, 0.402 mmol) in DCM (2.0 mL) was treated with TFA (1.0 mL, 12.06 mmol) at 0° C. to give TFA salt after evaporation of solvents. The TFA salt was basified to a free amine on Bond Elut SCX ion exchange column washed with methanol followed by 1 N ammonia/methanol to get the title compound. LCMS $[M+1]^+$=263.

INTERMEDIATE 100

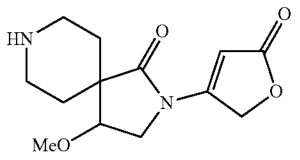 [SMILES: COC1CN(C2=CC(=O)OC2)C(=O)C12CCNCC2]

4-Methoxy-2-(5-oxo-2,5-dihydrofuran-3-yl)-2,8-diazaspiro[4.5]decan-1-one (racemic)

Step A: tert-Butyl 4-hydroxy-1-oxo-2-(5-oxo-2,5-dihydrofuran-3-yl)-2,8-diazaspiro[4.5]decane-8-carboxylate To a round bottom flask charged with tert-butyl 4-hydroxy-1-oxo-2,8-diazaspiro[4.5]decane-8-carboxylate (300 mg, 1.11 mmol) were added 4-bromofuran-2(5H)-one (271 mg, 1.66 mmol), $Pd(OAc)_2$ (24.9 mg, 0.111 mmol), Xantphos (96 mg, 0.166 mmol), and $K_2CO_3$ (307 mg, 2.22 mmol). Under $N_2$ dioxane (4.5 mL) and $H_2O$ (60.0 μL, 3.33 mmol) were added by injection. The reaction mixture was heated at 90° C. overnight, filtered through CELITE. The filtrate was purified by column chromatography (0-10% MeOH/DCM) to give the title compound. LCMS $[M+1]^+$=353.

Step B: tert-Butyl 4-methoxy-1-oxo-2-(5-oxo-2,5-dihydrofuran-3-yl)-2,8-diazaspiro[4.5]decane-8-carboxylate To a solution of tert-butyl 4-hydroxy-1-oxo-2-(5-oxo-2,5-dihydrofuran-3-yl)-2,8-diazaspiro[4.5]decane-8-carboxylate (200 mg, 0.568 mmol) in acetonitrile (2 mL) were added iodomethane (355 μl, 5.68 mmol) and silver oxide (158 mg, 0.681 mmol). The vial was sealed, wrapped with aluminum foil, and stirred at 58° C. for 17 h. The reaction mixture was filtered through CELITE, and concentrated to give the crude product, which was purified by column chromatography (0-10% MeOH/DCM) to afford the title compound LCMS $[M+1-56]^+=311$.

Step C: 4-Methoxy-2-(5-oxo-2,5-dihydrofuran-3-yl)-2,8-diazaspiro[4.5]decan-1-one To a solution of tert-butyl 4-methoxy-1-oxo-2-(5-oxo-2,5-dihydrofuran-3-yl)-2,8-diazaspiro[4.5]decane-8-carboxylate (150 mg) in dichloromethane (5 mL) was added trifluoroacetic acid (1 mL). The mixture was stirred at rt for 1h, and volatiles were removed under reduced pressure. The residue was basified to a free amine on Bond Elut SCX ion exchange column washed with methanol followed by 1 N ammonia/methanol to give title compound. LCMS $[M+1]^+=267$.

INTERMEDIATE 101

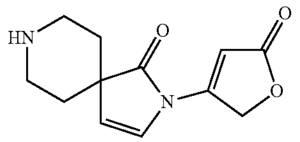 [SMILES: O=C1C=C(N2C=CC3(CCNCC3)C2=O)CO1]

2-(5-Oxo-2,5-dihydrofuran-3-yl)-2,8-diazaspiro[4.5]dec-3-en-1-one

Step A: tert-Butyl 1-oxo-2-(5-oxo-2,5-dihydrofuran-3-yl)-2,8-diazaspiro[4.5]dec-3-ene-8-carboxylate To a solution of tert-butyl 4-hydroxy-1-oxo-2-(5-oxo-2,5-dihydrofuran-3-yl)-2,8-diazaspiro[4.5]decane-8-carboxylate (210 mg, 0.596 mmol) in DCM (6 mL) were added DBU (269 μl, 1.79 mmol) and XtalFluor-E (409 mg, 1.79 mmol) at 0° C. The mixture was stirred overnight while warming up to rt, quenched with aqueous $NaHCO_3$. The organic layer was separated, and the aqueous layer was extracted with DCM (30 mL). The combined organic layers were dried ($MgSO_4$) and concentrated. The crude material was purified by column chromatography (0-100% EtOAc/hex) to the title compound. LCMS $[M+1]^+=335$.

Step B: 2-(5-Oxo-2,5-dihydrofuran-3-yl)-2,8-diazaspiro[4.5]dec-3-en-1-one

To a solution of tert-butyl 1-oxo-2-(5-oxo-2,5-dihydrofuran-3-yl)-2,8-diazaspiro[4.5]dec-3-ene-8-carboxylate (150 mg) in dichloromethane (5 mL) was added trifluoroacetic acid (1 mL). The mixture was stirred at rt for 1h, and volatiles were removed under reduced pressure. The residue was basified to a free amine on Bond Elut SCX ion exchange column washed with methanol followed by 1 N ammonia/methanol to give title compound. LCMS $[M+1]^+=235$.

INTERMEDIATE 102

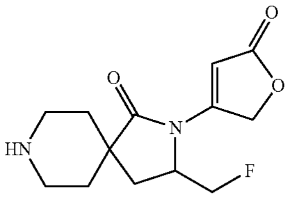 [SMILES: O=C1C=C(N2C(=O)C3(CCNCC3)CC2CF)CO1]

3-(Fluoromethyl)-2-(5-oxo-2,5-dihydrofuran-3-yl)-2,8-diazaspiro[4.5]decan-1-one (racemic)

Step A: 1-tert-Butyl 4-methyl 4-(2-(((tert-butyldimethylsilyl)oxy)methyl)allyl)piperidine-1,4-dicarboxylate (racemic)

To a solution of 1-tert-butyl 4-methyl piperidine-1,4-dicarboxylate (3 g, 12.33 mmol) in THF (50 ml) at −78° C. was added dropwise lithium bis(trimethylsilyl)amide (1M, 18.50 ml, 18.50 mmol) in THF. After the mixture was stirred at −78° C. for 30 minutes, a solution of ((2-(bromomethyl)allyl)oxy)(tert-butyl)dimethylsilane (4. g, 15.08 mmol) in THF (10 ml) was added. Stirring continued for 1 h at this temperature. The mixture was then allowed to warm up to rt, and stir over night. The reaction was quenched with saturated $NH_4Cl$ aqueous (20 ml), and the aqueous layer was extracted with EtOAc (30 ml×2). The combined organic layers were washed with brine, dried over anhydrous sodium sulfate, filtered and concentrated. The crude product was purified by column chromatography eluting with 0-30% EtOAc/hexane to give the title compound as an oil. LCMS $[M+23]^+=450.2$.

Step B: 1-tert-Butyl 4-methyl 4-(3-((tert-butyldimethylsilyl)oxy)-2-oxopropyl)piperidine-1,4-dicarboxylate To a solution of 1-tert-butyl 4-methyl 4-(2-(((tert-butyldimethylsilyl)oxy)methyl)allyl)piperidine-1,4-dicarboxylate (4.5 g, 10.52 mmol) in dioxane:water (80 ml, 1:1) were added osmium tetroxide (0.054 g, 0.210 mmol) and sodium periodate (4.10 g, 19.15 mmol) under nitrogen at rt. The mixture was stirred at rt for 3 h. Additional amount of osmium tetroxide (~100 mg) was added and the mixture was stirred at rt overnight until TLC showed the starting material was consumed. The mixture was diluted with EtOAc (200 ml). The organic layer was separated, and the aqueous layer was extracted with EtOAc. The combined organic layers were washed with 20% $Na_2S_2O_3$ (40 ml) and brine, dried over sodium sulfate, and concentrated. The crude product was purified by column chromatography eluting with 0-30% EtOAc/hexane to give the title compound as an oil.

Step C: tert-Butyl 3-4(tert-butyldimethylsilyl)oxy)methyl)-1-oxo-2,8-diazaspiro[4.5]decane-8-carboxylate To a solution of 1-tert-Butyl 4-methyl 4-(3-((tert-butyldimethylsilyl)oxy)-2-oxopropyl)piperidine-1,4-dicarboxylate (2.21 g, 5.14 mmol) in MeOH (51 ml) were added ammonium formate (6.49 g, 103 mmol), sodium cyanoborohydride (0.808 g, 12.86 mmol) and molecular sieves (4 A powder)(1 g). The mixture was stirred at 40° C. for 24 h in a sealed tube, cooled and filtered to remove solids. The filtrates were concentrated, and redissolved in DCM (100 ml). The organic solution was washed with water, brine, dried over sodium sulfate, and concentrated. The crude product was purified by column chromatography (Isco 120 g high performance silica column) eluting with 0-100% EtOAc/hexane to give the title compound. LCMS $[M+1]^+=399.4$.

Step D: (tert-Butyl 3-(((tert-butyldimethylsilyl)oxy)methyl)-1-oxo-2-(5-oxo-2,5-dihydrofuran-3-yl)-2,8-diazaspiro[4.5]decane-8-carboxylate To a microwave tube were added tert-butyl 3-(((tert-butyldimethylsilyl)oxy)methyl)-1-oxo-2,8-diazaspiro[4.5]

decane-8-carboxylate (426 mg, 1.069 mmol), 4-bromofuran-2-one (348 mg, 2.137 mmol), cesium carbonate (1045 mg, 3.21 mmol) and 2nd generation SPHOS precatalyst (154 mg, 0.214 mmol). The tube was purged with nitrogen for 15 minutes, then degased anhydrous dioxane (8 ml) was added. The tube was sealed and the mixture was heated at 100° C. for 48 h. After cooled to rt, the mixture was diluted with EtOAc and filtered. The filtrate was concentrated. The residue was purified by column chromatography (120 g HP silica by Isco) eluting with 0-60% EtOAc/hexane to give the title compound. LCMS $[M+1]^+$=481.4.

Step E: tert-Butyl 3-(hydroxymethyl)-1-oxo-2-(5-oxo-2,5-dihydrofuran-3-yl)-2,8-diazaspiro[4.5]decane-8-carboxylate To a solution of tert-Butyl 3-(((tert-butyldimethylsilyl)oxy)methyl)-1-oxo-2-(5-oxo-2,5-dihydrofuran-3-yl)-2,8-diazaspiro[4.5]decane-8-carboxylate (224 mg, 0.466 mmol) in THF (3 ml) was added TBAF (513 µl, 0.513 mmol). The mixture was stirred at rt for 10 minutes, and diluted with EtOAc. The organic layer was separated, and the aqueous layer was extracted with EtOAc. The combined layers were washed with water and brine, dried over sodium sulfate, and concentrated. The crude product was purified by column chromatography eluting with 0-5% MeOH/EtOAc to afford the title compound.

Step F: tert-Butyl 3-(fluoromethyl)-1-oxo-2-(5-oxo-2,5-dihydrofuran-3-yl)-2,8-diazaspiro[4.5]decane-8-carboxylate tert-Butyl 3-(hydroxymethyl)-1-oxo-2-(5-oxo-2,5-dihydrofuran-3-yl)-2,8-diazaspiro[4.5]decane-8-carboxylate (142 mg, 0.388 mmol) was suspended in DCM (3 ml) at −78° C., under nitrogen. To the suspension were added TEA (54.0 µl, 0.388 mmol), triethylamine trihydrofluoride (126 µl, 0.775 mmol) and, lastly, (diethylamino)difluorosulfonium tetrafluoroborate (133 mg, 0.581 mmol) at the same temperature. The mixture was allowed to warm up to room temperature overnight, quenched by with saturated $NaHCO_3$ aqueous solution. The organic layer was separated, and the aqueous layer was extracted with EtOAc. The combined layers were washed with water and brine, dried over sodium sulfate, and concentrated. The crude product was purified by column chromatography eluting with 0-100% EtOAc/hexane to afford the title compound. LCMS $[M+1]^+$=369.3.

Step G: 3-(Fluoromethyl)-2-(5-oxo-2,5-dihydrofuran-3-yl)-2,8-diazaspiro[4.5]decan-1-one To a solution of tert-butyl 3-(fluoromethyl)-1-oxo-2-(5-oxo-2,5-dihydrofuran-3-yl)-2,8-diazaspiro[4.5]decane-8-carboxylate (150 mg) in dichloromethane (2 mL) was added trifluoroacetic acid (1 mL), and the resulting solution was stirred at for 1h. After volatiles were removed under reduced pressure, the residue was redissolved in methanol and basified to free base on Bond Elut SCX ion exchange column washed with methanol followed by 1N ammonia/methanol to give 3-(fluoromethyl)-2-(5-oxo-2,5-dihydrofuran-3-yl)-2,8-diazaspiro[4.5]decan-1-one. LCMS $[M+1]^+$=369.2.

INTERMEDIATE 103

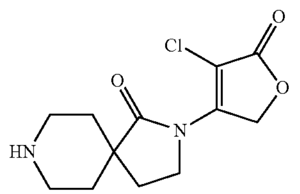 [SMILES: O=C1OCC(N2CCC3(CCNCC3)C2=O)=C1Cl]

2-(4-Chloro-5-oxo-2,5-dihydrofuran-3-yl)-2,8-diazaspiro[4.5]decan-1-one

Step A: tert-Butyl 2-(4-chloro-5-oxo-2,5-dihydrofuran-3-yl)-1-oxo-2,8-diazaspiro[4.5]decane-8-carboxylate To a solution of tert-butyl 1-oxo-2-(5-oxo-2,5-dihydrofuran-3-yl)-2,8-diazaspiro[4.5]decane-8-carboxylate (I-69, 2.1 g, 6.24 mmol) in chloroform (50 ml) was added NCS (1.000 g, 7.49 mmol) at rt. The mixture was heated at 60° C. overnight, and volatiles were removed under reduced pressure. The residue was purified on silica gel column using EtOAc/hexane as eluting solvents to give the title compound. LCMS $[M+1]^+$=371.11 and 372.9.

Step B: 2-(4-Chloro-5-oxo-2,5-dihydrofuran-3-yl)-2,8-diazaspiro[4.5]decan-1-one

To a solution of tert-butyl 2-(4-chloro-5-oxo-2,5-dihydrofuran-3-yl)-1-oxo-2,8-diazaspiro[4.5]decane-8-carboxylate (2.26 g, 6.09 mmol) in methylene chloride (10 ml) was added trifluoroacetic acid (9.39 ml, 122 mmol). The mixture was stirred at rt for 1h, and volatiles were removed under reduced pressure. The residue was partitioned between methylene chloride (100 mL) and 1N sodium hydroxide (100 mL). The organic layer was separated, and the alkaline phase was extracted with methylene chloride (2×100 mL). The combined organic layers were dried over sodium sulfate, and concentrated to give the title compound. LCMS $[M+1]^+$=271.07, 272.9.

INTERMEDIATE 104

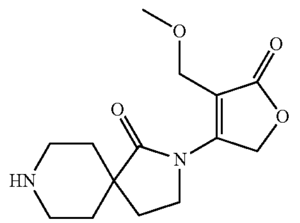 [SMILES: COCC1=C(N2CCC3(CCNCC3)C2=O)COC1=O]

2-(4-(Methoxymethyl)-5-oxo-2,5-dihydrofuran-3-yl)-2,8-diazaspiro[4.5]decan-1-one Step A: tert-Butyl 2-(4-bromo-5-oxo-2,5-dihydrofuran-3-yl)-1-oxo-2,8-diazaspiro[4.5]decane-8-carboxylate tert-Butyl 1-oxo-2-(5-oxo-2,5-dihydrofuran-3-yl)-2,8-diazaspiro[4.5]decane-8-carboxylate (2.73 g, 8.12 mmol) was dissolved in DCM (70 ml) and was treated with NBS (1.733 g, 9.74 mmol) at 25° C. The resulting mixture was stirred overnight at rt, diluted with DCM, washed with water and brine, and dried over $Na_2SO_4$. Removal of solvent under reduced pressure gave crude product that was purified by silica gel column chromatography (80 g RediSep Gold Column) using (25-80)% EtOAc/Hexanes as mobile phase.

Step B: tert-Butyl 1-oxo-2-(5-oxo-4-vinyl-2,5-dihydrofuran-3-yl)-2,8-diazaspiro[4.5]decane-8-carboxylate tert-Butyl 2-(4-bromo-5-oxo-2,5-dihydrofuran-3-yl)-1-oxo-2,8-diazaspiro[4.5]decane-8-carboxylate (2.2 g, 5.30 mmol), potassium trifluoro(vinyl)borate (1.064 g, 7.95 mmol), 1,1'-bis(di-tert-butylphosphino)ferrocene palladium dichloride (0.345 g, 0.530 mmol) and potassium phosphate tribasic (10.60 ml, 10.60 mmol) were taken up in THF (44.1 ml) in a sealed tube and de-gassed. The resulting mixture was heated overnight at 70° C., cooled to rt, diluted with EtOAc and water. After separation of layers, the aqueous layer was extracted with EtOAc (2×). The combined organic layers were dried over anhydrous $MgSO_4$, filtered, and concentrated. The crude material was purified by silica gel column chromatography using (30-100)% EtOAc/hexanes as mobile phase to give the title compound.

Step C: tert-Butyl 2-(4-formyl-5-oxo-2,5-dihydrofuran-3-yl)-1-oxo-2,8-diazaspiro[4.5]decane-8-carboxylate To a solution of tert-butyl 1-oxo-2-(5-oxo-4-vinyl-2,5-dihydrofuran-3-yl)-2,8-diazaspiro[4.5]decane-8-carboxylate (1.6 g, 4.41 mmol) in acetone (36 ml) and water (36 ml) was added $K_2OsO_4.2H_2O$. After stirred for ~5 min, solid sodium periodate (3.77 g, 17.61 mmol) was added to the above mixture in 4 portions during 1 h when the reaction temperature was maintained below 40° C. using ice-bath. The resulting mixture was stirred for another 1 h at room temperature, The suspension was filtered, and the filtrate was concentrated to remove acetone. The aqueous layer was extracted with DCM (3×). Combined organic layers were washed with 10% $Na_2S_2O_3$ solution (2×), dried over anhydrous $Na_2SO_4$, and concentrated to give the title compound, which was taken to the next step without further purification.

Step D: tert-Butyl 2-(4-(hydroxymethyl)-5-oxo-2,5-dihydrofuran-3-yl)-1-oxo-2,8-diazaspiro[4.5]decane-8-carboxylate To a solution of tert-butyl 2-(4-formyl-5-oxo-2,5-dihydrofuran-3-yl)-1-oxo-2,8-diazaspiro[4.5]decane-8-carboxylate (1.18 g, 3.24 mmol) in THF (13 ml) and MeOH (13 ml) was added at −78° C. sodium borohydride (0.147 g, 3.89 mmol) in two equal portions. The mixture was stirred for ~15 min at the same temperature, diluted with Ethyl Acetate and quenched with aqueous ammonium chloride at −78° C. After warmed up to rt, he aqueous layer was extracted with EtOAc (2×). The combined organic layers were washed with water and brine, dried ($MgSO_4$), filtered and concentrated under reduced pressure to get the title compound, which was taken to the next step without purification.

Step E: tert-Butyl 2-(4-(methoxymethyl)-5-oxo-2,5-dihydrofuran-3-yl)-1-oxo-2,8-diazaspiro[4.5]decane-8-carboxylate tert-Butyl 2-(4-(hydroxymethyl)-5-oxo-2,5-dihydrofuran-3-yl)-1-oxo-2,8-diazaspiro[4.5]decane-8-carboxylate (0.42 g, 1.146 mmol), silver oxide (0.292 g, 1.261 mmol) and methyl iodide (0.358 ml, 5.73 mmol) were taken up in DCM (5 ml). The mixture was stirred over night at rt under $N_2$. Additional silver oxide (0.292 g, 1.261 mmol) and methyl iodide (0.358 ml, 5.73 mmol) were added to the mixture in DCE (8 ml). The resulting mixture was heated at 54° C. overnight, filtered through CELITE to remove silver oxide, and concentrated under reduced pressure. The residue was purified on silica gel column chromatography (40 g RediSep Gold column) using (20-80)% EtOAc/DCM as mobile phase to give the title compound.

Step F: 2-(4-(Methoxymethyl)-5-oxo-2,5-dihydrofuran-3-yl)-2,8-diazaspiro[4.5]decan-1-one To a solution of tert-butyl 2-(4-chloro-5-oxo-2,5-dihydrofuran-3-yl)-1-oxo-2,8-diazaspiro[4.5]decane-8-carboxylate (0.15 g, 0.39 mmol) in methylene chloride (5 ml) was added trifluoroacetic acid (0.5 ml). The mixture was stirred at rt for 1h, and volatiles were removed under reduced pressure. The residue was partitioned between methylene chloride (10 mL) and 1N sodium hydroxide (10 mL). The organic layer was separated, and the alkaline phase was extracted with methylene chloride (2×10 mL). The combined organic layers were dried over sodium sulfate, and concentrated to give the title compound. LCMS $[M+1]^+$=281.4

INTERMEDIATE 105

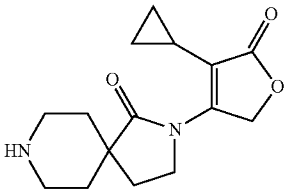 [SMILES: O=C1OCC(N2CCC3(CCNCC3)C2=O)=C1C1CC1]

2-(4-Cyclopropyl-5-oxo-2,5-dihydrofuran-3-yl)-2,8-diazaspiro[4.5]decan-1-one

Step A: tert-Butyl 2-(4-bromo-5-oxo-2,5-dihydrofuran-3-yl)-1-oxo-2,8-diazaspiro[4.5]decane-8-carboxylate tert-Butyl 1-oxo-2-(5-oxo-2,5-dihydrofuran-3-yl)-2,8-diazaspiro[4.5]decane-8-carboxylate (2.73 g, 8.12 mmol) was dissolved in DCM (70 ml) and was treated with NBS (1.733 g, 9.74 mmol) at 25° C. The resulting mixture was stirred overnight at rt, diluted with DCM, washed with water and brine, and dried over $Na_2SO_4$. Removal of solvent under reduced pressure gave crude product that was purified by silica gel column chromatography (80 g RediSep Gold Column) using (25-80)% EtOAc/Hexanes as mobile phase.

Step B: tert-Butyl 2-(4-cyclopropyl-5-oxo-2,5-dihydrofuran-3-yl)-1-oxo-2,8-diazaspiro[4.5]-decane-8-carboxylate To a micro wave vial charged with tert-butyl 2-(4-bromo-5-oxo-2,5-dihydrofuran-3-yl)-1-oxo-2,8-diazaspiro[4.5]decane-8-carboxylate (90 mg, 0.217 mmol) in toluene (2 mL) and water (0.2 mL) were added tricyclohexylphosphine (18.23 mg, 0.065 mmol), cyclopropylboronic acid (74.5 mg, 0.867 mmol), potassium phosphate (138 mg, 0.65 mmol) and palladium acetate (4.87 mg, 0.022 mmol). After degassing, the reaction mixture was heated at 100° C. overnight, cooled down to rt, and concentrated. The residue was redissolved in 30 mL of EtOAc. The solution was washed with water (30 mL) and brine (30 mL), dried over $Na_2SO_4$, and concentrated to give crude product that was purified by ISCO (0-100)% EtOAc/hexane as mobile phase.

Step C: 2-(4-Cyclopropyl-5-oxo-2,5-dihydrofuran-3-yl)-2,8-diazaspiro[4.5]decan-1-one To a solution of tert-butyl 2-(4-cyclopropyl-5-oxo-2,5-dihydrofuran-3-yl)-1-oxo-2,8-diazaspiro[4.5]decane-8-carboxylate (0.05 g, 0.13 mmol) in methylene chloride (2 ml) was added trifluoroacetic acid (0.2 ml). The mixture was stirred at rt for 1h, and volatiles were removed under reduced pressure. The residue was partitioned between methylene chloride (5 mL) and 1N sodium hydroxide (5 mL). The organic layer was separated, and the alkaline phase was extracted with methylene chloride (2×5 mL). The combined organic layers were dried over sodium sulfate, and concentrated to give the title compound. LCMS $[M+1]^+$=277.5

EXAMPLE 1

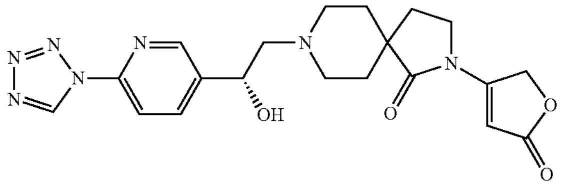

8-{(2R)-2-Hydroxy-2-[6-(1H-tetrazol-1-yl)pyridin-3-yl]ethyl}-1-oxo-2-(5-oxo-2,5-dihydrofuran-3-yl)-2-aza-8-azoniaspiro[4.5]decane 2-(5-Oxo-2,5-dihydrofuran-3-yl)-2,8-diazaspiro[4.5]decan-1-one (I-69, 0.06 g, 0.21 mmol), (5)-5-(oxiran-2-yl)-2-(1H-tetrazol-1-yl)pyridine (I-1A, 0.08 g, 0.41 mmol) and EtOH (2.5 mL) were added to a 5 ml microwave tube, and heated in a microwave reactor at 140° C. for 1 hr. The mixture was cooled to rt and concentrated. The crude material was purified over preparative TLC (25% methanol in EtOAc). LCMS $[M+1]^+$=479.

TABLE 8

Compounds prepared following a similar procedure as for EXAMPLE 1

| EXAMPLE | Epoxide Intermediate | Amine Intermediate | Structure, name and characterization |
|---|---|---|---|
| 2 | 1B | 69 | 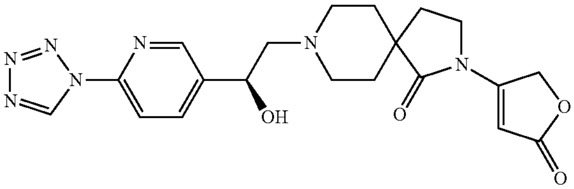 [SMILES: O=C1C=C(N2CCC3(CCN(C[C@@H](O)c4ccc(-n5cnnn5)nc4)CC3)C2=O)CO1] 8-{(2S)-2-hydroxy-2-[6-(1H-tetrazol-1-yl)pyridin-3-yl]ethyl}-1-oxo-2-(5-oxo-2,5-dihydrofuran-3-yl)-2-aza-8-azoniaspiro[4.5]decane, single isomer, LCMS $[M + 1 - 28]^+$ = 398.1 |
| 3 | 5A | 69 | 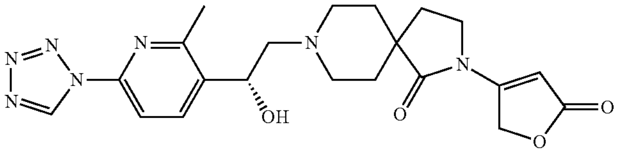 8-{(2R)-2-hydroxy-2-[2-methyl-6-(1H-tetrazol-1-yl)pyridin-3-yl]ethyl}-1-oxo-2-(5-oxo-2,5-dihydrofuran-3-yl)-2-aza-8-azoniaspiro[4.5]decane; LCMS $[M + 1 - 28]^+$ = 412.1 |
| 4 | 5B | 69 | 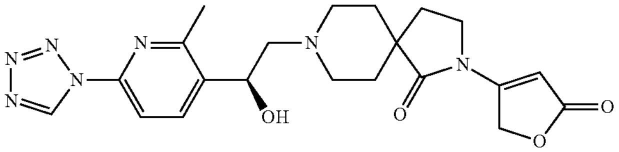 8-{(2S)-2-hydroxy-2-[2-methyl-6-(1H-tetrazol-1-yl)pyridin-3-yl]ethyl}-1-oxo-2-(5-oxo-2,5-dihydrofuran-3-yl)-2-aza-8-azoniaspiro[4.5]decane; LCMS $[M + 1 - 28]^+$ = 412.1 |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 5 | 12A | 69 | 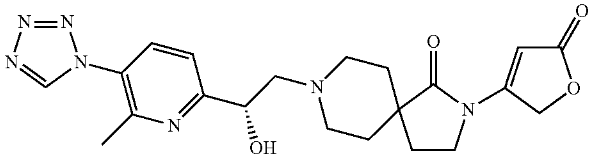 8-{(2S)-2-hydroxy-2-[6-methyl-5-(1H-tetrazol-1-yl)pyridin-2-yl]ethyl}-1-oxo-2-(5-oxo-2,5-dihydrofuran-3-yl)-2-aza-8-azoniaspiro[4.5]decane; LCMS $[M + 1 - 28]^+ = 412.2$ |
| 6 | 13B | 69 | 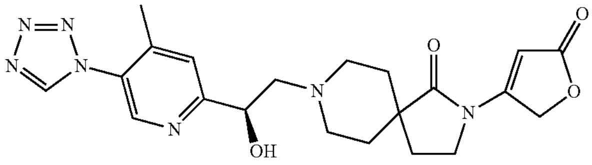 8-{(2R)-2-hydroxy-2-[4-methyl-5-(1H-tetrazol-1-yl)pyridin-2-yl]ethyl}-1-oxo-2-(5-oxo-2,5-dihydrofuran-3-yl)-2-aza-8-azoniaspiro[4.5]decane; LCMS $[M + 1 - 28]^+ = 412.2$ |
| 7 | 13A | 69 | 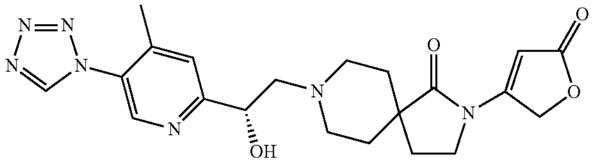 8-{(2S)-2-hydroxy-2-[4-methyl-5-(1H-tetrazol-1-yl)pyridin-2-yl]ethyl}-1-oxo-2-(5-oxo-2,5-dihydrofuran-3-yl)-2-aza-8-azoniaspiro[4.5]decane; LCMS $[M + 1 - 28]^+ = 412.1$ |
| 8 | 12B | 69 | 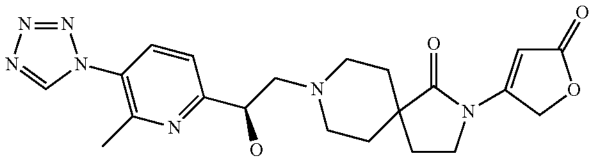 8-{(2R)-2-hydroxy-2-[6-methyl-5-(1H-tetrazol-1-yl)pyridin-2-yl]ethyl}-1-oxo-2-(5-oxo-2,5-dihydrofuran-3-yl)-2-aza-8-azoniaspiro[4.5]decane; LCMS $[M + 1 - 28]^+ = 412.1$ |
| 9 | 7A | 69 | 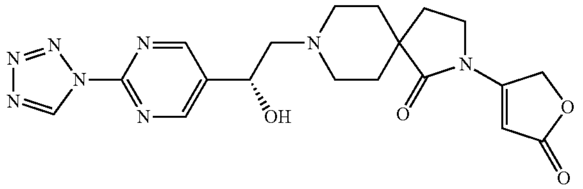 [SMILES: O=C1C=C(N2CCC3(CCN(C[C@H](O)c4cnc(-n5cnnn5)nc4)CC3)C2=O)CO1] 8-{(2R)-2-hydroxy-2-[2-(1H-tetrazol-1-yl)pyrimidin-5-yl]ethyl}-1-oxo-2-(5-oxo-2,5-dihydrofuran-3-yl)-2-aza-8-azoniaspiro[4.5]decane; LCMS $[M + 1 - 28]^+ = 399.1$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 10 | 7B | 69 | 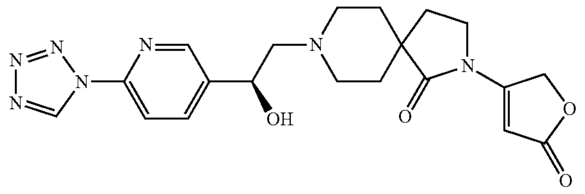 [SMILES: O=C1C=C(N2CCC3(CCN(C[C@@H](O)c4ccc(-n5cnnn5)nc4)CC3)C2=O)CO1] 8-{(2S)-2-hydroxy-2-[2-(1H-tetrazol-1-yl)pyrimidin-5-yl]ethyl}-1-oxo-2-(5-oxo-2,5-dihydrofuran-3-yl)-2-aza-8-azoniaspiro[4.5]decane; LCMS $[M + 1 - 28]^+ = 399.1$ |
| 11 | 15A | 69 | 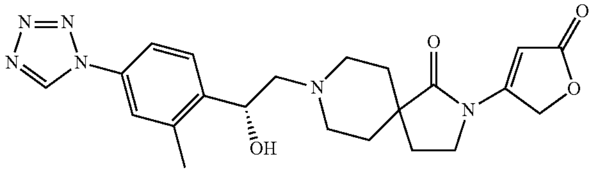 8-{(2R)-2-hydroxy-2-[2-methyl-4-(1H-tetrazol-1-yl)phenyl]ethyl}-1-oxo-2-(5-oxo-2,5-dihydrofuran-3-yl)-2-aza-8-azoniaspiro[4.5]decane; LCMS $[M + 1 - 28]^+ = 411.1$ |
| 12 | 15B | 69 | 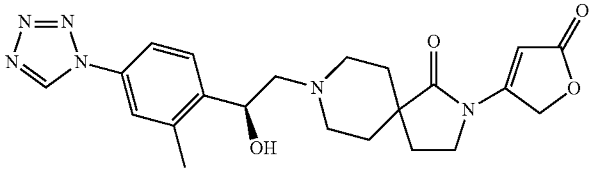 8-{(2S)-2-hydroxy-2-[2-methyl-4-(1H-tetrazol-1-yl)phenyl]ethyl}-1-oxo-2-(5-oxo-2,5-dihydrofuran-3-yl)-2-aza-8-azoniaspiro[4.5]decane; LCMS $[M + 1 - 28]^+ = 411.1$ |
| 13 | 32A | 69 | 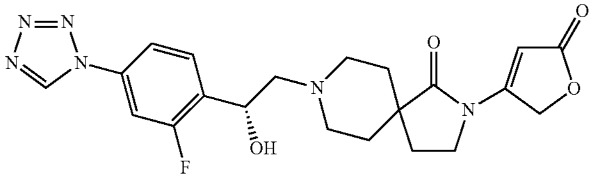 [SMILES: O=C1C=C(N2CCC3(CCN(C[C@H](O)c4ccc(-n5cnnn5)cc4F)CC3)C2=O)CO1] 8-{(2R)-2-[2-fluoro-4-(1H-tetrazol-1-yl)phenyl]-2-hydroxyethyl}-1-oxo-2-(5-oxo-2,5-dihydrofuran-3-yl)-2-aza-8-azoniaspiro[4.5]decane; LCMS $[M + 1 - 28]^+ = 415.1$ |
| 14 | 32B | 69 | 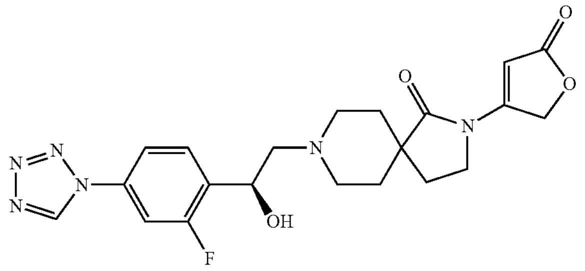 [SMILES: O=C1C=C(N2CCC3(CCN(C[C@@H](O)c4ccc(-n5cnnn5)cc4F)CC3)C2=O)CO1] 8-{(2S)-2-[2-fluoro-4-(1H-tetrazol-1-yl)phenyl]-2-hydroxyethyl}-1-oxo-2-(5-oxo-2,5-dihydrofuran-3-yl)-2-aza-8-azoniaspiro[4.5]decane; LCMS $[M + 1 - 28]^+ = 415.1$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 15 | 22A | 69 | 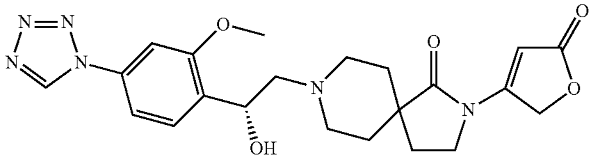 [SMILES: COc1cc(-n2cnnn2)ccc1[C@@H](O)CN1CCC2(CC1)CCN(C1=CC(=O)OC1)C2=O] 8-{(2R)-2-hydroxy-2-[2-methoxy-4-(1H-tetrazol-1-yl)phenyl]ethyl}-1-oxo-2-(5-oxo-2,5-dihydrofuran-3-yl)-2-aza-8-azoniaspiro[4.5]decane; LCMS $[M + 1]^+ = 455.2$ |
| 16 | 22B | 69 | 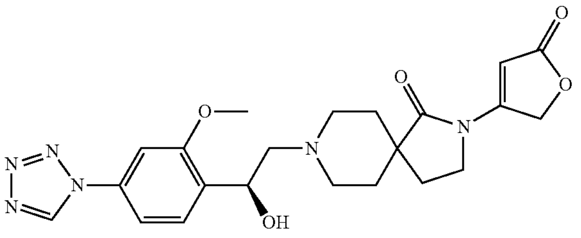 [SMILES: COc1cc(-n2cnnn2)ccc1[C@H](O)CN1CCC2(CC1)CCN(C1=CC(=O)OC1)C2=O] 8-{(2S)-2-hydroxy-2-[2-methoxy-4-(1H-tetrazol-1-yl)phenyl]ethyl}-1-oxo-2-(5-oxo-2,5-dihydrofuran-3-yl)-2-aza-8-azoniaspiro[4.5]decane; LCMS $[M + 1]^+ = 455.2$ |
| 17 | 7A | 68 | 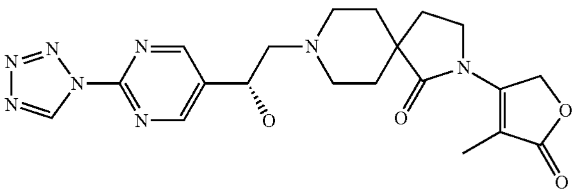 8-{(2R)-2-hydroxy-2-[2-(1H-tetrazol-1-yl)pyrimidin-5-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 413.0$ |
| 18 | 1A | 68 | 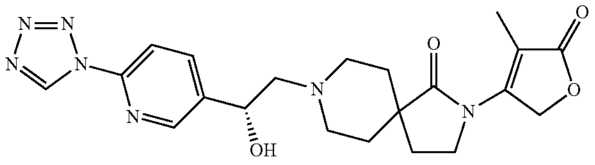 [SMILES: CC1=C(N2CCC3(CCN(C[C@H](O)c4ccc(-n5cnnn5)nc4)CC3)C2=O)COC1=O] 8-{(2R)-2-hydroxy-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane; LCMS $[M + 1]^+ = 440.1$ |
| 19 | 1B | 68 | 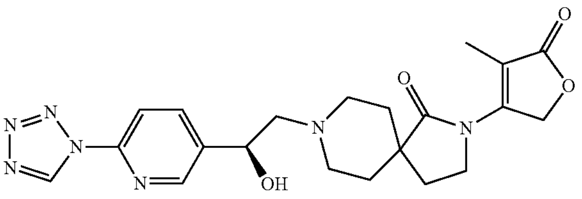 8-{(2S)-2-hydroxy-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 412.1$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 20 | 5A | 68 | 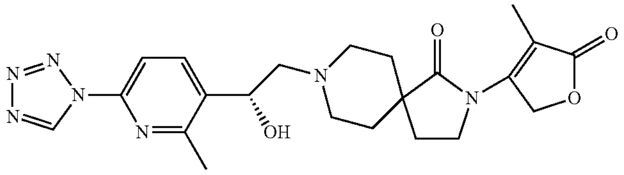 [SMILES: CC1=C(N2CCC3(CCN(C[C@H](O)c4ccc(-n5cnnn5)nc4C)CC3)C2=O)COC1=O]<br>8-{(2R)-2-hydroxy-2-[2-methyl-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane; LCMS $[M + 23]^+ = 476.1$ |
| 21 | 5B | 68 | 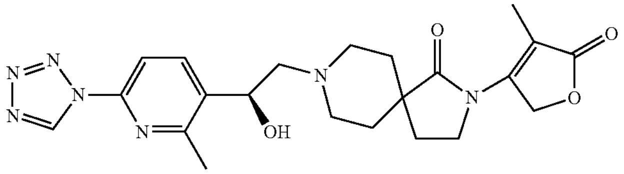 [SMILES: CC1=C(N2CCC3(CCN(C[C@@H](O)c4ccc(-n5cnnn5)nc4C)CC3)C2=O)COC1=O]<br>8-{(2S)-2-hydroxy-2-[2-methyl-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane; LCMS $[M + 23]^+ = 476.2$ |
| 22 | 4A | 68 | 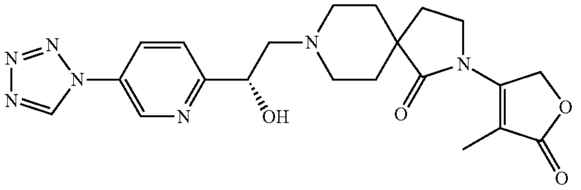<br>8-{(2S)-2-hydroxy-2-[5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 412.1$ |
| 23 | 4B | 68 | 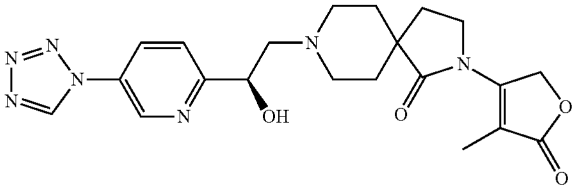<br>8-{(2R)-2-hydroxy-2-[5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 412.1$ |
| 24 | 2A | 68 | 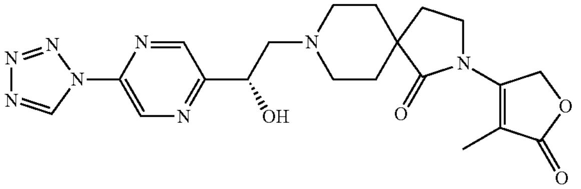<br>8-{(2S)-2-hydroxy-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 413.1$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 25 | 2B | 68 | 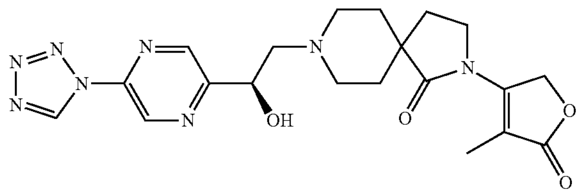 8-{(2R)-2-hydroxy-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+$ = 413.1 |
| 26 | 10A | 68 | 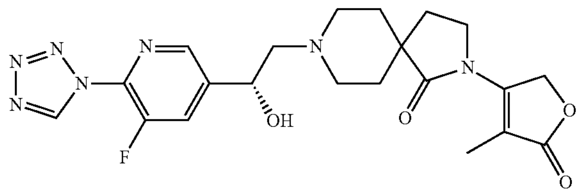 8-{(2R)-2-[5-fluoro-6-(1H-tetrazol-1-yl)pyridin-3-yl]-2-hydroxyethyl}-2-(4-methyl-5-oxo-2,5-dihydrofuran-3-yl)-1-oxo-2-aza-8-azoniaspiro[4.5]decane; LCMS $[M + 1 - 28]^+$ = 430.1 |
| 27 | 10B | 68 | 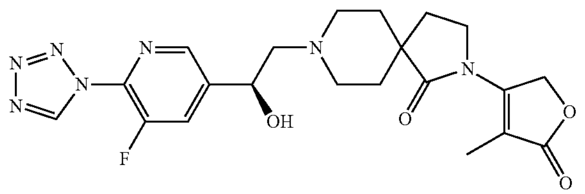 8-{(2S)-2-[5-fluoro-6-(1H-tetrazol-1-yl)pyridin-3-yl]-2-hydroxyethyl}-2-(4-methyl-5-oxo-2,5-dihydrofuran-3-yl)-1-oxo-2-aza-8-azoniaspiro[4.5]decane; LCMS $[M + 1 - 28]^+$ = 430.2 |
| 28 | 11A | 68 | 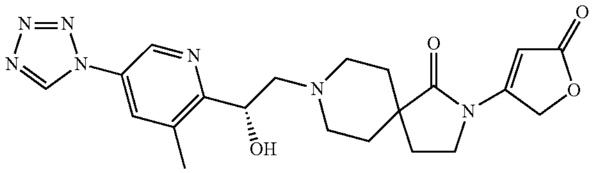 8-{(2S)-2-hydroxy-2-[3-methyl-5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+$ = 426.2 |
| 29 | 11B | 68 | 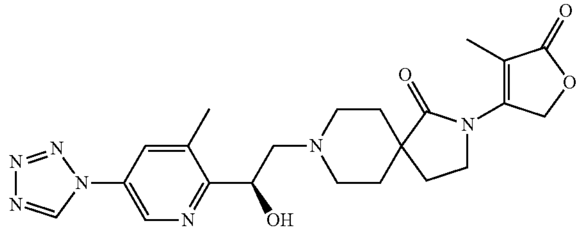 8-{(2R)-2-hydroxy-2-[3-methyl-5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+$ = 426.2 |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 30 | 12A | 68 | 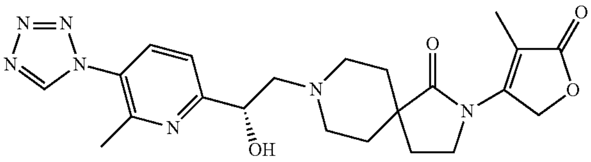 8-{(2S)-2-hydroxy-2-[6-methyl-5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 426.1$ |
| 31 | 12B | 68 | 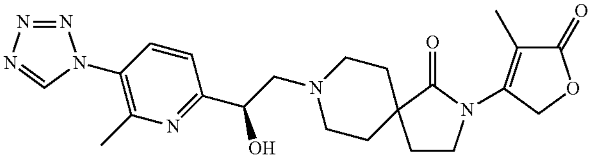 8-{(2R)-2-hydroxy-2-[6-methyl-5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 426.1$ |
| 32 | 6A | 68 | 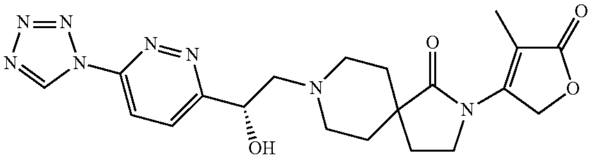 8-{(2S)-2-hydroxy-2-[6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 413.1$ |
| 33 | 6B | 68 | 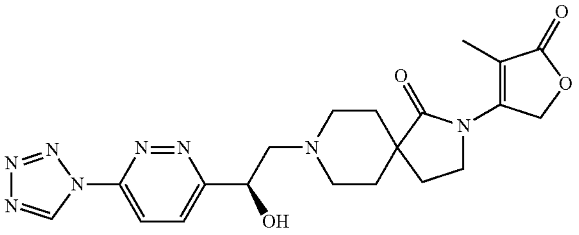 8-{(2R)-2-hydroxy-2-[6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 413.1$ |
| 34 | 8A | 68 | 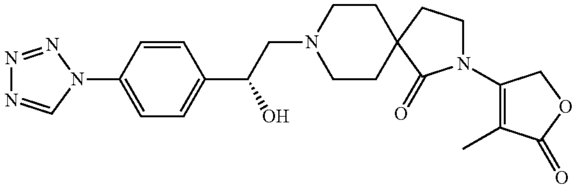 8-{(2R)-2-hydroxy-2-[4-(1H-tetrazol-1-yl)phenyl]ethyl}-2-(4-methyl-5-oxo-2,5-dihydrofuran-3-yl)-1-oxo-2-aza-8-azoniaspiro[4.5]decane; LCMS$[M + 1]^+ = 439.1$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 35 | 8B | 68 | 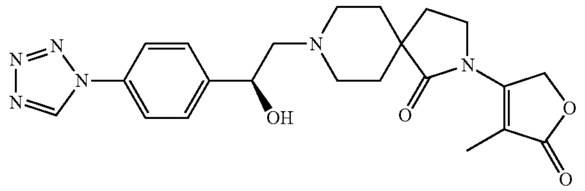 [SMILES: CC1=C(N2CCC3(CCN(C[C@@H](O)c4ccc(-n5cnnn5)cc4)CC3)C2=O)COC1=O] 8-{(2S)-2-hydroxy-2-[4-(1H-tetrazol-1-yl)phenyl]ethyl}-2-(4-methyl-5-oxo-2,5-dihydrofuran-3-yl)-1-oxo-2-aza-8-azoniaspiro[4.5]decane; LCMS $[M + 1]^+ = 439.1$ |
| 36 | 32A | 68 | 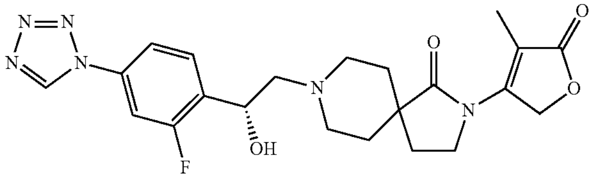 8-{(2R)-2-[2-fluoro-4-(1H-tetrazol-1-yl)phenyl]-2-hydroxyethyl}-2-(4-methyl-5-oxo-2,5-dihydrofuran-3-yl)-1-oxo-2-aza-8-azoniaspiro[4.5]decane; LCMS $[M + 1 - 28]^+ = 415.1$ |
| 37 | 32B | 68 | 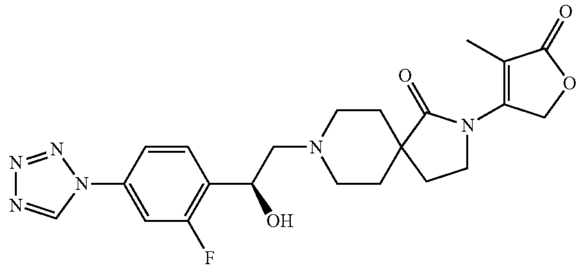 8-{(2S)-2-[2-fluoro-4-(1H-tetrazol-1-yl)phenyl]-2-hydroxyethyl}-2-(4-methyl-5-oxo-2,5-dihydrofuran-3-yl)-1-oxo-2-aza-8-azoniaspiro[4.5]decane; LCMS $[M + 1 - 28]^+ = 415.1$ |
| 38 | 14A | 68 | 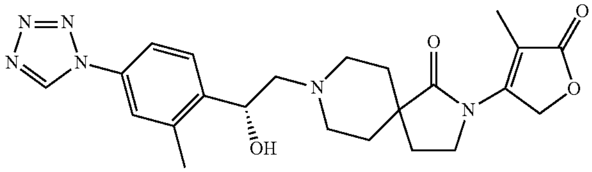 [SMILES: CC1=C(N2CCC3(CCN(C[C@H](O)c4ccc(-n5cnnn5)cc4C)CC3)C2=O)COC1=O] 8-{(2R)-2-hydroxy-2-[2-methyl-4-(1H-tetrazol-1-yl)phenyl]ethyl}-2-(4-methyl-5-oxo-2,5-dihydrofuran-3-yl)-1-oxo-2-aza-8-azoniaspiro[4.5]decane; LCMS $[M + 1]^+ = 453.2$ |
| 39 | 14B | 68 | 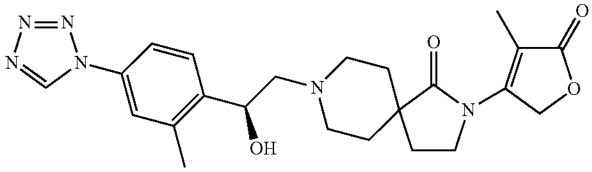 [SMILES: CC1=C(N2CCC3(CCN(C[C@@H](O)c4ccc(-n5cnnn5)cc4C)CC3)C2=O)COC1=O] 8-{(2S)-2-hydroxy-2-[2-methyl-4-(1H-tetrazol-1-yl)phenyl]ethyl}-2-(4-methyl-5-oxo-2,5-dihydrofuran-3-yl)-1-oxo-2-aza-8-azoniaspiro[4.5]decane; LCMS $[M + 1]^+ = 453.2$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 40 | 9A | 68 | 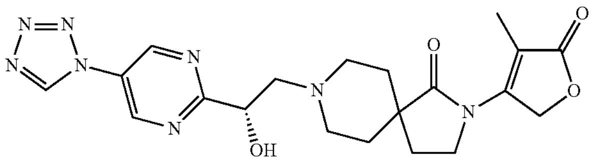 8-{(2S)-2-hydroxy-2-[5-(1H-tetrazol-1-yl)pyrimidin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 413.1$ |
| 41 | 9B | 68 | 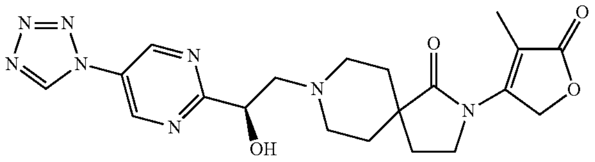 8-{(2R)-2-hydroxy-2-[5-(1H-tetrazol-1-yl)pyrimidin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 413.1$ |
| 42 | 5B | 71 | 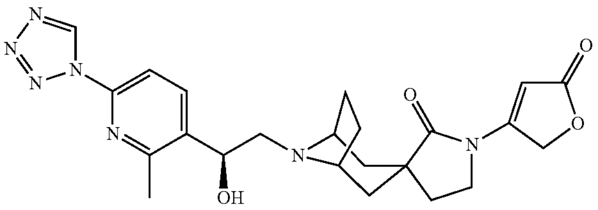 [SMILES: Cc1nc(-n2cnnn2)ccc1[C@H](O)CN1C2CCC1CC1(CCN(C3=CC(=O)OC3)C1=O)C2] (1R,5R)-8-{(2S)-2-hydroxy-2-[2-methyl-6-(1H-tetrazol-1-yl)pyridin-3-yl]ethyl}-2'-oxo-1'-(5-oxo-2,5-dihydrofuran-3-yl)spiro[8-azoniabicyclo[3.2.1]octane-3,3'-pyrrolidine]; LCMS $[M + 1]^+ = 466.1$ |
| 43 | 5A | 71 | 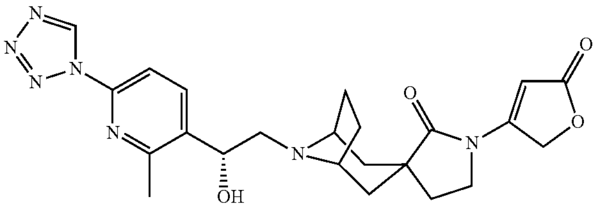 [SMILES: Cc1nc(-n2cnnn2)ccc1[C@@H](O)CN1C2CCC1CC1(CCN(C3=CC(=O)OC3)C1=O)C2] (1R,5R)-8-{(2R)-2-hydroxy-2-[2-methyl-6-(1H-tetrazol-1-yl)pyridin-3-yl]ethyl}-2'-oxo-1'-(5-oxo-2,5-dihydrofuran-3-yl)spiro[8-azoniabicyclo[3.2.1]octane-3,3'-pyrrolidine]; LCMS $[M + 1]^+ = 466.1$ |
| 44 | 6A | 71 | 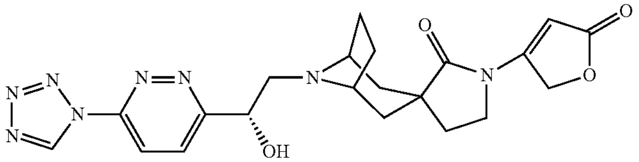 [SMILES: O=C1C=C(N2CCC3(CC4CCC(C3)N4C[C@H](O)c3ccc(-n4cnnn4)nn3)C2=O)CO1] (1R,5R)-8-{(2S)-2-hydroxy-2-[6-(1H-tetrazol-1-yl)pyridazin-3-yl]ethyl}-2'-oxo-1'-(5-oxo-2,5-dihydrofuran-3-yl)spiro[8-azoniabicyclo[3.2.1]octane-3,3'-pyrrolidine]; LCMS $[M + 1 - 28]^+ = 425.15$ |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 45 | 7A | 70 | 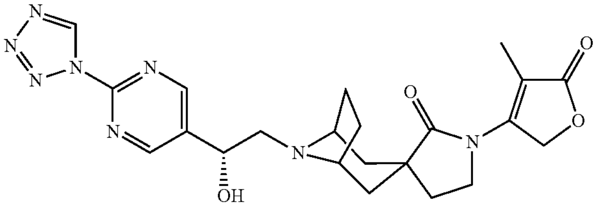 (1R,5R)-8-{(2R)-2-hydroxy-2-[2-(1H-tetrazol-1-yl)pyrimidin-5-yl]ethyl}-1'-(4-methyl-5-oxo-2,5-dihydrofuran-3-yl)-2'-oxospiro[8-azoniabicyclo[3.2.1]octane-3,3'-pyrrolidine]; LCMS $[M + 1]^+ = 439.1$ |
| 46 | 4B | 70 | 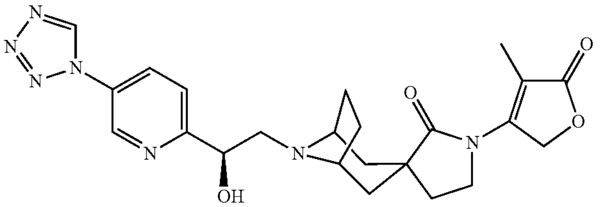 (1R,5R)-8-{(2R)-2-hydroxy-2-[5-(1H-tetrazol-1-yl)pyridin-2-yl]ethyl}-1'-(4-methyl-5-oxo-2,5-dihydrofuran-3-yl)-2'-oxospiro[8-azoniabicyclo[3.2.1]octane-3,3'-pyrrolidine]; LCMS $[M + 1]^+ = 438.1$ |
| 47 | 4A | 70 | 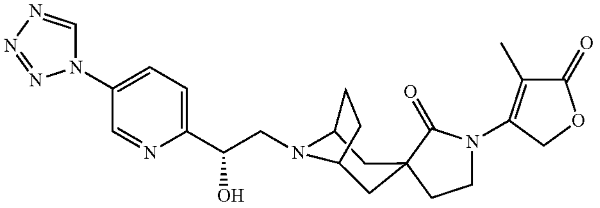 (1R,5R)-8-{(2S)-2-hydroxy-2-[5-(1H-tetrazol-1-yl)pyridin-2-yl]ethyl}-1'-(4-methyl-5-oxo-2,5-dihydrofuran-3-yl)-2'-oxospiro[8-azoniabicyclo[3.2.1]octane-3,3'-pyrrolidine]; LCMS $[M + 1 - 28]^+ = 438.1$ |
| 48 | 2A | 70 | 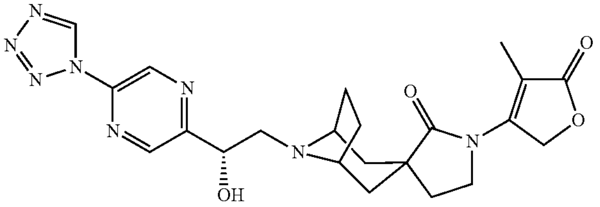 (1R,5R)-8-{(2S)-2-hydroxy-2-[5-(1H-tetrazol-1-yl)pyrazin-2-yl]ethyl}-1'-(4-methyl-5-oxo-2,5-dihydrofuran-3-yl)-2'-oxospiro[8-azoniabicyclo[3.2.1]octane-3,3'-pyrrolidine]; LCMS $[M + 1 - 28]^+ = 439.0$ |
| 49 | 2B | 70 | 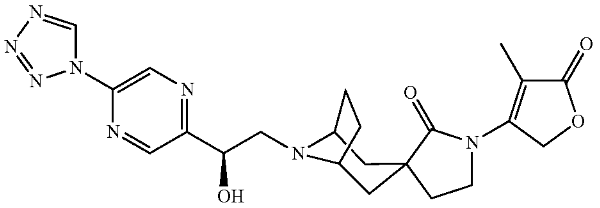 (1R,5R)-8-{(2R)-2-hydroxy-2-[5-(1H-tetrazol-1-yl)pyrazin-2-yl]ethyl}-1'-(4-methyl-5-oxo-2,5-dihydrofuran-3-yl)-2'-oxospiro[8-azoniabicyclo[3.2.1]octane-3,3'-pyrrolidine]; LCMS $[M + 1 - 28]^+ = 439.0$ |

TABLE 8-continued

| EXAMPLE | Epoxide Intermediate | Amine Intermediate | Structure, name and characterization |
|---|---|---|---|
| | | | Compounds prepared following a similar procedure as for EXAMPLE 1 |
| 50 | 17A | 70 | 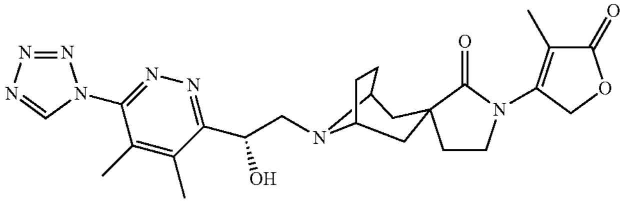 [SMILES: CC1=C(N2CCC3(CC4CCC(C3)N4C[C@H](O)c3nnc(-n4cnnn4)c(C)c3C)C2=O)COC1=O] (1R,5R)-8-{(2S)-2-[4,5-dimethyl-6-(1H-tetrazol-1-yl)pyridazin-3-yl]-2-hydroxyethyl}-1'-(4-methyl-5-oxo-2,5-dihydrofuran-3-yl)-2'-oxospiro[8-azoniabicyclo[3.2.1]octane-3,3'-pyrrolidine]; LCMS $[M + 1]^+ = 495.1$ |
| 51 | 17B | 70 | 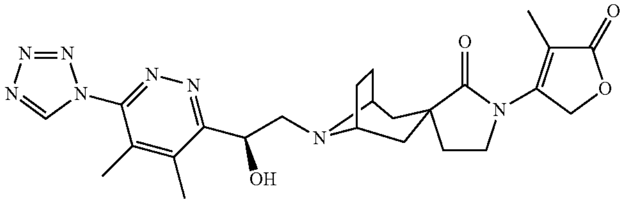 (1R,5R)-8-{(2R)-2-[4,5-dimethyl-6-(1H-tetrazol-1-yl)pyridazin-3-yl]-2-hydroxyethyl}-1'-(4-methyl-5-oxo-2,5-dihydrofuran-3-yl)-2'-oxospiro[8-azoniabicyclo[3.2.1]octane-3,3'-pyrrolidine]; LCMS $[M + 1 - 28]^+ = 467.1$ |
| 52 | 6A | 70 | 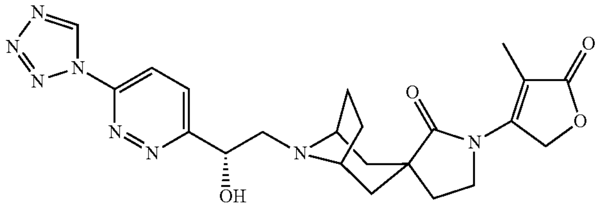 (1R,5R)-8-{(2S)-2-hydroxy-2-[6-(1H-tetrazol-1-yl)pyridazin-3-yl]ethyl}-1'-(4-methyl-5-oxo-2,5-dihydrofuran-3-yl)-2'-oxospiro[8-azoniabicyclo[3.2.1]octane-3,3'-pyrrolidine]; LCMS $[M + 1 - 28]^+ = 439.1$ |
| 53 | 6B | 70 | 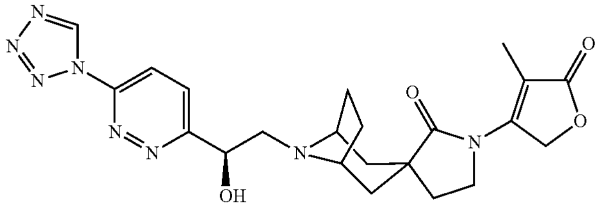 (1R,5R)-8-{(2R)-2-hydroxy-2-[6-(1H-tetrazol-1-yl)pyridazin-3-yl]ethyl}-1'-(4-methyl-5-oxo-2,5-dihydrofuran-3-yl)-2'-oxospiro[8-azoniabicyclo[3.2.1]octane-3,3'-pyrrolidine]; LCMS $[M + 1 - 28]^+ = 439.1$ |
| 54 | 20B | 70 | 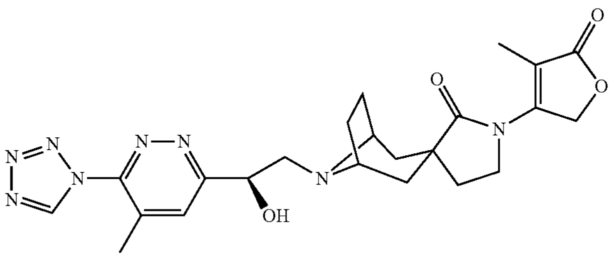 (1R,5R)-8-{(2R)-2-hydroxy-2-[5-methyl-6-(1H-tetrazol-1-yl)pyridazin-3-yl]ethyl}-1'-(4-methyl-5-oxo-2,5-dihydrofuran-3-yl)-2'-oxospiro[8-azoniabicyclo[3.2.1]octane-3,3'-pyrrolidine]; LCMS $[M + 1 - 28]^+ = 453.1$ |

TABLE 8-continued

| EXAMPLE | Epoxide Intermediate | Amine Intermediate | Structure, name and characterization |
|---|---|---|---|
| Compounds prepared following a similar procedure as for EXAMPLE 1 | | | |
| 55 | 20 | 70 | 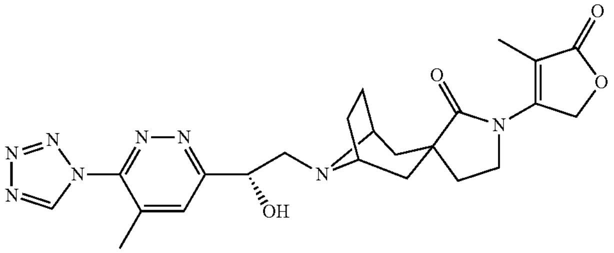 (1R,5R)-8-{(2S)-2-hydroxy-2-[5-methyl-6-(1H-tetrazol-1-yl)pyridazin-3-yl]ethyl}-1'-(4-methyl-5-oxo-2,5-dihydrofuran-3-yl)-2'-oxospiro[8-azoniabicyclo[3.2.1]octane-3,3'-pyrrolidine]; LCMS $[M + 1 - 28]^+ = 453.1$ |
| 56, 57 | 5A | 73 rac. | 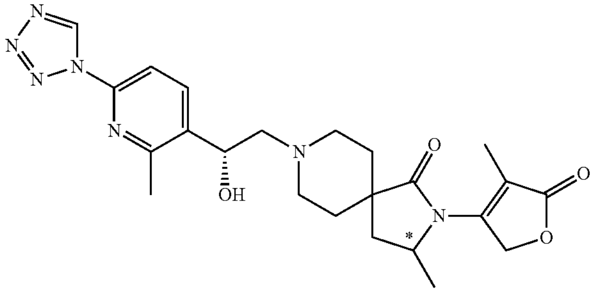 8-{(2R)-2-hydroxy-2-[2-methyl-6-(1H-tetrazol-1-yl)pyridin-3-yl]ethyl}-3-methyl-2-(4-methyl-5-oxo-2,5-dihydrofuran-3-yl)-1-oxo-2-aza-8-azoniaspiro[4.5]decane; LCMS $[M + 1 - 28]^+ = 440.3$ for each enantiomer. The racemic mixture was separated by chiral separation: AS-H (2 × 15 cm), 30% methanol(DEA)/$CO_2$, 100 bar, 60 ml/min, 220 nm |
| 58, 59 | 5B 5B | 73 rac. | 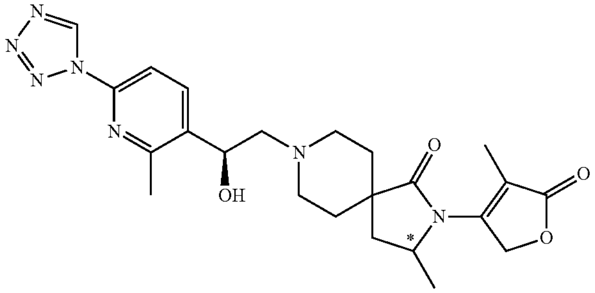 A "*" added 8-{(2S)-2-hydroxy-2-[2-methyl-6-(1H-tetrazol-1-yl)pyridin-3-yl]ethyl}-3-methyl-2-(4-methyl-5-oxo-2,5-dihydrofuran-3-yl)-1-oxo-2-aza-8-azoniaspiro[4.5]decane (enantiomer A); 8-{(2S)-2-hydroxy-2-[2-methyl-6-(1H-tetrazol-1-yl)pyridin-3-yl]ethyl}-3-methyl-2-(4-methyl-5-oxo-2,5-dihydrofuran-3-yl)-1-oxo-2-aza-8-azoniaspiro[4.5]decane (enantiomer B); LCMS $[M + 1 - 28]^+ = 440.3$ for each enantiomer. The racemic mixture was separated by chiral separation: AS-H (2 × 15 cm), 25% methanol(DEA)/$CO_2$, 100 bar, 60 ml/min, 220 nm |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 60 | 5A | 105 | 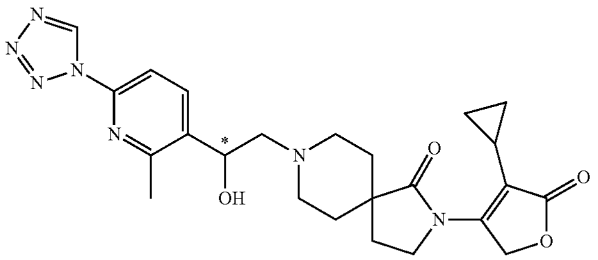<br>2-(4-cyclopropyl-5-oxo-2,5-dihydrofuran-3-yl)-8-{(2R)-2-hydroxy-2-[2-methyl-6-(1H-tetrazol-1-yl)pyridin-3-yl]ethyl}-1-oxo-2-aza-8-azoniaspiro[4.5]decane; LCMS $[M + 1 - 28]^+ = 452.3$ |
| 61 | 26A | 68 | 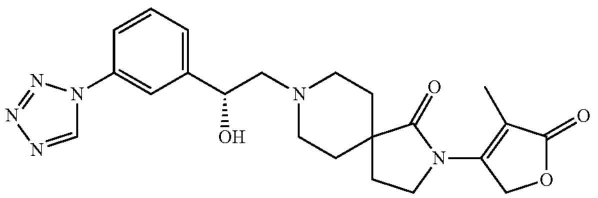 [SMILES: CC1=C(N2CCC3(CCN(C[C@H](O)c4cccc(-n5cnnn5)c4)CC3)C2=O)COC1=O]<br>8-{(2R)-2-hydroxy-2-[3-(1H-tetrazol-1-yl)phenyl]ethyl}-2-(4-methyl-5-oxo-2,5-dihydrofuran-3-yl)-1-oxo-2-aza-8-azoniaspiro[4.5]decane; LCMS $[M + 1]^+ = 439.0$ |
| 62 | 26B | 58 | 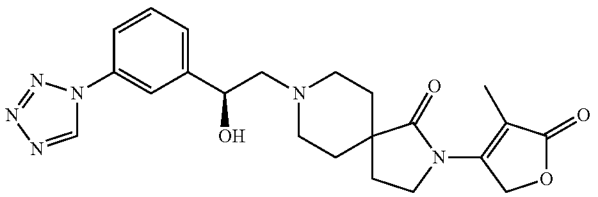 [SMILES: CC1=C(N2CCC3(CCN(C[C@@H](O)c4cccc(-n5cnnn5)c4)CC3)C2=O)COC1=O]<br>8-{(2S)-2-hydroxy-2-[3-(1H-tetrazol-1-yl)phenyl]ethyl}-2-(4-methyl-5-oxo-2,5-dihydrofuran-3-yl)-1-oxo-2-aza-8-azoniaspiro[4.5]decane; LCMS $[M + 1]^+ = 439.0$ |
| 63<br>64 | 1B<br>1B | 73A<br>73B | 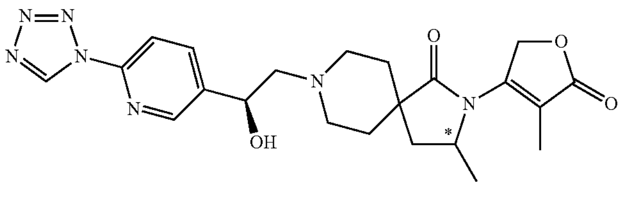<br>8-((S)-2-(6-(1H-tetrazol-1-yl)pyridin-3-yl)-2-hydroxyethyl)-3-methyl-2-(4-methyl-5-oxo-2,5-dihydrofuran-3-yl)-2,8-diazaspiro[4.5]decan-1-one (from fast enantiomer 73A);<br>8-((S)-2-(6-(1H-tetrazol-1-yl)pyridin-3-yl)-2-hydroxyethyl)-3-methyl-2-(4-methyl-5-oxo-2,5-dihydrofuran-3-yl)-2,8-diazaspiro[4.5]decan-1-one (from slower enantiomer 73B);<br>LCMS $[M + 1 - 28]^+ = 426.3$ for each enantiomer |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 65<br>66 | 1A<br>1A | 73A<br>73B | 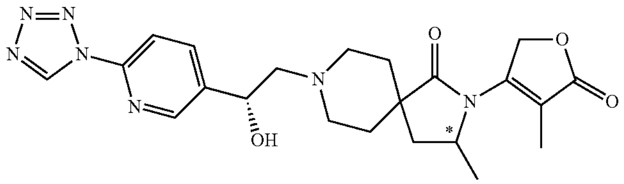<br>8-((R)-2-(6-(1H-tetrazol-1-yl)pyridin-3-yl)-2-hydroxyethyl)-3-methyl-2-(4-methyl-5-oxo-2,5-dihydrofuran-3-yl)-2,8-diazaspiro[4.5]decan-1-one (from fast enantiomer 73A);<br>8-((R)-2-(6-(1H-tetrazol-1-yl)pyridin-3-yl)-2-hydroxyethyl)-3-methyl-2-(4-methyl-5-oxo-2,5-dihydrofuran-3-yl)-2,8-diazaspiro[4.5]decan-1-one (from slower enantiomer 73B);<br>LCMS $[M + 1 - 28]^+$ = 426.2 for each enantiomer |
| 67 | 2A | 73A | 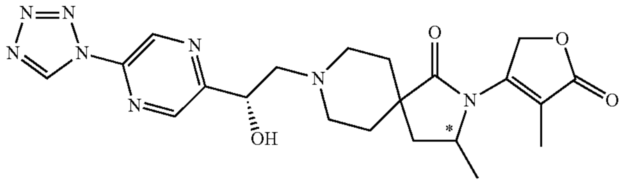<br>8-((S)-2-(5-(1H-tetrazol-1-yl)pyrazin-2-yl)-2-hydroxyethyl)-3-methyl-2-(4-methyl-5-oxo-2,5-dihydrofuran-3-yl)-2,8-diazaspiro[4.5]decan-1-one (from fast enantiomer 73A); LCMS $[M + 1 - 28]^+$ = 427.3 |
| 68 | 2B | 73A | 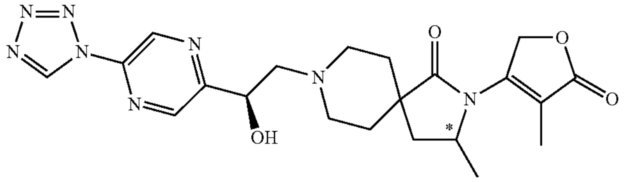<br>8-((R)-2-(5-(1H-tetrazol-1-yl)pyrazin-2-yl)-2-hydroxyethyl)-3-methyl-2-(4-methyl-5-oxo-2,5-dihydrofuran-3-yl)-2,8-diazaspiro[4.5]decan-1-one (from fast enantiomer 73A);<br>LCMS $[M + 1 - 28]^+$ = 427.3 |
| 69 | 17A | 68 | 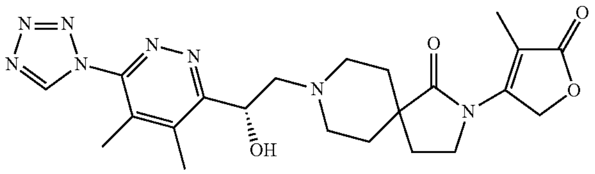<br>8-{(2S)-2-[4,5-dimethyl-6-(1H-tetrazol-1-yl)pyridazin-3-yl]-2-hydroxyethyl}-2-(4-methyl-5-oxo-2,5-dihydrofuran-3-yl)-1-oxo-2-aza-8-azoniaspiro[4.5]decane; LCMS $[M + 1 - 28]^+$ = 441.14 |
| 70 | 17B | 68 | 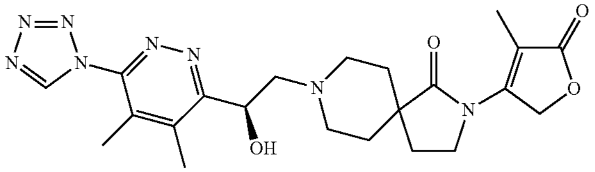<br>8-{(2R)-2-[4,5-dimethyl-6-(1H-tetrazol-1-yl)pyridazin-3-yl]-2-hydroxyethyl}-2-(4-methyl-5-oxo-2,5-dihydrofuran-3-yl)-1-oxo-2-aza-8-azoniaspiro[4.5]decane; LCMS $[M + 1 - 28]^+$ = 441.16 |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 71 | 25B | 68 | 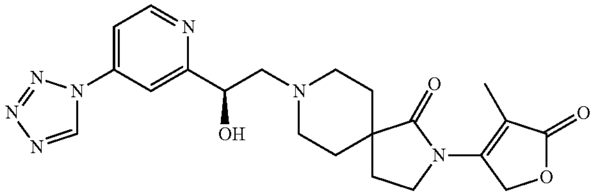 [SMILES: CC1=C(N2CCC3(CCN(C[C@@H](O)c4cc(-n5cnnn5)ccn4)CC3)C2=O)COC1=O] 8-{(2R)-2-hydroxy-2-[4-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane; LCMS $[M + 1]^+ = 440.2$ |
| 72 | 25A | 68 | 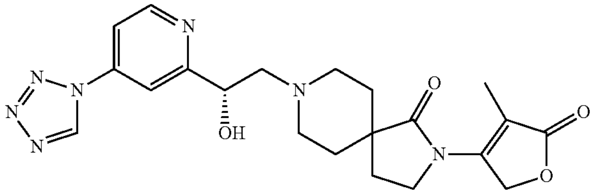 [SMILES: CC1=C(N2CCC3(CCN(C[C@H](O)c4cc(-n5cnnn5)ccn4)CC3)C2=O)COC1=O] 8-{(2S)-2-hydroxy-2-[4-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane; LCMS $[M + 1]^+ = 440.2$ |
| 73 | 27A | 68 | 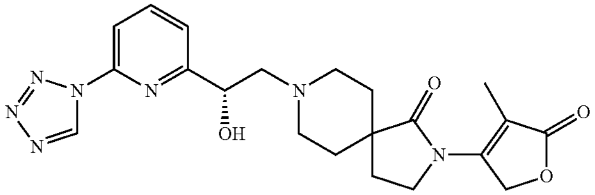 [SMILES: CC1=C(N2CCC3(CCN(C[C@H](O)c4cccc(-n5cnnn5)n4)CC3)C2=O)COC1=O] 8-{(2S)-2-hydroxy-2-[6-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane; LCMS $[M + 1]^+ = 440.1$ |
| 74 | 27B | 68 | 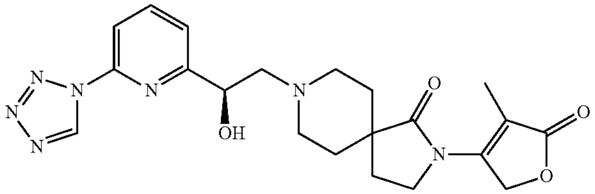 [SMILES: CC1=C(N2CCC3(CCN(C[C@@H](O)c4cccc(-n5cnnn5)n4)CC3)C2=O)COC1=O] 8-{(2R)-2-hydroxy-2-[6-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane; LCMS $[M + 1]^+ = 440.2$ |
| 75 | 28A | 68 | 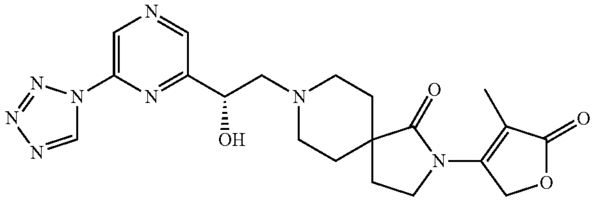 [SMILES: CC1=C(N2CCC3(CCN(C[C@H](O)c4cncc(-n5cnnn5)n4)CC3)C2=O)COC1=O] 8-{(2S)-2-hydroxy-2-[6-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane; LCMS $[M + 1]^+ = 441.1$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 76 | 19A | 68 | 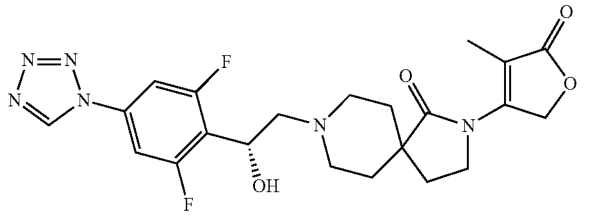 [SMILES: CC1=C(N2CCC3(CCN(C[C@H](O)c4c(F)cc(-n5cnnn5)cc4F)CC3)C2=O)COC1=O] 8-{(2R)-2-[2,6-difluoro-4-(1H-tetrazol-1-yl)phenyl]-2-hydroxyethyl}-2-(4-methyl-5-oxo-2,5-dihydrofuran-3-yl)-1-oxo-2-aza-8-azoniaspiro[4.5]decane; LCMS $[M + 1 - 28]^+ = 475.2$ |
| 77 | 2A | 74A | 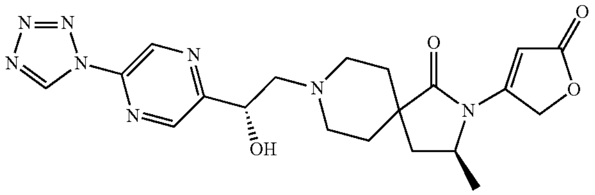 [SMILES: C[C@H]1CC2(CCN(C[C@H](O)c3cnc(-n4cnnn4)cn3)CC2)C(=O)N1C1=CC(=O)OC1] (3S)-8-{(2S)-2-hydroxy-2-[5-(1H-tetrazol-1-yl)pyrazin-2-yl]ethyl}-3-methyl-1-oxo-2-(5-oxo-2,5-dihydrofuran-3-yl)-2-aza-8-azoniaspiro[4.5]decane; LCMS $[M + 1 - 28]^+ = 441.3$ |
| 78 | 2B | 74A | 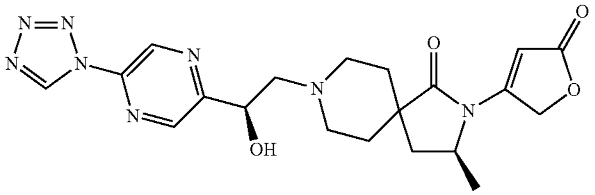 (3S)-8-{(2R)-2-hydroxy-2-[5-(1H-tetrazol-1-yl)pyrazin-2-yl]ethyl}-3-methyl-1-oxo-2-(5-oxo-2,5-dihydrofuran-3-yl)-2-aza-8-azoniaspiro[4.5]decane; LCMS $[M + 1]^+ = 441.3$ |
| 79 | 2A | 74B | 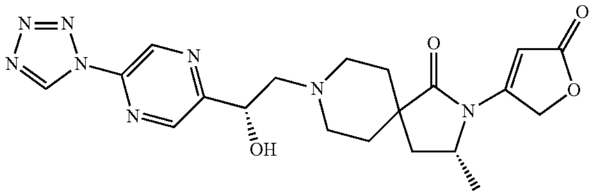 (3R)-8-{(2S)-2-hydroxy-2-[5-(1H-tetrazol-1-yl)pyrazin-2-yl]ethyl}-3-methyl-1-oxo-2-(5-oxo-2,5-dihydrofuran-3-yl)-2-aza-8-azoniaspiro[4.5]decane; LCMS $[M + 1 - 28]^+ = 413.2$ |
| 80 | 2B | 74B | 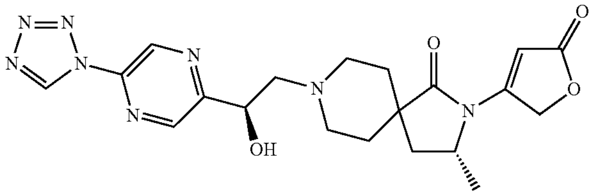 (3R)-8-{(2R)-2-hydroxy-2-[5-(1H-tetrazol-1-yl)pyrazin-2-yl]ethyl}-3-methyl-1-oxo-2-(5-oxo-2,5-dihydrofuran-3-yl)-2-aza-8-azoniaspiro[4.5]decane; LCMS $[M + 1 - 28]^+ = 413.1$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 81 | 1A | 74A | 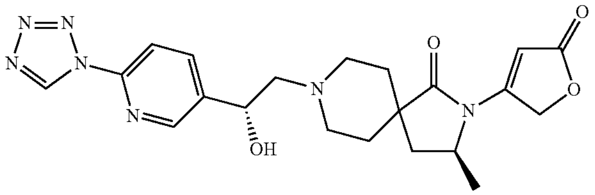 [SMILES: C[C@H]1CC2(CCN(C[C@H](O)c3ccc(-n4cnnn4)nc3)CC2)C(=O)N1C1=CC(=O)OC1] (3S)-8-{(2R)-2-hydroxy-2-[6-(1H-tetrazol-1-yl)pyridin-3-yl]ethyl}-3-methyl-1-oxo-2-(5-oxo-2,5-dihydrofuran-3-yl)-2-aza-8-azoniaspiro[4.5]decane; LCMS $[M + 23]^+ = 462.1$ |
| 82 | 1B | 74A | 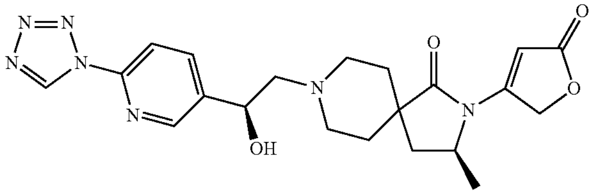 [SMILES: C[C@H]1CC2(CCN(C[C@@H](O)c3ccc(-n4cnnn4)nc3)CC2)C(=O)N1C1=CC(=O)OC1] (3S)-8-{(2S)-2-hydroxy-2-[6-(1H-tetrazol-1-yl)pyridin-3-yl]ethyl}-3-methyl-1-oxo-2-(5-oxo-2,5-dihydrofuran-3-yl)-2-aza-8-azoniaspiro[4.5]decane; LCMS $[M + 1]^+ = 439.9$ |
| 83 | 1A | 74B | 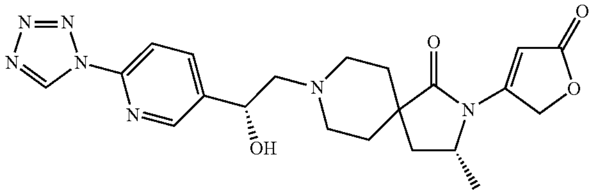 [SMILES: C[C@@H]1CC2(CCN(C[C@H](O)c3ccc(-n4cnnn4)nc3)CC2)C(=O)N1C1=CC(=O)OC1] (3R)-8-{(2R)-2-hydroxy-2-[6-(1H-tetrazol-1-yl)pyridin-3-yl]ethyl}-3-methyl-1-oxo-2-(5-oxo-2,5-dihydrofuran-3-yl)-2-aza-8-azoniaspiro[4.5]decane; LCMS $[M + 1]^+ = 440.1$ |
| 84 | 1 B | 74B | 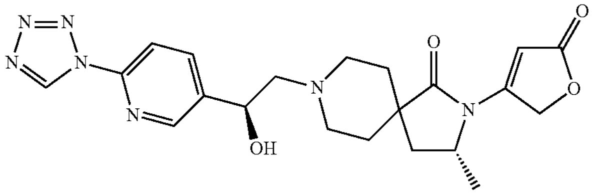 [SMILES: C[C@@H]1CC2(CCN(C[C@@H](O)c3ccc(-n4cnnn4)nc3)CC2)C(=O)N1C1=CC(=O)OC1] (3R)-8-{(2S)-2-hydroxy-2-[6-(1H-tetrazol-1-yl)pyridin-3-yl]ethyl}-3-methyl-1-oxo-2-(5-oxo-2,5-dihydrofuran-3-yl)-2-aza-8-azoniaspiro[4.5]decane; LCMS $[M + 1]^+ = 440.1$ |
| 85 | 21A | 68 | 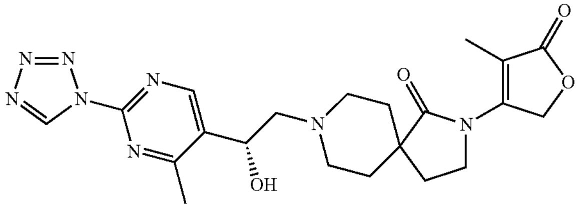 [SMILES: CC1=C(N2CCC3(CCN(C[C@H](O)c4cnc(-n5cnnn5)nc4C)CC3)C2=O)COC1=O] 8-{(2R)-2-hydroxy-2-[4-methyl-2-(1H-tetrazol-1-yl)pyrimidin-5-yl]ethyl}-2-(4-methyl-5-oxo-2,5-dihydrofuran-3-yl)-1-oxo-2-aza-8-azoniaspiro[4.5]decane; LCMS $[M + 1]^+ = 455.2$ |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 86 | 21B | 68 | 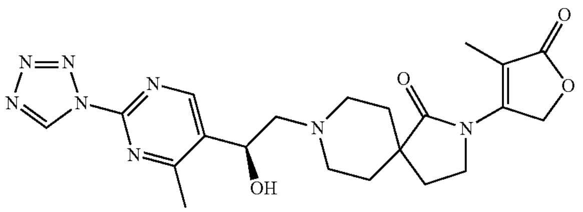 [SMILES: CC1=C(N2CCC3(CCN(C[C@@H](O)c4cnc(-n5cnnn5)nc4C)CC3)C2=O)COC1=O] 8-{(2S)-2-hydroxy-2-[4-methyl-2-(1H-tetrazol-1-yl)pyrimidin-5-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 455.2$ |
| 87 | 3A | 68 | 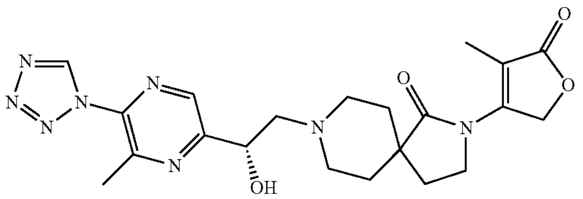 [SMILES: CC1=C(N2CCC3(CCN(C[C@H](O)c4cnc(-n5cnnn5)c(C)n4)CC3)C2=O)COC1=O] 8-{(2S)-2-hydroxy-2-[6-methyl-5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 455.1$ |
| 88 | 3B | 68 | 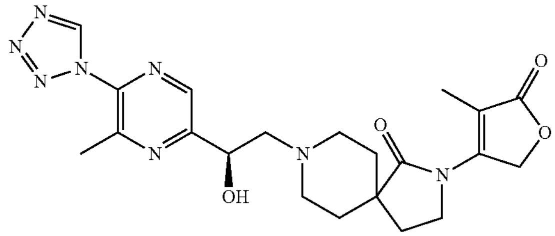 [SMILES: CC1=C(N2CCC3(CCN(C[C@@H](O)c4cnc(-n5cnnn5)c(C)n4)CC3)C2=O)COC1=O] 8-{(2R)-2-hydroxy-2-[6-methyl-5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 455.2$ |
| 89<br>91 | 2A<br>2A | 84A<br>84B | 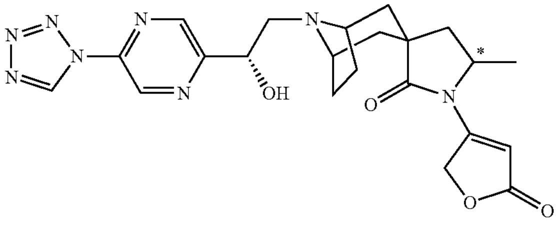 (1R,5R)-8-{(2S)-2-hydroxy-2-[5-(1H-tetrazol-1-yl)pyrazin-2-yl]ethyl}-5'-methyl-2'-oxo-1'-(5-oxo-2,5-dihydrofuran-3-yl)spiro[8-azoniabicyclo[3.2.1]octane-3,3'-pyrrolidine](from fast enantiomer 84A); (1R,5R)-8-{(2S)-2-hydroxy-2-[5-(1H-tetrazol-1-yl)pyrazin-2-yl]ethyl}-5'-methyl-2'-oxo-1'-(5-oxo-2,5-dihydrofuran-3-yl)spiro[8-azoniabicyclo[3.2.1]octane-3,3'-pyrrolidine](from slower enantiomer 84B); LCMS $[M + 1 - 28]^+ = 439.1$ for each enantiomer |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 90<br>92 | 2B<br>2B | 84A<br>84B | 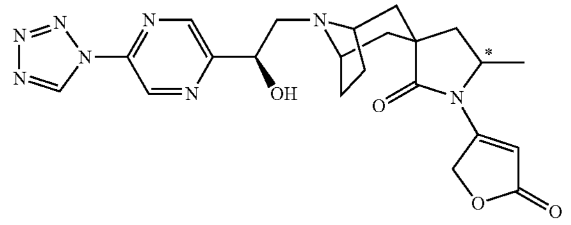<br>(1R,5R)-8-{(2R)-2-hydroxy-2-[5-(1H-tetrazol-1-yl)pyrazin-2-yl]ethyl}-5'-methyl-2'-oxo-1'-(5-oxo-2,5-dihydrofuran-3-yl)spiro[8-azoniabicyclo[3.2.1]octane-3,3'-pyrrolidine] (from fast enantiomer 84A); (1R,5R)-8-{(2R)-2-hydroxy-2-[5-(1H-tetrazol-1-yl)pyrazin-2-yl]ethyl}-5'-methyl-2'-oxo-1'-(5-oxo-2,5-dihydrofuran-3-yl)spiro[8-azoniabicyclo[3.2.1]octane-3,3'-pyrrolidine] (from slower enantiomer 84B); LCMS $[M + 1 - 28]^+ = 439.1$ for each enantiomer |
| 93 | 22A | 68 | 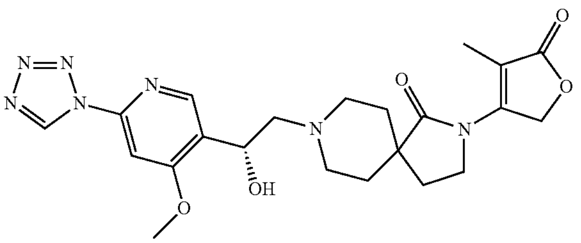 [SMILES: COc1cc(-n2cnnn2)ncc1[C@@H](O)CN1CCC2(CC1)CCN(C1=C(C)C(=O)OC1)C2=O]<br>8-{(2R)-2-hydroxy-2-[4-methoxy-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane; LCMS $[M + 1]^+ = 470.2$ |
| 94 | 22B | 68 | 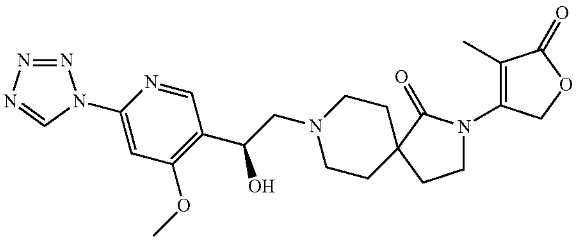 [SMILES: COc1cc(-n2cnnn2)ncc1[C@H](O)CN1CCC2(CC1)CCN(C1=C(C)C(=O)OC1)C2=O]<br>8-{(2S)-2-hydroxy-2-[4-methoxy-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane; LCMS $[M + 1]^+ = 470.2$ |
| 95 | 24A | 68 | 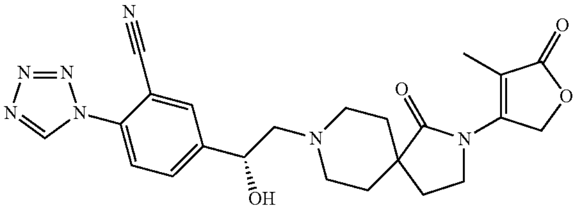 [SMILES: CC1=C(N2CCC3(CCN(C[C@H](O)c4ccc(-n5cnnn5)c(C#N)c4)CC3)C2=O)COC1=O]<br>8-{(2R)-2-[3-cyano-4-(1H-tetrazol-1-yl)phenyl]-2-hydroxyethyl}-2-(4-methyl-5-oxo-2,5-dihydrofuran-3-yl)-1-oxo-2-aza-8-azoniaspiro[4.5]decane; LCMS $[M + 1 - 28]^+ = 464$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 96 | 24B | 68 | 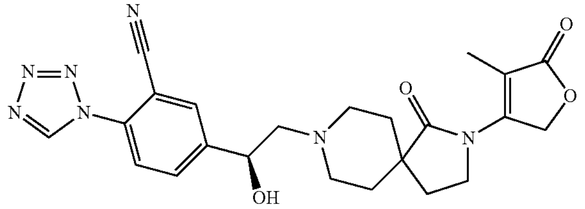 [SMILES: CC1=C(N2CCC3(CCN(C[C@@H](O)c4ccc(-n5cnnn5)c(C#N)c4)CC3)C2=O)COC1=O] 8-{(2S)-2-[3-cyano-4-(1H-tetrazol-1-yl)phenyl]-2-hydroxyethyl}-2-(4-methyl-5-oxo-2,5-dihydrofuran-3-yl)-1-oxo-2-aza-8-azoniaspiro[4.5]decane; LCMS $[M + 1 - 28]^+ = 464$ |
| 97 | 1A | 92 | 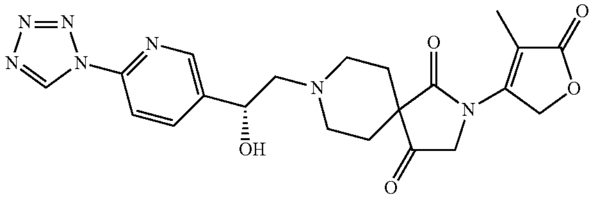 [SMILES: CC1=C(N2CC(=O)C3(CCN(C[C@H](O)c4ccc(-n5cnnn5)nc4)CC3)C2=O)COC1=O] 8-{(2R)-2-hydroxy-2-[6-(1H-tetrazol-1-yl)pyridin-3-yl]ethyl}-2-[4-methyl-5-oxo-2,5-dihydrofuran-3-yl)-1,4-dioxo-2-aza-8-azoniaspiro[4.5]decane; LCMS $[M + 1]^+ = 453.9$ |
| 98 | 23A | 68 | 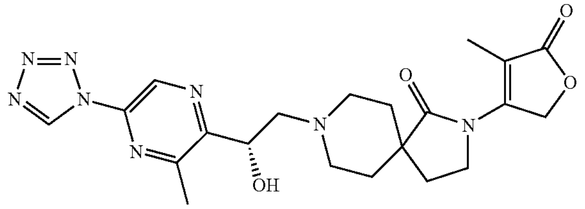 [SMILES: CC1=C(N2CCC3(CCN(C[C@H](O)c4ncc(-n5cnnn5)nc4C)CC3)C2=O)COC1=O] 8-{(2S)-2-hydroxy-2-[3-methyl-5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 455.2$ |
| 99 | 23B | 68 | 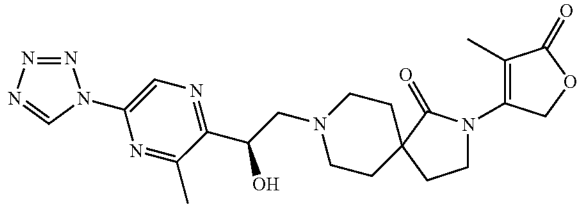 [SMILES: CC1=C(N2CCC3(CCN(C[C@@H](O)c4ncc(-n5cnnn5)nc4C)CC3)C2=O)COC1=O] 8-{(2R)-2-hydroxy-2-[3-methyl-5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 455.2$ |
| 100<br>102 | 1A<br>1A | 84A<br>84B | 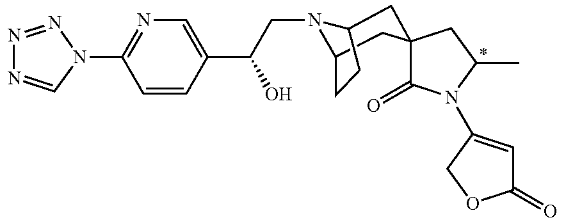 (1R,5R)-8-{(2R)-2-hydroxy-2-[6-(1H-tetrazol-1-yl)pyridin-3-yl]ethyl}-5'-methyl-2'-oxo-1'-(5-oxo-2,5-dihydrofuran-3-yl)spiro[8-azoniabicyclo[3.2.1]octane-3,3'-pyrrolidine] (from fast enantiomer 84A); LCMS $[M + 1 - 28]^+ = 438.1$; |

TABLE 8-continued

Compounds prepared following a similar procedure as for EXAMPLE 1

| EXAMPLE | Epoxide Intermediate | Amine Intermediate | Structure, name and characterization |
|---|---|---|---|
| | | | (1R,5R)-8-{(2R)-2-hydroxy-2-[6-(1H-tetrazol-1-yl)pyridin-3-yl]ethyl}-5'-methyl-2'-oxo-1'-(5-oxo-2,5-dihydrofuran-3-yl)spiro[8-azoniabicyclo[3.2.1]octane-3,3'-pyrrolidine](from slower enantiomer 84B); LCMS $[M + 1]^+ = 466.1$ |
| 101<br>103 | 1B<br>1B | 84A<br>84B | 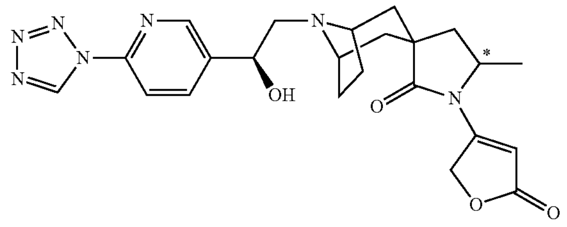 [SMILES: CC1CC2(CC3CCC(C2)N3C[C@@H](O)c2ccc(-n3cnnn3)nc2)C(=O)N1C1=CC(=O)OC1]<br>(1R,5R)-8-{(2S)-2-hydroxy-2-[6-(1H-tetrazol-1-yl)pyridin-3-yl]ethyl}-5'-methyl-2'-oxo-1'-(5-oxo-2,5-dihydrofuran-3-yl)spiro[8-azoniabicyclo[3.2.1]octane-3,3'-pyrrolidine] (from fast enantiomer 84A); LCMS $[M + 1 - 28]^+ = 438.1$; (1R,5R)-8-{(2S)-2-hydroxy-2-[6-(1H-tetrazol-1-yl)pyridin-3-yl]ethyl}-5'-methyl-2'-oxo-1'-(5-oxo-2,5-dihydrofuran-3-yl)spiro[8-azoniabicyclo[3.2.1]octane-3,3'-pyrrolidine] (from slower enantiomer 84B); LCMS $[M + 1]^+ = 466.1$ |
| 104<br>106 | 1A<br>1A | 87A<br>87B | 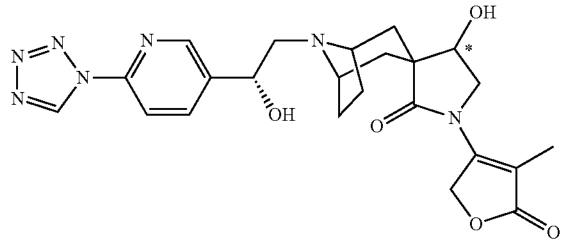 [SMILES: CC1=C(N2CC(O)C3(CC4CCC(C3)N4C[C@H](O)c3ccc(-n4cnnn4)nc3)C2=O)COC1=O]<br>(1R,5R)-4'-hydroxy-8-{(2R)-2-hydroxy-2-[6-(1H-tetrazol-1-yl)pyridin-3-yl]ethyl}-1'-(4-methyl-5-oxo-2,5-dihydrofuran-3-yl)-2'-oxospiro[8-azoniabicyclo[3.2.1]octane-3,3'-pyrrolidine] (from fast enantiomer 87A); (1R,,5R)-4'-hydroxy-8-{(2R)-2-hydroxy-2-[6-(1H-tetrazol-1-yl)pyridin-3-yl]ethyl}-1'-(4-methyl-5-oxo-2,5-dihydrofuran-3-yl)-2'-oxospiro[8-azoniabicyclo[3.2.1]octane-3,3'-pyrrolidine] (from slower enantiomer 87B); LCMS $[M + 1]^+ = 482.2$ for both enantiomers |
| 105<br>107 | 1B<br>1B | 87A<br>87B | 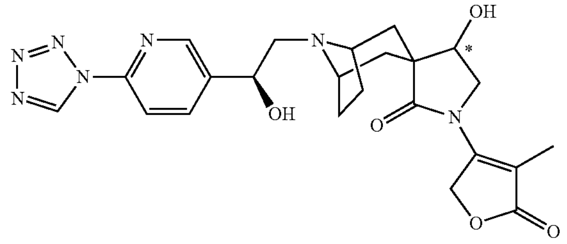 [SMILES: CC1=C(N2CC(O)C3(CC4CCC(C3)N4C[C@@H](O)c3ccc(-n4cnnn4)nc3)C2=O)COC1=O]<br>(1R,5R)-4'-hydroxy-8-{(2S)-2-hydroxy-2-[6-(1H-tetrazol-1-yl)pyridin-3-yl]ethyl}-1'-(4-methyl-5-oxo-2,5-dihydrofuran-3-yl)-2'-oxospiro[8-azoniabicyclo[3.2.1]octane-3,3'-pyrrolidine] (from fast enantiomer 87A); (1R,5R)-4'-hydroxy-8-{(2S)-2-hydroxy-2-[6-(1H-tetrazol-1-yl)pyridin-3-yl]ethyl}-1'-(4-methyl-5-oxo-2,5-dihydrofuran-3-yl)-2'-oxospiro[8-azoniabicyclo[3.2.1]octane-3,3'-pyrrolidine] (from slower enantiomer 87B); LCMS $[M + 1]^+ = 482.2$ for each enantiomer |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 108 | 1A | 94A | 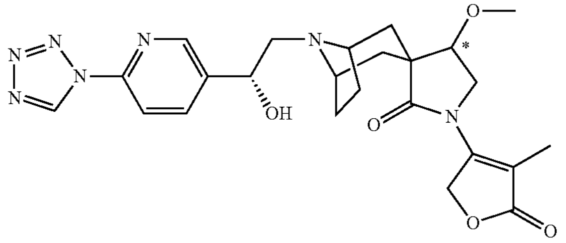 [SMILES: COC1CN(C2=C(C)C(=O)OC2)C(=O)C12CC1CCC(C2)N1C[C@H](O)c1ccc(-n2cnnn2)nc1] (1R,5R)-8-{(2R)-2-hydroxy-2-[6-(1H-tetrazol-1-yl)pyridin-3-yl]ethyl}-4'-methoxy-1'-(4-methyl-5-oxo-2,5-dihydrofuran-3-yl)-2'-oxospiro[8-azoniabicyclo[3.2.1]octane-3,3'-pyrrolidine] (from fast enantiomer 94A); LCMS $[M + 1]^+ = 496.1$ |
| 109 | 1B | 94A | 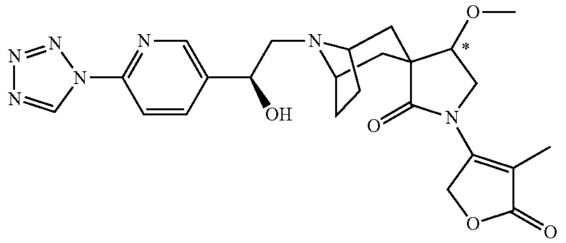 [SMILES: COC1CN(C2=C(C)C(=O)OC2)C(=O)C12CC1CCC(C2)N1C[C@@H](O)c1ccc(-n2cnnn2)nc1] (1R,5R)-8-{(2S)-2-hydroxy-2-[6-(1H-tetrazol-1-yl)pyridin-3-yl]ethyl}-4'-methoxy-1'-(4-methyl-5-oxo-2,5-dihydrofuran-3-yl)-2'-oxospiro[8-azoniabicyclo[3.2.1]octane-3,3'-pyrrolidine] (from fast enantiomer 94A); LCMS $[M + 1]^+ = 496.1$ |
| 110 | 1A | 86A | 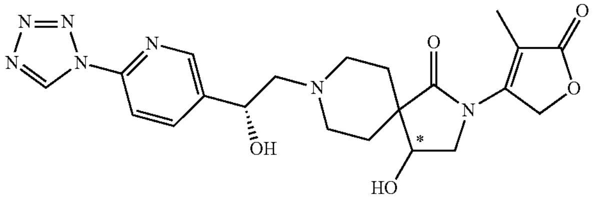 4-hydroxy-8-{(2R)-2-hydroxy-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane (from fast enantiomer 86A); LCMS $[M + 1 - 28]^+ = 428.3$ |
| 111 | 1A | 86B | 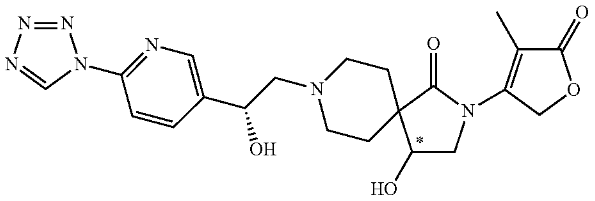 4-hydroxy-8-{(2R)-2-hydroxy-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane (from slower enantiomer 86B);; LCMS $[M + 1 - 28]^+ = 428.3$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 112 | 1A | 72 | 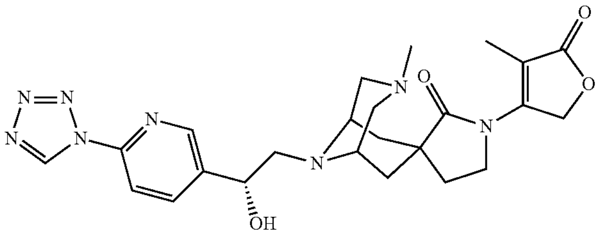 [SMILES: CC1=C(N2CCC3(CC4CN(C)CC(C3)N4C[C@H](O)c3ccc(-n4cnnn4)nc3)C2=O)COC1=O] (1R,5R,7R,9R)-9-{(2R)-2-hydroxy-2-[6-(1H-tetrazol-1-yl)pyridin-3-yl]ethyl}-7-methyl-1'-(4-methyl-5-oxo-2,5-dihydrofuran-3-yl)-2'-oxospiro[7,9-diazoniabicyclo[3.3.1]nonane-3,3'-pyrrolidine]; LCMS $[M + 1]^+ = 495.2$ |
| 113 | 7B | 73A | 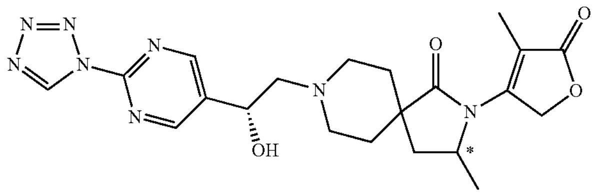 [SMILES: CC1=C(N2C(=O)C3(CCN(C[C@H](O)c4cnc(-n5cnnn5)nc4)CC3)CC2C)COC1=O] 8-{(2R)-2-hydroxy-2-[2-(1H-tetrazol-1-yl)pyrimidin-5-yl]ethyl}-3-methyl-2-(4-methyl-5-oxo-2,5-dihydrofuran-3-yl)-1-oxo-2-aza-8-azoniaspiro[4.5]decane (from fast enantiomer 73A); LCMS $[M + 1]^+ = 455.1$ |
| 114 | 1A | 93A | 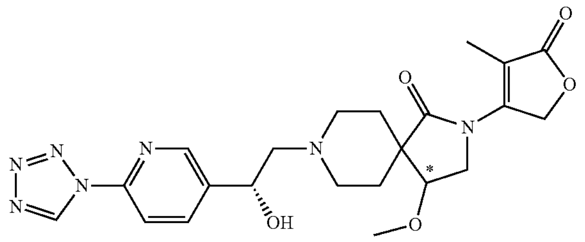 8-{(2R)-2-hydroxy-2-[6-(1H-tetrazol-1-yl)pyridin-3-yl]ethyl}-4-methoxy-2-(4-methyl-5-oxo-2,5-dihydrofuran-3-yl)-1-oxo-2-aza-8-azoniaspiro[4.5]decane (from fast enantiomer 93A);; LCMS $[M + 1 - 28]^+ = 442$ |
| 115 | 1A | 93B | 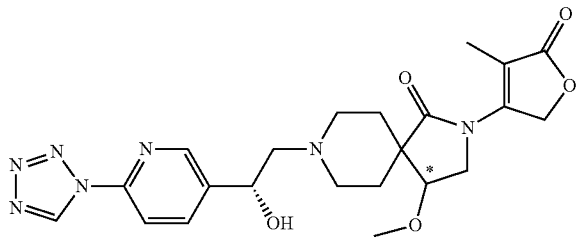 8-{(2R)-2-hydroxy-2-[6-(1H-tetrazol-1-yl)pyridin-3-yl]ethyl}-4-methoxy-2-(4-methyl-5-oxo-2,5-dihydrofuran-3-yl)-1-oxo-2-aza-8-azoniaspiro[4.5]decane (from slower enantiomer 93B);; LCMS $[M + 1 - 28]^+ = 442$ |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 116 | 1A | 83 | 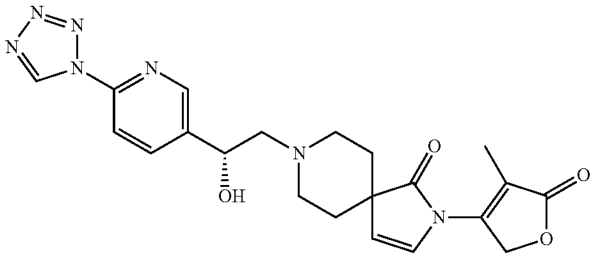<br>8-{(2R)-2-hydroxy-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]dec-3-ene; LCMS $[M + 1 - 28]^+ = 410$ |
| 117 | 5A | 90 (trans, race-mic) | 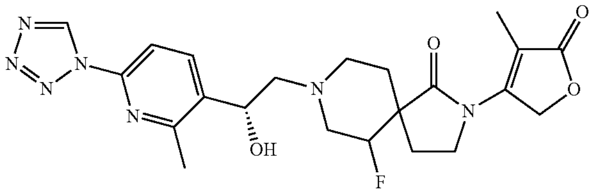<br>6-fluoro-8-{(2R)-2-hydroxy-2-[2-methyl-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane (trans, two isomers); LCMS $[M + 1 - 28]^+ = 444$ |
| 118 | 5A | 91 (cis, race-mic) | 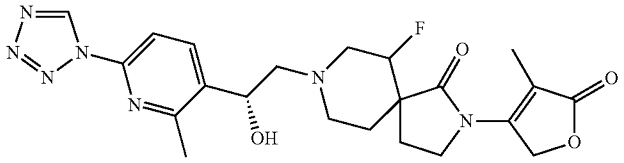<br>6-fluoro-8-{(2R)-2-hydroxy-2-[2-methyl-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane (cis, two isomers); LCMS $[M + 1 - 28]^+ = 444$ |
| 119 | 16A | 68 | 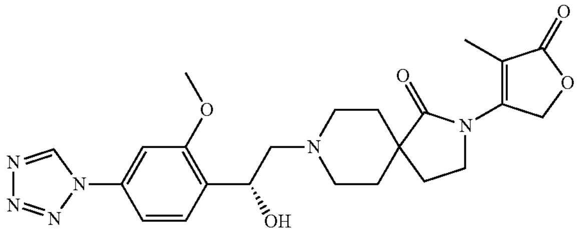 [SMILES: COc1cc(-n2cnnn2)ccc1[C@@H](O)CN1CCC2(CC1)CCN(C1=C(C)C(=O)OC1)C2=O]<br>8-{(2R)-2-hydroxy-2-[2-methoxy-4-(1H-tetrazol-1-yl)phenyl]ethyl}-2-(4-methyl-5-oxo-2,5-dihydrofuran-3-yl)-1-oxo-2-aza-8-azoniaspiro[4.5]decane; LCMS $[M + 1]^+ = 469.2$ |
| 120 | 16B | 68 | 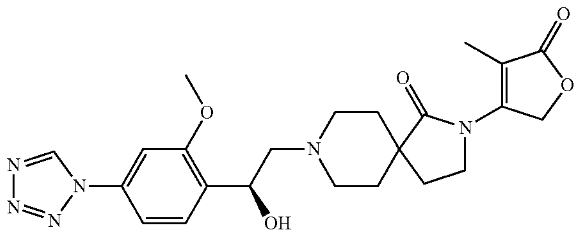 [SMILES: COc1cc(-n2cnnn2)ccc1[C@H](O)CN1CCC2(CC1)CCN(C1=C(C)C(=O)OC1)C2=O]<br>8-{(2S)-2-hydroxy-2-[2-methoxy-4-(1H-tetrazol-1-yl)phenyl]ethyl}-2-(4-methyl-5-oxo-2,5-dihydrofuran-3-yl)-1-oxo-2-aza-8-azoniaspiro[4.5]decane; LCMS $[M + 1]^+ = 469.2$ |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 121 | 18A | 68 | 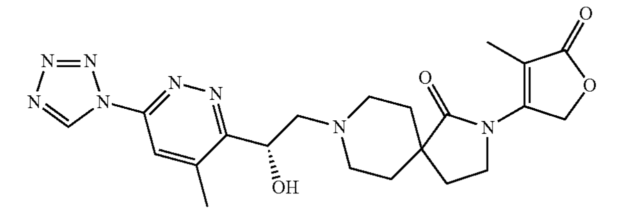<br>8-{(2S)-2-hydroxy-2-[4-methyl-6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane; LCMS $[M + 1]^+ = 445.1$ |
| 122 | 18B | 68 | 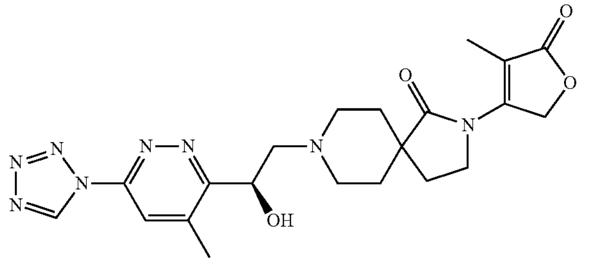<br>8-{(2R)-2-hydroxy-2-[4-methyl-6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane; LCMS $[M + 1]^+ = 445.1$ |
| 123<br>125 | 6A<br>6A | 73A<br>73B | 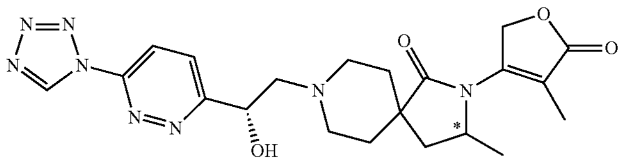<br>8-{(2S)-2-hydroxy-2-[6-(1H-tetrazol-1-yl)pyridazin-3-yl]ethyl}-3-methyl-2-(4-methyl-5-oxo-2,5-dihydrofuran-3-yl)-1-oxo-2-aza-8-azoniaspiro[4.5]decane (from fast enantiomer 73A);<br>8-{(2S)-2-hydroxy-2-[6-(1H-tetrazol-1-yl)pyridazin-3-yl]ethyl}-3-methyl-2-(4-methyl-5-oxo-2,5-dihydrofuran-3-yl)-1-oxo-2-aza-8-azoniaspiro[4.5]decane (from slower enantiomer 73B);<br>LCMS $[M + 1 - 28]^+ = 427.3$ for each enantiomer |
| 124<br>126 | 6B<br>6B | 73A<br>73B | 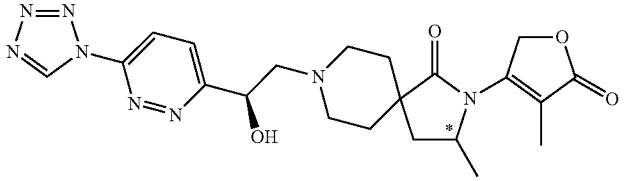<br>8-{(2R)-2-hydroxy-2-[6-(1H-tetrazol-1-yl)pyridazin-3-yl]ethyl}-3-methyl-2-(4-methyl-5-oxo-2,5-dihydrofuran-3-yl)-1-oxo-2-aza-8-azoniaspiro[4.5]decane (from fast enantiomer 73A);<br>8-{(2R)-2-hydroxy-2-[6-(1H-tetrazol-1-yl)pyridazin-3-yl]ethyl}-3-methyl-2-(4-methyl-5-oxo-2,5-dihydrofuran-3-yl)-1-oxo-2-aza-8-azoniaspiro[4.5]decane (from slower enantiomer 73B);<br>LCMS $[M + 1 - 28]^+ = 427.3$ for each enantiomer |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 127 | 20B | 68 | 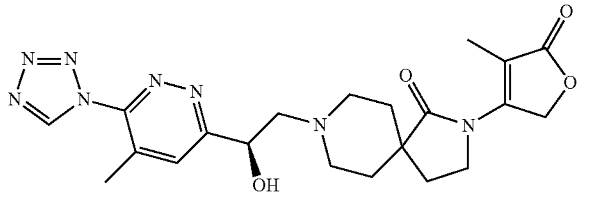 8-{(2R)-2-hydroxy-2-[5-methyl-6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane; LCMS $[M+1-28]^+ = 427.19$ |
| 128 | 20A | 68 | 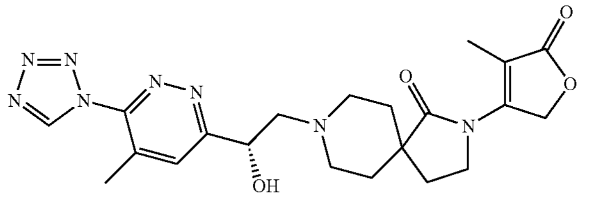 8-{(2S)-2-hydroxy-2-[5-methyl-6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane; LCMS $[M+1-28]^+ = 427.0$ |
| 129 | 29A | 68 | 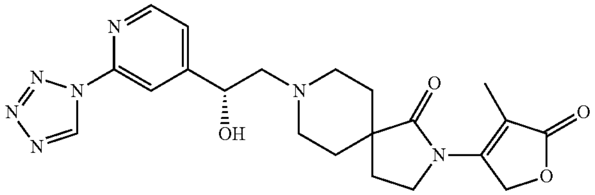 8-{(2R)-2-hydroxy-2-[2-(1H-tetrazol-1-yl)pyridin-4-yl]ethyl}-2-(4-methyl-5-oxo-2,5-dihydrofuran-3-yl)-1-oxo-2-aza-8-azoniaspiro[4.5]decane; LCMS $[M+1-28]^+ = 412$ |
| 130 | 29B | 68 | 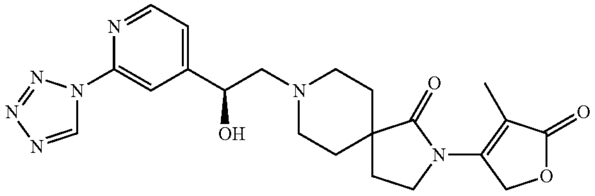 8-{(2S)-2-hydroxy-2-[2-(1H-tetrazol-1-yl)pyridin-4-yl]ethyl}-2-(4-methyl-5-oxo-2,5-dihydrofuran-3-yl)-1-oxo-2-aza-8-azoniaspiro[4.5]decane; LCMS $[M+1-28]^+ = 412$ |
| 131 | 30A | 68 | 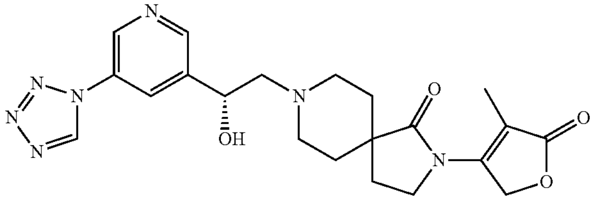 8-{(2R)-2-hydroxy-2-[5-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane; LCMS $[M+1-28]^+ = 412$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 132 | 30B | 68 | 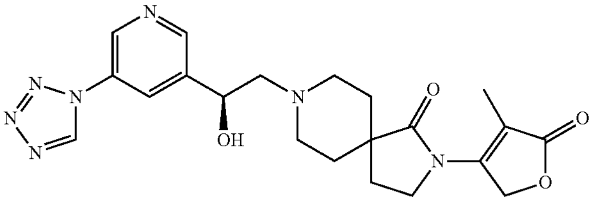 8-{(2S)-2-hydroxy-2-[5-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 412$ |
| 133 | 1A | 85A | 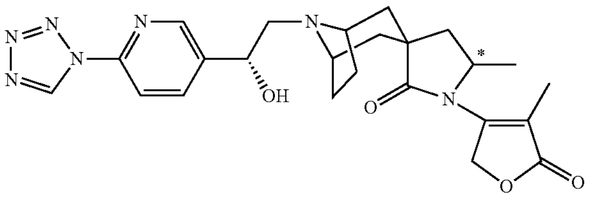 (1R,5R,5'R)-8-{(2R)-2-hydroxy-2-[6-(1H-tetrazol-1-yl)pyridin-3-yl]ethyl}-5'-methyl-1'-(4-methyl-5-oxo-2,5-dihydrofuran-3-yl)-2'-oxospiro[8-azoniabicyclo[3.2.1]octane-3,3'-pyrrolidine] (from fast enantiomer 85A); LCMS $[M + 1 - 28]^+ = 452.2$ |
| 134 | 1B | 85A | 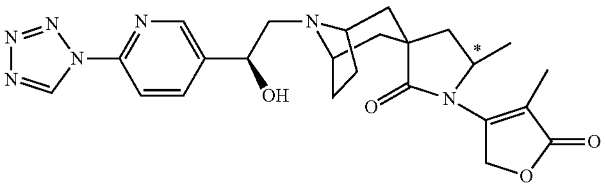 [SMILES: CC1=C(N2C(=O)C3(CC2C)CC2CCC(C3)N2C[C@@H](O)c2ccc(-n3cnnn3)nc2)COC1=O] (1R,5R,5'R)-8-{(2S)-2-hydroxy-2-[6-(1H-tetrazol-1-yl)pyridin-3-yl]ethyl}-5'-methyl-1'-(4-methyl-5-oxo-2,5-dihydrofuran-3-yl)-2'-oxospiro[8-azoniabicyclo[3.2.1]octane-3,3'-pyrrolidine] (from fast enantiomer 85A); LCMS $[M + 1]^+ = 480.1$ |
| 135 | 1A | 85B | 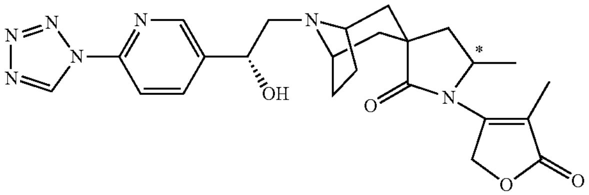 [SMILES: CC1=C(N2C(=O)C3(CC2C)CC2CCC(C3)N2C[C@H](O)c2ccc(-n3cnnn3)nc2)COC1=O] (1R,5R,5'R)-8-{(2R)-2-hydroxy-2-[6-(1H-tetrazol-1-yl)pyridin-3-yl]ethyl}-5'-methyl-1'-(4-methyl-5-oxo-2,5-dihydrofuran-3-yl)-2'-oxospiro[8-azoniabicyclo[3.2.1]octane-3,3'-pyrrolidine] (from slower enantiomer 85B); LCMS $[M + 1]^+ = 480.1$ |
| 136 | 1B | 85B | 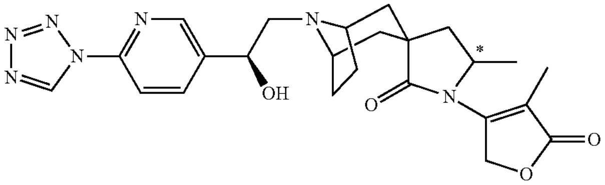 [SMILES: CC1=C(N2C(=O)C3(CC2C)CC2CCC(C3)N2C[C@@H](O)c2ccc(-n3cnnn3)nc2)COC1=O] (1R,5R,5'R)-8-{(2S)-2-hydroxy-2-[6-(1H-tetrazol-1-yl)pyridin-3-yl]ethyl}-5'-methyl-1'-(4-methyl-5-oxo-2,5-dihydrofuran-3-yl)-2'-oxospiro[8-azoniabicyclo[3.2.1]octane-3,3'-pyrrolidine] (from slower enantiomer 85B); LCMS $[M + 1]^+ = 480.1$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 137 | 11A | 73A | 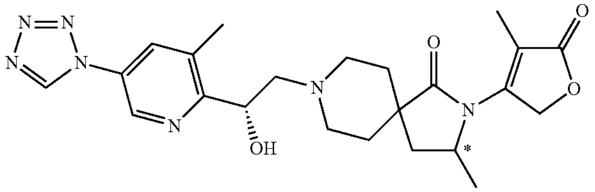<br>8-{(2S)-2-hydroxy-2-[3-methyl-5-(1H-tetrazol-1-yl)pyridin-2-yl]ethyl}-3-methyl-2-(4-methyl-5-oxo-2,5-dihydrofuran-3-yl)-1-oxo-2-aza-8-azoniaspiro[4.5]decane(from fast enantiomer 73A); LCMS $[M + 1]^+$ = 468.2 |
| 138 | 11B | 73A | 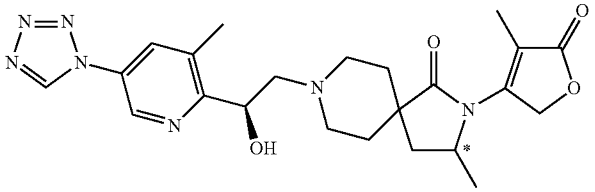 [SMILES: CC1=C(N2C(=O)C3(CCN(C[C@@H](O)c4ncc(-n5cnnn5)cc4C)CC3)CC2C)COC1=O]<br>8-{(2R)-2-hydroxy-2-[3-methyl-5-(1H-tetrazol-1-yl)pyridin-2-yl]ethyl}-3-methyl-2-(4-methyl-5-oxo-2,5-dihydrofuran-3-yl)-1-oxo-2-aza-8-azoniaspiro[4.5]decane (from fast enantiomer 73A); ; LCMS $[M + 1]^+$ = 468.2 |
| 139 | 14A | 73A | 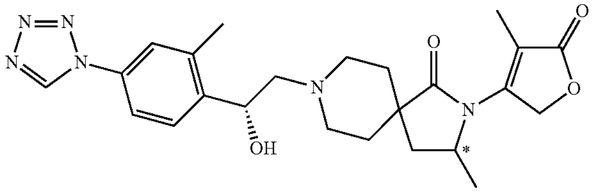 [SMILES: CC1=C(N2C(=O)C3(CCN(C[C@H](O)c4ccc(-n5cnnn5)cc4C)CC3)CC2C)COC1=O]<br>8-{(2R)-2-hydroxy-2-[2-methyl-4-(1H-tetrazol-1-yl)phenyl]ethyl}-3-methyl-2-(4-methyl-5-oxo-2,5-dihydrofuran-3-yl)-1-oxo-2-aza-8-azoniaspiro[4.5]decane (from fast enantiomer 73A); ; LCMS $[M + 1]^+$ = 467.1 |
| 140 | 14B | 73A | 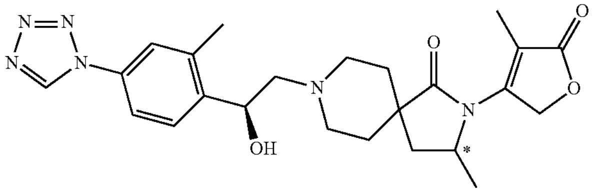 [SMILES: CC1=C(N2C(=O)C3(CCN(C[C@@H](O)c4ccc(-n5cnnn5)cc4C)CC3)CC2C)COC1=O]<br>8-{(2S)-2-hydroxy-2-[2-methyl-4-(1H-tetrazol-1-yl)phenyl]ethyl}-3-methyl-2-(4-methyl-5-oxo-2,5-dihydrofuran-3-yl)-1-oxo-2-aza-8-azoniaspiro[4.5]decane (from fast enantiomer 73A); ; LCMS $[M + 1]^+$ = 467.3 |
| 141 | 32A | 73A | 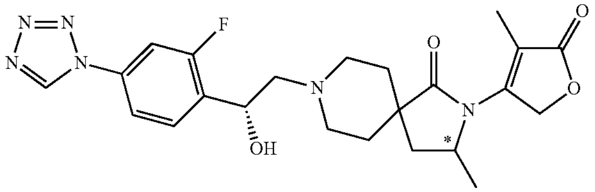 [SMILES: CC1=C(N2C(=O)C3(CCN(C[C@H](O)c4ccc(-n5cnnn5)cc4F)CC3)CC2C)COC1=O]<br>8-{(2R)-2-[2-fluoro-4-(1H-tetrazol-1-yl)phenyl]-2-hydroxyethyl}-3-methyl-2-(4-methyl-5-oxo-2,5-dihydrofuran-3-yl)-1-oxo-2-aza-8-azoniaspiro[4.5]decane (from fast enantiomer 73A); ; LCMS $[M + 1]^+$ = 471.3 |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 142 | 32B | 73A | 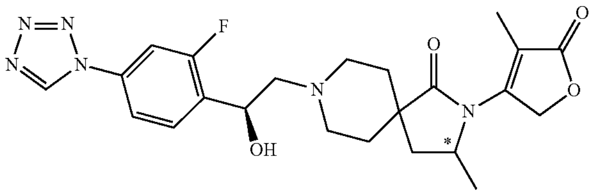 [SMILES: CC1=C(N2C(=O)C3(CCN(C[C@@H](O)c4ccc(-n5cnnn5)cc4F)CC3)CC2C)COC1=O] 8-{(2S)-2-[2-fluoro-4-(1H-tetrazol-1-yl)phenyl]-2-hydroxyethyl}-3-methyl-2-(4-methyl-5-oxo-2,5-dihydrofuran-3-yl)-1-oxo-2-aza-8-azoniaspiro[4.5]decane (from fast enantiomer 73A); ; LCMS $[M + 1 - 28]^+$ = 471.3 |
| 143 | 19B | 68 | 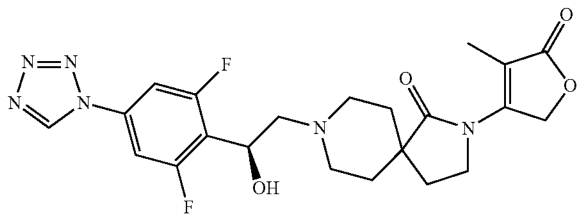 [SMILES: CC1=C(N2CCC3(CCN(C[C@@H](O)c4c(F)cc(-n5cnnn5)cc4F)CC3)C2=O)COC1=O] 8-{(2S)-2-[2,6-difluoro-4-(1H-tetrazol-1-yl)phenyl]-2-hydroxyethyl}-2-(4-methyl-5-oxo-2,5-dihydrofuran-3-yl)-1-oxo-2-aza-8-azoniaspiro[4.5]decane; LCMS $[M + 1]^+$ = 475.1 |
| 144 | 5A | 103 | 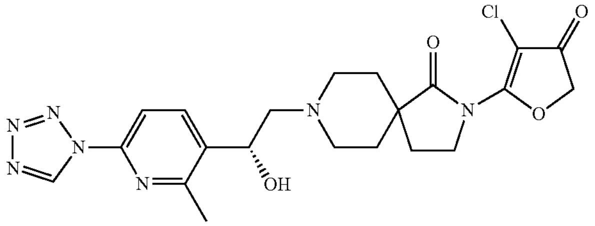 [SMILES: Cc1nc(-n2cnnn2)ccc1[C@@H](O)CN1CCC2(CC1)CCN(C1=C(Cl)C(=O)CO1)C2=O] 2-(4-chloro-5-oxo-2,5-dihydrofuran-3-yl)-8-{(2R)-2-hydroxy-2-[2-methyl-6-(1H-tetrazol-1-yl)pyridin-3-yl]ethyl}-1-oxo-2-aza-8-azoniaspiro[4.5]decane; LCMS $[M + 23]^+$ = 496.1 |
| 145 | 5B | 103 | 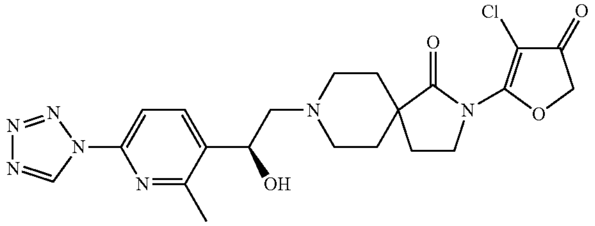 [SMILES: Cc1nc(-n2cnnn2)ccc1[C@H](O)CN1CCC2(CC1)CCN(C1=C(Cl)C(=O)CO1)C2=O] 2-(4-chloro-5-oxo-2,5-dihydrofuran-3-yl)-8-{(2S)-2-hydroxy-2-[2-methyl-6-(1H-tetrazol-1-yl)pyridin-3-yl]ethyl}-1-oxo-2-aza-8-azoniaspiro[4.5]decane; LCMS $[M + 23]^+$ = 496.1 |

TABLE 8-continued

Compounds prepared following a similar procedure as for EXAMPLE 1

| EXAMPLE | Epoxide Intermediate | Amine Intermediate | Structure, name and characterization |
| --- | --- | --- | --- |
| 146 | 6A | 96 | 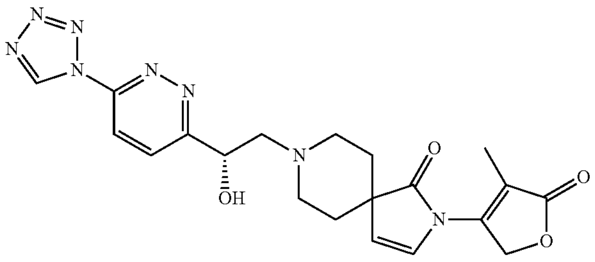 8-{(2S)-2-hydroxy-2-[6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]dec-3-ene; LCMS $[M + 1 - 28]^+ = 411$ |
| 147 | 31A | 68 | 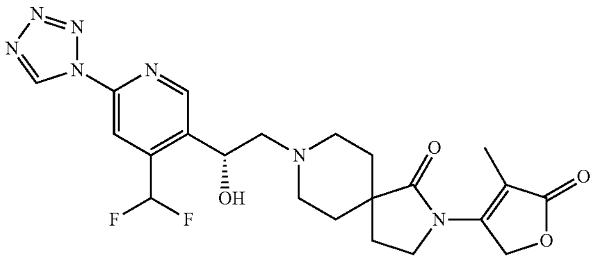 [SMILES: CC1=C(N2CCC3(CCN(C[C@H](O)c4cnc(-n5cnnn5)cc4C(F)F)CC3)C2=O)COC1=O] 8-{2-[4-(difluoromethyl)-6-(1H-tetrazol-1-yl)pyridin-3-yl]-2-hydroxyethyl}-2-(4-methyl-5-oxo-2,5-dihydrofuran-3-yl)-2,8-diazaspiro[4.5]decan-1-one; LCMS $[M + 1 - 28]^+ = 490.2$ |
| 148 | 32B | 68 | 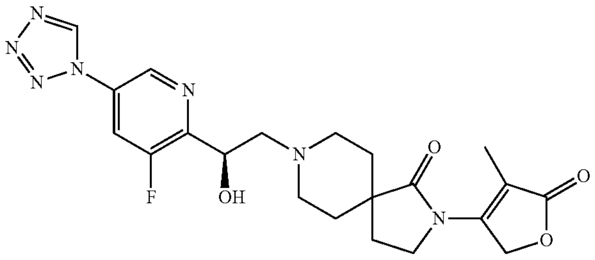 [SMILES: CC1=C(N2CCC3(CCN(C[C@@H](O)c4ncc(-n5cnnn5)cc4F)CC3)C2=O)COC1=O] 8-{(2R)-2-[3-fluoro-5-(1H-tetrazol-1-yl)pyridin-2-yl]-2-hydroxyethyl}-2-(4-methyl-5-oxo-2,5-dihydrofuran-3-yl)-2,8-diazaspiro[4.5]decan-1-one; LCMS: $[M + 1]^+ = 458.2$ |
| 149 | 33A | 68 | 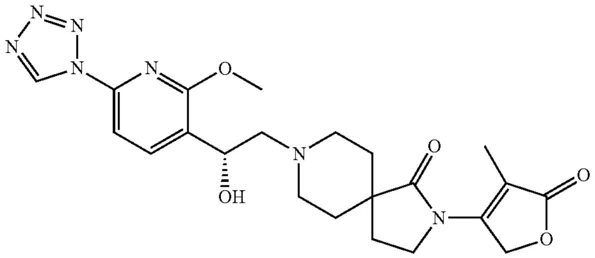 8-{(2R)-2-hydroxy-2-[2-methoxy-6-(1H-tetrazol-1-yl)pyridin-3-yl]ethyl}-2-(4-methyl-5-oxo-2,5-dihydrofuran-3-yl)-2,8-diazaspiro[4.5]decan-1-one; LCMS $[M + 1 - 28]^+ = 442$ |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 150 | 33B | 68 | 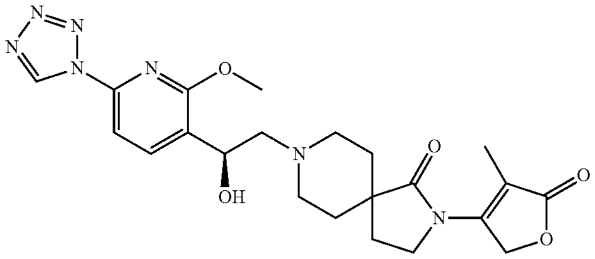 8-{(2S)-2-hydroxy-2-[2-methoxy-6-(1H-tetrazol-1-yl)pyridin-3-yl]ethyl}-2-(4-methyl-5-oxo-2,5-dihydrofuran-3-yl)-2,8-diazaspiro[4.5]decan-1-one; LCMS $[M + 1 - 28]^+ = 442$ |
| 151 | 1A | 101 | 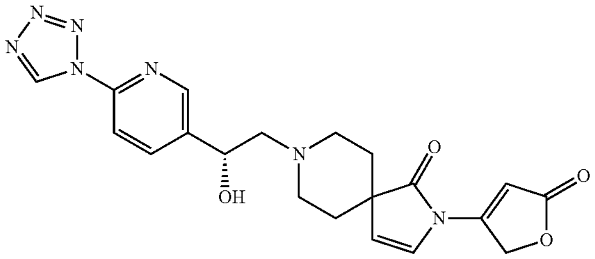 [SMILES: O=C1C=C(N2C=CC3(CCN(C[C@H](O)c4ccc(-n5cnnn5)nc4)CC3)C2=O)CO1] 8-{(2R)-2-hydroxy-2-[6-(1H-tetrazol-1-yl)pyridin-3-yl]ethyl}-1-oxo-2-(5-oxo-2,5-dihydrofuran-3-yl)-2-aza-8-azoniaspiro[4.5]dec-3-ene; LCMS $[M + 1 - 28]^+ = 396$ |
| 152 | 2A | 101 | 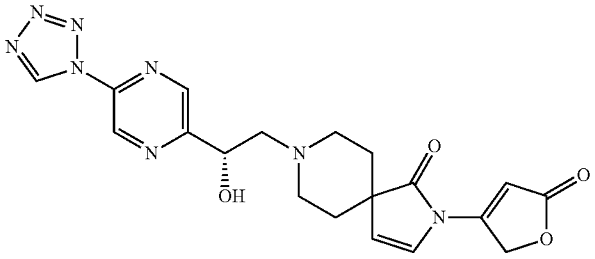 [SMILES: O=C1C=C(N2C=CC3(CCN(C[C@H](O)c4cnc(-n5cnnn5)cn4)CC3)C2=O)CO1] 8-{(2S)-2-hydroxy-2-[5-(1H-tetrazol-1-yl)pyrazin-2-yl]ethyl}-1-oxo-2-(5-oxo-2,5-dihydrofuran-3-yl)-2-aza-8-azoniaspiro[4.5]dec-3-ene; LCMS $[M + 1 - 28]^+ = 397$ |
| 153 | 18B | 96 | 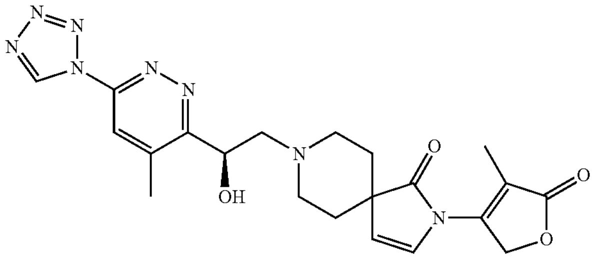 8-{(2R)-2-hydroxy-2-[4-methyl-6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]dec-3-ene; LCMS $[M + 1 - 28]^+ = 425$ |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 154 | 18A | 96 | 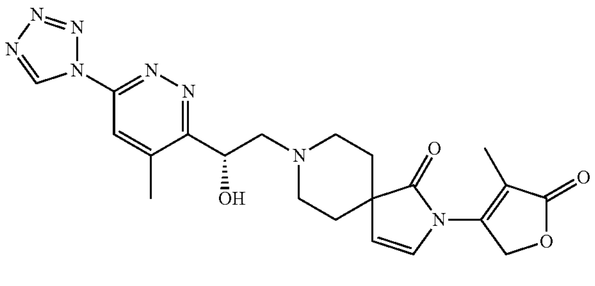 8-{(2S)-2-hydroxy-2-[4-methyl-6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]dec-3-ene; LCMS $[M + 1 - 28]^+ = 425$ |
| 155 | 1A | 101 | 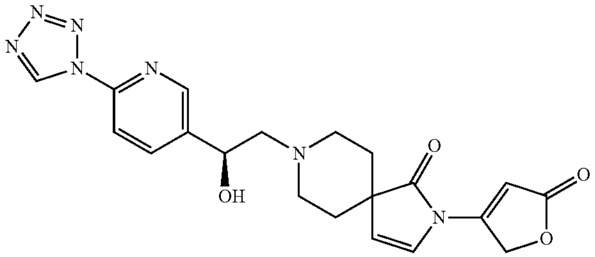 [SMILES: O=C1C=C(N2C=CC3(CCN(C[C@@H](O)c4ccc(-n5cnnn5)nc4)CC3)C2=O)CO1] 8-{(2S)-2-hydroxy-2-[6-(1H-tetrazol-1-yl)pyridin-3-yl]ethyl}-1-oxo-2-(5-oxo-2,5-dihydrofuran-3-yl)-2-aza-8-azoniaspiro[4.5]dec-3-ene; LCMS $[M + 1 - 28]^+ = 396$ |
| 156 | 1B | 96 | 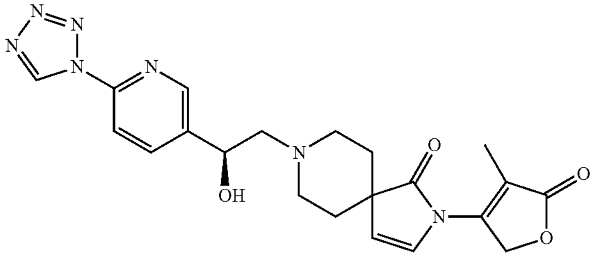 8-{(2S)-2-hydroxy-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]dec-3-ene; LCMS $[M + 1 - 28]^+ = 410$ |
| 157 | 1A | 98 | 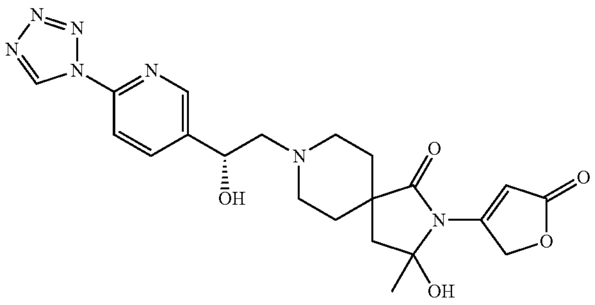 3-hydroxy-8-{(2R)-2-hydroxy-2-[6-(1H-tetrazol-1-yl)pyridin-3-yl]ethyl}-3-methyl-1-oxo-2-(5-oxo-2,5-dihydrofuran-3-yl)-2-aza-8-azoniaspiro[4.5]decane (two isomers); LCMS $[M + 1 - 28]^+ = 428$ |

TABLE 8-continued

| EXAMPLE | Epoxide Intermediate | Amine Intermediate | Structure, name and characterization |
|---|---|---|---|
| | | | Compounds prepared following a similar procedure as for EXAMPLE 1 |
| 158 | 6A | 98 | 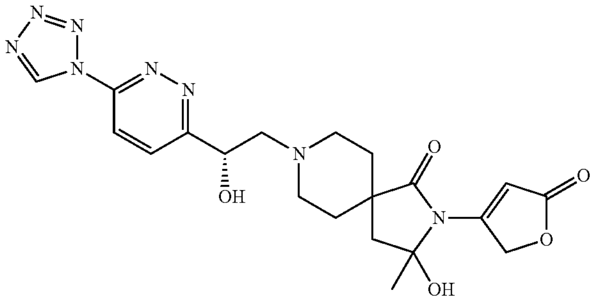 3-hydroxy-8-{(2S)-2-hydroxy-2-[6-(1H-tetrazol-1-yl)pyridazin-3-yl]ethyl}-3-methyl-1-oxo-2-(5-oxo-2,5-dihydrofuran-3-yl)-2-aza-8-azoniaspiro[4.5]decane (two isomers); LCMS $[M + 1 - 28]^+ = 429$ |
| 159 | 1A | 94A | 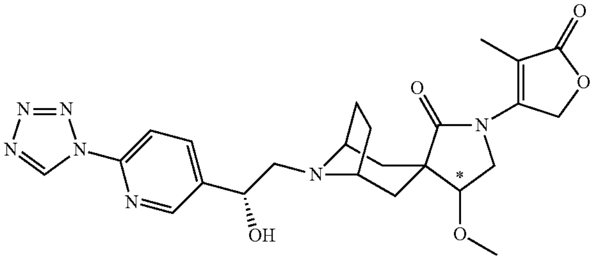 8-{(2R)-2-hydroxy-2-[6-(1H-tetrazol-1-yl)pyridin-3-yl]ethyl}-4'-methoxy-1'-(4-methyl-5-oxo-2,5-dihydrofuran-3-yl)-2'H-spiro[8-azabicyclo[3.2.1]octane-3,3'-pyrrolidin]-2'-one (from fast enantiomer 94A); LCMS $[M + 1 - 28]^+ = 468$ |
| 160 | 2A | 94A | 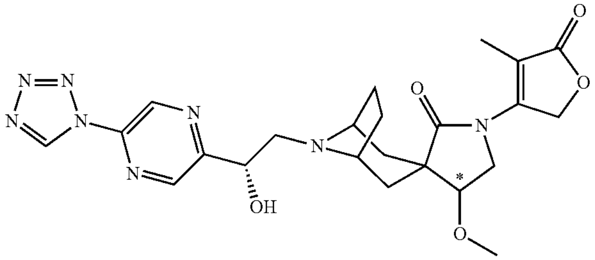 8-{(2S)-2-hydroxy-2-[5-(1H-tetrazol-1-yl)pyrazin-2-yl]ethyl}-4'-methoxy-1'-(4-methyl-5-oxo-2,5-dihydrofuran-3-yl)-2'H-spiro[8-azabicyclo[3.2.1]octane-3,3'-pyrrolidin]-2'-one (from fast enantiomer 94A); LCMS $[M + 1 - 28]^+ = 469$ |
| 161 | 1A | 94B | 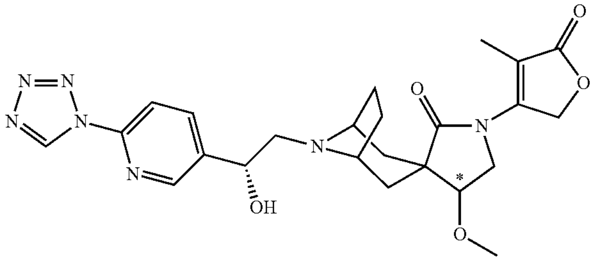 8-{(2R)-2-hydroxy-2-[6-(1H-tetrazol-1-yl)pyridin-3-yl]ethyl}-4'-methoxy-1'-(4-methyl-5-oxo-2,5-dihydrofuran-3-yl)-2'H-spiro[8-azabicyclo[3.2.1]octane-3,3'-pyrrolidin]-2'-one (from slower enantiomer 94B); LCMS $[M + 1 - 28]^+ = 468$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 162 | 2A | 94B | 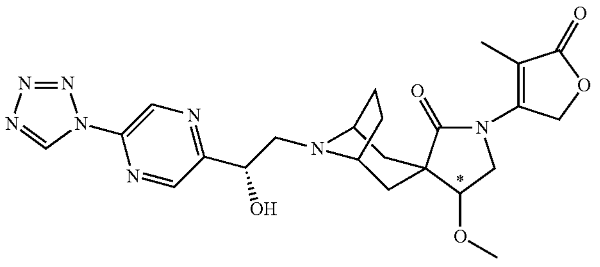 8-{(2S)-2-hydroxy-2-[5-(1H-tetrazol-1-yl)pyrazin-2-yl]ethyl}-4'-methoxy-1'-(4-methyl-5-oxo-2,5-dihydrofuran-3-yl)-2'H-spiro[8-azabicyclo[3.2.1]octane-3,3'-pyrrolidin]-2'-one (from slower enantiomer 94B); LCMS $[M + 1 - 28]^+ = 469$ |
| 163 | 2A | 96 | 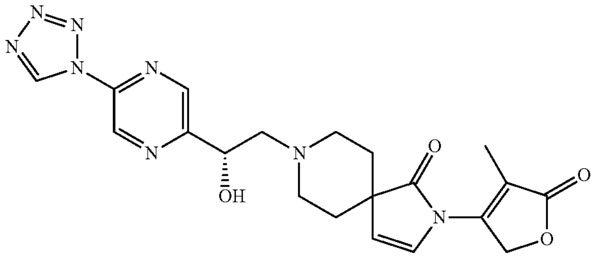 8-{(2S)-2-hydroxy-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]dec-3-ene; LCMS $[M + 1 - 28]^+ = 411$ |
| 164 | 2A | 77 | 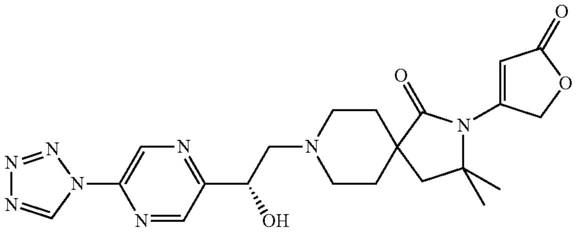 [SMILES: CC1(C)CC2(CCN(C[C@H](O)c3cnc(-n4cnnn4)cn3)CC2)C(=O)N1C1=CC(=O)OC1] 8-{(2S)-2-hydroxy-2-[5-(1H-tetrazol-1-yl)pyrazin-2-yl]ethyl}-3,3-dimethyl-1-oxo-2-(5-oxo-2,5-dihydrofuran-3-yl)-2-aza-8-azoniaspiro[4.5]decane; LCMS $[M + 1]^+ = 455$ |
| 165 | 23 | 74A | 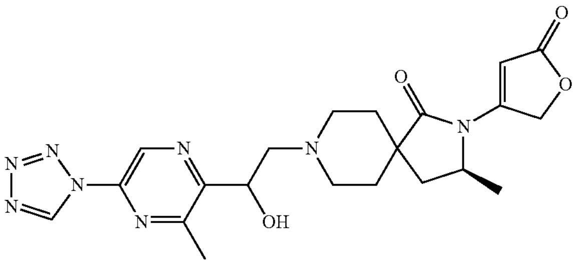 (3S)-8-{2-hydroxy-2-[3-methyl-5-(1H-tetrazol-1-yl)pyrazin-2-yl]ethyl}-3-methyl-2-(5-oxo-2,5-dihydrofuran-3-yl)-2,8-diazaspiro[4.5]decan-1-one (racemic); LCMS $[M + 1 - 28]^+ = 427.5$ |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 166 | 6A | 99 | 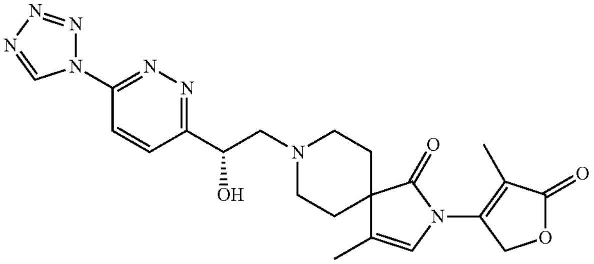 8-{(2S)-2-hydroxy-2-[6-(1H-tetrazol-1-yl)pyridazin-3-yl]ethyl}-4-methyl-2-(4-methyl-5-oxo-2,5-dihydrofuran-3-yl)-1-oxo-2-aza-8-azoniaspiro[4.5]dec-3-ene; LCMS $[M + 1 - 28]^+ = 425$ |
| 167 | 2A | 80 | 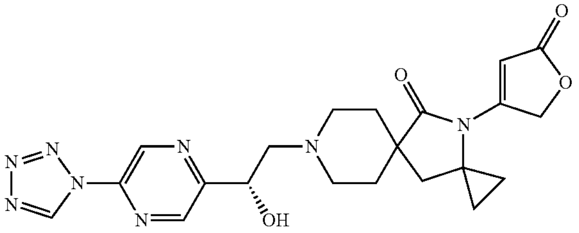 [SMILES: O=C1C=C(N2C(=O)C3(CCN(C[C@H](O)c4cnc(-n5cnnn5)cn4)CC3)CC23CC3)CO1] 8-{(2S)-2-hydroxy-2-[5-(1H-tetrazol-1-yl)pyrazin-2-yl]ethyl}-12-(5-oxo-2,5-dihydrofuran-3-yl)-8,12-diazadispiro[2.1.5.2]dodecan-11-one; LCMS $[M + 1]^+ = 453$ |
| 168 | 23 rac. | 74A | 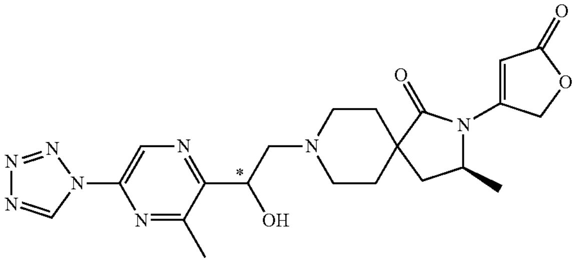 [SMILES: Cc1nc(-n2cnnn2)cnc1C(O)CN1CCC2(CC1)C[C@H](C)N(C1=CC(=O)OC1)C2=O] (3S)-8-{2-hydroxy-2-[3-methyl-5-(1H-tetrazol-1-yl)pyrazin-2-yl]ethyl}-3-methyl-2-(5-oxo-2,5-dihydrofuran-3-yl)-2,8-diazaspiro[4.5]decan-1-one (enantiomer A); (3S)-8-{2-hydroxy-2-[3-methyl-5-(1H-tetrazol-1-yl)pyrazin-2-yl]ethyl}-3-methyl-2-(5-oxo-2,5-dihydrofuran-3-yl)-2,8-diazaspiro[4.5]decan-1-one (enantiomer B) LCMS $[M + 1]^+ = 455.5$ for both enantiomers. The racemic mixture was separated by chiral separation: OJ-H(2 × 25 cm), 30% methanol(0.1% DEA)/$CO_2$, 100 bar, 70 mL/min, 220 nm |
| 169 | 23 rac. | 74A | |
| 170 | 1A | 89A | 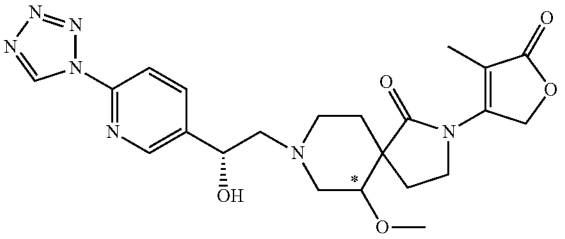 8-{(2R)-2-hydroxy-2-[6-(1H-tetrazol-1-yl)pyridin-3-yl]ethyl}-6-methoxy-2-(4-methyl-5-oxo-2,5-dihydrofuran-3-yl)-2,8-diazaspiro[4.5]decan-1-one (from cis, fast enantiomer 89A); LCMS $[M + 1 - 28]^+ = 442$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 171 | 1B | 89A | 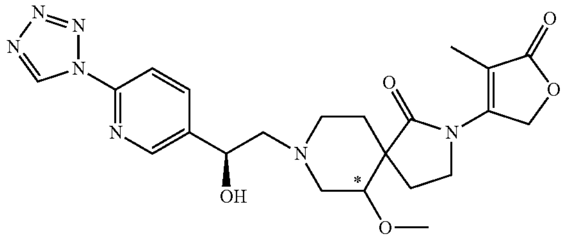 8-{(2S)-2-hydroxy-2-[6-(1H-tetrazol-1-yl)pyridin-3-yl]ethyl}-6-methoxy-2-(4-methyl-5-oxo-2,5-dihydrofuran-3-yl)-2,8-diazaspiro[4.5]decan-1-one(from cis, fast enantiomer 89A); LCMS $[M + 1 - 28]^+ = 442$ |
| 172 | 2A | 89A | 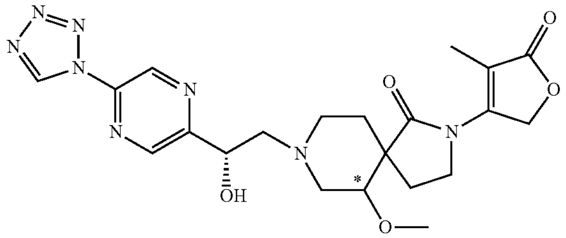 8-{(2S)-2-hydroxy-2-[5-(1H-tetrazol-1-yl)pyrazin-2-yl]ethyl}-6-methoxy-2-(4-methyl-5-oxo-2,5-dihydrofuran-3-yl)-2,8-diazaspiro[4.5]decan-1-one(from cis, fast enantiomer 89A); LCMS $[M + 1 - 28]^+ = 443$ |
| 173 | 2B | 89A | 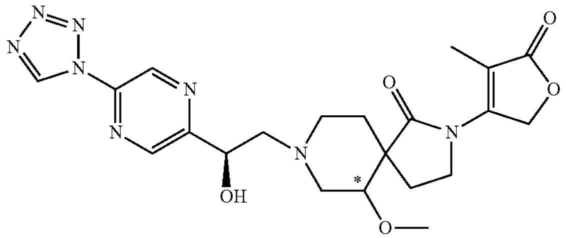 8-{(2R)-2-hydroxy-2-[5-(1H-tetrazol-1-yl)pyrazin-2-yl]ethyl}-6-methoxy-2-(4-methyl-5-oxo-2,5-dihydrofuran-3-yl)-2,8-diazaspiro[4.5]decan-1-one(from cis, fast enantiomer 89A); LCMS $[M + 1 - 28]^+ = 443$ |
| 174 | 1A | 97 | 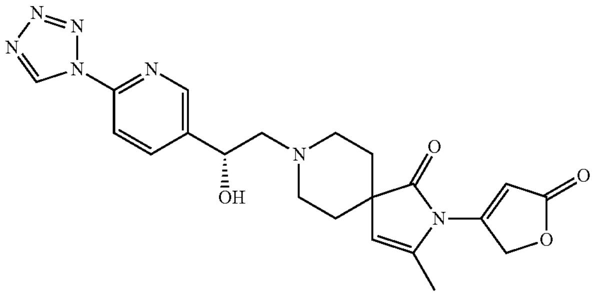 8-{(2R)-2-hydroxy-2-[6-(1H-tetrazol-1-yl)pyridin-3-yl]ethyl}-3-methyl-2-(5-oxo-2,5-dihydrofuran-3-yl)-2,8-diazaspiro[4.5]dec-3-en-1-one; LCMS $[M + 1 - 28]^+ = 410$ |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 175 | 1A | 99 | 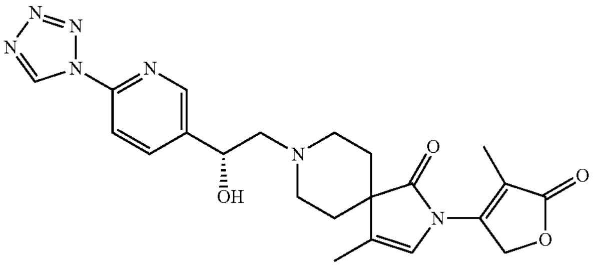 8-{(2R)-2-hydroxy-2-[6-(1H-tetrazol-1-yl)pyridin-3-yl]ethyl}-4-methyl-2-(4-methyl-5-oxo-2,5-dihydrofuran-3-yl)-1-oxo-2-aza-8-azoniaspiro[4.5]dec-3-ene; LCMS $[M + 1 - 28]^+ = 424$ |
| 176 | 1A | 89B | 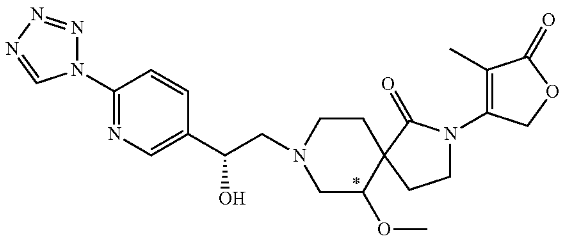 8-{(2R)-2-hydroxy-2-[6-(1H-tetrazol-1-yl)pyridin-3-yl]ethyl}-6-methoxy-2-(4-methyl-5-oxo-2,5-dihydrofuran-3-yl)-2,8-diazaspiro[4.5]decan-1-one (from cis, slower enantiomer 89B); LCMS $[M + 1 - 28]^+ = 442$ |
| 177 | 1B | 89B | 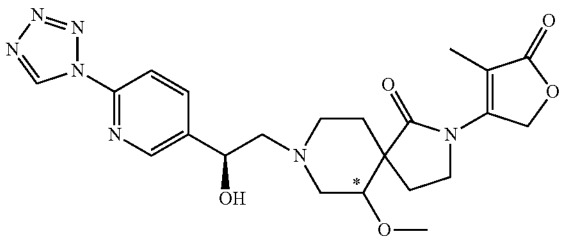 8-{(2S)-2-hydroxy-2-[6-(1H-tetrazol-1-yl)pyridin-3-yl]ethyl}-6-methoxy-2-(4-methyl-5-oxo-2,5-dihydrofuran-3-yl)-2,8-diazaspiro[4.5]decan-1-one(from cis, slower enantiomer 89B); LCMS $[M + 1 - 28]^+ = 442$ |
| 178 | 2A | 89B | 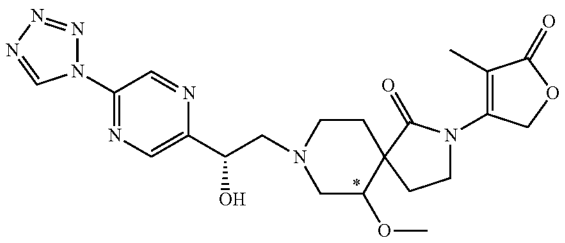 8-{(2S)-2-hydroxy-2-[5-(1H-tetrazol-1-yl)pyrazin-2-yl]ethyl}-6-methoxy-2-(4-methyl-5-oxo-2,5-dihydrofuran-3-yl)-2,8-diazaspiro[4.5]decan-1-one (from cis, slower enantiomer 89B); LCMS $[M + 1 - 28]^+ = 443$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 179 | 2B | 89B | 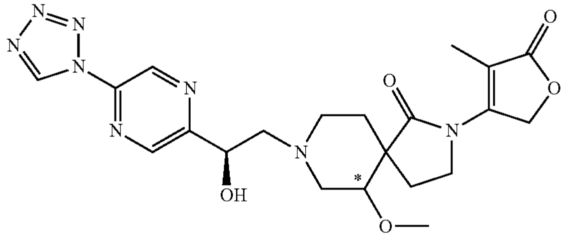 8-{(2R)-2-hydroxy-2-[5-(1H-tetrazol-1-yl)pyrazin-2-yl]ethyl}-6-methoxy-2-(4-methyl-5-oxo-2,5-dihydrofuran-3-yl)-2,8-diazaspiro[4.5]decan-1-one(from cis, slower enantiomer 89B); LCMS $[M + 1 - 28]^+ = 443$ |
| 180 | 1A | 76 | 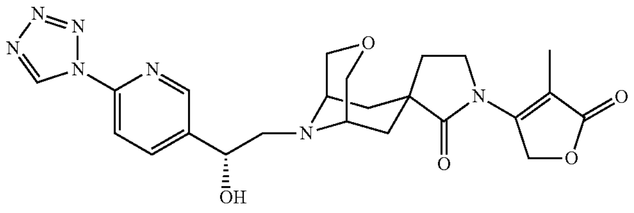 9-{(2R)-2-hydroxy-2-[6-(1H-tetrazol-1-yl)pyridin-3-yl]ethyl}-1'-(4-methyl-5-oxo-2,5-dihydrofuran-3-yl)-2'H-spiro[7-oxa-9-azabicyclo[3.3.1]nonane-3,3'-pyrrolidin]-2'-one; LCMS $[M + 1 - 28]^+ = 454$ |
| 181 | 2A | 76 | 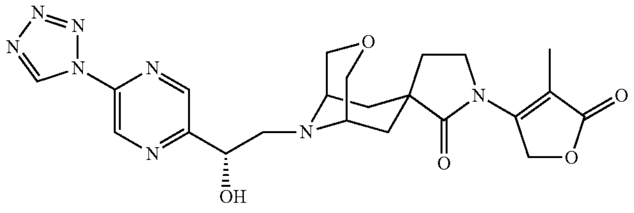 9-{(2S)-2-hydroxy-2-[5-(1H-tetrazol-1-yl)pyrazin-2-yl]ethyl}-1'-(4-methyl-5-oxo-2,5-dihydrofuran-3-yl)-2'H-spiro[7-oxa-9-azabicyclo[3.3.1]nonane-3,3'-pyrrolidin]-2'-one; LCMS $[M + 1 - 28]^+ = 455$ |
| 182 | 1A | 104 | 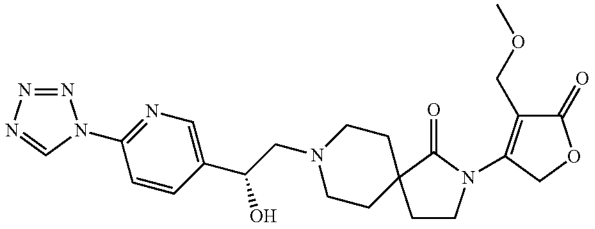 8-{(2R)-2-hydroxy-2-[6-(1H-tetrazol-1-yl)pyridin-3-yl]ethyl}-2-[4-(methoxymethyl)-5-oxo-2,5-dihydrofuran-3-yl]-2,8-diazaspiro[4.5]decan-1-one; LCMS $[M + 1 - 28]^+ = 442.3$ |

TABLE 8-continued

Compounds prepared following a similar procedure as for EXAMPLE 1

| EXAMPLE | Epoxide Intermediate | Amine Intermediate | Structure, name and characterization |
|---|---|---|---|
| 183 | 6A | 90A | 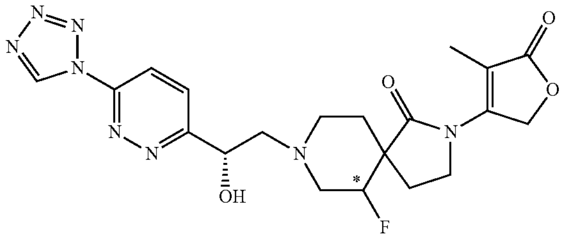 6-fluoro-8-{(2S)-2-hydroxy-2-[6-(1H-tetrazol-1-yl)pyridazin-3-yl]ethyl}-2-(4-methyl-5-oxo-2,5-dihydrofuran-3-yl)-2,8-diazaspiro[4.5]decan-1-one (from trans, fast enantiomer 90A); LCMS $[M + 1 - 28]^+ = 431$ |
| 184 | 6B | 90A | 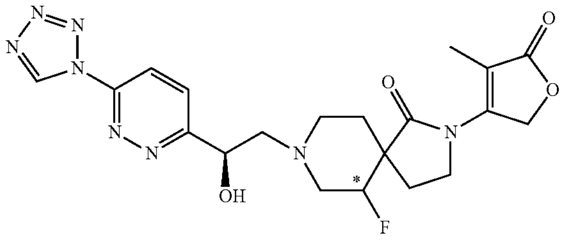 6-fluoro-8-{(2R)-2-hydroxy-2-[6-(1H-tetrazol-1-yl)pyridazin-3-yl]ethyl}-2-(4-methyl-5-oxo-2,5-dihydrofuran-3-yl)-2,8-diazaspiro[4.5]decan-1-one (from trans, fast enantiomer 90A); LCMS $[M + 1 - 28]^+ = 431$ |
| 185 | 18A | 90A | 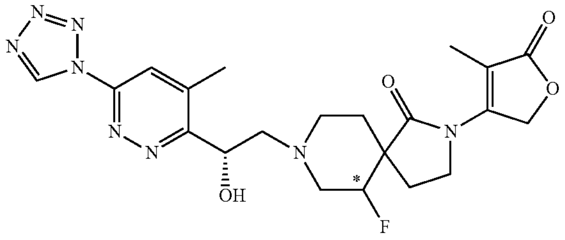 6-fluoro-8-{(2S)-2-hydroxy-2-[4-methyl-6-(1H-tetrazol-1-yl)pyridazin-3-yl]ethyl}-2-(4-methyl-5-oxo-2,5-dihydrofuran-3-yl)-2,8-diazaspiro[4.5]decan-1-one(from trans, fast enantiomer 90A); ; LCMS $[M + 1 - 28]^+ = 445$ |
| 186 | 18B | 90A | 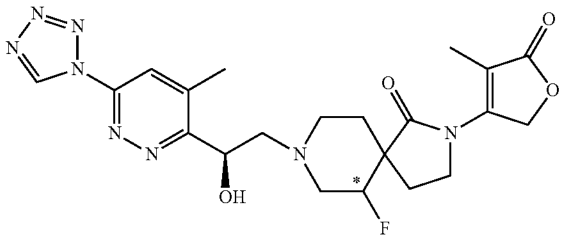 6-fluoro-8-{(2R)-2-hydroxy-2-[4-methyl-6-(1H-tetrazol-1-yl)pyridazin-3-yl]ethyl}-2-(4-methyl-5-oxo-2,5-dihydrofuran-3-yl)-2,8-diazaspiro[4.5]decan-1-one(from trans, fast enantiomer 90A);); LCMS $[M + 1 - 28]^+ = 445$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 187 | 2A | 97 | 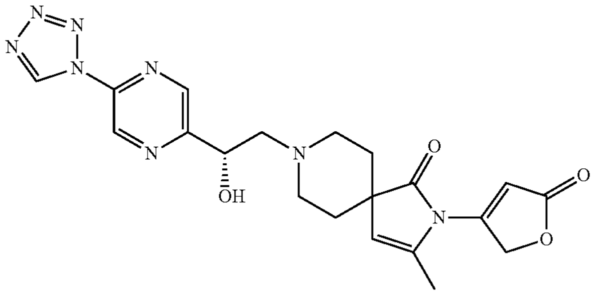 8-{(2S)-2-hydroxy-2-[5-(1H-tetrazol-1-yl)pyrazin-2-yl]ethyl}-3-methyl-2-(5-oxo-2,5-dihydrofuran-3-yl)-2,8-diazaspiro[4.5]dec-3-en-1-one; LCMS $[M + 1 - 28]^+ = 411$ |
| 188 | 6A | 97 | 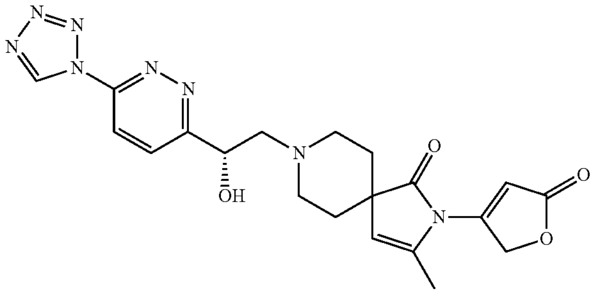 8-{(2S)-2-hydroxy-2-[6-(1H-tetrazol-1-yl)pyridazin-3-yl]ethyl}-3-methyl-2-(5-oxo-2,5-dihydrofuran-3-yl)-2,8-diazaspiro[4.5]dec-3-en-1-one; LCMS $[M + 1 - 28]^+ = 411$ |
| 189 | 6A | 77 | 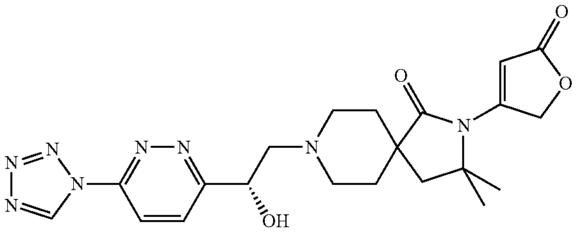 [SMILES: CC1(C)CC2(CCN(C[C@H](O)c3ccc(-n4cnnn4)nn3)CC2)C(=O)N1C1=CC(=O)OC1] 8-{(2S)-2-hydroxy-2-[6-(1H-tetrazol-1-yl)pyridazin-3-yl]ethyl}-3,3-dimethyl-1-oxo-2-(5-oxo-2,5-dihydrofuran-3-yl)-2-aza-8-azoniaspiro[4.5]decane; LCMS $[M + 1]^+ = 455$ |
| 190 | 6B | 77 | 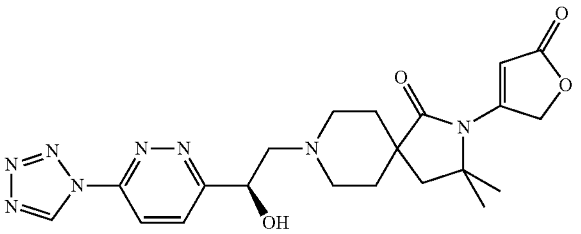 [SMILES: CC1(C)CC2(CCN(C[C@@H](O)c3ccc(-n4cnnn4)nn3)CC2)C(=O)N1C1=CC(=O)OC1] 8-{(2R)-2-hydroxy-2-[6-(1H-tetrazol-1-yl)pyridazin-3-yl]ethyl}-3,3-dimethyl-1-oxo-2-(5-oxo-2,5-dihydrofuran-3-yl)-2-aza-8-azoniaspiro[4.5]decane; LCMS $[M + 1 - 28]^+ = 455$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 191 | 6A | 104 | 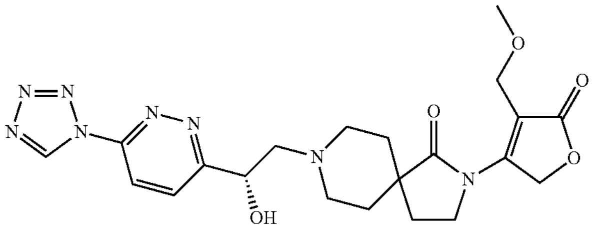 8-{(2S)-2-hydroxy-2-[6-(1H-tetrazol-1-yl)pyridazin-3-yl]ethyl}-2-[4-(methoxymethyl)-5-oxo-2,5-dihydrofuran-3-yl]-2,8-diazaspiro[4.5]decan-1-one; LCMS $[M + 1 - 28]^+ = 443.5$ |
| 192 | 1A | 90A | 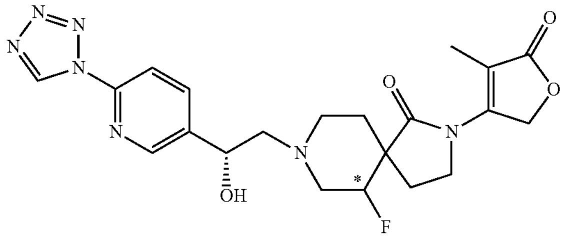 6-fluoro-8-{(2R)-2-hydroxy-2-[6-(1H-tetrazol-1-yl)pyridin-3-yl]ethyl}-2-(4-methyl-5-oxo-2,5-dihydrofuran-3-yl)-2,8-diazaspiro[4.5]decan-1-one (from trans, fast enantiomer 90A);); LCMS $[M + 1 - 28]^+ = 430$ |
| 193 | 1B | 90A | 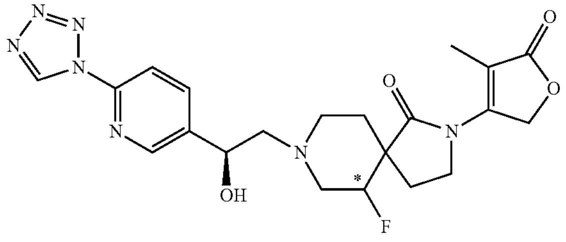 6-fluoro-8-{(2S)-2-hydroxy-2-[6-(1H-tetrazol-1-yl)pyridin-3-yl]ethyl}-2-(4-methyl-5-oxo-2,5-dihydrofuran-3-yl)-2,8-diazaspiro[4.5]decan-1-one (from trans, fast enantiomer 90A);); LCMS $[M + 1 - 28]^+ = 430$ |
| 194 | 1A | 90B | 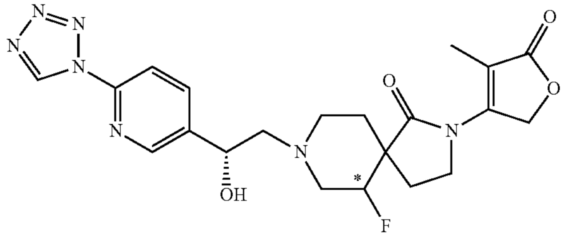 6-fluoro-8-{(2R)-2-hydroxy-2-[6-(1H-tetrazol-1-yl)pyridin-3-yl]ethyl}-2-(4-methyl-5-oxo-2,5-dihydrofuran-3-yl)-2,8-diazaspiro[4.5]decan-1-one(from trans, slower enantiomer 90B);); LCMS $[M + 1 - 28]^+ = 430$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 195 | 1B | 90B | 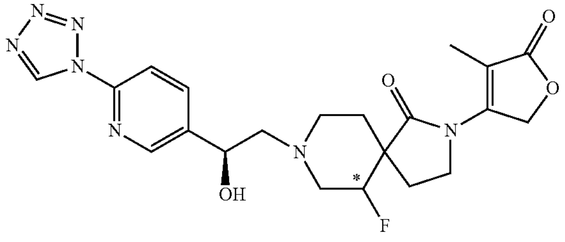 6-fluoro-8-{(2S)-2-hydroxy-2-[6-(1H-tetrazol-1-yl)pyridin-3-yl]ethyl}-2-(4-methyl-5-oxo-2,5-dihydrofuran-3-yl)-2,8-diazaspiro[4.5]decan-1-one (from trans, slower enantiomer 90B);); LCMS $[M + 1 - 28]^+ = 430$ |
| 196 | 6A | 90B | 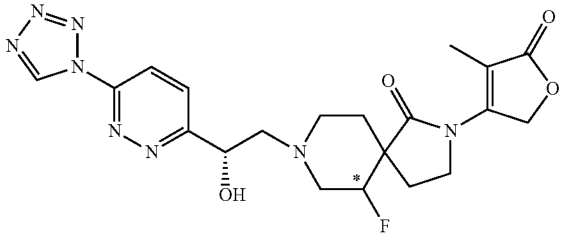 6-fluoro-8-{(2S)-2-hydroxy-2-[6-(1H-tetrazol-1-yl)pyridazin-3-yl]ethyl}-2-(4-methyl-5-oxo-2,5-dihydrofuran-3-yl)-2,8-diazaspiro[4.5]decan-1-one(from trans, slower enantiomer 90B);); LCMS $[M + 1 - 28]^+ = 431$ |
| 197 | 6B | 90B | 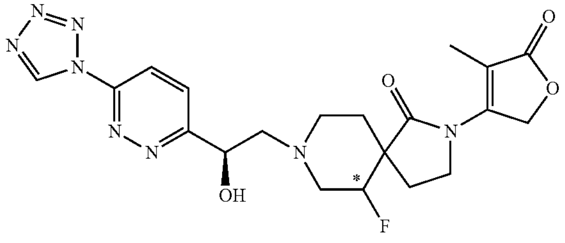 6-fluoro-8-{(2R)-2-hydroxy-2-[6-(1H-tetrazol-1-yl)pyridazin-3-yl]ethyl}-2-(4-methyl-5-oxo-2,5-dihydrofuran-3-yl)-2,8-diazaspiro[4.5]decan-1-one(from trans, slower enantiomer 90B);); LCMS $[M + 1 - 28]^+ = 431$ |
| 198 | 18A | 90B | 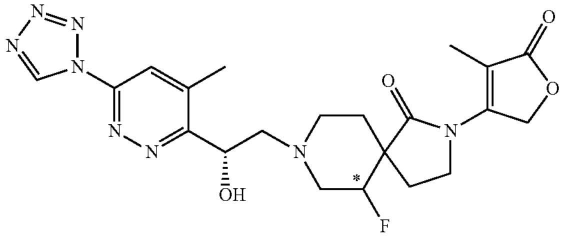 6-fluoro-8-{(2S)-2-hydroxy-2-[4-methyl-6-(1H-tetrazol-1-yl)pyridazin-3-yl]ethyl}-2-(4-methyl-5-oxo-2,5-dihydrofuran-3-yl)-2,8-diazaspiro[4.5]decan-1-one(from trans, slower enantiomer 90B);); LCMS $[M + 1 - 28]^+ = 445$ |

TABLE 8-continued

| Compounds prepared following a similar procedure as for EXAMPLE 1 | | | |
|---|---|---|---|
| EXAMPLE | Epoxide Intermediate | Amine Intermediate | Structure, name and characterization |
| 199 | 18B | 90B | 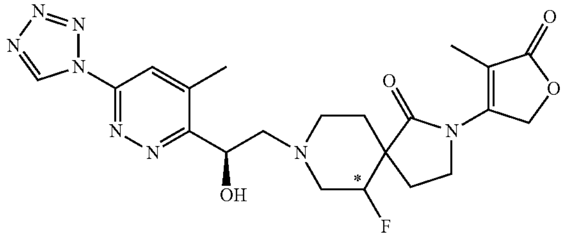 6-fluoro-8-{(2R)-2-hydroxy-2-[4-methyl-6-(1H-tetrazol-1-yl)pyridazin-3-yl]ethyl}-2-(4-methyl-5-oxo-2,5-dihydrofuran-3-yl)-2,8-diazaspiro[4.5]decan-1-one (from trans, slower enantiomer 90B); LCMS $[M + 1 - 28]^+ = 445$ |
| 200 | 2A | 104 | 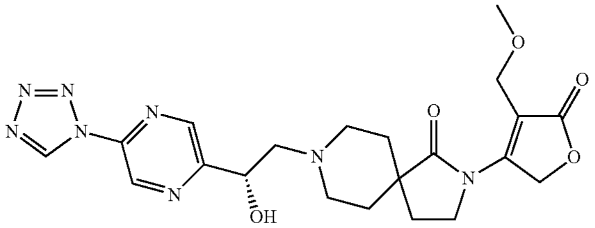 8-{(2S)-2-hydroxy-2-[5-(1H-tetrazol-1-yl)pyrazin-2-yl]ethyl}-2-[4-(methoxymethyl)-5-oxo-2,5-dihydrofuran-3-yl]-2,8-diazaspiro[4.5]decan-1-one; LCMS $[M + 1 - 28]^+ = 443.5$ |
| 201 | 2A | 101 | 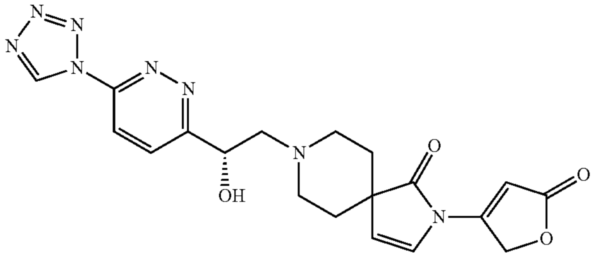 [SMILES: O=C1C=C(N2C=CC3(CCN(C[C@H](O)c4ccc(-n5cnnn5)nn4)CC3)C2=O)CO1] 8-{(2S)-2-hydroxy-2-[6-(1H-tetrazol-1-yl)pyridazin-3-yl]ethyl}-1-oxo-2-(5-oxo-2,5-dihydrofuran-3-yl)-2-aza-8-azoniaspiro[4.5]dec-3-ene; LCMS $[M + 1 - 28]^+ = 397$ |

EXAMPLE 202 and 203

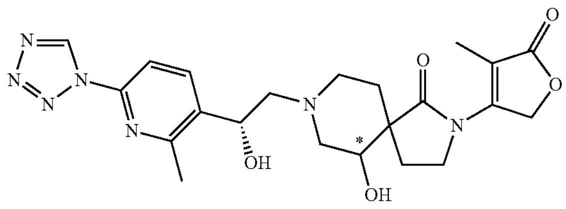

Example 202 (cis enantiomer A)
Example 203 (cis enantiomer B)

6-Hydroxy-8-((R)-2-hydroxy-2-(2-methyl-6-(1H-tetrazol-1-yl)pyridin-3-yl)ethyl)-2-(4-methyl-5-oxo-2,5-dihydrofuran-3-yl)-2,8-diazaspiro[4.5]decan-1-one; and 6-Hydroxy-8-((R)-2-hydroxy-2-(2-methyl-6-(1H-tetrazol-1-yl)pyridin-3-yl)ethyl)-2-(4-methyl-5-oxo-2,5-dihydrofuran-3-yl)-2,8-diazaspiro[4.5]decan-1-one (cis, enantiomer A and cis, enantiomer B)

(S)-2-Methyl-3-(oxiran-2-yl)-6-(1H-tetrazol-1-yl)pyridine (I-5A, 68.7 mg, 0.338 mmol), 6-Hydroxy-2-(4-methyl-5-oxo-2,5-dihydrofuran-3-yl)-2,8-diazaspiro[4.5]decan-1-one (cis, racemic, 1-90, 90 mg, 0.338 mmol) and ethanol (1 mL) were added to a 5 ml microwave tube and heated at 140° C. for 1 h. The reaction mixture was concentrated, and purified over preparative TLC (5% methanol in DCM). The racemic mixture was resolved chirally (1A 30×250 mm, 60% MeOH (0.2% DEA) to give fast eluted isomer (enantiomer A), and slow eluted isomer (enantiomer B). LCMS $[M+1]^+$=470.11. Absolute stereochemistry of the two enantiomers was not determined.

TABLE 9

| Compounds were prepared following a similar procedure as for EXAMPLE 202 and 203 | | | |
|---|---|---|---|
| Example | Intermediate Epoxide | Amine Intermediate | Chemical Structure, Name and Characterization |
| 204 | 2A | 102 (rac.) | 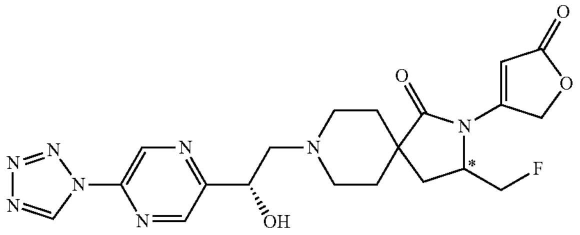 [SMILES: O=C1C=C(N2C(=O)C3(CCN(C[C@H](O)c4cnc(-n5cnnn5)cn4)CC3)CC2CF)CO1]<br>8-((S)-2-(5-(1H-tetrazol-1-yl)pyrazin-2-yl)-2-hydroxyethyl)-3-(fluoromethyl)-2-(5-oxo-2,5-dihydrofuran-3-yl)-2,8-diazaspiro[4.5]decan-1-one (enantiomer A); LCMS $[M + 1 - 28]^+ = 431.2$ Chiral separation: AS-H (25 × 0.46 cm) 35% methanol (0.1% DEA)/$CO_2$, 100 bar, 40% methanol(DEA)/$CO_2$, 70 mL/min, 220 nm |
| 205 | 2A | 102 (rac.) | 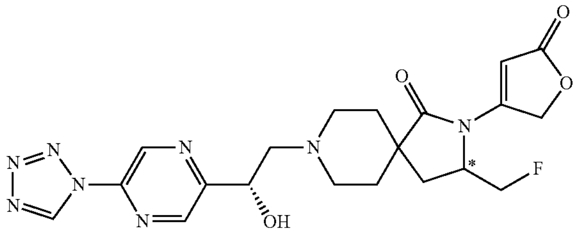 [SMILES: O=C1C=C(N2C(=O)C3(CCN(C[C@H](O)c4cnc(-n5cnnn5)cn4)CC3)CC2CF)CO1]<br>8-(S)-2-(5-(1H-tetrazol-1-yl)pyrazin-2-yl)-2-hydroxyethyl)-3-(fluoromethyl)-2-(5-oxo-2,5-dihydrofuran-3-yl)-2,8-diazaspiro[4.5]decan-1-one (enantiomer B); LCMS $[M + 1 - 28]^+ = 431.2$ Chiral separation: AS-H (25 × 0.46 cm) 35% methanol (0.1% DEA)/$CO_2$, 100 bar, 40% methanol(DEA)/$CO_2$, 70 mL/min, 220 nm |
| 206 | 1A | 100 (rac.) | 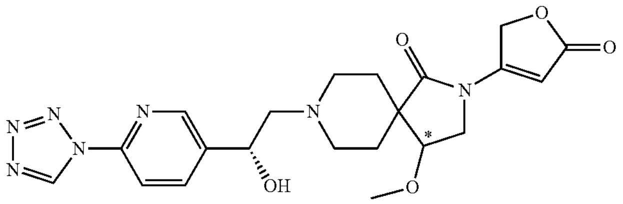<br>8-((R)-2-(6-(1H-tetrazol-1-yl)pyridin-3-yl)-2-hydroxyethyl)-4-methoxy-2-(5-oxo-2,5-dihydrofuran-3-yl)-2,8-diazaspiro[4.5]decan-1-one (enantiomer A); LCMS $[M + 1 - 28]^+ = 428$ Chiral separation: AS-H (25 × 0.46 cm) 35% methanol (0.1% DEA)/$CO_2$, 100 bar, 40% methanol(DEA)/$CO_2$, 70 mL/min, 220 nm |
| 207 | 1A | 100 (rac.) | 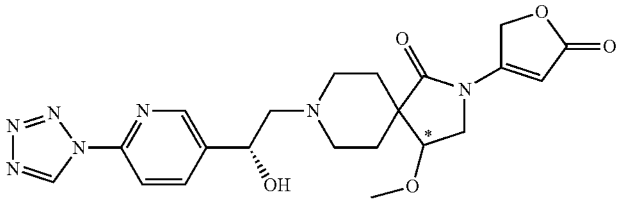<br>8-((R)-2-(6-(1H-tetrazol-1-yl)pyridin-3-yl)-2-hydroxyethyl)-4-methoxy-2-(5-oxo-2,5-dihydrofuran-3-yl)-2,8-diazaspiro[4.5]decan-1-one (enantiomer B);; LCMS $[M + 1 - 28]^+ = 428$ Chiral separation: AS-H (25 × 0.46 cm) 35% methanol (0.1% DEA)/$CO_2$, 100 bar, 40% methanol(DEA)/$CO_2$, 70 mL/min, 220 nm |

TABLE 9-continued

Compounds were prepared following a similar procedure as for EXAMPLE 202 and 203

| Example | Intermediate Epoxide | Amine Intermediate | Chemical Structure, Name and Characterization |
|---|---|---|---|
| 210 | 6A | 79 (rac.) | 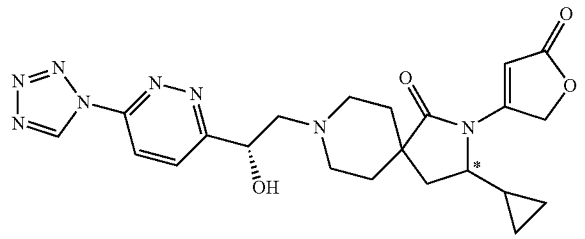 3-cyclopropyl-8-{(2S)-2-hydroxy-2-[6-(1H-tetrazol-1-yl)pyridazin-3-yl]ethyl}-2-(5-oxo-2,5-dihydrofuran-3-yl)-2,8-diazaspiro[4.5]decan-1-one (enantiomer A); LCMS $[M + 1]^+ = 439.2$ Chiral separation: AS-H (25 × 0.46 cm) 35% methanol (0.1% DEA)/$CO_2$, 100 bar, 35% methanol(DEA)/$CO_2$, 70 mL/min, 220 nm |
| 211 | 6A | 79 (rac.) | 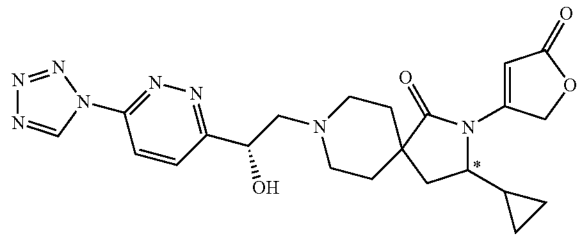 3-cyclopropyl-8-{(2S)-2-hydroxy-2-[6-(1H-tetrazol-1-yl)pyridazin-3-yl]ethyl}-2-(5-oxo-2,5-dihydrofuran-3-yl)-2,8-diazaspiro[4.5]decan-1-one (enantiomer B); LCMS $[M + 1]^+ = 439.2$ Chiral separation: AS-H (25 × 0.46 cm) 35% methanol (0.1% DEA)/$CO_2$, 100 bar, 35% methanol(DEA)/$CO_2$, 70 mL/min, 220 nm |
| 212 | 2A | 79 (rac.) | 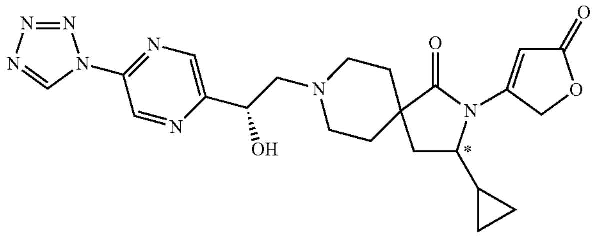 3-cyclopropyl-8-{(2S)-2-hydroxy-2-[5-(1H-tetrazol-1-yl)pyrazin-2-yl]ethyl}-2-(5-oxo-2,5-dihydrofuran-3-yl)-2,8-diazaspiro[4.5]decan-1-one (enantiomer A); LCMS $[M + 1]^+ = 439.3$ Chiral separation: AS-H (25 × 0.46 cm) 35% methanol (0.1% DEA)/$CO_2$, 100 bar, 35% methanol(DEA)/$CO_2$, 50 mL/min, 220 nm |
| 213 | 2A | 79 (rac.) | 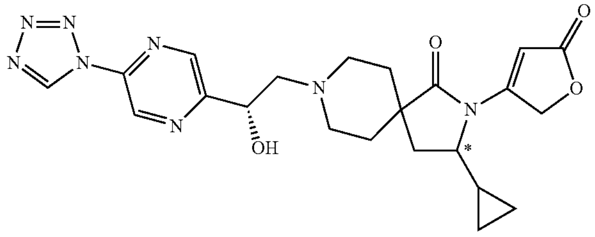 3-cyclopropyl-8-{(2S)-2-hydroxy-2-[5-(1H-tetrazol-1-yl)pyrazin-2-yl]ethyl}-2-(5-oxo-2,5-dihydrofuran-3-yl)-2,8-diazaspiro[4.5]decan-1-one (enantiomer B); LCMS $[M + 1]^+ = 439.3$ Chiral separation: AS-H (25 × 0.46 cm) 35% methanol (0.1% DEA)/$CO_2$, 100 bar, 35% methanol(DEA)/$CO_2$, 50 mL/min, 220 nm |

TABLE 9-continued

Compounds were prepared following a similar procedure as for EXAMPLE 202 and 203

| Example | Intermediate Epoxide | Amine Intermediate | Chemical Structure, Name and Characterization |
| --- | --- | --- | --- |
| 214 | 1A | 79 (rac.) | 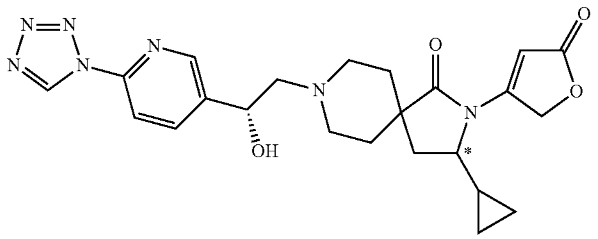<br>3-cyclopropyl-8-{(2R)-2-hydroxy-2-[6-(1H-tetrazol-1-yl)pyridin-3-yl]ethyl}-2-(5-oxo-2,5-dihydrofuran-3-yl)-2,8-diazaspiro[4.5]decan-1-one (enantiomer A); LCMS $[M + 1]^+ = 438.3$<br>Chiral separation: AS-H (25 × 0.46 cm) 35% methanol (0.1% DEA)/$CO_2$, 100 bar, 35% methanol(DEA)/$CO_2$, 50 mL/min, 220 nm |
| 215 | 1A | 79 (rac.) | 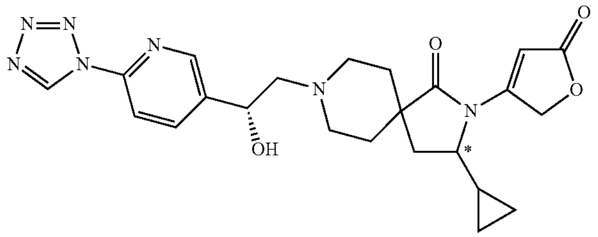<br>3-cyclopropyl-8-{(2R)-2-hydroxy-2-[6-(1H-tetrazol-1-yl)pyridin-3-yl]ethyl}-2-(5-oxo-2,5-dihydrofuran-3-yl)-2,8-diazaspiro[4.5]decan-1-one (enantiomer B); LCMS $[M + 1]^+ = 438.3$<br>Chiral separation: AS-H (25 × 0.46 cm) 35% methanol (0.1% DEA)/$CO_2$, 100 bar, 35% methanol(DEA)/$CO_2$, 50 mL/min, 220 nm |
| 218 | 1A | 78 (rac.) | 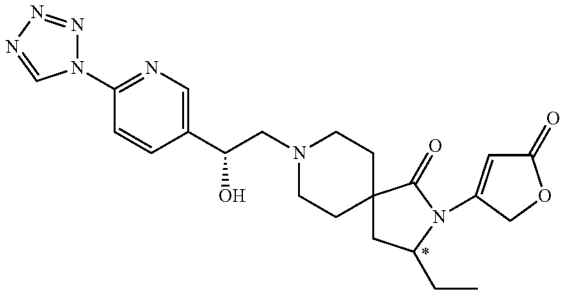<br>3-ethyl-8-{(2R)-2-hydroxy-2-[6-(1H-tetrazol-1-yl)pyridin-3-yl]ethyl}-2-(5-oxo-2,5-dihydrofuran-3-yl)-2,8-diazaspiro[4.5]decan-1-one (enantiomer A); LCMS $[M + 1]^+ = 426.3$<br>Chiral separation: AS-H (25 × 0.46 cm) 40% methanol (0.1% DEA)/$CO_2$, 100 bar, 35% methanol(DEA)/$CO_2$, 50 mL/min, 220 nm |
| 219 | 1A | 78 (rac.) | 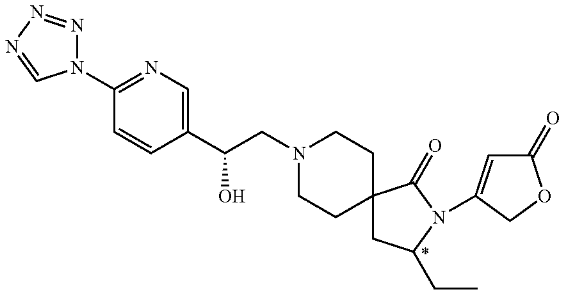<br>3-ethyl-8-{(2R)-2-hydroxy-2-[6-(1H-tetrazol-1-yl)pyridin-3-yl]ethyl}-2-(5-oxo-2,5-dihydrofuran-3-yl)-2,8-diazaspiro[4.5]decan-1-one (enantiomer B); LCMS $[M + 1]^+ = 426.3$<br>Chiral separation: AS-H (25 × 0.46 cm) 40% methanol (0.1% DEA)/$CO_2$, 100 bar, 35% methanol(DEA)/$CO_2$, 50 mL/min, 220 nm |

TABLE 9-continued

Compounds were prepared following a similar procedure as for EXAMPLE 202 and 203

| Example | Intermediate Epoxide | Amine Intermediate | Chemical Structure, Name and Characterization |
|---|---|---|---|
| 220 | 2A | 78 (rac.) | 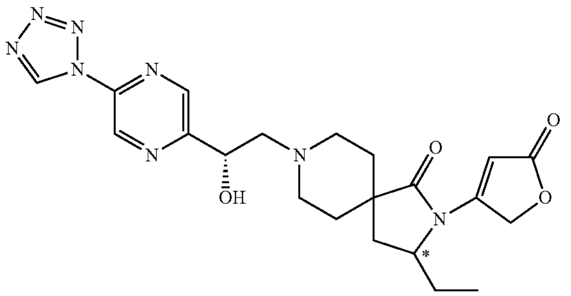<br>3-ethyl-8-{(2S)-2-hydroxy-2-[5-(1H-tetrazol-1-yl)pyrazin-2-yl]ethyl}-2-(5-oxo-2,5-dihydrofuran-3-yl)-2,8-diazaspiro[4.5]decan-1-one (enantiomer A); LCMS $[M + 1]^+ = 427.3$<br>Chiral separation: AS-H (25 × 0.46 cm) 30% methanol (0.1% DEA)/$CO_2$, 100 bar, 35% methanol(DEA)/$CO_2$, 60 mL/min, 220 nm |
| 221 | 2A | 78 (rac.) | 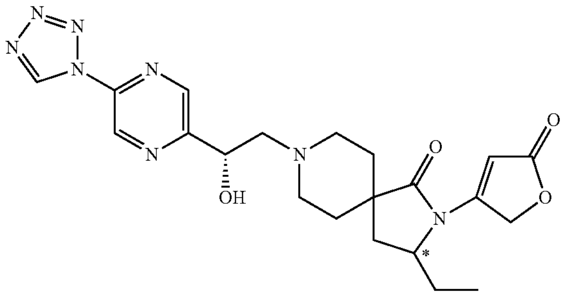<br>3-ethyl-8-{(2S)-2-hydroxy-2-[5-(1H-tetrazol-1-yl)pyrazin-2-yl]ethyl}-2-(5-oxo-2,5-dihydrofuran-3-yl)-2,8-diazaspiro[4.5]decan-1-one (enantiomer B); LCMS $[M + 1]^+ = 427.3$<br>Chiral separation: AS-H (25 × 0.46 cm) 30% methanol (0.1% DEA)/$CO_2$, 100 bar, 35% methanol(DEA)/$CO_2$, 60 mL/min, 220 nm |
| 222 | 1A | 79 (rac.) | 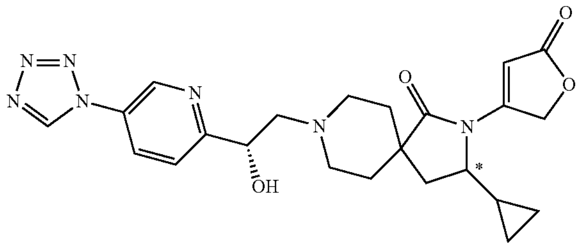<br>3-cyclopropyl-8-{(2S)-2-hydroxy-2-[5-(1H-tetrazol-1-yl)pyridin-2-yl]ethyl}-2-(5-oxo-2,5-dihydrofuran-3-yl)-2,8-diazaspiro[4.5]decan-1-one (enantiomer A); LCMS $[M + 1]^+ = 466.3$<br>Chiral separation: AS-H (25 × 0.46 cm) 30% methanol (0.1% DEA)/$CO_2$, 100 bar, 35% methanol(DEA)/$CO_2$, 60 mL/min, 220 nm |
| 223 | 1A | 79 (rac.) | 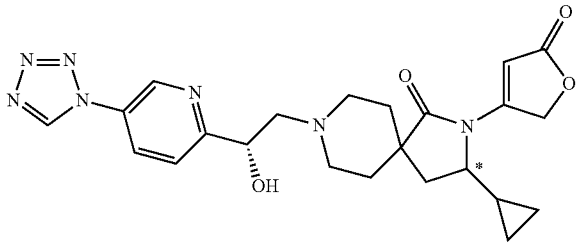<br>3-cyclopropyl-8-{(2S)-2-hydroxy-2-[5-(1H-tetrazol-1-yl)pyridin-2-yl]ethyl}-2-(5-oxo-2,5-dihydrofuran-3-yl)-2,8-diazaspiro[4.5]decan-1-one (enantiomer B); LCMS $[M + 1]^+ = 466.2$<br>Chiral separation: AS-H (25 × 0.46 cm) 30% methanol (0.1% DEA)/$CO_2$, 100 bar, 35% methanol(DEA)/$CO_2$, 60 mL/min, 220 nm |

TABLE 9-continued

| Example | Intermediate Epoxide | Amine Intermediate | Chemical Structure, Name and Characterization |
|---|---|---|---|
| | | | Compounds were prepared following a similar procedure as for EXAMPLE 202 and 203 |
| 224 | 2A | 90 (trans, rac.) | 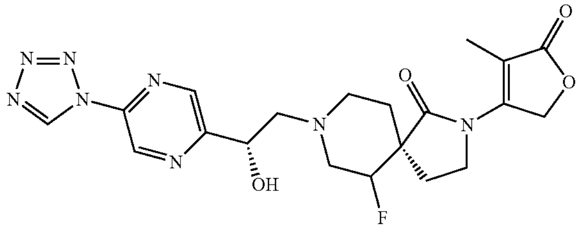 6-fluoro-8-{(2S)-2-hydroxy-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane (trans, two isomers); LCMS $[M + 1]^+ = 459$ |
| 225 | 2A | 91 (cis, rac.) | 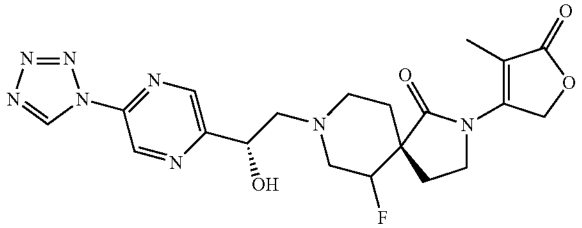 6-fluoro-8-{(2S)-2-hydroxy-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane (cis, two isomers); LCMS $[M + 1]^+ = 459$ |
| 226 | 1A | 81 (rac.) | 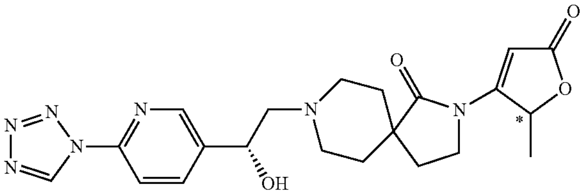 8-((R)-2-(6-(1H-tetrazol-1-yl)pyridin-3-yl)-2-hydroxyethyl)-2-(2-methyl-5-oxo-2,5-dihydrofuran-3-yl)-2,8-diazaspiro[4.5]decan-1-one (enantiomer A); LCMS $[M + 1 - 28]^+ = 412$ Chiral separation: AS-H (25 × 0.46 cm) 35% methanol (0.1% DEA)/$CO_2$, 100 bar, 40% methanol(DEA)/$CO_2$, 50 mL/min, 220 nm |
| 227 | 1A | 81 (rac.) | 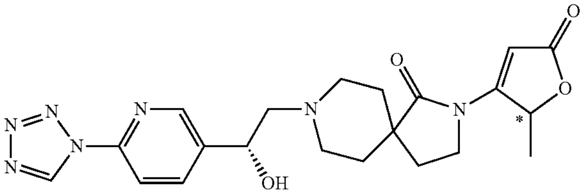 [SMILES: CC1OC(=O)C=C1N1CCC2(CCN(C[C@H](O)c3ccc(-n4cnnn4)nc3)CC2)C1=O] 8-((R)-2-(6-(1H-tetrazol-1-yl)pyridin-3-yl)-2-hydroxyethyl)-2-(2-methyl-5-oxo-2,5-dihydrofuran-3-yl)-2,8-diazaspiro[4.5]decan-1-one (enantiomer B); LCMS $[M + 1 - 28]^+ = 412$ Chiral separation: AS-H (25 × 0.46 cm) 35% methanol (0.1% DEA)/$CO_2$, 100 bar, 40% methanol(DEA)/$CO_2$, 50 mL/min, 220 nm |
| 228 | 1A | 82 (rac.) | 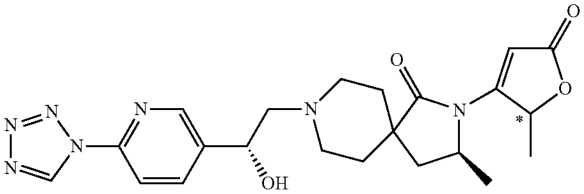 (3S)-8-((R)-2-(6-(1H-tetrazol-1-yl)pyridin-3-yl)-2-hydroxyethyl)-3-methyl-2-(2-methyl-5-oxo-2,5-dihydrofuran-3-yl)-2,8-diazaspiro[4.5]decan-1-one (enantiomer A); LCMS $[M + 1 - 28]^+ = 426$ Chiral separation: AS-H (25 × 0.46 cm) 35% methanol (0.1% DEA)/$CO_2$, 100 bar, 40% methanol(DEA)/$CO_2$, 70 mL/min, 220 nm |

TABLE 9-continued

Compounds were prepared following a similar procedure as for EXAMPLE 202 and 203

| Example | Intermediate Epoxide | Amine Intermediate | Chemical Structure, Name and Characterization |
|---|---|---|---|
| 229 | 1A | 82 (rac.) | 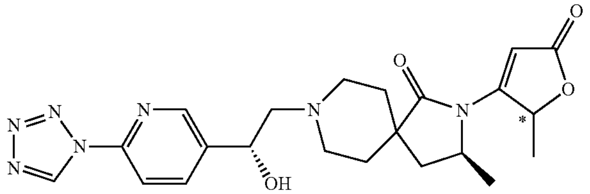 3S)-8-((R)-2-(6-(1H-tetrazol-1-yl)pyridin-3-yl)-2-hydroxyethyl)-3-methyl-2-(2-methyl-5-oxo-2,5-dihydrofuran-3-yl)-2,8-diazaspiro[4.5]decan-1-one (enantiomer B); LCMS $[M + 1 - 28]^+ = 426$ Chiral separation: AS-H (25 x 0.46 cm) 35% methanol (0.1% DEA)/$CO_2$, 100 bar, 40% methanol(DEA)/$CO_2$, 70 mL/min, 220 nm |
| 230 | 1A | 83 (rac.) | 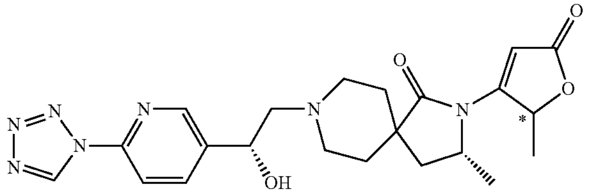 (3R)-8-((R)-2-(6-(1H-tetrazol-1-yl)pyridin-3-yl)-2-hydroxyethyl)-3-methyl-2-(2-methyl-5-oxo-2,5-dihydrofuran-3-yl)-2,8-diazaspiro[4.5]decan-1-one (enantiomer A); LCMS $[M + 1 - 28]^+ = 426$ Chiral separation: OJ-H (25 x 0.46 cm) 35% methanol (0.1% DEA)/$CO_2$, 100 bar, 40% methanol(DEA)/$CO_2$, 70 mL/min, 220 nm |
| 231 | 1A | 83 (rac.) | 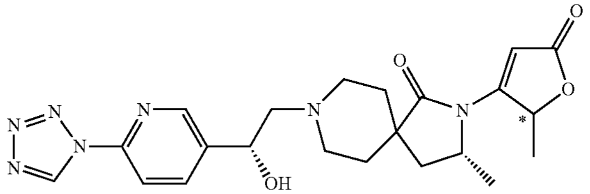 (3R)-8-((R)-2-(6-1H-tetrazol-1-yl)pyridin-3-yl)-2-hydroxyethyl)-3-methyl-2-(2-methyl-5-oxo-2,5-dihydrofuran-3-yl)-2,8-diazaspiro[4.5]decan-1-one (enantiomer B); LCMS $[M + 1 - 28]^+ = 426$ Chiral separation: OJ-H (25 x 0.46 cm) 35% methanol (0.1% DEA)/$CO_2$, 100 bar, 40% methanol(DEA)/$CO_2$, 70 mL/min, 220 nm |

EXAMPLE 232

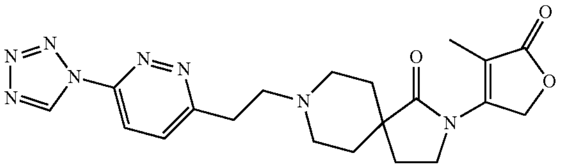 [SMILES: CC1=C(N2CCC3(CCN(CCc4ccc(-n5cnnn5)nn4)CC3)C2=O)COC1=O]

8-(2-(6-(1H-Tetrazol-1-yl)pyridazin-3-yl)ethyl)-2-(4-methyl-5-oxo-2,5-dihydrofuran-3-yl)-2,8-diazaspiro[4.5]decan-1-one To a microwave vial were added 3-(1H-tetrazol-1-yl)-6-vinylpyridazine (167 mg, 0.959 mmol), 2-(4-methyl-5-oxo-2,5-dihydrofuran-3-yl)-2,8-diazaspiro[4.5]decan-1-one (60 mg, 0.240 mmol), DPEPhos (12.9 mg, 0.024 mmol) and $Rh(COD)_2BF_4$ (9.73 mg, 0.024 mmol). The vial was sealed, vacuumed and back-filled with $N_2$ and toluene (0.6 mL). The reaction mixture was heated at 70° C. for 48 h, purified with column chromatography (0-10% MeOH/DCM) to give the title compound. LCMS $[(M+1)]^+=425$.

EXAMPLE 233

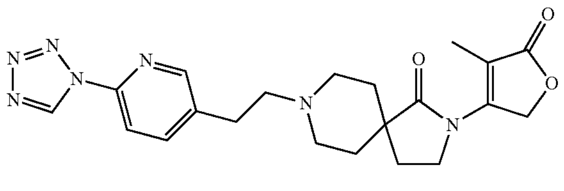 [SMILES: CC1=C(N2CCC3(CCN(CCc4ccc(-n5cnnn5)nc4)CC3)C2=O)COC1=O]

8-(2-(6-(1H-Tetrazol-1-yl)pyridazin-3)ethyl)-2-(4-methyl-5-oxo-2,5-dihydrofuran-3-yl)-2,8-diazaspiro[4.5]decan-1-one To a solution of 2-(4-methyl-5-oxo-2,5-dihydrofuran-3-yl)-2,8-diazaspiro[4.5]decan-1-one (30 mg, 0.120 mmol) and 2-(6-(1H-tetrazol-1-yl)pyridin-3-yl)acetaldehyde (34.0 mg, 0.180 mmol) in THF (4.8 mL) were added AcOH (41.2 μl, 0.719 mmol) and MP-cyanoborohydride (MP designates highly crosslinked, macroporous polystyrene) (2.19 mmol/g) (181 mg, 0.396 mmol). The mixture was put on shaker overnight. The insoluble material was filtered off, washed with MeOH. The filtrate was concentrated and purified over prep-TLC (5% MeOH/DCM) to give the title compound. LCMS $[M+1-28]^+$=396.

TABLE 10 compounds prepared following a similar procedure as for EXAMPLE 232 or 233

| EXAMPLE | Olefin or Aldehyde Intermediate | Amine Intermediate | Structure, name and characterization |
|---|---|---|---|
| 234 | 46 | 68 | 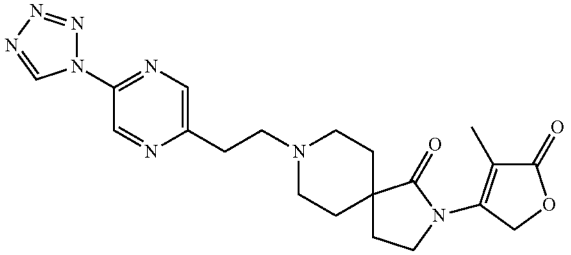<br>2-(4-methyl-5-oxo-2,5-dihydrofuran-3-yl)-1-oxo-8-{2-[5-(1H-tetrazol-1-yl)pyrazin-2-yl]ethyl}-2-aza-8-azoniaspiro[4.5]decane, LCMS $[M + 1 - 28]^+ = 397$ |
| 235 | 38 | 70 | 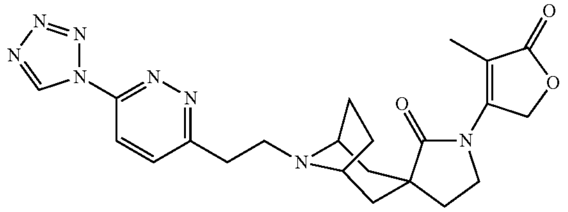<br>(1S,5S)-1'-(4-methyl-5-oxo-2,5-dihydrofuran-3-yl)-2'-oxo-8-{2-[6-(1H-tetrazol-1-yl)pyridazin-3-yl]ethyl}spiro[8-azoniabicyclo[3.2.1]octane-3,3'-pyrrolidine]; LCMS $[M + 1 - 28]^+ = 423$ |
| 236 | 39 | 68 | 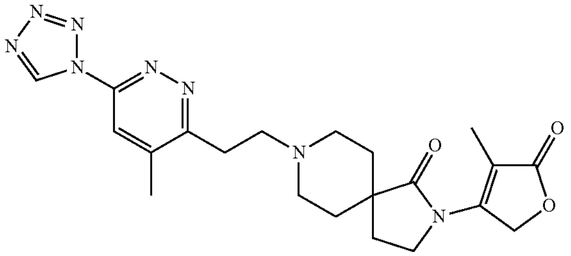 [SMILES: CC1=C(N2CCC3(CCN(CCc4nnc(-n5cnnn5)cc4C)CC3)C2=O)COC1=O]<br>2-(4-methyl-5-oxo-2,5-dihydrofuran-3-yl)-8-{2-[4-methyl-6-(1H-tetrazol-1-yl)pyridazin-3-yl]ethyl}-1-oxo-2-aza-8-azoniaspiro[4.5]decane; LCMS $[M + 1 - 28]^+ = 439$ |
| 237 | 40 | 68 | 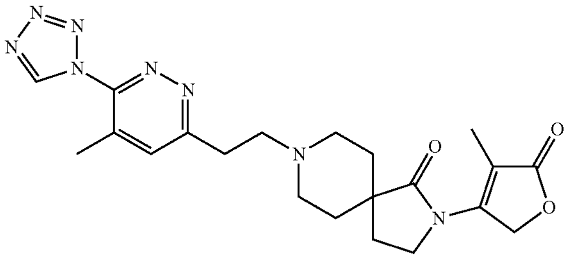<br>2-(4-methyl-5-oxo-2,5-dihydrofuran-3-yl)-8-{2-[5-methyl-6-(1H-tetrazol-1-yl)pyridazin-3-yl]ethyl}-1-oxo-2-aza-8-azoniaspiro[4.5]decane; LCMS $[M + 1]^+ = 411$ |

TABLE 10-continued

| compounds prepared following a similar procedure as for EXAMPLE 232 or 233 | | | |
|---|---|---|---|
| EXAMPLE | Olefin or Aldehyde Intermediate | Amine Intermediate | Structure, name and characterization |
| 238 | 41 | 68 | 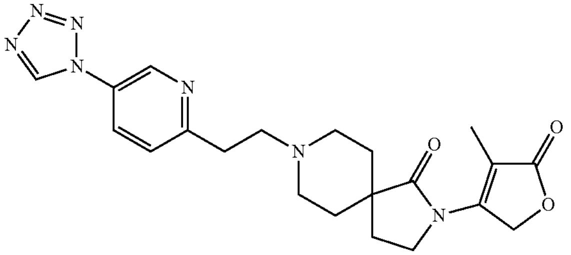 [SMILES: CC1=C(N2CCC3(CCN(CCc4ccc(-n5cnnn5)cn4)CC3)C2=O)COC1=O]<br>2-(4-methyl-5-oxo-2,5-dihydrofuran-3-yl)-1-oxo-8-{2-[5-(1H-tetrazol-1-yl)pyridin-2-yl]ethyl}-2-aza-8-azoniaspiro[4.5]decane: $[M + 1]^+ = 424$ |
| 239 | 38 | 75 | 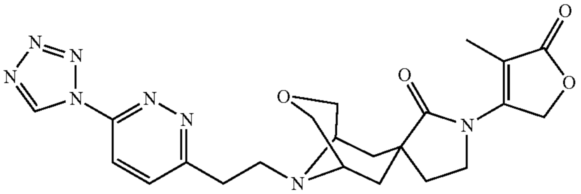<br>(1R,5S,9r)-1'-(4-methyl-5-oxo-2,5-(dihydrofuran-3-yl)-2'-oxo-9-{2-[6-(1H-tetrazol-1-yl)pyridazin-3-yl]ethyl}spiro[7-oxa-9-azoniabicyclo[3.3.1]nonane-3,3'-pyrrolidine]; LCMS $[M + 1 - 28]^+ = 439$ |
| 240 | 38 | 73 (rac.) | 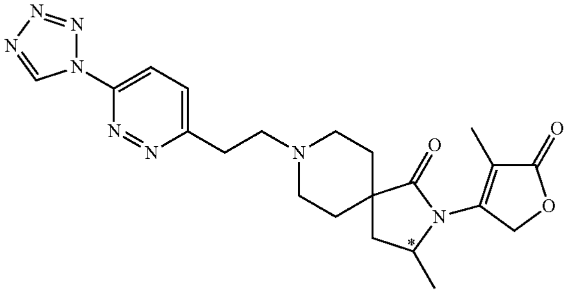 [SMILES: CC1=C(N2C(=O)C3(CCN(CCc4ccc(-n5cnnn5)nn4)CC3)CC2C)COC1=O]<br>3-methyl-2-(4-methyl-5-oxo-2,5-dihydrofuran-3-yl)-1-oxo-8-{2-[6-(1H-tetrazol-1-yl)pyridazin-3-yl]ethyl}-2-aza-8-azoniaspiro[4.5]decane (enantiomer A); LCMS $[M + 1 - 28]^+ = 411.3$<br>The racemic mixture was separated by chiral separation:<br>AS-H (25 × 0.46), 40% MeOH(0.2% TEA)/$CO_2$, 50 mL/min, 220 nM |
| 241 | 38 | 73 (rac.) | 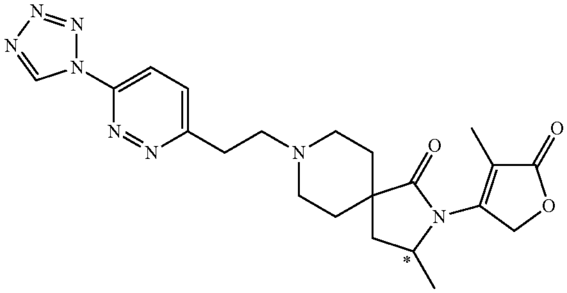 [SMILES: CC1=C(N2C(=O)C3(CCN(CCc4ccc(-n5cnnn5)nn4)CC3)CC2C)COC1=O]<br>3-methyl-2-(4-methyl-5-oxo-2,5-dihydrofuran-3-yl)-1-oxo-8-{2-[6-(1H-tetrazol-1-yl)pyridazin-3-yl]ethyl}-2-aza-8-azoniaspiro[4.5]decane (enantiomer B); LCMS $[M + 1 - 28]^+ = 411.3$<br>The racemic mixture was separated by chiral separation:<br>AS-H (25 × 0.46), 40% MeOH(0.2% TEA)/$CO_2$, 50 mL/min, 220 nM |

TABLE 10-continued compounds prepared following a similar procedure as for EXAMPLE 232 or 233

| EXAMPLE | Olefin or Aldehyde Intermediate | Amine Intermediate | Structure, name and characterization |
|---|---|---|---|
| 242 | 36 | 74B | 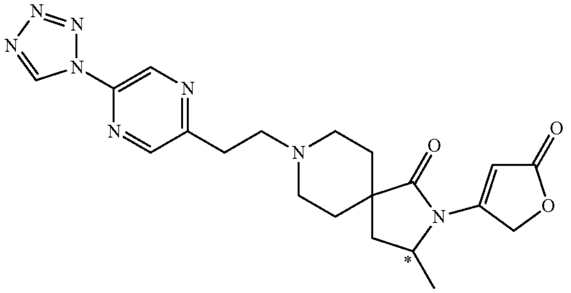 3-methyl-1-oxo-2-(5-oxo-2,5-dihydrofuran-3-yl)-8-{2-[5-(1H-tetrazol-1-yl)pyrazin-2-yl]ethyl}-2-aza-8-azoniaspiro[4.5]decane (from slower enantiomer 74B);; LCMS $[M + 1 - 28]^+ = 397.2$ |
| 243 | 38 | 86A | 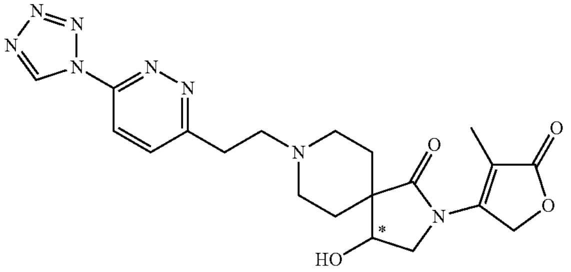 4-hydroxy-2-(4-methyl-5-oxo-2,5-dihydrofuran-3-yl)-1-oxo-8-{2-[6-(1H-tetrazol-1-yl)pyridazin-3-yl]ethyl}-2-aza-8-azoniaspiro[4.5]decane (from fast enantiomer 86A);; LCMS $[M + 1 - 28]^+ = 413$ |
| 244 | 50 | 86A | 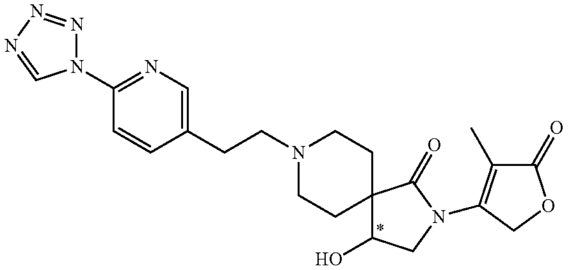 4-hydroxy-2-(4-methyl-5-oxo-2,5-dihydrofuran-3-yl)-1-oxo-8-{2-[6-(1H-tetrazol-1-yl)pyridin-3-yl]ethyl}-2-aza-8-azoniaspiro[4.5]decane (from fast enantiomer 86A); LCMS $[M + 1 - 28]^+ = 412$ |
| 245 | 50 | 86B | 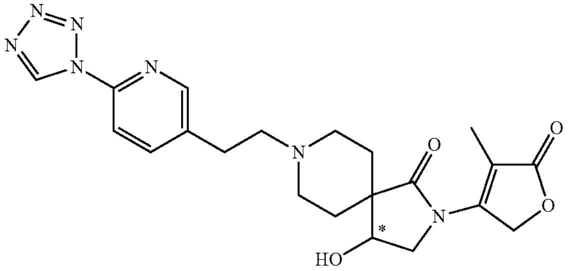 4-hydroxy-2-(4-methyl-5-oxo-2,5-dihydrofuran-3-yl)-1-oxo-8-{2-[6-(1H-tetrazol-1-yl)pyridin-3-yl]ethyl}-2-aza-8-azoniaspiro[4.5]decane (from slower enantiomer 86B);; LCMS $[M + 1 - 28]^+ = 412$ |

TABLE 10-continued

| compounds prepared following a similar procedure as for EXAMPLE 232 or 233 | | | |
|---|---|---|---|
| EXAMPLE | Olefin or Aldehyde Intermediate | Amine Intermediate | Structure, name and characterization |
| 246 | 36 | 74A | 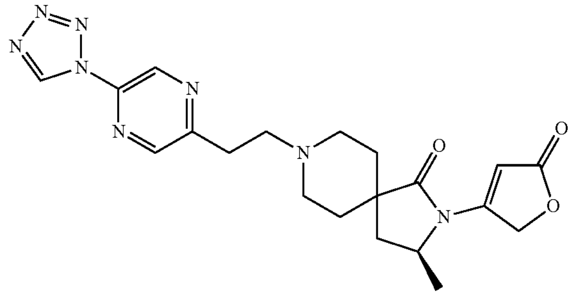 [SMILES: C[C@H]1CC2(CCN(CCc3cnc(-n4cnnn4)cn3)CC2)C(=O)N1C1=CC(=O)OC1] 3(S)-methyl-1-oxo-2-(5-oxo-2,5-dihydrofuran-3-yl)-8-{2-[5-(1H-tetrazol-1-yl)pyrazin-2-yl]ethyl}-2-aza-8-azoniaspiro[4.5]decane; LCMS [M + 1 − 28]+ = 425 |
| 247 | 36 | 96 | 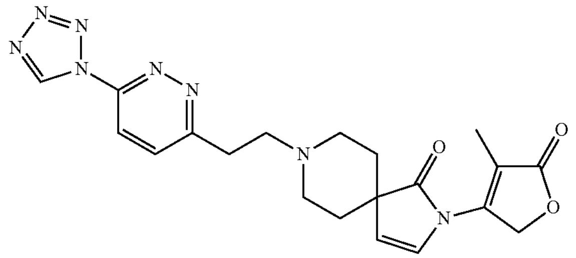 2-(4-methyl-5-oxo-2,5-dihydrofuran-3-yl)-1-oxo-8-{2-[6-(1H-tetrazol-1-yl)pyridazin-3-yl]ethyl}-2-aza-8-azoniaspiro[4.5]dec-3-ene; LCMS [M + 1 − 28]+ = 395 |
| 248 | 39 | 96 | 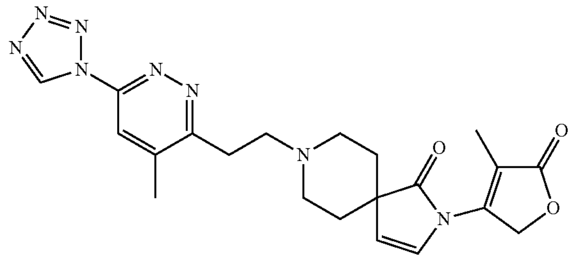 2-(4-methyl-5-oxo-2,5-dihydrofuran-3-yl)-8-{2-[4-methyl-6-(1H-tetrazol-1-yl)pyridazin-3-yl]ethyl}-1-oxo-2-aza-8-azoniaspiro[4.5]dec-3-ene; LCMS [M + 1 − 28]+ = 409 |
| 249 | 38 | 101 | 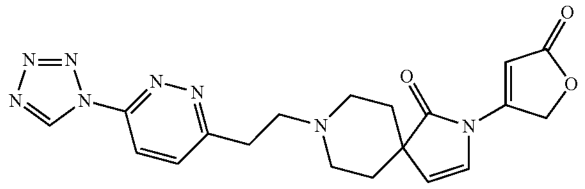 1-oxo-2-(5-oxo-2,5-dihydrofuran-3-yl)-8-{2-[6-(1H-tetrazol-1-yl)pyridazin-3-yl]ethyl}-2-aza-8-azoniaspiro[4.5]dec-3-ene; LCMS [M + 1 − 28]+ = 381 |

TABLE 10-continued compounds prepared following a similar procedure as for EXAMPLE 232 or 233

| EXAMPLE | Olefin or Aldehyde Intermediate | Amine Intermediate | Structure, name and characterization |
|---|---|---|---|
| 250 | 52 | 68 | 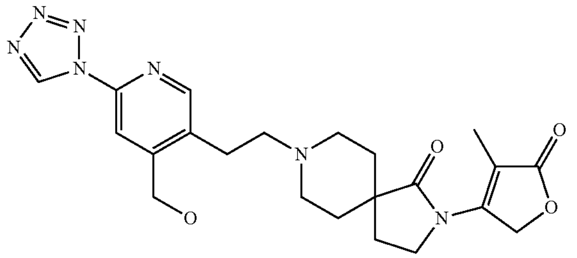 [SMILES: CC1=C(N2CCC3(CCN(CCc4cnc(-n5cnnn5)cc4CO)CC3)C2=O)COC1=O] 8-{2-[4-(hydroxymethyl)-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane; LCMS $[M + 1]^+ = 454$ |
| 251 | 36 | 96 | 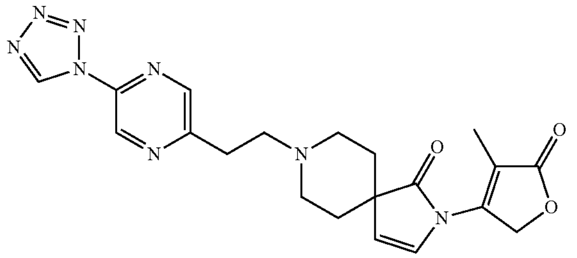 2-(4-methyl-5-oxo-2,5-dihydrofuran-3-yl)-1-oxo-8-{2-[5-(1H-tetrazol-1-yl)pyrazin-2-yl]ethyl}-2-aza-8-azoniaspiro[4.5]dec-3-ene; LCMS $[M + 1 - 28]^+ = 395$ |
| 252 | 37 | 68 | 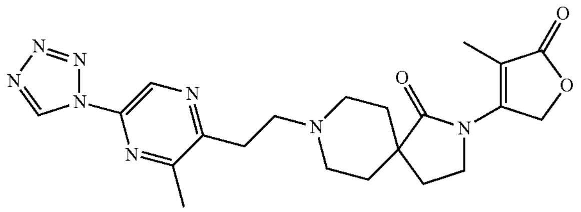 2-(4-methyl-5-oxo-2,5-dihydrofuran-3-yl)-8-{2-[3-methyl-5-(1H-tetrazol-1-yl)pyrazin-2-yl]ethyl}-2,8-diazaspiro[4.5]decan-1-one; LCMS $[M + 1 - 28]^+ = 411$ |
| 253 | 33 | 99 | 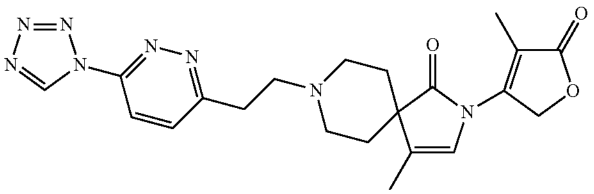 4-methyl-2-(4-methyl-5-oxo-2,5-dihydrofuran-3-yl)-1-oxo-8-{2-[6-(1H-tetrazol-1-yl)pyridazin-3-yl]ethyl}-2-aza-8-azoniaspiro[4.5]dec-3-ene; LCMS $[M + 1 - 28]^+ = 409$ |
| 254 | 51 | 68 | 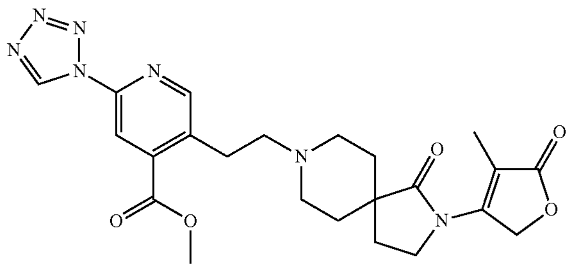 [SMILES: COC(=O)c1cc(-n2cnnn2)ncc1CCN1CCC2(CC1)CCN(C1=C(C)C(=O)OC1)C2=O] methyl 5-(2-(2-(4-methyl-5-oxo-2,5-dihydrofuran-3-yl)-1-oxo-2,8-diazaspiro[4.5]decan-8-yl)ethyl)-2-(1H-tetrazol-1-yl)isonicotinate; LCMS $[M + 1]^+ = 482$ |

TABLE 10-continued compounds prepared following a similar procedure as for EXAMPLE 232 or 233

| EXAMPLE | Olefin or Aldehyde Intermediate | Amine Intermediate | Structure, name and characterization |
|---|---|---|---|
| 255 | 38 | 97 | 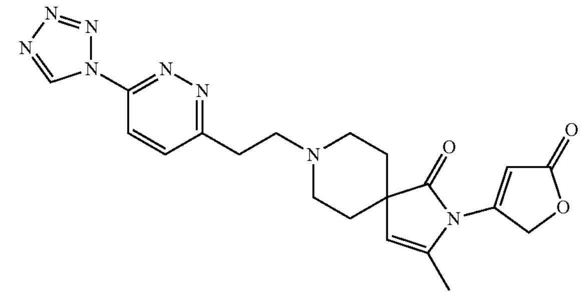 3-methyl-2-(5-oxo-2,5-dihydrofuran-3-yl)-8-{2-[6-(1H-tetrazol-1-yl)pyridazin-3-yl]ethyl}-2,8-diazaspiro[4.5]dec-3-en-1-one; LCMS $[M + 1 - 28]^+ = 395$ |
| 256 | 39 | 99 | 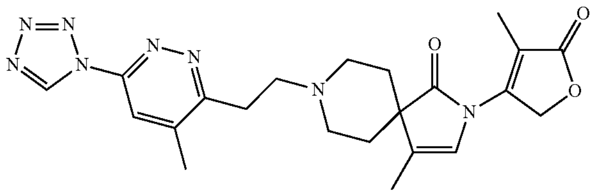 4-methyl-2-(4-methyl-5-oxo-2,5-dihydrofuran-3-yl)-8-{2-[4-methyl-6-(1H-tetrazol-1-yl)pyridazin-3-yl]ethyl}-1-oxo-2-aza-8-azoniaspiro[4.5]dec-3-ene; LCMS $[M + 1 - 28]^+ = 423$ |
| 257 | 38 | 89A | 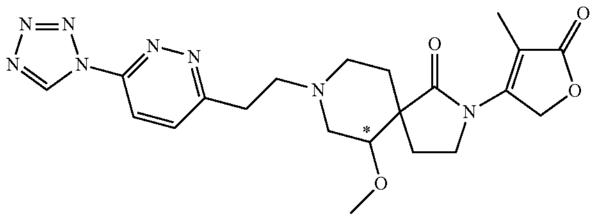 6-methoxy-2-(4-methyl-5-oxo-2,5-dihydrofuran-3-yl)-8-{2-[6-(1H-tetrazol-1-yl)pyridazin-3-yl]ethyl}-2,8-diazaspiro[4.5]decan-1-one (from cis, fast enantiomer 89A); LCMS $[M + 1 - 28]^+ = 427$ |
| 258 | 38 | 89B | 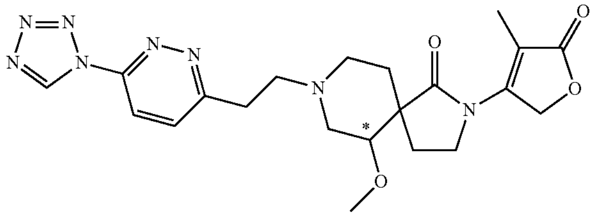 6-methoxy-2-(4-methyl-5-oxo-2,5-dihydrofuran-3-yl)-8-{2-[6-(1H-tetrazol-1-yl)pyridazin-3-yl]ethyl}-2,8-diazaspiro[4.5]decan-1-one (from cis, slower enantiomer 89B); LCMS $[M + 1 - 28]^+ = 427$ |

TABLE 10-continued

| compounds prepared following a similar procedure as for EXAMPLE 232 or 233 | | | |
|---|---|---|---|
| EXAMPLE | Olefin or Aldehyde Intermediate | Amine Intermediate | Structure, name and characterization |
| 259 | 39 | 89A | 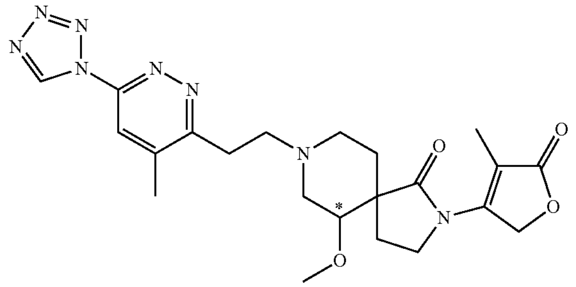 6-methoxy-2-(4-methyl-5-oxo-2,5-dihydrofuran-3-yl)-8-{2-[4-methyl-6-(1H-tetrazol-1-yl)pyridazin-3-yl]ethyl}-2,8-diazaspiro[4.5]decan-1-one (from cis, fast enantiomer 89A); LCMS $[M + 1 - 28]^+ = 441$ |
| 260 | 39 | 89B | 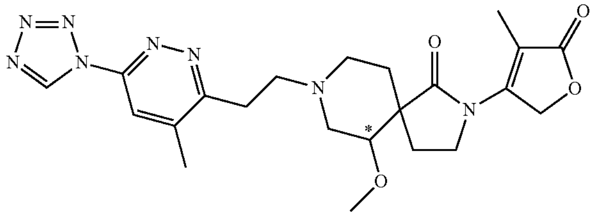 6-methoxy-2-(4-methyl-5-oxo-2,5-dihydrofuran-3-yl)-8-{2-[4-methyl-6-(1H-tetrazol-1-yl)pyridazin-3-yl]ethyl}-2,8-diazaspiro[4.5]decan-1-one (from cis, enantiomer 89B); LCMS $[M + 1 - 28]^+ = 441$ |
| 261 | 37 | 74A | 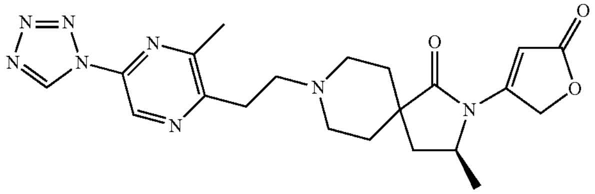 (3S)-3-methyl-8-{2-[3-methyl-5-(1H-tetrazol-1-yl)pyrazin-2-yl]ethyl}-2-(5-oxo-2,5-dihydrofuran-3-yl)-2,8-diazaspiro[4.5]decan-1-one; LCMS $[M + 1 - 28]^+ = 411.1$ |
| 262 | 39 | 74A | 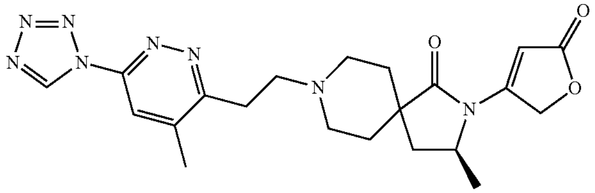 (3S)-3-methyl-8-{2-[4-methyl-6-(1H-tetrazol-1-yl)pyridazin-3-yl]ethyl}-2-(5-oxo-2,5-dihydrofuran-3-yl)-2,8-diazaspiro[4.5]decan-1-one; LCMS $[M + 1 - 28]^+ = 411.2$ |
| 263 | 37 | 96 | 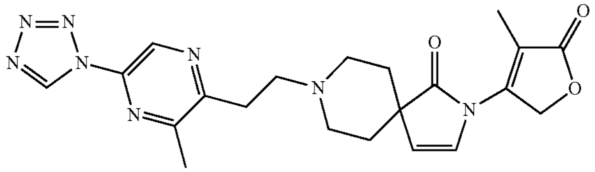 2-(4-methyl-5-oxo-2,5-dihydrofuran-3-yl)-8-{2-[3-methyl-5-(1H-tetrazol-1-yl)pyrazin-2-yl]ethyl}-1-oxo-2-aza-8-azoniaspiro[4.5]dec-3-ene; LCMS $[M + 1 - 28]^+ = 409$ |

TABLE 10-continued compounds prepared following a similar procedure as for EXAMPLE 232 or 233

| EXAMPLE | Olefin or Aldehyde Intermediate | Amine Intermediate | Structure, name and characterization |
|---|---|---|---|
| 264 | 38 | 74A | 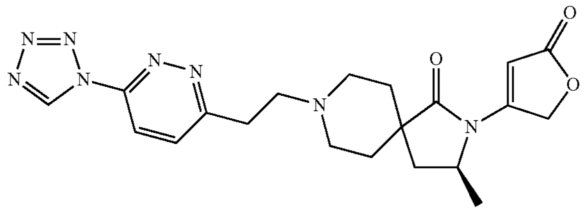 (3S)-3-methyl-2-(5-oxo-2,5-dihydrofuran-3-yl)-8-{2-[6-(1H-tetrazol-1-yl)pyridazin-3-yl]ethyl}-2,8-diazaspiro[4.5]decan-1-one; LCMS $[M + 1 - 28]^+ = 397.4$ |
| 265 | 38 | 90A | 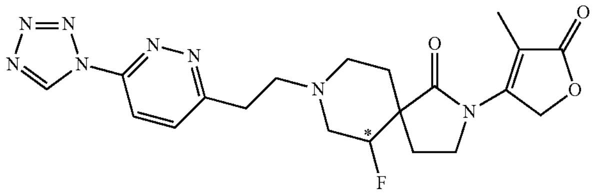 6-fluoro-2-(4-methyl-5-oxo-2,5-dihydrofuran-3-yl)-8-{2-[6-(1H-tetrazol-1-yl)pyridazin-3-yl]ethyl}-2,8-diazaspiro[4.5]decan-1-one (from trans, fast enantiomer 90A); LCMS $[M + 1 - 28]^+ = 415$ |
| 266 | 38 | 90B | 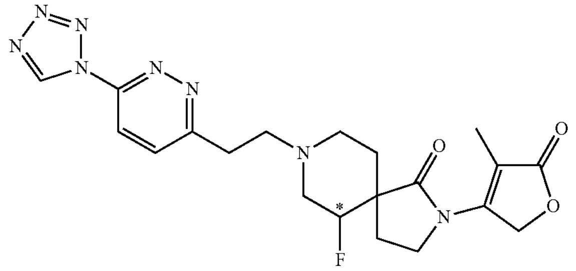 6-fluoro-2-(4-methyl-5-oxo-2,5-dihydrofuran-3-yl)-8-{2-[6-(1H-tetrazol-1-yl)pyridazin-3-yl]ethyl}-2,8-diazaspiro[4.5]decan-1-one (from trans, slower enantiomer 90B); LCMS $[M + 1 - 28]^+ = 415$ |
| 267 | 39 | 90A | 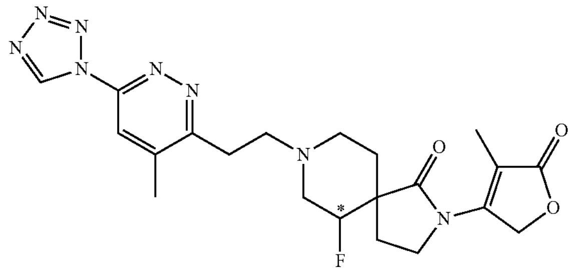 6-fluoro-2-(4-methyl-5-oxo-2,5-dihydrofuran-3-yl)-8-{2-[4-methyl-6-(1H-tetrazol-1-yl)pyridazin-3-yl]ethyl}-2,8-diazaspiro[4.5]decan-1-one (from trans, fast enantiomer 90A); LCMS $[M + 1 - 28]^+ = 429$ |

TABLE 10-continued compounds prepared following a similar procedure as for EXAMPLE 232 or 233

| EXAMPLE | Olefin or Aldehyde Intermediate | Amine Intermediate | Structure, name and characterization |
|---|---|---|---|
| 268 | 39 | 90B | 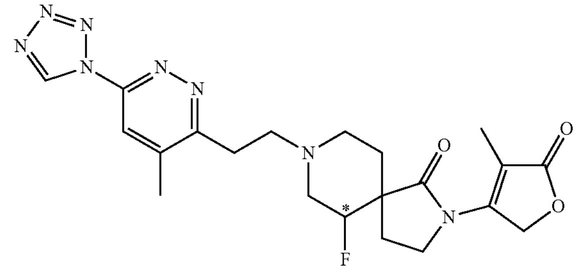 6-fluoro-2-(4-methyl-5-oxo-2,5-dihydrofuran-3-yl)-8-{2-[4-methyl-6-(1H-tetrazol-1-yl)pyridazin-3-yl]ethyl}-2,8-diazaspiro[4.5]decan-1-one (from trans, slower enantiomer 90B); LCMS $[M+1-28]^+ = 429$ |
| 269 | 37 | 69 | 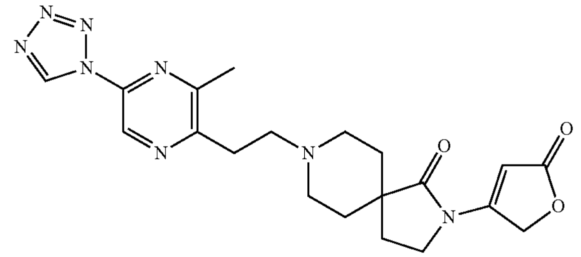 [SMILES: Cc1nc(-n2cnnn2)cnc1CCN1CCC2(CC1)CCN(C1=CC(=O)OC1)C2=O] 8-{2-[3-methyl-5-(1H-tetrazol-1-yl)pyrazin-2-yl]ethyl}-2-(5-oxo-2,5-dihydrofuran-3-yl)-2,8-diazaspiro[4.5]decan-1-one; LCMS $[M+1]^+ = 425$ |
| 270 | 44 | 74A | 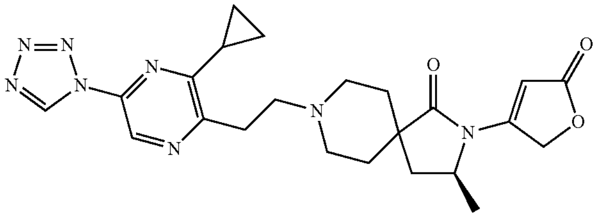 [SMILES: C[C@H]1CC2(CCN(CCc3ncc(-n4cnnn4)nc3C3CC3)CC2)C(=O)N1C1=CC(=O)OC1] (S)-8-(2-(3-cyclopropyl-5-(1H-tetrazol-1-yl)pyrazin-2-yl)ethyl)-3-methyl-2-(5-oxo-2,5-dihydrofuran-3-yl)-2,8-diazaspiro[4.5]decan-1-one; LCMS $[M+1]^+ = 465.1$ |
| 271 | 45 | 74A | 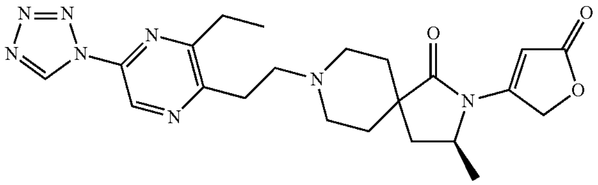 [SMILES: CCc1nc(-n2cnnn2)cnc1CCN1CCC2(CC1)C[C@H](C)N(C1=CC(=O)OC1)C2=O] (S)-8-(2-(3-ethyl-5-(1H-tetrazol-1-yl)pyrazin-2-yl)ethyl)-3-methyl-2-(5-oxo-2,5-dihydrofuran-3-yl)-2,8-diazaspiro[4.5]decan-1-one; LCMS $[M+1]^+ = 453.2$ |
| 272 | 42 | 96 | 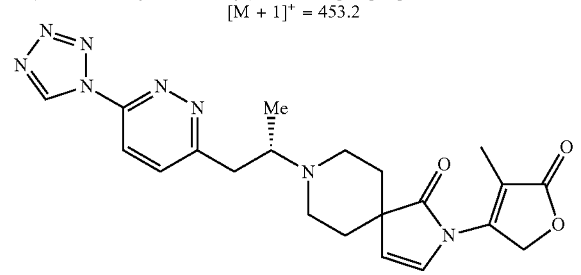 (S)-8-(1-(6-(1H-tetrazol-1-yl)pyridazin-3-yl)propan-2-yl)-2-(4-methyl-5-oxo-2,5-dihydrofuran-3-yl)-2,8-diazaspiro[4.5]dec-3-en-1-one (enantiomer A); LCMS $[M+1]^+ = 409$ The recemate was resolved on chiral AS column, using conditions 40% MeOH (0.2% $NH_4OH$)/$CO_2$, 220 nm |

TABLE 10-continued compounds prepared following a similar procedure as for EXAMPLE 232 or 233

| EXAMPLE | Olefin or Aldehyde Intermediate | Amine Intermediate | Structure, name and characterization |
|---|---|---|---|
| 273 | 42 | 96 | 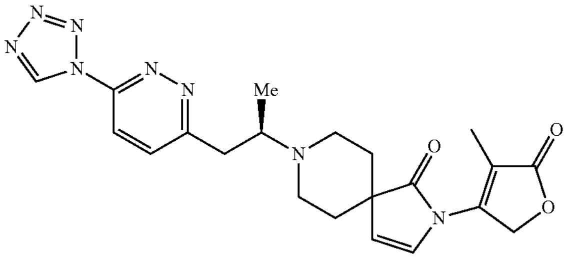<br>(R)-8-(1-(6-(1H-tetrazol-1-yl)pyridazin-3-yl)propan-2-yl)-2-(4-methyl-5-oxo-2,5-dihydrofuran-3-yl)-2,8-diazaspiro[4.5]dec-3-en-1-one (enantiomer B); LCMS $[M + 1]^+ = 409$<br>The recemate was resolved on chiral AS column, using conditions 40% MeOH (0.2% $NH_4OH$)/$CO_2$, 220 nm |
| 274 | 43 | 96 | 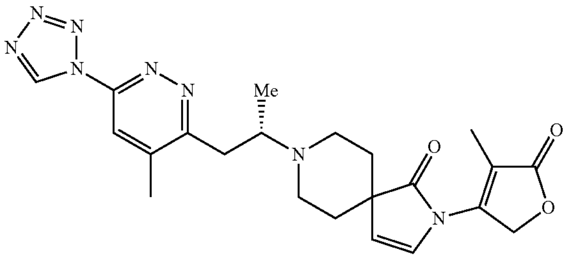<br>(S)-2-(4-methyl-5-oxo-2,5-dihydrofuran-3-yl)-8-(1-(4-methyl-6-(1H-tetrazol-1-yl)pyridazin-3-yl)propan-2-yl)-2,8-diazaspiro[4.5]dec-3-en-1-one (enantiomer A); LCMS $[M + 1]^+ = 423$<br>The recemate was resolved on chiral AS column, using conditions 40% MeOH (0.2% $NH_4OH$)/$CO_2$, 220 nm |
| 275 | 43 | 96 | 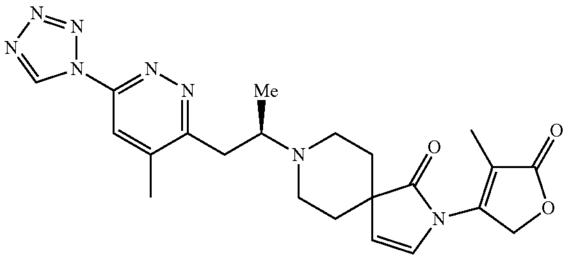<br>(R)-2-(4-methyl-5-oxo-2,5-dihydrofuran-3-yl)-8-(1-(4-methyl-6-(1H-tetrazol-1-yl)pyridazin-3-yl)propan-2-yl)-2,8-diazaspiro[4.5]dec-3-en-1-one (enantiomer B); LCMS $[M + 1]^+ = 423$<br>The recemate was resolved on chiral AS column, using conditions 40% MeOH (0.2% $NH_4OH$)/$CO_2$, 220 nm |

EXAMPLE 276

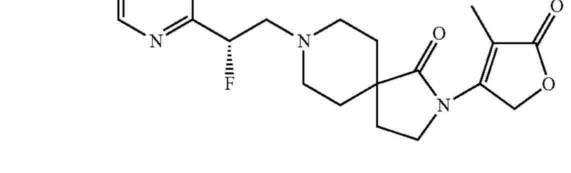

(S)-8-(2-(5-(1H-Tetrazol-1-yl)pyrazin-2-yl)-2-fluoroethyl)-2-(4-methyl-5-oxo-2,5-dihydrofuran-3-yl)-2,8-diazaspiro[4.5]decan-1-one To a solution of $Et_3N.3HF$ (185 μL, 1.14 mmol) and $Et_3N$ (79 μL, 0.568 mmol) in DCM (5.7 mL) were added Xtal-Fluor-E (195 mg, 0.851 mmol) and 8-{(2R)-2-hydroxy-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane (250 mg, 0.568 mmol) at −78° C. The mixture was stirred overnight while warmed to rt, and quenched with $NaHCO_3$ aqueous. The organic layer was separated, and the aqueous layer was extracted with DCM (30 mL). The combined organic layers were dried ($MgSO_4$) and concentrated. The residue was purified by column chromatography (0-10% MeOH/DCM) to give the title compound. LCMS $[M+1-28]^+=415$.

TABLE 11

| compounds prepared following a similar procedure as for EXAMPLE 276 | | |
|---|---|---|
| EXAMPLE | Starting Material | Structure, name and characterization |
| 277 | Example 24 | 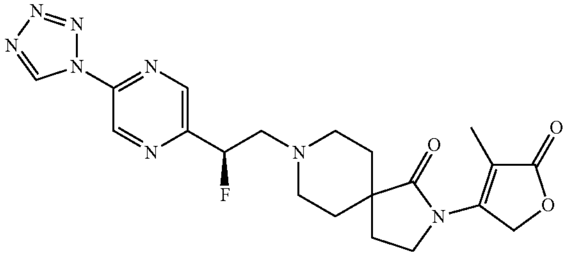 8-{(2R)-2-fluoro-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 415$ |
| 278 | Example 33 | 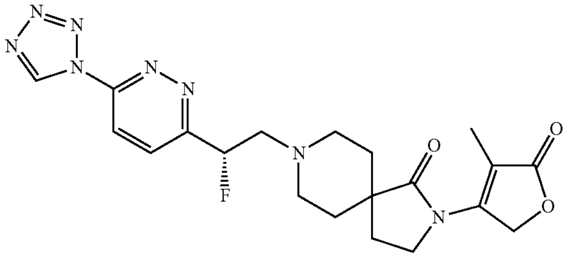 8-{(2S)-2-fluoro-2-[6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 415$ |
| 279 | Example 23 | 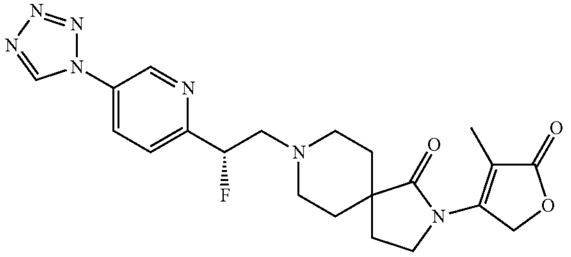 [SMILES: CC1=C(N2CCC3(CCN(C[C@H](F)c4ccc(-n5cnnn5)cn4)CC3)C2=O)COC1=O] 8-{(2S)-2-fluoro-2-[5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane; LCMS $[M + 1]^+ = 442$ |
| 280 | Example 22 | 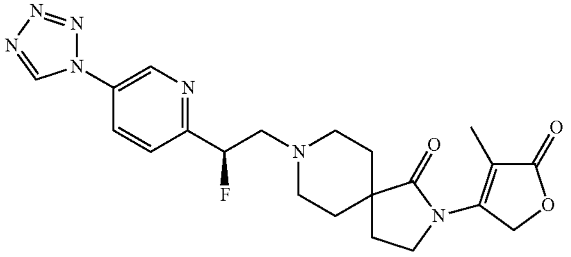 [SMILES: CC1=C(N2CCC3(CCN(C[C@@H](F)c4ccc(-n5cnnn5)cn4)CC3)C2=O)COC1=O] 8-{(2R)-2-fluoro-2-[5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane; LCMS $[M + 1]^+ = 442$ |

EXAMPLE 281

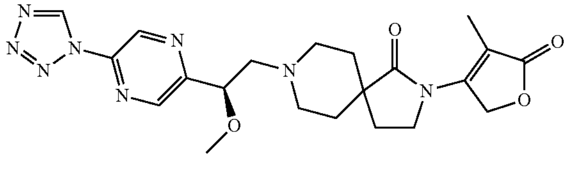 [SMILES: CO[C@H](CN1CCC2(CC1)CCN(C1=C(C)C(=O)OC1)C2=O)c1cnc(-n2cnnn2)cn1]

8-{(2R)-2-methoxy-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane 8-{(2R)-2-Methoxy-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane To a solution of 2-(4-methyl-5-oxo-2,5-dihydrofuran-3-yl)-2,8-diazaspiro[4.5]decan-1-one (105 mg, 0.418 mmol) and (S)-2-(5-(1H-tetrazol-1-yl)pyrazin-2-yl)-2-methoxyacetaldehyde (111 mg, 0.502 mmol) in DCM (25 ml) were added sodium triacetoxyhydroborate (266 mg, 1.255 mmol) and a few drops of AcOH at rt. The mixture was stirred at the same temperature for 20 min, quenched with $NaHCO_3$ aqueous. The organic layer was separated, and the aqueous layer was extracted with DCM (20 ml). The combined organic layers were dried (MgSO4) and concentrated. The residue was purified over preparative TLC (20% MeOH in EtOAc. LCMS $[M+1-28]^+$=426.92.

TABLE 12 compounds prepared following a similar procedure as for EXAMPLE 281

| EXAMPLE | Aldehyde | Amine | Structure, name and characterization |
|---|---|---|---|
| 282 | 49 | 68 | 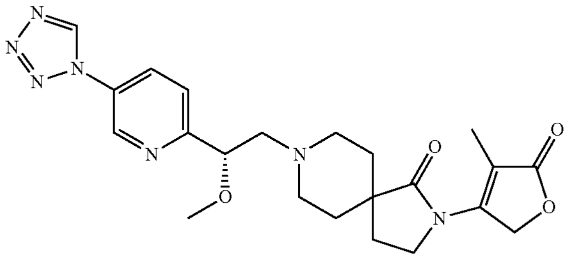 [SMILES: CO[C@@H](CN1CCC2(CC1)CCN(C1=C(C)C(=O)OC1)C2=O)c1ccc(-n2cnnn2)cn1] 8-{(2S)-2-methoxy-2-[5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane LCMS $[M + 1]^+$ = 454.5 |
| 283 | 46 | 68 | 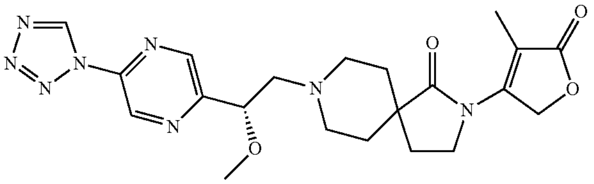 [SMILES: CO[C@@H](CN1CCC2(CC1)CCN(C1=C(C)C(=O)OC1)C2=O)c1cnc(-n2cnnn2)cn1] 8-{(2S)-2-hydroxy-2-[2-methyl-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane; LCMS $[M + 1]^+$ = 455.6 |
| 284 | 49 (rac.) | 69 | 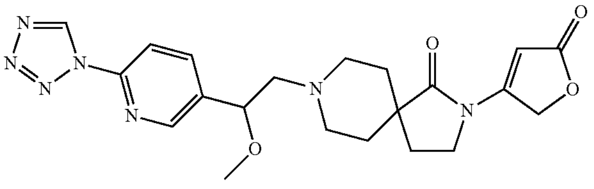 [SMILES: COC(CN1CCC2(CC1)CCN(C1=CC(=O)OC1)C2=O)c1ccc(-n2cnnn2)nc1] 8-{(2R)-2-methoxy-2-[6-(1H-tetrazol-1-yl)pyridinium-3-yl]ethyl}-1-oxo-2-(5-oxo-2,5-dihydrofuran-3-yl)-2-aza-8-azoniaspiro[4.5]decane (racemic); LCMS $[M + 1]^+$ = 440.2 |

TABLE 12-continued

| EXAMPLE | Aldehyde | Amine | Structure, name and characterization |
|---|---|---|---|
| | | | compounds prepared following a similar procedure as for EXAMPLE 281 |
| 285 | 47 | 68 | 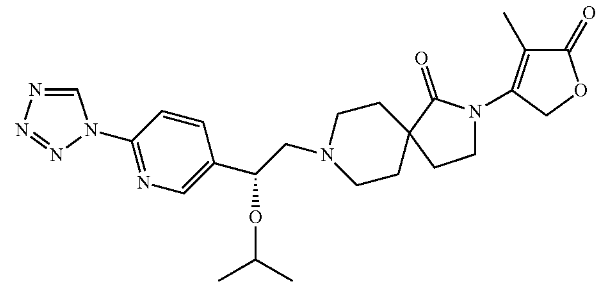 8-{(2R)-2-(1-methylethoxy)-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane; LCMS $[M + 1 - 28]^+ = 454.2$ |
| 286 | 46 | 74A | 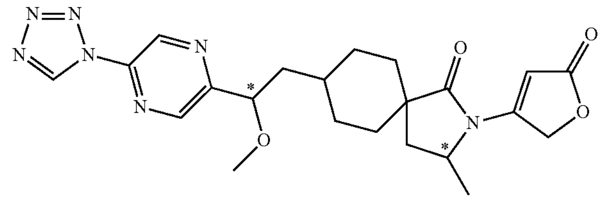 (3R)-8-{(2R)-2-methoxy-2-[5-(1H-tetrazol-1-yl)pyrazin-2-yl]ethyl}-3-methyl-1-oxo-2-(5-oxo-2,5-dihydrofuran-3-yl)-2-aza-8-azoniaspiro[4.5]decane (from 2R-enantiomer 46 and fast enantiomer 74A); LCMS $[M + 1 - 28]^+ = 427.5$ |
| 287 | 48 | 74A | 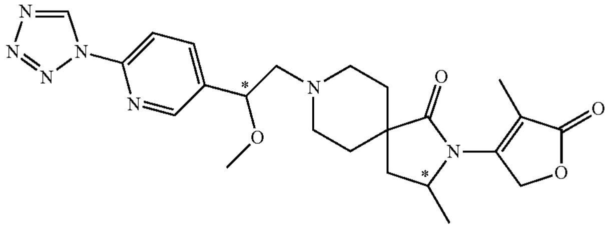 (3R)-8-{(2S)-2-methoxy-2-[6-(1H-tetrazol-1-yl)pyridin-3-yl]ethyl}-3-methyl-2-(4-methyl-5-oxo-2,5-dihydrofuran-3-yl)-1-oxo-2-aza-8-azoniaspiro[4.5]decane (from 2S-enatiomer 48, and fast enantiomer 74A);; LCMS $[M + 1 - 28]^+ = 440.2$ |
| 288 | 48 | 70 | 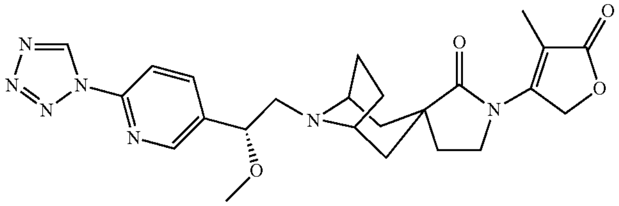 [SMILES: CO[C@@H](CN1C2CCC1CC1(CCN(C3=C(C)C(=O)OC3)C1=O)C2)c1ccc(-n2cnnn2)nc1] (1R,3R,5S)-S-((R)-2-(6-(1H-tetrazol-1-yl)pyridin-3-yl)-2-methoxyethyl)-1'-(4-methyl-5-oxo-2,5-dihydrofuran-3-yl)-8-azaspiro[bicyclo[3.2.1]octane-3,3'-pyrrolidin]-2'-one; LCMS $[M + 1]^+ = 480.5$ |
| 289 | 49 | 70 | 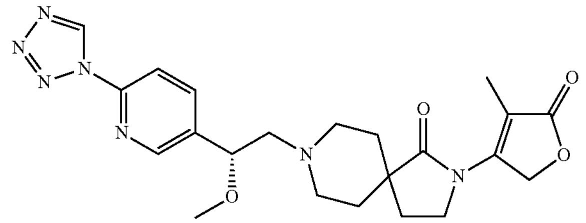 [SMILES: CO[C@@H](CN1CCC2(CC1)CCN(C1=C(C)C(=O)OC1)C2=O)c1ccc(-n2cnnn2)nc1] (R)-8-(2-(6-(1H-tetrazol-1-yl)pyridin-3-yl)-2-methoxyethyl)-2-(4-methyl-5-oxo-2,5-dihydrofuran-3-yl)-2,8-diazaspiro[4.5]decan-1-one; LCMS $[M + 1]^+ = 454.5$ |

EXAMPLE 290 and 291

290

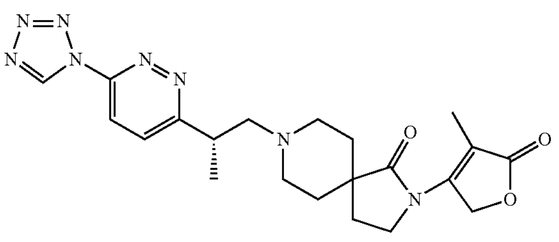

291

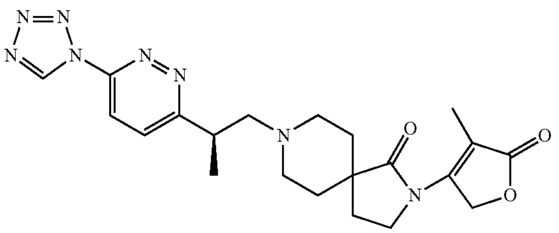

EXAMPLE 290

2-(4-methyl-5-oxo-2,5-dihydrofuran-3-yl)-8-{(2S)-2-[6-(1H-tetrazol-1-yl)pyridazin-3-yl]propyl}-2,8-diazaspiro[4.5]decan-1-one (enantiomer A, faster eluting)

EXAMPLE 291

2-(4-methyl-5-oxo-2,5-dihydrofuran-3-yl)-8-{(2R)-2-[6-(1H-tetrazol-1-yl)pyridazin-3-yl]propyl}-2,8-diazaspiro[4.5]decan-1-one (Enantiomer B, slower eluting)

Step A: 3-chloro-6-(1H-tetrazol-1-yl)pyridazine

To a solution of 6-chloropyridazin-3-amine (7.45 g, 57.5 mmol) in ethyl acetate (150 ml) was added trimethylsilyl 2,2,2-trifluoroacetate (16.88 ml, 98 mmol). After the mixture was stirred for 5 min, triethoxymethane (17.21 ml, 103 mmol) was added. The resulting mixture was stirred another five min, and azidotrimethylsilane (12.09 ml, 92 mmol) was added. Stirring continued at rt for 2 days, and the mixture was concentrated under reduced pressure. Recrystallization of the residue from ethyl acetate afforded the title compound.

Step B: 3-(prop-1-en-2-yl)-6-(1H-tetrazol-1-yl)pyridazine

A mixture of 3-chloro-6-(1H-tetrazol-1-yl)pyridazine (2.00 g, 11.0 mmol), 4,4,5,5-tetramethyl-2-(prop-1-en-2-yl)-1,3,2-dioxaborolane (2.24 mL, 11.5 mmol), KF (1.28 g, 22.0 mmol) and $PdCl_2$(dppf) (0.40 g, 0.55 mmol) in a solvent mixture of dioxane (80 mL) and water (20 mL) was stirred at 80° C. for 16 hours under $N_2$. The mixture was cooled to rt, diluted with EtOAc (100 mL) and filtered. The filtrate was concentrated and the residue was purified by silica gel (PE/EtOAc=5:1 to 3:1) to afford the title compound.

Step C: 3-(2-methyloxiran-2-yl)-6-(1H-tetrazol-1-yl)pyridazine

A mixture of 3-(prop-1-en-2-yl)-6-(1H-tetrazol-1-yl)pyridazine (800 mg, 4.25 mmol) and NBS (908 mg, 5.10 mmol) in a solution of t-butanol (15 mL) and water (30 mL) was heated at 80° C. for 2 hours. The mixture was cooled to 5° C., and a solution of NaOH (510 mg, 12.8 mmol) in water (41 mL) was added over 10 min. After stirring at 5° C. for 1 h, the mixture was extracted with $CH_2Cl_2$ (50 mL×2). The combined organic layers were washed with brine, dried over $Na_2SO_4$, and concentrated to afford the title compound.

Step D: 2-(6-(1H-tetrazol-1-yl)pyridazin-3-yl)propan-1-ol

A mixture of 3-(2-methyloxiran-2-yl)-6-(1H-tetrazol-1-yl)pyridazine (590 mg, 2.89 mmol) and Pd/C (590 mg, 10%) in EtOH (20 mL) and THF (60 mL) was stirred at rt for 2 h under hydrogen atmosphere (1 atm). The mixture was filtered, and the filter cake was washed with EtOH (50 mL). The filtrate was concentrated and the residue was purified via Biotage column (EtOAc in DCM: 0 to 60%) to afford the title compound.

Step E: 2-(6-(1H-tetrazol-1-yl)pyridazin-3-yl)propanal

A mixture of 2-(6-(1H-tetrazol-1-yl)pyridazin-3-yl)propan-1-ol (220 mg, 1.07 mmol) and DMP (678 mg, 1.60 mmol) in $CHCl_3$ (20 mL) was stirred at rt for 2 h. Excess DMP was quenched with saturated aqueous $Na_2S_2O_3$ (20 mL). The organic layer was separated, dried over $Na_2SO_4$, and concentrated to afford the title compound.

Step F: 8-(2-(6-(1H-tetrazol-1-yl)pyridazin-3-yl)propyl)-2-(4-methyl-5-oxo-2,5-dihydrofuran-3-yl)-2,8-diazaspiro[4.5]decan-1-one A mixture of 2-(6-(1H-tetrazol-1-yl)pyridazin-3-yl)propanal (217 mg, 1.06 mmol), 2-(4-methyl-5-oxo-2,5-dihydrofuran-3-yl)-2,8-diazaspiro[4.5]decan-1-one (132 mg, 0.54 mmol) and three drops of HOAc in $CHCl_3$ (20 mL) was stirred at 20° C. for 1 hour, then $NaBH(OAc)_3$ (674 mg, 3.18 mmol) was added. The resulting mixture was stirred at rt for 16 h, and quenched with water (5 mL). The organic layer was separated and concentrated. The residue was purified by preparative TLC (EtOAc:MeOH=5:1) to give the racemic title compound which was separated by SFC (Chiralpak AS-H 150*4.6 mm I.D., 5 um; 40% ethanol (0.05% DEA) in $CO_2$) to afford single enantiomer A (Ex. 290, faster eluting); and enantiomer B (Ex. 291, slower eluting). $^1$H-NMR (400 MHz, $CDCl_3$) δ ppm 9.75 (s, 1 H), 8.23 (d, J=9.2 Hz, 1 H), 7.69 (d, J=9.2 Hz, 1 H), 5.19 (s, 2 H), 3.96 (m, 2 H), 3.50 (m, 1 H), 2.98 (m, 1 H), 2.80 (m, 1 H), 2.65 (m, 2 H), 2.25 (m, 1 H), 2.10 (m, 3 H), 2.05 (s, 3 H), 1.75 (m, 2 H), 1.40 (m, 5 H). LCMS $[M+1]^+$=439.

EXAMPLE 293 and 294

293

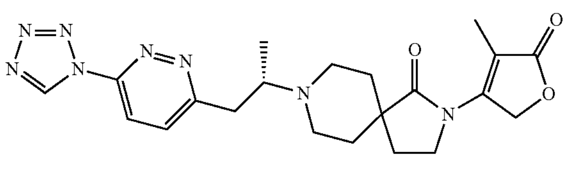

-continued

294

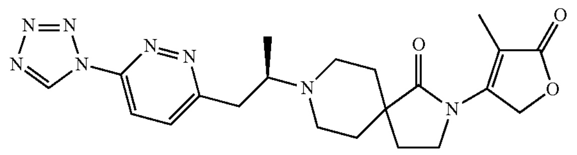

EXAMPLE 293

2-(4-Methyl-5-oxo-2,5-dihydrofuran-3-yl)-8-{(1S)-1-methyl-2-[6-(1H-tetrazol-1-yl)pyridazin-3-yl]ethyl}-2,8-diazaspiro[4.5]decan-1-one (enantiomer A)

EXAMPLE 294

2-(4-Methyl-5-oxo-2,5-dihydrofuran-3-yl)-8-{(1R)-1-methyl-2-[6-(1H-tetrazol-1-yl)pyridazin-3-yl]ethyl}-2,8-diazaspiro[4.5]decan-1-one (enantiomer B)

A solution of 3-(prop-1-en-1-yl)-6-(1H-tetrazol-1-yl)pyridazine (500 mg, 2.66 mmol), 2-(4-methyl-5-oxo-2,5-dihydrofuran-3-yl)-2,8-diazaspiro[4.5]decan-1-one (332 mg, 1.33 mmol), Rh(COD)$BF_4$ (80 mg, 0.037 mmol) and DPEphos (80 mg, 0.049 mmol) in toluene (8 mL) was purged air three times with $N_2$, and heated at 70° C. for 48 h. The reaction mixture was purified by preparative TLC to afford the racemate of the title compound which was then separated by SFC (Chiralpak AS-H 150*4.6 mm I.D., 5 um, methanol (0.05% DEA) in $CO_2$ from 5% to 40%) to give Ex. 293 (enantiomer A, fast eluted) and Ex. 294 (enantiomer B, slow eluted). $^1$H-NMR (400 MHz, $CDCl_3$) δ ppm 9.76 (s, 1 H), 8.26 (d, J=9.0 Hz, 1 H), 7.87 (br, 1 H), 5.22 (s, 2 H), 4.03 (t, J=6.8 Hz, 2H), 3.58-3.08 (m, 4 H), 2.15 (t, J=6.8 Hz, 2 H), 2.05 (s, 3 H), 2.00-1.71 (m, 7 H), 1.26 (br, 5 H). LCMS $[M+1]^+$=439.

EXAMPLE 295 and 296

295

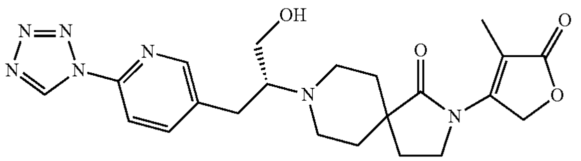

296

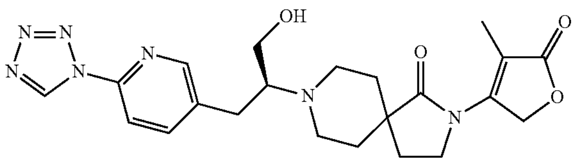

EXAMPLE 295

8-[(1R)-2-hydroxy-1-{[6-(1H-tetrazol-1-yl)pyridin-3-yl]methyl}ethyl]-2-(4-methyl-5-oxo-2,5-dihydrofuran-3-yl)-2,8-diazaspiro[4.5]decan-1-one (enantimer A)

EXAMPLE 296

8-[(1S)-2-hydroxy-1-{[6-(1H-tetrazol-1-yl)pyridin-3-yl]methyl}ethyl]-2-(4-methyl-5-oxo-2,5-dihydrofuran-3-yl)-2,8-diazaspiro[4.5]decan-1-one (enantiomer B)

Step A: 5-bromo-2-(1H-tetrazol-1-yl)pyridine

To solution of 5-bromopyridin-2-amine (5.00 g, 29 mmol) in AcOH (100 mL) was added $CH(OEt)_3$ (21.50 g, 145 mmol), followed by addition of $NaN_3$ (1.90 g, 29 mmol). The mixture was stirred at 80° C. for 2 h, cooled to rt, and adjusted to about pH=6. The mixture was filtered, and the cake was washed with water. The filtered cake was purified by flash column chromatography (0-30% ethyl acetate in petroleum ether) to give the title compound.

Step B: 5-allyl-2-(1H-tetrazol-1-yl)pyridine

To a solution of 5-bromo-2-(1H-tetrazol-1-yl)pyridine (3.00 g, 13.3 mmol) in THF (50 mL) were added allyltributylstannane (5.30 g, 15.9 mmol), LiCl (1.60 g, 39.9 mmol) and $Pd(PPh_3)_4$(1.53 g, 1.33 mmol) under nitrogen atmosphere. The mixture was stirred at reflux for 18 h, poured into ice-water, and extracted with ethyl acetate. The organic extract was separated, washed with water and brine, dried over $MgSO_4$, and concentrated. The crude material was purified by flash column chromatography (0-40% ethyl acetate in petroleum ether) to give the title compound.

Step C: 3-(6-(1H-tetrazol-1-yl)pyridin-3-yl)propane-1,2-diol

To a solution of 5-allyl-2-(1H-tetrazol-1-yl)pyridine (1.50 g, 8.0 mmol) in acetone (30 mL) and water (10 mL) were added $OsO_4$ (0.21 g, 0.8 mmol) and NMO (5.50 g, 9.6 mmol). The mixture was stirred at 25° C. for 18 h, diluted with water (30 mL) and extracted with $CH_2Cl_2$ (3×40 mL). The combined organic layers were washed with brine (2×40 mL), dried over $MgSO_4$, and concentrated. The residue was purified by flash column chromatography (0-10% methanol in dichloromethane) to give the title compound.

Step D: 1-(6-(1H-tetrazol-1-yl)pyridin-3-yl)-3-((tert-butyldimethylsilyl)oxy)propan-2-ol To a solution of 5-(2,3-dihydroxypropyl)-4-methylisobenzofuran-1(3H)-one (2.00 g, 9.0 mmol) in dry DMF (20 mL) were added imidazole (1.20 g, 18.0 mmol) and TBS-C1 (1.50 g, 9.9 mmol). After stirred at rt for 2.5 h, the reaction mixture was diluted with $CH_2Cl_2$, washed with water (20 mL) and saturated $NaHCO_3$ (20 mL). The combined aqueous layers were extracted five times with $CH_2Cl_2$. The combined organic layers were washed with brine (50 mL), dried over $Na_2SO_4$, and concentrated. The residue was purified by flash column chromatography (0-60% ethyl acetate in petroleum ether) to give the title compound.

Step E: 1-(6-(1H-tetrazol-1-yl)pyridin-3-yl)-3-((tert-butyldimethylsilyl)oxy)propan-2-one To a solution of 1-(6-(1H-tetrazol-1-yl)pyridin-3-yl)-3-((tert-butyldimethylsilyl)oxy)propan-2-ol (1.00 g, 3.0 mmol) in $CH_2Cl_2$(30 mL) was added DMP (6.20 g, 15.0 mmol). The mixture was stirred at rt for 12 h, filtered through a short pad of $SiO_2$. The filtrate was concentrated. The crude product was purified by flash column chromatography (0-60% ethyl acetate in petroleum ether) to give the title compound.

Step F: 8-(1-(6-(1H-tetrazol-1-yl)pyridin-3-yl)-3-((tert-butyldimethylsilyl)oxy)propan-2-yl)-2-(4-methyl-5-oxo-2,5-dihydrofuran-3-yl)-2,8-diazaspiro[4.5]decan-1-one To a solution of 1-(6-(1H-tetrazol-1-yl)pyridin-3-yl)-3-((tert-butyldimethylsilyl)oxy)propan-2-one (0.50 g, 1.5 mmol) in methanol (20 mL) were added 2-(4-methyl-5-oxo-2,5-dihydrofuran-3-yl)-2,8-diazaspiro[4.5]decan-1-one (0.45 g, 1.8 mmol) and titanium(IV) isopropoxide (2.10 g, 7.5 mmol). The mixture was stirred at rt for 48 h, and sodium cyanoborohyride (190 mg, 3.0 mmol) was added. The resulting reaction mixture was stirred at rt for further 20 h. Water (10 mL) was added while stirring. The inorganic precipitate was filtered off, and washed with methanol. The filtrate was concentrated to give the crude product which was dissolved in ethyl acetate to remove the remaining inorganic solids by filtration. The filtrate was concentrated, and the residue was purified by flash column chromatography (0-10% methanol in dichloromethane) to give the title compound.

Step G: 8-(1-(6-(1H-tetrazol-1-yl)pyridin-3-yl)-3-hydroxypropan-2-yl)-2-(4-methyl-5-oxo-2,5-dihydrofuran-3-yl)-2,8-diazaspiro[4.5]decan-1-one To a solution of 8-(1-(6-(1H-tetrazol-1-yl)pyridin-3-yl)-3-((tert-butyldimethylsilyl)oxy)propan-2-yl)-2-(4-methyl-5-oxo-2,5-dihydrofuran-3-yl)-2,8-diazaspiro[4.5]decan-1-one (0.10 g, 0.18 mmol) in DCM (3 mL) was added trifluoroacetic acid (3 mL). After stirred at rt for 24 h, the mixture was removed solvent under reduced pressure. The residue was purified by pre-HPLC to give the racemic title compound which was separate by SFC (CHIRALPAK AD 250×30 mm I.D., 20 μm; Supercritical $CO_2$/MeOH (0.2% $NH_3H_2O$), 45/55) to give Ex. 295 (enantiomer A, faster eluted; and Ex. 296 (enantiomer B, slower eluted). $^1$H-NMR (400 Hz, $CDCl_3$) 6 ppm 9.52 (s, 1 H), 8.36 (s, 1 H), 8.04 (d, J=8.0 Hz, 1 H), 8.04 (d, J=8.4 Hz, 1 H), 5.25 (s, 2 H), 4.04-3.90 (m, 2 H), 3.53-3.44 (m, 2 H), 3.08-2.96 (m, 3 H), 2.96-2.88 (m, 1 H), 2.72-2.68 (m, 1 H), 2.58-2.49 (m, 2 H), 2.13 (s, 3 H), 2.11-2.00 (m, 3 H), 1.99-1.94 (m, 3 H), 1.68-1.51 (m, 2 H). LCMS $[M+1]^+$=454.

EXAMPLE 297 and 298

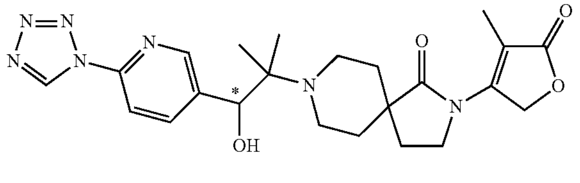 [SMILES: CC1=C(N2CCC3(CCN(C(C)(C)C(O)c4ccc(-n5cnnn5)nc4)CC3)C2=O)COC1=O]

(S)-8-(1-(6-(1H-tetrazol-1-yl)pyridin-3-yl)-1-hydroxy-2-methylpropan-2-yl)-2-(4-methyl-5-oxo-2,5-dihydrofuran-3-yl)-2,8-diazaspiro[4.5]decan-1-one; and (R)-8-(1-(6-(1H-tetrazol-1-yl)pyridin-3-yl)-1-hydroxy-2-methylpropan-2-yl)-2-(4-methyl-5-oxo-2,5-dihydrofuran-3-yl)-2,8-diazaspiro[4.5]decan-1-one Step A: 2,8-diazaspiro[4.5]decan-1-one To a solution of tert-butyl 1-oxo-2,8-diazaspiro[4.5]decane-8-carboxylate (5 g, 19.66 mmol) in methylene chloride (10 ml) was added trifluoroacetic acid (15.15 ml, 197 mmol). The resulting solution was stirred at rt for 1 h. Volatiles were removed, and the residue was basified to a free amine on Bond Elut SCX ion exchange column washed with methanol followed by 1 N ammonia in methanol to give 2,8-diazaspiro[4.5]decan-1-one. LCMS $[M+1]^+$=155.11.

Step B: ethyl 2-methyl-2-(1-oxo-2,8-diazaspiro[4.5]decan-8-yl)propionate

A mixture of 2,8-diazaspiro[4.5]decan-1-one (3.03 g, 19.65 mmol), triethylamine (5.48 ml, 39.3 mmol) and ethyl 2-bromo-2-methylpropanoate (5.77 ml, 39.3 mmol) was heated at 80° C. overnight. The reaction mixture was partitioned between methylene chloride (200 mL) and aqueous saturated sodium bicarbonate. The organic layer was separated, and the aqueous layer was extracted with methylene chloride (3×100 mL). The combined organic layers were dried over magnesium sulfate, and concentrated. The residue was purified on silica gel column using methanol/methylene chloride to provide the title compound. LCMS $[M+1]^+$=269.4

Step C: 2-methyl-2-(1-oxo-2,8-diazaspiro[4.5]decan-8-yl)propanal

To a solution of ethyl 2-methyl-2-(1-oxo-2,8-diazaspiro[4.5]decan-8-yl)propionate (3.77 g, 14.05 mmol) in toluene (100 ml) at −78° C. was added DIBAL-H (45.0 ml, 45.0 mmol) dropwise. The mixture was stirred at the same temperature for 2 h, then quenched with methanol (10 mL) dropwise, and warmed to rt. This was followed by addition of saturated sodium sulfate aqueous (30 mL). The suspension was vigorously stirred at rt for 1 h and filtered. The organic layer was separated, and the aqueous layer was extracted with methylene chloride. The combined organic layers were washed with saturated sodium bicarbonate, dried over sodium sulfate, and concentrated to give the title compound. LCMS $[M+1+18]^+$=243.3; $[M+1+32]^+$=257.4.

Step D: tert-butyl (5-(1-hydroxy-2-methyl-2-(1-oxo-2,8-diazaspiro[4.5]decan-8-yl)propyl)pyridin-2-yl)carbamate To a solution of tert-butyl (5-bromopyridin-2-yl)carbamate (2.155 g, 7.89 mmol) in tetrahydrofuran (60 ml) at −78° C. was added N-butyllithium (8.02 ml, 16.05 mmol) dropwise. The mixture was stirred at −78° C. for 30 min. To the resulting mixture was added a solution of 2-methyl-2-(1-oxo-2,8-diazaspiro[4.5]decan-8-yl)propanal (0.59 g, 2.63 mmol) in tetrahydrofuran (20 mL) dropwise. After stirring at −78° C. for 1 h, the reaction was quenched by methanol (4 mL), and warmed to rt. The mixture was partitioned between ethyl acetate and saturated sodium bicarbonate. The alkaline phase was extracted with methylene chloride twice. The combined organic layers were dried over sodium sulfate, and concentrated. The residue solidified after standing at rt overnight. The solid was treated with methylene chloride and the solid was collected by filtration to obtain the title compound. The filtrate was purified on silica gel using methanol/methylene chloride to give more of the title compound. LCMS $[M+1]^+$=419.20.

Step E: tert-butyl (5-(1-hydroxy-2-methyl-2-(2-(4-methyl-5-oxo-2,5-dihydrofuran-3-yl)-1-oxo-2,8-diazaspiro[4.5]decan-8-yl)propyl)pyridin-2-yl)carbamate A mixture of tert-butyl (5-(1-hydroxy-2-methyl-2-(1-oxo-2,8-diazaspiro[4.5]decan-8-yl)propyl)pyridin-2-yl)carbamate (480 mg, 1.147 mmol), 4-methyl-5-oxo-2,5-dihydrofuran-3-yl trifluoromethanesulfonate (367 mg, 1.491 mmol), potassium carbonate (476 mg, 3.44 mmol) and Xantphos (133 mg, 0.229 mmol) in dioxane (10 ml) was flushed with $N_2$ for 30 min, followed by addition of palladium (II) acetate (25.7 mg, 0.115 mmol). The mixture was heated under $N_2$ at 90° C. overnight. After cooling to rt, the mixture was filtered through CELITE. The filtrate was concentrated, and the residue was purified on silica gel using ethyl acetate eluting first followed by 10% methanol in methylene chloride as eluting solvents to give the title compound. LCMS $[M+1]^+$=515.18.

Step F: 8-(1-(6-aminopyridin-3-yl)-1-hydroxy-2-methylpropan-2-yl)-2-(4-methyl-5-oxo-2,5-dihydrofuran-3-yl)-2,8-diazaspiro[4.5]decan-1-one To a solution of tert-butyl (5-(1-hydroxy-2-methyl-2-(2-(4-methyl-5-oxo-2,5-dihydrofuran-3-yl)-1-oxo-2,8-diazaspiro[4.5]decan-8-yl)propyl)pyridin-2-yl)carbamate (590 mg, 1.146 mmol) in methylene chloride (4 ml) was added trifluoroacetic acid (8.83 ml, 115 mmol). The solution was stirred at rt for 2 h, and volatiles were evaporated under reduced pressure. The TFA salt was basified to free amine on Bond Elut SCX ion exchange column using methanol followed by 1 N ammonia in methanol as eluting solvents to give the title compound. LCMS $[M+1]^+$=415.12.

Step G: 8-(1-(6-(1H-tetrazol-1-yl)pyridin-3-yl)-1-hydroxy-2-methylpropan-2-yl)-2-(4-methyl-5-oxo-2,5-dihydrofuran-3-yl)-2,8-diazaspiro[4.5]decan-1-one (enantiomer A and enantiomer B)

To a solution of 8-(1-(6-aminopyridin-3-yl)-1-hydroxy-2-methylpropan-2-yl)-2-(4-methyl-5-oxo-2,5-dihydrofuran-3-yl)-2,8-diazaspiro[4.5]decan-1-one (343 mg, 0.828 mmol) in ethyl acetate (10 ml) was added trimethylsilyl trifluoroacetate (0.529 ml, 3.06 mmol). The mixture was stirred for 5 min, and triethyl orthoformate (0.275 ml, 1.655 mmol) was added. After stirring another 5 min, to the mixture was added azidotrimethylsilane (0.198 ml, 1.490 mmol), and it stirred at rt for 3 days. The mixture was concentrated, and the residue was purified on silica gel using methanol (contained 0.7M ammonia)/methylene chloride as eluting solvents to give the product which was further purified on TLC using 10% methanol in methylene chloride as developing solvents to give the title compound as a racemate, LCMS $[M+1]^+$=468.17. The racemate was chirally separated (AS column) to give enantiomer A (fast eluted isomer) and enantiomer B (slow eluted isomer). Absolute stereochemistry of each enantiomer was not determined. LCMS $[M+1]^+$=468.14. $^1$HNMR (500 MHz, $CDCl_3$), δ 9.55 (s, 1 H), 8.52 (s, 1H), 8.09-8.05 (m, 2 H), 5.29 (s, 2 H), 4.82 (s, 1 H), 4.08-4.053 (m, 2 H), 3.14-3.05 (m, 2 H), 2.516-2.45 (m, 2 H), 2.20-2.17 (t, J=6.8 Hz, 2 H), 2.082 (s, 3 H), 2.04-2.02 (m, 2 H), 1.69-1.67 (m, 2 H), 1.04 (s, 3 H), 0.89 (s, 3 H)

EXAMPLE 299 and 300

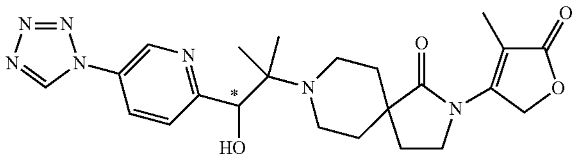 [SMILES: CC1=C(N2CCC3(CCN(C(C)(C)C(O)c4ccc(-n5cnnn5)cn4)CC3)C2=O)COC1=O]

(S)-8-(1-(5-(1H-tetrazol-1-yl)pyridin-2-yl)-1-hydroxy-2-methylpropan-2-yl)-2-(4-methyl-5-oxo-2,5-dihydrofuran-3-yl)-2,8-diazaspiro[4.5]decan-1-one; and (S)-8-(1-(5-(1H-tetrazol-1-yl)pyridin-2-yl)-1-hydroxy-2-methylpropan-2-yl)-2-(4-methyl-5-oxo-2,5-dihydrofuran-3-yl)-2,8-diazaspiro[4.5]decan-1-one 8-(1-(5-(1H-Tetrazol-1-yl)pyridin-2-yl)-1-hydroxy-2-methylpropan-2-yl)-2-(4-methyl-5-oxo-2,5-dihydrofuran-3-yl)-2,8-diazaspiro[4.5]decan-1-one was synthesized following the procedure as described for the synthesis of 8-(1-(6-(1H-tetrazol-1-yl)pyridin-3-yl)-1-hydroxy-2-methylpropan-2-yl)-2-(4-methyl-5-oxo-2,5-dihydrofuran-3-yl)-2,8-diazaspiro[4.5]decan-1-one. The racemate was separated on an OD-H chiral column to give enantiomer A (fast eluted isomer) and enantiomer B (slow eluted isomer). Absolute stereochemistry of each enantiomer was not determined. LCMS $[M+1]^+$=468.5; $^1$ HNMR (500 MHz, $CDCl_3$), δ 9.353 (s, 1 H), 8.895-8.891 (m, 1 H), 8.111-8.089 (m, 1 H), 7.853-7.788 (m, 1 H), 5.231 (s, 2 H), 4.788 (s, 1 H), 4.019-3.991 (m, 2 H), 3.056-2.994 (m, 2 H), 2.441-2.370 (m, 2 H), 2.142-2.114 (m, 2 H), 2.000-1.977 (m, 2 H), 1.935 (s, 3 H), 1.607-1.581 (m, 2 H), 1.052 (s, 3 H), 0.795 (s, 3 H).

EXAMPLE 301, 302, 303, and 304

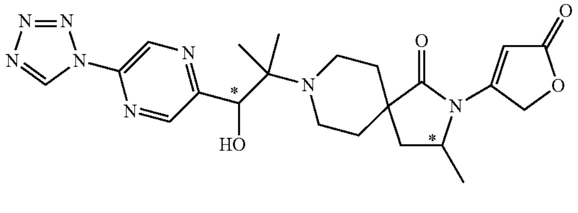 [SMILES: CC1CC2(CCN(C(C)(C)C(O)c3cnc(-n4cnnn4)cn3)CC2)C(=O)N1C1=CC(=O)OC1]

8-(1-(5-(1H-tetrazol-1-yl)pyrazin-2-yl)-1-hydroxy-2-methylpropan-2-yl)-3-methyl-2-(5-oxo-2,5-dihydrofuran-3-yl)-2,8-diazaspiro[4.5]decan-1-one (racemate and four separated enantiomers)

Step A: 1-tert-butyl 4-ethyl 4-(2-methylallyl)piperidine-1,4-dicarboxylate

To a solution of diisopropylamine (16.62 ml, 117 mmol) in tetrahydrofuran (20 ml) at 0° C. was added N-butyllithium (46.6 ml, 117 mmol). The resulting solution was stirred at ° C. for 0.5 h. To a solution of 1-tert-butyl 4-ethyl piperidine-1,4-dicarboxylate (20 g, 78 mmol) in tetrahydrofuran (200 ml) at −78° C. was added the above LDA solution dropwise. The resulting mixture was stirred at −78° C. for 1 h. This was followed by addition of 3-bromo-2-methylpropene (11.28 ml, 112 mmol) dropwise. The mixture was stirred at −78° C. for 1.5 h, quenched with saturated ammonium acetate, and diluted with ethyl acetate (200 mL). The organic layer was separated, washed with saturated ammonium acetate, and concentrated. The residue was purified on silica gel using ethyl acetate/Hexane as eluting solvent to give the title compound. LCMS $[M+23]^+$=334.21.

Step B: 1-tert-butyl 4-ethyl 4-(2-oxopropyl)piperidine-1,4-dicarboxylate

To a solution of 1-tert-butyl 4-ethyl 4-(2-methylallyl) piperidine-1,4-dicarboxylate (23.48 g, 75 mmol) in dioxane (200 ml) and water (100 ml) were added sodium periodate (32.3 g, 151 mmol) and osmium tetroxide (0.473 ml, 1.508 mmol). The mixture was stirred at rt over the weekend, filtrated, and the filtrate was concentrated. The residue was partitioned between ethyl acetate and saturated sodium bicarbonate. The aqueous layer was extracted with ethyl acetate. The combined organic layers were dried over sodium sulfate, and concentrated. The crude product was purified on silica gel using ethyl acetate/hexane as eluting solvents to give the title compound. LCMS $[M+23]^+$=336.23.

Step C: tert-butyl 3-methyl-1-oxo-2,8-diazaspiro[4.5]decane-8-carboxylate

To a solution of 1-tert-butyl 4-ethyl 4-(2-oxopropyl)piperidine-1,4-dicarboxylate (18.74 g, 59.8 mmol) in methanol (100 ml) were added magnesium sulfate (14.40 g, 120 mmol), ammonium acetate (9.22 g, 120 mmol) and sodium cyanoborohydride (7.52 g, 120 mmol). The mixture was heated at 80° C. in a sealed tube overnight, and filtered. The filtrate was concentrated, and the residue was partitioned between methylene chloride and saturated sodium bicarbonate. The aqueous layer was extracted with methylene chloride. The combined organic layers were dried over sodium sulfate, concentrated, and the residue was purified on silica gel using ethyl acetate as eluting solvent to give the title compound. LCMS $[M+1-56]^+$=213.25.

Step D: 3-methyl-2,8-diazaspiro[4.5]decan-1-one

To a solution of tert-butyl 3-methyl-1-oxo-2,8-diazaspiro[4.5]decane-8-carboxylate (4.9 g, 18.26 mmol) in methylene chloride (5 ml) was added trifluoroacetic acid (10 ml, 130 mmol) dropwise. The mixture was stirred at rt for 3 h. Volatiles were removed under reduced pressure, and the residue was converted to a free base using Bond Elut SCX ion exchange column washed with methanol to remove TFA followed by 1N ammonia in methanol to collect the title compound. LCMS $[M+1]^+$=169.35.

Step E: ethyl 2-methyl-2-(3-methyl-1-oxo-2,8-diazaspiro[4.5]decan-8-yl)propanoate A mixture of 3-methyl-2,8-diazaspiro[4.5]decan-1-one (2.76 g, 16.41 mmol), triethylamine (4.57 ml, 32.8 mmol) and ethyl 2-bromo-2-methylpropanoate (4.82 ml, 32.8 mmol) was heated at 80° C. overnight. The mixture was partitioned between methylene chloride (200 mL) and saturated sodium bicarbonate. The organic layer was separated, and the aqueous layer was extracted with methylene chloride three times. The combined organic layers were dried over magnesium sulfate, and concentrated. The residue was purified on silica gel using methanol/methylene chloride to give the title compound. LCMS $[M+1]^+$=283.4.

Step F: 2-methyl-2-(3-methyl-1-oxo-2,8-diazaspiro[4.5]decan-8-yl)propanal

To a solution of ethyl 2-methyl-2-(3-methyl-1-oxo-2,8-diazaspiro[4.5]decan-8-yl)propanoate (2.09 g, 7.40 mmol) in toluene (30 ml) was added DIBAL-H (23.68 ml, 23.68 mmol) at −78° C. The mixture was stirred at −78° C. for 2 h, and quenched with methanol (7 mL) at −78° C. After warmed to rt, saturated sodium sulfate (20 mL) was added. The resulting mixture was vigorously stirred for 30 min, filtered, and washed with methylene chloride. The filtrate was partitioned between saturated sodium bicarbonate and methylene chloride. The alkaline layer was extracted with methylene chloride. The combined organic layers were dried over sodium sulfate, and concentrated to the title compound. LCMS $[M+1+18]^+$=257.4.

Step G: 8-(1-(5-(diallylamino)pyrazin-2-yl)-1-hydroxy-2-methylpropan-2-yl)-3-methyl-2,8-diazaspiro[4.5]decan-1-one To a solution of N,N-diallyl-5-bromopyrazin-2-amine (2.93 g, 11.52 mmol) in tetrahydrofuran (120 ml) was added n-butyllithium (4.61 ml, 11.52 mmol) at −78° C. After the mixture was stirred for 3 min, 2-methyl-2-(3-methyl-1-oxo-2,8-diazaspiro[4.5]decan-8-yl)propanal (915 mg, 3.84 mmol) was added in one portion. The resulting solution was stirred at −78° C. for 60 min, and quenched with methanol. The mixture was partitioned between ethyl acetate and saturated bicarbonate. The aqueous phase was extracted with 30% isopropanol/methylene chloride (4×200 ml). The combined organic layers were dried over sodium sulfate, and concentrated. The residue was purified on silica gel column using methanol/methylene chloride to give the title compound. LCMS $[M+1]^+$=414.7.

N,N-diallyl-5-bromopyrazin-2-amine was prepared as follows: A solution of 2,5-dibromopyrazine (11.32 g, 47.6 mmol) and diallylamine (12.92 ml, 105 mmol) in DMF (40 ml) was heated at 100° C. for 2 days. The mixture was cooled to rt, and partitioned between ethyl acetate (200 mL) and saturated sodium bicarbonate. The organic layer was washed with saturated sodium bicarbonate, dried over sodium sulfate, and concentrated. The crude product was purified on silica gel column using ethyl acetate/hexane as eluting solvents to give N,N-diallyl-5-bromopyrazin-2-amine. LCMS $[M+1]^+$=254.2.

Step H: 8-(1-(5-(diallylamino)pyrazin-2-yl)-1-hydroxy-2-methylpropan-2-yl)-3-methyl-2-(5-oxo-2,5-dihydrofuran-3-yl)-2,8-diazaspiro[4.5]decan-1-one A mixture of 8-(1-(5-(diallylamino)pyrazin-2-yl)-1-hydroxy-2-methylpropan-2-yl)-3-methyl-2,8-diazaspiro[4.5]decan-1-one (0.62 g, 1.499 mmol), 4-bromofuran-2(5H)-one (0.318 g, 1.949 mmol), Xantphos (0.260 g, 0.450 mmol), potassium carbonate (0.414 g, 3.00 mmol) in dioxane (15 ml) was flushed with nitrogen followed by addition of palladium(ii) acetate (0.101 g, 0.450 mmol). The mixture was heated at 90° C. for 24 h, and filtered. The filtrate was concentrated, and the residue was purified on silica gel using methanol/methylene chloride as eluting solvents to give the title compound. LCMS $[M+1]^+$=496.11.

Step I: 8-(1-(5-aminopyrazin-2-yl)-1-hydroxy-2-methylpropan-2-yl)-3-methyl-2-(5-oxo-2,5-dihydrofuran-3-yl)-2,8-diazaspiro[4.5]decan-1-one To a mixture of 1,3-dimethylbarbituric acid (1869 mg, 11.94 mmol) and 8-(1-(5-(diallylamino)pyrazin-2-yl)-1-hydroxy-2-methylpropan-2-yl)-3-methyl-2-(5-oxo-2,5-dihydrofuran-3-yl)-2,8-diazaspiro[4.5]decan-1-one (740 mg, 1.493 mmol) in methylene chloride (50 ml) was added tetrakis(triphenylphosphine)palladium(0) (518 mg, 0.448 mmol) under nitrogen. The mixture was heated under nitrogen at 40° C. for 2 days, diluted with methylene chloride (50 mL), and basified slowly with saturated sodium bicarbonate. After bubbling stopped, additional saturated sodium bicarbonate (200 mL) was added. The aqueous layer was extracted with methylene chloride three times. The combined organic layers were dried over sodium sulfate, and concentrated. The residue was purified on silica gel chromatography using methanol/methylene as eluting solvents to give the title compound. LCMS [M+1]=416.04.

Step J: 8-(1-(5-(1H-tetrazol-1-yl)pyrazin-2-yl)-1-hydroxy-2-methylpropan-2-yl)-3-methyl-2-(5-oxo-2,5-dihydrofuran-3-yl)-2,8-diazaspiro[4.5]decan-1-one To a solution of 8-(1-(5-aminopyrazin-2-yl)-1-hydroxy-2-methylpropan-2-yl)-3-methyl-2-(5-oxo-2,5-dihydrofuran-3-yl)-2,8-diazaspiro[4.5]decan-1-one (243 mg, 0.585 mmol) in DMF (4.00 ml) was added trimethylsilyl trifluoroacetate (0.576 ml, 3.33 mmol) at rt. The mixture was stirred for 5 min. Triethyl orthoformate (0.389 ml, 2.339 mmol) was added followed by addition of azidotrimethylsilane (0.279 ml, 2.105 mmol) after another 5 min stirring. The resulting solution was stirred for 2 days, and concentrated. The residue was purified on silica gel column using methanol (contains 0.7 M ammonia)/methylene chloride to give the racemic product which was further purified on preparative TLC using 10% methanol/methylene chloride as developing solvents to give the title compound as a mixture of four isomers. The mixture was separated on OD column using 50% MeOH/MeCN (3:1) (0.2% DEA)/$CO_2$ to give the four enantiomers of the title compound. LCMS $[M+1]^+$=469.5. Absolute stereochemistry of each enantiomer was not determined. The first eluted isomer: $^1$HNMR (500 MHz, $CDCl_3$), δ 9.562 (s, 1 H), 9.325 (s, 1H), 8.862 (s, 1 H), 5.492-5.456 (m, 1 H), 5.342-5.303 (m, 1 H), 4.905 (s, 1 H), 4.120-4.103 (m, 1H), 3.111-3.067 (m, 2 H), 2.506-2.463 (m, 2 H), 2.418-2.373 (m, 1 H), 2.099-2.059 (m, 1 H), 1.980-1.946 (m, 1 H), 1.769-1.742 (m, 1 H), 2.642-1.616 (m, 2 H), 1.491-1.478 (d, J=6.4 Hz, 3H), 1.141 (s, 3 H), 0.875 (s, 3 H).

The following Thallium Flux Assay was performed on each of the final product compounds in the Examples.

Thallium Flux Assay

Cell Culture Conditions—HEK293 cells stably expressing hROMK ($hK_{ir}1.1$) were grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 mL Calcium/Magnesium-free PBS. Add 5 mL of 1× trypsin (prepared in Ca/Mg Free PBS) to T-225 flask and return flask to 37° C./$CO_2$ incubator for 2-3 minutes. To dislodge the cell, gently bang the side of the flask with your hand. Triturate the cells completely and then transfer the cells to 25 mL complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)

- FluxOR™ Reagent (Component A)
- FluxOR™ Assay Buffer (Component B)—10× Concentrate
- PowerLoad™ Concentrate (Component C)—100× Concentrate
- Probenecid (Component D)—Lyophilized sample is kept at −20° C. Water soluble, 100× after solubilization in 1 mL water. Store at 4° C.
- FluxOR™ Chloride-free Buffer (Component E)—5× Concentrate
- Potassium sulfate ($K_2SO_4$) Concentrate (Component F)—125 mM in water. Store at 4° C.
- Thallium sulfate ($Tl_2SO_4$) Concentrate (Component G)—50 mM in water. Store at 4° C.
- DMSO (dimethyl sulfoxide, Component H)—1 mL (100%)

Reagent Preparation: FluxOR Working Solutions

- 1000× FluxOR™ Reagent: Reconstitute a vial of component A in 100 μl DMSO; Mix well; Store 10 μl aliquots at −20° C.
- 1× FluxOR™ Assay Buffer: Dilute Component B 10-fold with water; Adjust pH to 7.4 with Hepes/NaOH; Filter and store at 4° C.
- Probenecid/Assay Buffer: 100 mL of 1× FluxOR™ Assay Buffer; 1 mL of reconstituted component D; Store at 4° C.
- Loading Buffer (per microplate): 10 μl 1000× FluxOR™ Reagent; 100 μl component C; 10 mL Probenecid/Assay Buffer
- Compound Buffer (per microplate): 20 mL Probenecid/Assay Buffer; 0.3 mM ouabain (10 mM ouabain in water can be stored in amber bottle/aluminum foil at room temperature); Test compound
- 1× FluxOR™ Chloride-Free Buffer: Prepare 1× working solution in water. Can be stored at room temperature
- Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Store at 4° C. when not in use. If kept sterile, this solution is good for months.

Assay Protocol—The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol

1. Seed HEK-hKir1.1 cells (50 μl at 20,000 cells/well) in 384-well PDL coated Microplates
2. Allow cells to adhere overnight in humidified 37° C./10% $CO_2$ incubator
3. Completely remove cell growth media from microplate and replace with 25 μl loading buffer
4. Incubate Microplate at room temperature, protected form light, for 90 min
5. Remove loading buffer and replace with 25 μl 1× Assay Buffer±test compound.
6. Incubate microplate at room temperature, protected from light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—The fluorescence intensity of wells containing 3 μM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 μM in this assay.

Alternatively, the control could be another compound (outside the scope of Formula I) that has an $IC_{50}$ potency in this assay of less than 1 μM.

Data collected for compounds in the Examples of the present invention using the Thallium Flux Assay are shown in Table 13 below. All of the tested final product compounds in the Examples (diastereomeric mixtures and individual diastereomers) had $IC_{50}$ potencies less than 1 μM the Thallium Flux Assay.

TABLE 13

| Example No. | Thallium Flux IC50 (μM) | Example No. | Thallium Flux IC50 (μM) | Example No. | Thallium Flux IC50 (μM) |
|---|---|---|---|---|---|
| 1 | 0.01 | 2 | 0.05 | 3 | 0.02 |
| 4 | 0.05 | 5 | 0.04 | 6 | 0.05 |
| 7 | 0.08 | 8 | 0.06 | 9 | 0.08 |
| 10 | 0.12 | 11 | 0.02 | 12 | 0.01 |
| 13 | 0.02 | 14 | 0.02 | 15 | 0.01 |
| 16 | 0.02 | 17 | 0.03 | 18 | 0.01 |
| 19 | 0.03 | 20 | 0.03 | 21 | 0.04 |
| 22 | 0.01 | 23 | 0.02 | 24 | 0.02 |
| 25 | 0.03 | 26 | 0.04 | 27 | 0.02 |
| 28 | 0.03 | 29 | 0.04 | 30 | 0.02 |
| 31 | 0.03 | 32 | 0.02 | 33 | 0.02 |
| 34 | 0.01 | 35 | 0.01 | 36 | 0.01 |
| 37 | 0.01 | 38 | 0.01 | 39 | 0.01 |
| 40 | 0.20 | 41 | 0.16 | 42 | 0.02 |
| 43 | 0.01 | 44 | 0.01 | 45 | 0.03 |
| 46 | 0.02 | 47 | 0.02 | 48 | 0.03 |
| 49 | 0.09 | 50 | 0.02 | 51 | 0.03 |
| 52 | 0.01 | 53 | 0.01 | 54 | 0.02 |
| 55 | 0.05 | 56 | 0.02 | 57 | 0.02 |
| 58 | 0.06 | 59 | 0.05 | 60 | 0.04 |
| 61 | 0.07 | 62 | 0.04 | 63 | 0.04 |
| 64 | 0.05 | 65 | 0.01 | 66 | 0.01 |
| 67 | 0.17 | 68 | 0.23 | 69 | 0.04 |
| 70 | 0.03 | 71 | 0.07 | 72 | 0.04 |
| 73 | 0.17 | 74 | 0.09 | 75 | 0.44 |
| 76 | 0.02 | 77 | 0.01 | 78 | 0.01 |
| 79 | 0.10 | 80 | 0.13 | 81 | 0.01 |
| 82 | 0.01 | 83 | 0.01 | 84 | 0.01 |
| 85 | 0.03 | 86 | 0.04 | 87 | 0.05 |
| 88 | 0.04 | 89 | 0.03 | 90 | 0.04 |
| 91 | 0.03 | 92 | 0.02 | 93 | 0.03 |
| 94 | 0.02 | 95 | 0.05 | 96 | 0.07 |
| 97 | 0.02 | 98 | 0.04 | 99 | 0.05 |
| 100 | 0.01 | 101 | 0.006 | 102 | 0.01 |
| 103 | 0.01 | 104 | 0.12 | 105 | 0.13 |
| 106 | 0.06 | 107 | 0.11 | 108 | 0.04 |
| 109 | 0.06 | 110 | 0.12 | 111 | 0.09 |
| 112 | 0.41 | 113 | 0.08 | 114 | 0.06 |
| 115 | 0.06 | 116 | 0.03 | 117 | 0.05 |
| 118 | 0.18 | 119 | 0.01 | 120 | 0.01 |
| 121 | 0.02 | 122 | 0.01 | 123 | 0.06 |
| 124 | 0.04 | 125 | 0.06 | 126 | 0.09 |
| 127 | 0.02 | 128 | 0.08 | 129 | 0.14 |
| 130 | 0.16 | 131 | 0.68 | 132 | 0.64 |
| 133 | 0.01 | 134 | 0.06 | 135 | 0.05 |
| 136 | 0.08 | 137 | 0.08 | 138 | 0.08 |
| 139 | 0.04 | 140 | 0.01 | 141 | 0.03 |
| 142 | 0.03 | 143 | 0.19 | 144 | 0.02 |
| 145 | 0.02 | 146 | 0.05 | 147 | 0.04 |
| 148 | 0.10 | 149 | 0.02 | 150 | 0.02 |
| 151 | 0.03 | 152 | 0.27 | 153 | 0.04 |
| 154 | 0.03 | 155 | 0.06 | 156 | 0.02 |
| 157 | 0.07 | 158 | 0.56 | 159 | 0.04 |
| 160 | 0.11 | 161 | 0.03 | 162 | 0.04 |
| 163 | 0.10 | 164 | 0.04 | 165 | 0.01 |
| 166 | 0.10 | 167 | 0.01 | 168 | 0.01 |
| 169 | 0.01 | 170 | 0.04 | 171 | 0.06 |
| 172 | 0.18 | 173 | 0.77 | 174 | 0.02 |
| 175 | 0.04 | 176 | 0.09 | 177 | 0.07 |
| 178 | 0.79 | 179 | 0.33 | 180 | 0.04 |
| 181 | 0.15 | 182 | 0.05 | 183 | 0.08 |
| 184 | 0.07 | 185 | 0.05 | 186 | 0.07 |
| 187 | 0.10 | 188 | 0.05 | 189 | 0.05 |
| 190 | 0.05 | 191 | 0.07 | 192 | 0.01 |
| 193 | 0.02 | 194 | 0.01 | 195 | 0.01 |
| 196 | 0.04 | 197 | 0.03 | 198 | 0.01 |
| 199 | 0.02 | 200 | 0.08 | 201 | 0.12 |
| 202 | 0.06 | 203 | 0.15 | 204 | 0.30 |
| 205 | 0.03 | 206 | 0.05 | 207 | 0.04 |
| | | | | 210 | 0.07 |
| 211 | 0.04 | 212 | 0.12 | 213 | 0.04 |
| 214 | 0.03 | 215 | 0.03 | | |
| | | 218 | 0.01 | 219 | 0.01 |
| 220 | 0.04 | 221 | 0.03 | 222 | 0.10 |
| 223 | 0.05 | 224 | 0.11 | 225 | 0.15 |
| 226 | 0.33 | 227 | 0.18 | 228 | 0.02 |
| 229 | 0.28 | 230 | 0.08 | 231 | 1.53 |
| 232 | 0.01 | 233 | 0.01 | 234 | 0.01 |
| 235 | 0.01 | 236 | 0.004 | 237 | 0.02 |
| 238 | 0.01 | 239 | 0.32 | 240 | 0.03 |
| 241 | 0.02 | 242 | 0.04 | 243 | 0.21 |
| 344 | 0.03 | 345 | 0.02 | 246 | 0.02 |
| 247 | 0.02 | 248 | 0.02 | 249 | 0.04 |
| 250 | 0.08 | 251 | 0.05 | 252 | 0.01 |
| 253 | 0.02 | 254 | 0.03 | 255 | 0.02 |
| 256 | 0.03 | 257 | 0.10 | 258 | 0.12 |
| 259 | 0.10 | 260 | 0.12 | 261 | 0.003 |
| 262 | 0.004 | 263 | 0.01 | 264 | 0.003 |
| 265 | 0.01 | 266 | 0.01 | 267 | 0.01 |
| 268 | 0.01 | 269 | 0.02 | 270 | 0.01 |
| 271 | 0.005 | 272 | 0.01 | 273 | 0.004 |
| 274 | 0.01 | 275 | 0.004 | 276 | 0.05 |
| 277 | 0.08 | 278 | 0.03 | 279 | 0.02 |
| 280 | 0.03 | 281 | 0.14 | 282 | 0.07 |
| 283 | 0.06 | 284 | 0.08 | 285 | 0.05 |
| 286 | 0.06 | 287 | 0.10 | 288 | 0.03 |
| 289 | 0.02 | 290 | 0.09 | 291 | 0.08 |
| 293 | 0.01 | 294 | 0.004 | 295 | 0.02 |
| 296 | 0.02 | 297 | 0.01 | 298 | 0.01 |

TABLE 13-continued

| Example No. | Thallium Flux IC50 (μM) | Example No. | Thallium Flux IC50 (μM) | Example No. | Thallium Flux IC50 (μM) |
|---|---|---|---|---|---|
| 299 | 0.01 | 300 | 0.02 | 301 | 0.01 |
| 302 | 0.10 | 303 | 2.00 | 304 | 0.91 |

Spontaneously Hypertensive Rat (SHR) Assay

The spontaneously hypertensive rat (SHR) exhibits age-dependent hypertension that does not require administration of exogenous agents to elevate blood pressure nor does it require the use of a high salt diet to elevate blood pressure. Thus it resembles human essential hypertension and provides an opportunity to assess the dose-dependence of novel agents for their ability to lower blood pressure.

Experimental protocols for evaluating blood pressure lowering efficacy of compounds of the present invention in spontaneously hypertensive rats (SHR):

Spontaneously hypertensive rats (SHR, male, 6 months, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. HCTZ (25 mg/kg/day, PO) was included as a reference diuretic at a dose giving approximately maximal efficacy in SHR. The blood pressure lowering efficacy of compounds of the present invention compared to vehicle control was evaluated following a single oral gavage each day for a typical duration of three to fourteen days. Data were collected as hourly averages, and changes in blood pressure were calculated by subtracting vehicle control baseline data on an hourly basis. Examples 1, 3, 4, 18, 24, 32, 65, 77, 122, 146, 151, 232, 247, 248, 252, 261, 263, 277 and 291 were evaluated at PO, QD doses at one or more doses within the range of 0.1 to 10 mg/kg and resulted in typical reductions in daily (24 h) mean systolic blood pressure ranging from 5 mmHg to 33 mmHg at the doses used by the last day of the studies.

The Spontaneously Hypertensive Rat Assay is well known and often used in the art as an experimental model simulating human hypertension (see, e.g., Lerman, L. O., et al., *J Lab Clin Med,* 2005; 146:160-173).

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I

I

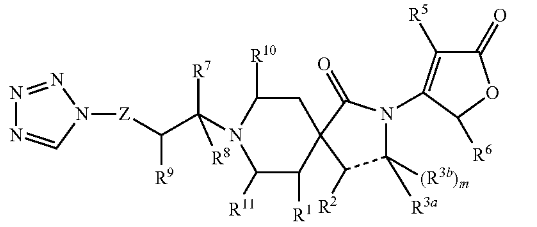

or a pharmaceutically acceptable salt thereof wherein:

Z is

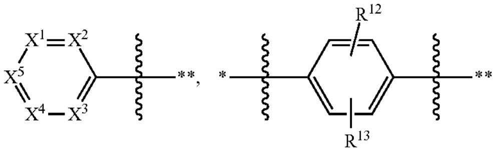

or

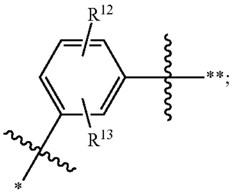

$X^1$, $X^2$ and $X^3$ are each independently selected from $C(R^4)$ or N;

one of $X^4$ and $X^5$ is * —C and the other is $C(R^4)$ or N;

provided that at least one and at most two of $X^1$, $X^2$, $X^3$, $X^4$ and $X^5$ is N;

Each $R^4$ is independently —H, halo (particularly —F or —Cl), —CN, —$C_{3-6}$ cycloalkyl, —$C(O)OC_{1-4}$alkyl, —$OC_{1-4}$alkyl, or —$C_{1-4}$alkyl optionally substituted with —OH or 1-3 of —F;

wherein * indicates the point of attachment to the N-tetrazolyl ring and ** indicates the point Of attachment to —$CH(R^9)$—;

$R^1$ is —H, halo particularly —F, —OH, or —$OC_{1-3}$alkyl particularly —$OCH_3$;

m is an integer selected from zero ($R^{3b}$ is absent) and 1 ($R^{3b}$ is present);

$R^2$ is —H, ═O (oxo), —OH, —$C_{1-3}$alkyl or —$OC_{1-3}$alkyl;

$R^{3a}$ is —H, —$C_{3-4}$cycloalkyl or —$C_{1-3}$alkyl optionally substituted with —$OCH_3$ or 1 to 3 of —F;

$R^{3b}$ is —H or —$C_{1-3}$alkyl, or $R^{3b}$ is absent when the dashed bond is a double bond;

or $R^{3a}$ and $R^{3b}$ are joined together with the carbon to which they are both attached to form cyclopropyl or cyclobutyl;

$R^5$ is —H, halo, —$C_{3-6}$ cycloalkyl or —$C_{1-3}$alkyl optionally substituted with —O—$C_{1-3}$alkyl;

$R^6$ is —H or —$C_{1-3}$alkyl;

$R^7$ is —H or —$C_{1-3}$alkyl optionally substituted with —OH, —$OCH_3$ or 1 to 3 of —F;

$R^8$ is —H or —$C_{1-3}$alkyl;

or $R^7$ and $R^8$ are joined together with the carbon to which they are both attached to form —$C_{3-4}$cycloalkyl;

$R^9$ is —H, —F, —OH, —$C_{1-3}$alkyl, —$OC_{1-3}$alkyl or —$CH_2OH$;

$R^{10}$ is —H, —$C_{1-3}$alkyl optionally substituted with —OH, —$OCH_3$, or 1 to 3 of —F;

$R^{11}$ is —H, —$C_{1-3}$alkyl optionally substituted with —OH, —$OCH_3$, or 1 to 3 of —F;

or $R^{10}$ and $R^{11}$ are joined together to represent —$CH_2$—$CH_2$—, —$CH_2$—$N(CH_3)$—$CH_2$— or —$CH_2OCH_2$—;

$R^{12}$ and $R^{13}$ are each independently —H, halo (particularly —F or —Cl), —CN, —$C_{3-6}$cycloalkyl, —C(O)$OC_{1-4}$alkyl, —$OC_{1-4}$alkyl, or —$C_{1-4}$alkyl optionally substituted with or —OH or 1-3 of —F; and the dashed bond (" - - - ") represents a single or double bond provided that:

(i) when m is 1, then the dashed bond is a single bond; and (ii) when m is zero and $R^2$ is not =O, then the dashed bond is a double bond.

2. The compound of claim 1 having structural Formula II or a pharmaceutically acceptable salt thereof:

II

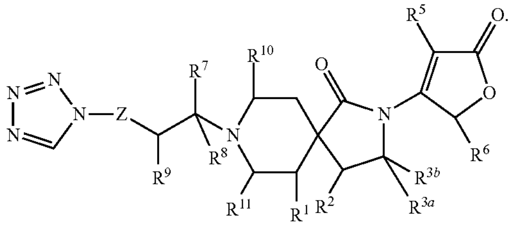

3. The compound of claim 1 having structural Formula III or a pharmaceutically acceptable salt thereof:

III

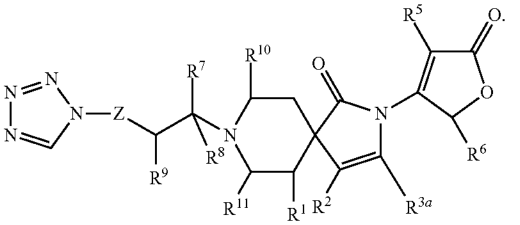

4. The compound of claim 1 or a pharmaceutically acceptable salt thereof wherein Z is:

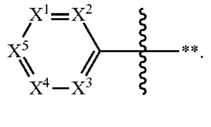

5. The compound of claim 1 or a pharmaceutically acceptable salt thereof wherein Z is

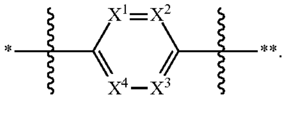

6. The compound of claim 1 or a pharmaceutically acceptable salt thereof wherein Z is

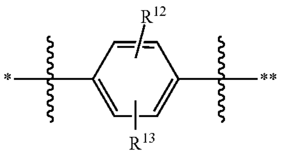

or

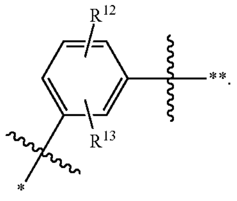

7. The compound of claim 1 having structural Formula IV or a pharmaceutically acceptable salt thereof:

IV

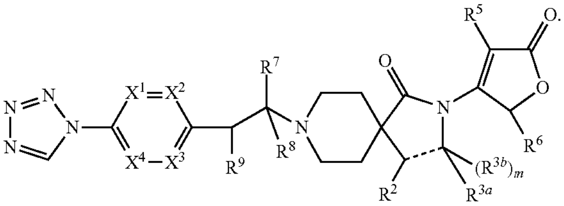

8. The compound of claim 7 or a pharmaceutically acceptable salt thereof wherein:

$X^1$, $X^2$, $X^3$ and $X^4$ are each independently selected from $C(R^4)$ or N; provided that at least one and at most two of $X^1$, $X^2$, $X^3$ and $X^4$ is N;

each $R^4$ is independently —H or —$C_{1-4}$alkyl optionally substituted with 1-3 of —F;

$R^2$ is —H, =O, —OH, —$C_{1-3}$alkyl or —$OC_{1-3}$alkyl;

$R^{3a}$ is —H, —$C_{3-4}$cycloalkyl or —$C_{1-3}$alkyl optionally substituted with —$OCH_3$ or 1 to 3 of —F;

$R^{3b}$ is —H or —$C_{1-3}$alkyl, or $R^{3b}$ is absent when the dashed bond is a double bond;

$R^5$ is —H or —$CH_3$;

$R^6$ is —H or —$CH_3$;

$R^7$ is —H, —$CH_3$ or —$CH_2OH$;

$R^8$ is —H or —$CH_3$;

$R^9$ is —H, —F, —OH, —$C_{1-3}$alkyl, —$OC_{1-3}$alkyl; and the dashed bond ("- - - ") represents a single or double bond provided that:

(i) when m is 1, then the dashed bond is a single bond; and (ii) when m is zero and $R^2$ is not =O, then the dashed bond is a double bond.

9. The compound of claim 1 selected from:

8-{(2R)-2-hydroxy-2-[6-(1H-tetrazol-1-yl)pyridin-3-yl]ethyl}-1-oxo-2-(5-oxo-2,5-dihydrofuran-3-yl)-2-aza-8-azoniaspiro[4.5]decane, 8-{(2S)-2-hydroxy-2-[6-(1H-tetrazol-1-yl)pyridin-3-yl]ethyl}-1-oxo-2-(5-oxo-2,5-dihydrofuran-3-yl)-2-aza-8-azoniaspiro[4.5]decane, single isomer, 8-{(2R)-2-hydroxy-2-[2-methyl-6-(1H-tetrazol-1-yl)pyridin-3-yl]ethyl}-1-oxo-2-(5-oxo-2,5-dihydrofuran-3-yl)-2-aza-8-azoniaspiro[4.5]decane, 8-{(2S)-2-hydroxy-2-[2-methyl-6-(1H-tetrazol-1-yl)pyridin-3-yl]ethyl}-1-oxo-2-(5-oxo-2,5-dihydrofuran-3-yl)-2-aza-8-azoniaspiro[4.5]decane, 8-{(2S)-2-hydroxy-2-[6-methyl-5-(1H-tetrazol-1-yl)pyridin-2-yl]ethyl}-1-oxo-2-(5-oxo-2,5-dihydrofuran-3-yl)-2-aza-8-azoniaspiro[4.5]decane, 8-{(2R)-2-hydroxy-2-[4-methyl-5-(1H-tetrazol-1-yl)pyridin-2-yl]ethyl}-1-oxo-2-(5-oxo-2,5-dihydrofuran-3-yl)-2-aza-8-azoniaspiro[4.5]decane, 8-{(2S)-2-hydroxy-2-[4-methyl-5-(1H-tetrazol-1-yl)pyridin-2-yl]ethyl}-1-oxo-2-(5-oxo-2,5-dihydrofuran-3-yl)-2-aza-8-azoniaspiro[4.5]decane, 8-{(2R)-2-hydroxy-2-[6-methyl-5-(1H-tetrazol-1-yl)pyridin-2-yl]ethyl}-1-oxo-2-(5-oxo-2,5-dihydrofuran-3-yl)-2-aza-8-azoniaspiro[4.5]decane, 8-{(2R)-2-hydroxy-2-[2-(1H-tetrazol-1-yl)pyrimidin-5-yl]ethyl}-1-oxo-2-(5-oxo-2,5-dihydrofuran-3-yl)-2-aza-8-azoniaspiro[4.5]decane, 8-{(2S)-2-hydroxy-2-[2-(1H-tetrazol-1-yl)pyrimidin-5-yl]ethyl}-1-oxo-2-(5-oxo-2,5-dihydrofuran-3-yl)-2-aza-8-azoniaspiro[4.5]decane, 8-{(2R)-2-hydroxy-2-[2-methyl-4-(1H-tetrazol-1-yl)phenyl]ethyl}-1-oxo-2-(5-oxo-2,5-dihydrofuran-3-yl)-2-aza-8-azoniaspiro[4.5]decane, 8-{(2S)-2-hydroxy-2-[2-methyl-4-(1H-tetrazol-1-yl)phenyl]ethyl}-1-oxo-2-(5-oxo-2,5-dihydrofuran-3-yl)-2-aza-8-azoniaspiro[4.5]decane, 8-{(2R)-2-[2-fluoro-4-(1H-tetrazol-1-yl)phenyl]-2-hydroxyethyl}-1-oxo-2-(5-oxo-2,5-dihydrofuran-3-yl)-2-aza-8-azoniaspiro[4.5]decane, 8-{(2S)-2-[2-fluoro-4-(1H-tetrazol-1-yl)phenyl]-2-hydroxyethyl}-1-oxo-2-(5-oxo-2,5-dihydrofuran-3-yl)-2-aza-8-azoniaspiro[4.5]decane, 8-{(2R)-2-hydroxy-2-[2-methoxy-4-(1H-tetrazol-1-yl)phenyl]ethyl}-1-oxo-2-(5-oxo-2,5-dihydrofuran-3-yl)-2-aza-8-azoniaspiro[4.5]decane, 8-{(2S)-2-hydroxy-2-[2-methoxy-4-(1H-tetrazol-1-yl)phenyl]ethyl}-1-oxo-2-(5-oxo-2,5-dihydrofuran-3-yl)-2-aza-8-azoniaspiro[4.5]decane, 8-{(2R)-2-hydroxy-2-[2-(1H-tetrazol-1-yl)pyrimidin-5-yl]ethyl}-2-(4-methyl-5-oxo-2,5-dihydrofuran-3-yl)-1-oxo-2-aza-8-azoniaspiro[4.5]decane, 8-{(2R)-2-hydroxy-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane, 8-{(2S)-2-hydroxy-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane, 8-{(2R)-2-hydroxy-2-[2-methyl-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane, 8-{(2S)-2-hydroxy-2-[2-methyl-6-(1H-tetrazol-1-yl)pyridin-3-yl]ethyl}-2-(4-methyl-5-oxo-2,5-dihydrofuran-3-yl)-1-oxo-2-aza-8-azoniaspiro [4.5]decane, 8-{(2S)-2-hydroxy-2-[5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2R)-2-hydroxy-2-[5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2S)-2-hydroxy-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane, 8-{(2R)-2-hydroxy-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane, 8-{(2R)-2-[5-fluoro-6-(1H-tetrazol-1-yl)pyridin-3-yl]-2-hydroxyethyl}-2-(4-methyl-5-oxo-2,5-dihydrofuran-3-yl)-1-oxo-2-aza-8-azoniaspiro[4.5]decane, 8-{(2S)-2-[5-fluoro-6-(1H-tetrazol-1-yl)pyridin-3-yl]-2-hydroxyethyl}-2-(4-methyl-5-oxo-2,5-dihydrofuran-3-yl)-1-oxo-2-aza-8-azoniaspiro[4.5]decane, 8-{(2S)-2-hydroxy-2-[3-methyl-5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2R)-2-hydroxy-2-[3-methyl-5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2S)-2-hydroxy-2-[6-methyl-5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2R)-2-hydroxy-2-[6-methyl-5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2S)-2-hydroxy-2-[6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane, 8-{(2R)-2-hydroxy-2-[6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane, -{(2R)-2-hydroxy-2-[4-(1H-tetrazol-1-yl)phenyl]ethyl}-2-(4-methyl-5-oxo-2,5-dihydrofuran-3-yl)-1-oxo-2-aza-8-azoniaspiro[4.5]decane, 8-{(2S)-2-hydroxy-2-[4-(1H-tetrazol-1-yl)phenyl]ethyl}-2-(4-methyl-5-oxo-2,5-dihydrofuran-3-yl)-1-oxo-2-aza-8-azoniaspiro[4.5]decane, 8-{(2R)-2-[2-fluoro-4-(1H-tetrazol-1-yl)phenyl]-2-hydroxyethyl}-2-(4-methyl-5-oxo-2,5-dihydrofuran-3-yl)-1-oxo-2-aza-8-azoniaspiro[4.5]decane, 8-{(2S)-2-[2-fluoro-4-(1H-tetrazol-1-yl)phenyl]-2-hydroxyethyl}-2-(4-methyl-5-oxo-2,5-dihydrofuran-3-yl)-1-oxo-2-aza-8-azoniaspiro[4.5]decane;

8-{(2R)-2-hydroxy-2-[2-methyl-4-(1H-tetrazol-1-yl)phenyl]ethyl}-2-(4-methyl-5-oxo-2,5-dihydrofuran-3-yl)-1-oxo-2-aza-8-azoniaspiro[4.5]decane, 8-{(2S)-2-hydroxy-2-[2-methyl-4-(1H-tetrazol-1-yl)phenyl]ethyl}-2-(4-methyl-5-oxo-2,5-dihydrofuran-3-yl)-1-oxo-2-aza-8-azoniaspiro[4.5]decane, 8-{(2S)-2-hydroxy-2-[5-(1H-tetrazol-1-yl)pyrimidin-2-yl]ethyl}-2-(4-methyl-5-oxo-2,5-dihydrofuran-3-yl)-1-oxo-2-aza-8-azoniaspiro[4.5]decane, 8-{(2R)-2-hydroxy-2-[5-(1H-tetrazol-1-yl)pyrimidin-2-yl]ethyl}-2-(4-methyl-5-oxo-2,5-dihydrofuran-3-yl)-1-oxo-2-aza-8-azoniaspiro[4.5]decane, (1R,5R)-8-{(2S)-2-hydroxy-2-[2-methyl-6-(1H-tetrazol-1-yl)pyridin-3-yl]ethyl}-2'-oxo-1'-(5-oxo-2,5-dihydrofuran-3-yl)spiro[8-azoniabicyclo[3.2.1]octane-3,3'-pyrrolidine], (1R,5R)-8-{(2R)-2-hydroxy-2-[2-methyl-6-(1H-tetrazol-1-yl)pyridin-3-yl]ethyl}-2'-oxo-1'-(5-oxo-2,5-dihydrofuran-3-yl)spiro[8-azoniabicyclo[3.2.1]octane-3,3'-pyrrolidine], 2-hydroxy-2-[6-(1H-tetrazol-1-yl)pyridazin-3-yl]ethyl}-2'-oxo-1'-(5-oxo-2,5-dihydrofuran-3-yl)spiro[8-azoniabicyclo[3.2.1]octane-3,3'-pyrrolidine], (1R,5R)-8-{(2R)-2-hydroxy-2-[2-(1H-tetrazol-1-yl)pyrimidin-5-yl]ethyl}-1'-(4-methyl-5-oxo-2,5-dihydrofuran-3-yl)-2'-oxospiro[8-azoniabicyclo[3.2.1]octane-3,3'-pyrrolidine], (1R,5R)-8-{(2R)-2-hydroxy-2-[5-(1H-tetrazol-1-yl)pyridin-2-yl]ethyl}-1'-(4-methyl-5-oxo-2,5-dihydrofuran-3-yl)-2'-oxospiro[8-azoniabicyclo[3.2.1]octane-3,3'-pyrrolidine], (1R,5R)-8-{(2S)-2-hydroxy-2-[5-(1H-tetrazol-1-yl)pyridin-2-yl]ethyl}-1'-(4-methyl-5-oxo-2,5-dihydrofuran-3-yl)-2'-oxospiro[8-azoniabicyclo[3.2.1]octane-3,3'-pyrrolidine], (1R,5R)-8-{(2S)-2-hydroxy-2-[5-(1H-tetrazol-1-yl)pyrazin-2-yl]ethyl}-1'-(4-methyl-5-oxo-2,5-dihydrofuran-3-yl)-2'-oxospiro[8-azoniabicyclo[3.2.1]octane-3,3'-pyrrolidine], (1R,5R)-8-{(2R)-2-hydroxy-2-[5-(1H-tetrazol-1-yl)pyrazin-2-yl]ethyl}-1'-(4-methyl-5-oxo-2,5-dihydrofuran-3-yl)-2'-oxospiro[8-azoniabicyclo[3.2.1]octane-3,3'-pyrrolidine], (1R,5R)-8-{(2S)-2-[4,5-dimethyl-6-(1H-tetrazol-1-yl)pyridazin-3-yl]-2-hydroxyethyl}-1'-(4-methyl-5-oxo-2,5-dihydrofuran-3-yl)-2'-oxospiro[8-azoniabicyclo[3.2.1]octane-3,3'-pyrrolidine], (1R,5R)-8-{(2R)-2-[4,5-dimethyl-6-(1H-tetrazol-1-yl)pyridazin-3-yl]-2-hydroxyethyl}-1'-(4-methyl-5-oxo-2,5-dihydrofuran-3-yl)-2'-oxospiro[8-azoniabicyclo[3.2.1]octane-3,3'-pyrrolidine], (1R,5R)-8-{(2S)-2-hydroxy-2-[6-(1H-tetrazol-1-yl)pyridazin-3-yl]ethyl}-1'-(4-methyl-5-oxo-2,5-dihydrofuran-3-yl)-2'-oxospiro[8-azoniabicyclo[3.2.1]octane-3,3'-pyrrolidine], (1R,5R)-8-{(2R)-2-hydroxy-2-[6-(1H-tetrazol-1-yl)pyridazin-3-yl]ethyl}-1'-(4-methyl-5-oxo-2,5-dihydrofuran-3-yl)-2'-oxospiro[8-azoniabicyclo[3.2.1]octane-3,3'-pyrrolidine], (1R,5R)-8-{(2R)-2-hydroxy-2-[5-methyl-6-(1H-tetrazol-1-yl)pyridazin-3-yl]ethyl}-1'-(4-methyl-5-oxo-2,5-dihydrofuran-3-yl)-2'-oxospiro[8-azoniabicyclo[3.2.1]octane-3,3'-pyrrolidine], (1R,5R)-8-{(2S)-2-hydroxy-2-[5-methyl-6-(1H-tetrazol-1-yl)pyridazin-3-yl]ethyl}-1'-(4-methyl-5-oxo-2,5-dihydrofuran-3-yl)-2'-oxospiro[8-azoniabicyclo[3.2.1]octane-3,3'-pyrrolidine], 8-{(2R)-2-hydroxy-2-[2-methyl-6-(1H-tetrazol-1-yl)pyridin-3-yl]ethyl}-3-methyl-2-(4-methyl-5-oxo-2,5-dihydrofuran-3-yl)-1-oxo-2-aza-8-azoniaspiro[4.5]decane, 8-{(2S)-2-hydroxy-2-[2-methyl-6-(1H-tetrazol-1-yl)pyridin-3-yl]ethyl}-3-methyl-2-(4-methyl-5-oxo-2,5-dihydrofuran-3-yl)-1-oxo-2-aza-8-azoniaspiro[4.5]decane, 2-(4-cyclopropyl-5-oxo-2,5-dihydrofuran-3-yl)-8-{(2R)-2-hydroxy-2-[2-methyl-6-(1H-tetrazol-1-yl)pyridin-3-yl]ethyl}-1-oxo-2-aza-8-azoniaspiro[4.5]decane, 8-{(2R)-2-hydroxy-2-[3-(1H-tetrazol-1-yl)phenyl]ethyl}-2-(4-methyl-5-oxo-2,5-dihydrofuran-3-yl)-1-oxo-2-aza-8-azoniaspiro[4.5]decane, 8-{(2S)-2-hydroxy-2-[3-(1H-tetrazol-1-yl)phenyl]ethyl}-2-(4-methyl-5-oxo-2,5-dihydrofuran-3-yl)-1-oxo-2-aza-8-azoniaspiro[4.5]decane, 8-((S)-2-(6-(1H-tetrazol-1-yl)pyridin-3-yl)-2-hydroxyethyl)-3-methyl-2-(4-methyl-5-oxo-2,5-dihydrofuran-3-yl)-2,8-diazaspiro[4.5]decan-1-one, 8-((R)-2-(6-(1H-tetrazol-1-yl)pyridin-3-yl)-2-hydroxyethyl)-3-methyl-2-(4-methyl-5-oxo-2,5-dihydrofuran-3-yl)-2,8-diazaspiro[4.5]decan-1-one, 8-((S)-2-(5-(1H-tetrazol-1-yl)pyrazin-2-yl)-2-hydroxyethyl)-3-methyl-2-(4-methyl-5-oxo-2,5-dihydrofuran-3-yl)-2,8-diazaspiro[4.5]decan-1-one, 8-((R)-2-(5-(1H-tetrazol-1-yl)pyrazin-2-yl)-2-hydroxyethyl)-3-methyl-2-(4-methyl-5-oxo-2,5-dihydrofuran-3-yl)-2,8-diazaspiro[4.5]decan-1-one, 8-{(2S)-2-[4,5-dimethyl-6-(1H-tetrazol-1-yl)pyridazin-3-yl]-2-hydroxyethyl}-2-(4-methyl-5-oxo-2,5-dihydrofuran-3-yl)-1-oxo-2-aza-8-azoniaspiro[4.5]decane, 8-{(2R)-2-[4,5-dimethyl-6-(1H-tetrazol-1-yl)pyridazin-3-yl]-2-hydroxyethyl}-2-(4-methyl-5-oxo-2,5-dihydrofuran-3-yl)-1-oxo-2-aza-8-azoniaspiro[4.5]decane, 8-{(2R)-2-hydroxy-2-[4-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2S)-2-hydroxy-2-[4-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2S)-2-hydroxy-2-[6-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2R)-2-hydroxy-2-[6-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2S)-2-hydroxy-2-[6-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane, 8-{(2R)-2-[2,6-difluoro-4-(1H-tetrazol-1-yl)phenyl]-2-hydroxyethyl}-2-(4-methyl-5-oxo-2,5-dihydrofuran-3-yl)-1-oxo-2-aza-8-azoniaspiro[4.5]decane, (3S)-8-{(2S)-2-hydroxy-2-[5-(1H-tetrazol-1-yl)pyrazin-2-yl]ethyl}-3-methyl-1-oxo-2-(5-oxo-2,5-dihydrofuran-3-yl)-2-aza-8-azoniaspiro[4.5]decane, (3S)-8-{(2R)-2-hydroxy-2-[5-(1H-tetrazol-1-yl)pyrazin-2-yl]ethyl}-3-methyl-1-oxo-2-(5-oxo-2,5-dihydrofuran-3-yl)-2-aza-8-azoniaspiro[4.5]decane, (3R)-8-{(2S)-2-hydroxy-2-[5-(1H-tetrazol-1-yl)pyrazin-2-yl]ethyl}-3-methyl-1-oxo-2-(5-oxo-2,5-dihydrofuran-3-yl)-2-aza-8-azoniaspiro[4.5]decane, (3R)-8-{(2R)-2-hydroxy-2-[5-(1H-tetrazol-1-yl)pyrazin-2-yl]ethyl}-3-methyl-1-oxo-2-(5-oxo-2,5-dihydrofuran-3-yl)-2-aza-8-azoniaspiro[4.5]decane, (3S)-8-{(2R)-2-hydroxy-2-[6-(1H-tetrazol-1-yl)pyridin-3-yl]ethyl}-3-methyl-1-oxo-2-(5-oxo-2,5-dihydrofuran-3-yl)-2-aza-8-azoniaspiro[4.5]decane, (3S)-8-{(2S)-2-hydroxy-2-[6-(1H-tetrazol-1-yl)pyridin-3-yl]ethyl}-3-methyl-1-oxo-2-(5-oxo-2,5-dihydrofuran-3-yl)-2-aza-8-azoniaspiro[4.5]decane, (3R)-8-{(2R)-2-hydroxy-2-[6-(1H-tetrazol-1-yl)pyridin-3-yl]ethyl}-3-methyl-1-oxo-2-(5-oxo-2,5-dihydrofuran-3-yl)-2-aza-8-azoniaspiro[4.5]decane, (3R)-8-{(2S)-2-hydroxy-2-[6-(1H-tetrazol-1-yl)pyridin-3-yl]ethyl}-3-methyl-1-oxo-2-(5-oxo-2,5-dihydrofuran-3-yl)-2-aza-8-azoniaspiro[4.5]decane, 8-{(2R)-2-hydroxy-2-[4-methyl-2-(1H-tetrazol-1-yl)pyrimidin-5-yl]ethyl}-2-(4-methyl-5-oxo-2,5-dihydrofuran-3-yl)-1-oxo-2-aza-8-azoniaspiro[4.5]decane, 8-{(2S)-2-hydroxy-2-[4-methyl-2-(1H-tetrazol-1-yl)pyrimidin-5-yl]ethyl}-2-(4-methyl-5-oxo-2,5-dihydrofuran-3-yl)-1-oxo-2-aza-8-azoniaspiro[4.5]decane, 8-{(2S)-2-hydroxy-2-[6-methyl-5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane, 8-{(2R)-2-hydroxy-2-[6-methyl-5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane, (1R,5R)-8-{(2S)-2-hydroxy-2-[5-(1H-tetrazol-1-yl)pyrazin-2-yl]ethyl}-5'-methyl-2'-oxo- l'-(5-oxo-2,5-dihydrofuran-3-yl)spiro [8-azoniabicyclo[3.2.1]octane-3,3'-pyrrolidine], (1R,5R)-8-{(2R)-2-hydroxy-2-[5-(1H-tetrazol-1-yl)pyrazin-2-yl]ethyl}-5'-methyl-2'-oxo- l'-(5-oxo-2,5-dihydrofuran-3-yl)spiro [8-azoniabicyclo[3.2.1]octane-3,3'-pyrrolidine], 8-{(2R)-2-hydroxy-2-[4-methoxy-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane, 8-{(2S)-2-hydroxy-2-[4-methoxy-6-(1H-tetrazol-1-y Opyridin-3-yl]ethyl}-2-(4-methyl-5-oxo-2,5-dihydrofuran-3-yl)-1-oxo-2-aza-8-azoniaspiro[4.5]decane, 8-{(2R)-2-[3-cyano-4-(1H-tetrazol-1-yl)phenyl]-2-hydroxyethyl}-2-(4-methyl-5-oxo-2,5-dihydrofuran-3-yl)-1-oxo-2-aza-8-azoniaspiro[4.5]decane,
8-{(2S)-2-[3-cyano-4-(1H-tetrazol-1-yl)phenyl]-2-hydroxyethyl}-2-(4-methyl-5-oxo-2,5-dihydrofuran-3-yl)-1-oxo-2-aza-8-azoniaspiro[4.5]decane,
8-{(2R)-2-hydroxy-2-[6-(1H-tetrazol-1-yl)pyridin-3-yl]ethyl}-2-(4-methyl-5-oxo-2,5-dihydrofuran-3-yl)-1,4-dioxo-2-aza-8-azoniaspiro[4.5]decane,
8-{(2S)-2-hydroxy-2-[3-methyl-5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane,
8-{(2R)-2-hydroxy-2-[3-methyl-5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane,
(1R,5R)-8-{(2R)-2-hydroxy-2-[6-(1H-tetrazol-1-yl)pyridin-3-yl]ethyl}-5'-methyl-2'-oxo- l'-(5-oxo-2,5-dihydrofuran-3-yl)spiro [8-azoniabicyclo[3.2.1]octane-3,3'-pyrrolidine],
(1R,5R)-8-{(2S)-2-hydroxy-2-[6-(1H-tetrazol-1-yl)pyridin-3-yl]ethyl}-5'-methyl-2'-oxo-1'-(5-oxo-2,5-dihydrofuran-3-yl)spiro [8-azoniabicyclo[3.2.1]octane-3,3'-pyrrolidine],
(1R,5R)-4'-hydroxy-8-{(2R)-2-hydroxy-2-[6-(1H-tetrazol-1-yl)pyridin-3-yl]ethyl}-1'-(4-methyl-5-oxo-2,5-dihydrofuran-3-yl)-2'-oxospiro[8-azoniabicyclo[3.2.1]octane-3,3'-pyrrolidine],
(1R,5R)-4'-hydroxy-8-{(2S)-2-hydroxy-2-[6-(1H-tetrazol-1-yl)pyridin-3-yl]ethyl}-1'-(4-methyl-5-oxo-2,5-dihydrofuran-3-yl)-2'-oxospiro[8-azoniabicyclo[3.2.1]octane-3,3'-pyrrolidine],
(1R,5R)-8-{(2R)-2-hydroxy-2-[6-(1H-tetrazol-1-yl)pyridin-3-yl]ethyl}-4'-methoxy-1'-(4-methyl-5-oxo-2,5-dihydrofuran-3-yl)-2'-oxospiro[8-azoniabicyclo[3.2.1]octane-3,3'-pyrrolidine](two isomers),
(1R,5R)-8-{(2S)-2-hydroxy-2-[6-(1H-tetrazol-1-yl)pyridin-3-yl]ethyl}-4'-methoxy-1'-(4-methyl-5-oxo-2,5-dihydrofuran-3-yl)-2'-oxospiro[8-azoniabicyclo[3.2.1]octane-3,3'-pyrrolidine](two isomers),
4-hydroxy-8-{(2R)-2-hydroxy-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane,
(1R,5R,7R,9R)-9-{(2R)-2-hydroxy-2-[6-(1H-tetrazol-1-yl)pyridin-3-yl]ethyl}-7-methyl-1'-(4-methyl-5-oxo-2,5-dihydrofuran-3-yl)-2'-oxospiro[7,9-diazoniabicyclo[3.3.1]nonane-3,3'-pyrrolidine],
8-{(2R)-2-hydroxy-2-[2-(1H-tetrazol-1-yl)pyrimidin-5-yl]ethyl}-3-methyl-2-(4-methyl-5-oxo-2,5-dihydrofuran-3-yl)-1-oxo-2-aza-8-azoniaspiro[4.5]decane,
8-{(2R)-2-hydroxy-2-[6-(1H-tetrazol-1-yl)pyridin-3-yl]ethyl}-4-methoxy-2-(4-methyl-5-oxo-2,5-dihydrofuran-3-yl)-1-oxo-2-aza-8-azoniaspiro[4.5]decane,
8-{(2R)-2-hydroxy-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]dec-3-ene,
6-fluoro-8-{(2R)-2-hydroxy-2-[2-methyl-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane,
8-{(2R)-2-hydroxy-2-[2-methoxy-4-(1H-tetrazol-1-yl)phenyl]ethyl}-2-(4-methyl-5-oxo-2,5-dihydrofuran-3-yl)-1-oxo-2-aza-8-azoniaspiro[4.5]decane,
8-{(2S)-2-hydroxy-2-[2-methoxy-4-(1H-tetrazol-1-yl)phenyl]ethyl}-2-(4-methyl-5-oxo-2,5-dihydrofuran-3-yl)-1-oxo-2-aza-8-azoniaspiro[4.5]decane,
8-{(2S)-2-hydroxy-2-[4-methyl-6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane,
8-{(2R)-2-hydroxy-2-[4-methyl-6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane,
8-{(2S)-2-hydroxy-2-[6-(1H-tetrazol-1-yl)pyridazin-3-yl]ethyl}-3-methyl-2-(4-methyl-5-oxo-2,5-dihydrofuran-3-yl)-1-oxo-2-aza-8-azoniaspiro[4.5]decane,
8-{(2R)-2-hydroxy-2-[6-(1H-tetrazol-1-yl)pyridazin-3-yl]ethyl}-3-methyl-2-(4-methyl-5-oxo-2,5-dihydrofuran-3-yl)-1-oxo-2-aza-8-azoniaspiro[4.5]decane,
8-{(2R)-2-hydroxy-2-[5-methyl-6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane,
8-{(2S)-2-hydroxy-2-[5-methyl-6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane,
8-{(2R)-2-hydroxy-2-[2-(1H-tetrazol-1-yl)pyridin-4-yl]ethyl}-2-(4-methyl-5-oxo-2,5-dihydrofuran-3-yl)-1-oxo-2-aza-8-azoniaspiro[4.5]decane,
8-{(2S)-2-hydroxy-2-[2-(1H-tetrazol-1-yl)pyridin-4-yl]ethyl}-2-(4-methyl-5-oxo-2,5-dihydrofuran-3-yl)-1-oxo-2-aza-8-azoniaspiro[4.5]decane,
8-{(2R)-2-hydroxy-2-[5-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane,
8-{(2S)-2-hydroxy-2-[5-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane,
(1R,5R,5'R)-8-{(2R)-2-hydroxy-2-[6-(1H-tetrazol-1-yl)pyridin-3-yl]ethyl}-5'-methyl-1'-(4-methyl-5-oxo-2,5-dihydrofuran-3-yl)-2'-oxospiro[8-azoniabicyclo[3.2.1]octane-3,3'-pyrrolidine],
(1R,5R,5'R)-8-{(2S)-2-hydroxy-2-[6-(1H-tetrazol-1-yl)pyridin-3-yl]ethyl}-5'-methyl-1'-(4-methyl-5-oxo-2,5-dihydrofuran-3-yl)-2'-oxospiro[8-azoniabicyclo[3.2.1]octane-3,3'-pyrrolidine],
8-{(2S)-2-hydroxy-2-[3-methyl-5-(1H-tetrazol-1-yl)pyridin-2-yl]ethyl}-3-methyl-2-(4-methyl-5-oxo-2,5-dihydrofuran-3-yl)-1-oxo-2-aza-8-azoniaspiro[4.5]decane,
8-{(2R)-2-hydroxy-2-[3-methyl-5-(1H-tetrazol-1-yl)pyridin-2-yl]ethyl}-3-methyl-2-(4-methyl-5-oxo-2,5-dihydrofuran-3-yl)-1-oxo-2-aza-8-azoniaspiro[4.5]decane,
8-{(2R)-2-hydroxy-2-[2-methyl-4-(1H-tetrazol-1-yl)phenyl]ethyl}-3-methyl-2-(4-methyl-5-oxo-2,5-dihydrofuran-3-yl)-1-oxo-2-aza-8-azoniaspiro[4.5]decane,
8-{(2S)-2-hydroxy-2-[2-methyl-4-(1H-tetrazol-1-yl)phenyl]ethyl}-3-methyl-2-(4-methyl-5-oxo-2,5-dihydrofuran-3-yl)-1-oxo-2-aza-8-azoniaspiro[4.5]decane,
8-{(2R)-2-[2-fluoro-4-(1H-tetrazol-1-yl)phenyl]-2-hydroxyethyl}-3-methyl-2-(4-methyl-5-oxo-2,5-dihydrofuran-3-yl)-1-oxo-2-aza-8-azoniaspiro[4.5]decane,
8-{(2S)-2-[2-fluoro-4-(1H-tetrazol-1-yl)phenyl]-2-hydroxyethyl}-3-methyl-2-(4-methyl-5-oxo-2,5-dihydrofuran-3-yl)-1-oxo-2-aza-8-azoniaspiro[4.5]decane,
8-{(2S)-2-[2,6-difluoro-4-(1H-tetrazol-1-yl)phenyl]-2-hydroxyethyl}-2-(4-methyl-5-oxo-2,5-dihydrofuran-3-yl)-1-oxo-2-aza-8-azoniaspiro[4.5]decane,
2-(4-chloro-5-oxo-2,5-dihydrofuran-3-yl)-8-{(2S)-2-hydroxy-2-[2-methyl-6-(1H-tetrazol-1-yl)pyridin-3-yl]ethyl}-1-oxo-2-aza-8-azoniaspiro[4.5]decane,
2-(4-chloro-5-oxo-2,5-dihydrofuran-3-yl)-8-{(2R)-2-hydroxy-2-[2-methyl-6-(1H-tetrazol-1-yl)pyridin-3-yl]ethyl}-1-oxo-2-aza-8-azoniaspiro[4.5]decane,
8-{(2S)-2-hydroxy-2-[6-(1H-tetrazol-1-yl)pyridazin-3-yl]ethyl-}2-(4-methyl-5-oxo-2,5-dihydrofuran-3-yl)-1-oxo-2-aza-8-azoniaspiro[4.5]dec-3-ene, 8-{2-[4-(difluoromethyl)-6-(1H-tetrazol-1-yl)pyridin-3-yl]-2-hydroxyethyl}-2-(4-methyl-5-oxo-2,5-dihydrofuran-3-yl)-2,8-diazaspiro[4.5]decan-1-one, 8-{(2R)-2-[3-fluoro-5-(1H-tetrazol-1-yl)pyridin-2-yl]-2-hydroxyethyl}-2-(4-methyl-5-oxo-2,5-dihydrofuran-3-yl)-2,8-diazaspiro[4.5]decan-1-one;

8-{(2R)-2-hydroxy-2-[2-methoxy-6-(1H-tetrazol-1-yl)pyridin-3-yl]ethyl}-2-(4-methyl-5-oxo-2,5-dihydrofuran-3-yl)-2,8-diazaspiro[4.5]decan-1-one, 8-{(2S)-2-hydroxy-2-[2-methoxy-6-(1H-tetrazol-1-yl)pyridin-3-yl]ethyl}-2-(4-methyl-5-oxo-2,5-dihydrofuran-3-yl)-2,8-diazaspiro[4.5]decan-1-one, 8-{(2R)-2-hydroxy-2-[6-(1H-tetrazol-1-yl)pyridin-3-yl]ethyl}-1-oxo-2-(5-oxo-2,5-dihydrofuran-3-yl)-2-aza-8-azoniaspiro[4.5]dec-3-ene, 8-{(2S)-2-hydroxy-2-[5-(1H-tetrazol-1-yl)pyrazin-2-yl]ethyl}-1-oxo-2-(5-oxo-2,5-dihydrofuran-3-yl)-2-aza-8-azoniaspiro[4.5]dec-3-ene, 8-{(2R)-2-hydroxy-2-[4-methyl-6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]dec-3-ene, 8-{(2S)-2-hydroxy-2-[4-methyl-6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]dec-3-ene, 8-{(2S)-2-hydroxy-2-[6-(1H-tetrazol-1-yl)pyridin-3-yl]ethyl}-1-oxo-2-(5-oxo-2,5-dihydrofuran-3-yl)-2-aza-8-azoniaspiro [4.5]dec-3-ene, 8-{(2S)-2-hydroxy-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]dec-3-ene, 3-hydroxy-8-{(2R)-2-hydroxy-2-[6-(1H-tetrazol-1-yl)pyridin-3-yl]ethyl}-3-methyl-1-oxo-2-(5-oxo-2,5-dihydrofuran-3-yl)-2-aza-8-azoniaspiro[4.5]decane (two isomers), 3-hydroxy-8-{(2S)-2-hydroxy-2-[6-(1H-tetrazol-1-yl)pyridazin-3-yl]ethyl}-3-methyl-1-oxo-2-(5-oxo-2,5-dihydrofuran-3-yl)-2-aza-8-azoniaspiro[4.5]decane (two isomers), 8-{(2R)-2-hydroxy-2-[6-(1H-tetrazol-1-yl)pyridin-3-yl]ethyl}-4'-methoxy-1'-(4-methyl-5-oxo-2,5-dihydrofuran-3-yl)-2'H-spiro [8-azabicyclo[3.2.1]octane-3,3'-pyrrolidin]-2'-one, 8-{(2S)-2-hydroxy-2-[5-(1H-tetrazol-1-yl)pyrazin-2-yl]ethyl}-4'-methoxy -1'-(4-methyl-5-oxo-2,5-dihydrofuran-3-yl)-2'H-spiro [8-azabicyclo[3.2.1]octane-3,3'-pyrrolidin]-2'-one, 8-{(2S)-2-hydroxy-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]dec-3-ene, 8-{(2S)-2-hydroxy-2-[5-(1H-tetrazol-1-yl)pyrazin-2-yl]ethyl}-3,3-dimethyl-1-oxo-2-(5-oxo-2,5-dihydrofuran-3-yl)-2-aza-8-azoniaspiro[4.5]decane, (3S)-8-{2-hydroxy-2-[3-methyl-5-(1H-tetrazol-1-yl)pyrazin-2-yl]ethyl}-3-methyl-2-(5-oxo-2,5-dihydrofuran-3-yl)-2,8-diazaspiro[4.5]decan-1-one (racemic) , 8-{(2S)-2-hydroxy-2-[6-(1H-tetrazol-1-yl)pyridazin-3-yl]ethyl}-4-methyl-2-(4-methyl-5-oxo-2,5-dihydrofuran-3-yl)-1-oxo-2-aza-8-azoniaspiro[4.5]dec-3-ene, 8-{(2S)-2-hydroxy-2-[5-(1H-tetrazol-1-yl)pyrazin-2-yl]ethyl}-12-(5-oxo-2,5-dihydrofuran-3-yl)-8,12-diazadispiro [2.1.5.2]dodecan-11-one, (3S)-8-{2-hydroxy-2-[3-methyl-5-(1H-tetrazol-1-yl)pyrazin-2-yl]ethyl}-3-methyl-2-(5-oxo-2,5-dihydrofuran-3-yl)-2,8-diazaspiro[4.5]decan-1-one, 8-{(2R)-2-hydroxy-2-[6-(1H-tetrazol-1-yl)pyridin-3-yl]ethyl}-6-methoxy -2-(4-methyl-5-oxo-2,5-dihydrofuran-3-yl)-2,8-diazaspiro[4.5]decan-1-one, 8-{(2S)-2-hydroxy-2-[6-(1H-tetrazol-1-yl)pyridin-3-yl]ethyl}-6-methoxy -2-(4-methyl-5-oxo-2,5-dihydrofuran-3-yl)-2,8-diazaspiro[4.5]decan-1-one, 8-{(2S)-2-hydroxy-2-[5-(1H-tetrazol-1-yl)pyrazin-2-yl]ethyl}-6-methoxy -2-(4-methyl-5-oxo-2,5-dihydrofuran-3-yl)-2,8-diazaspiro[4.5]decan-1-one, 8-{(2R)-2-hydroxy-2-[5-(1H-tetrazol-1-yl)pyrazin-2-yl]ethyl}-6-methoxy -2-(4-methyl-5-oxo-2,5-dihydrofuran-3-yl)-2,8-diazaspiro[4.5]decan-1-one, 8-{(2R)-2-hydroxy-2-[6-(1H-tetrazol-1-yl)pyridin-3-yl]ethyl}-3-methyl-2-(5-oxo-2,5-dihydrofuran-3-yl)-2,8-diazaspiro[4.5]dec-3-en-1-one, 8-{(2R)-2-hydroxy-2-[6-(1H-tetrazol-1-yl)pyridin-3-yl]ethyl}-4-methyl-2-(4-methyl-5-oxo-2,5-dihydrofuran-3-yl)-1-oxo-2-aza-8-azoniaspiro[4.5]dec-3-ene, 8-{(2R)-2-hydroxy-2-[6-(1H-tetrazol-1-yl)pyridin-3-yl]ethyl}-6-methoxy -2-(4-methyl-5-oxo-2,5-dihydrofuran-3-yl)-2,8-diazaspiro[4.5]decan-1-one, 8-{(2S)-2-hydroxy-2-[6-(1H-tetrazol-1-yl)pyridin-3-yl]ethyl}-6-methoxy -2-(4-methyl-5-oxo-2,5-dihydrofuran-3-yl)-2,8-diazaspiro[4.5]decan-1-one, 8-{(2S)-2-hydroxy-2-[5-(1H-tetrazol-1-yl)pyrazin-2-yl]ethyl}-6-methoxy -2-(4-methyl-5-oxo-2,5-dihydrofuran-3-yl)-2,8-diazaspiro[4.5]decan-1-one, 8-{(2R)-2-hydroxy-2-[5-(1H-tetrazol-1-yl)pyrazin-2-yl]ethyl}-6-methoxy -2-(4-methyl-5-oxo-2,5-dihydrofuran-3-yl)-2,8-diazaspiro[4.5]decan-1-one, 9-{(2R)-2-hydroxy-2-[6-(1H-tetrazol-1-yl)pyridin-3-yl]ethyl}-1'-(4-methyl-5-oxo-2,5-dihydrofuran-3-yl)-2'H-spiro [7-oxa-9-azabicyclo[3.3.1]nonane-3,3'-pyrrolidin]-2'-one, 9-{(2S)-2-hydroxy-2-[5-(1H-tetrazol-1-yl)pyrazin-2-yl]ethyl}-1'-(4-methyl-5-oxo-2,5-dihydrofuran-3-yl)-2'H-spiro [7-oxa-9-azabicyclo[3.3.1]nonane-3,3'-pyrrolidin]-2'-one, 8-{(2R)-2-hydroxy-2-[6-(1H-tetrazol-1-yl)pyridin-3-yl]ethyl}-2-[4-(methoxymethyl)-5-oxo-2,5-dihydrofuran-3-yl]-2,8-diazaspiro[4.5]decan-1-one, 6-fluoro-8-{(2S)-2-hydroxy-2-[6-(1H-tetrazol-1-yl)pyridazin-3-yl]ethyl}-2-(4-methyl-5-oxo-2,5-dihydrofuran-3-yl)-2,8-diazaspiro[4.5]decan-1-one, 6-fluoro-8-{(2R)-2-hydroxy-2-[6-(1H-tetrazol-1-yl)pyridazin-3-yl]ethyl}-2-(4-methyl-5-oxo-2,5-dihydrofuran-3-yl)-2,8-diazaspiro[4.5]decan-1-one, 6-fluoro-8-{(2S)-2-hydroxy-2-[4-methyl-6-(1H-tetrazol-1-yl)pyridazin-3-yl]ethyl}-2-(4-methyl-5-oxo-2,5-dihydrofuran-3-yl)-2,8-diazaspiro[4.5]decan-1-one, 6-fluoro-8-{(2R)-2-hydroxy-2-[4-methyl-6-(1H-tetrazol-1-yl)pyridazin-3-yl]ethyl}-2-(4-methyl-5-oxo-2,5-dihydrofuran-3-yl)-2,8-diazaspiro[4.5]decan-1-one, 8-{(2S)-2-hydroxy-2-[5-(1H-tetrazol-1-yl)pyrazin-2-yl]ethyl}-3-methyl-2-(5-oxo-2,5-dihydrofuran-3-yl)-2,8-diazaspiro[4.5]dec-3-en-1-one, 8-{(2S)-2-hydroxy-2-[6-(1H-tetrazol-1-yl)pyridazin-3-yl]ethyl}-3,3-dimethyl-1-oxo-2-(5-oxo-2,5-dihydrofuran-3-yl)-2-aza-8-azoniaspiro[4.5]decane, 8-{(2S)-2-hydroxy-2-[6-(1H-tetrazol-1-yl)pyridazin-3-yl]ethyl}-3-methyl-2-(5-oxo-2,5-dihydrofuran-3-yl)-2,8-diazaspiro[4.5]dec-3-en-1-one, 8-{(2R)-2-hydroxy-2-[6-(1H-tetrazol-1-yl)pyridazin-3-yl]ethyl}-3,3-dimethyl-1-oxo-2-(5-oxo-2,5-dihydrofuran-3-yl)-2-aza-8-azoniaspiro[4.5]decane, 8-{(2S)-2-hydroxy-2-[6-(1H-tetrazol-1-yl)pyridazin-3-yl]ethyl}-2-[4-(methoxymethyl)-5-oxo-2,5-dihydrofuran-3-yl]-2,8-diazaspiro[4.5]decan-1-one, 6-fluoro-8-{(2R)-2-hydroxy-2-[6-(1H-tetrazol-1-yl)pyridin-3-yl]ethyl}-2-(4-methyl-5-oxo-2,5-dihydrofuran-3-yl)-2,8-diazaspiro[4.5]decan-1-one, 6-fluoro-8-{(2S)-2-hydroxy-2-[6-(1H-tetrazol-1-yl)pyridin-3-yl]ethyl}-2-(4-methyl-5-oxo-2,5-dihydrofuran-3-yl)-2,8-diazaspiro[4.5]decan-1-one, 6-fluoro-8-{(2R)-2-hydroxy-2-[6-(1H-tetrazol-1-yl)pyridin-3-yl]ethyl}-2-(4-methyl-5-oxo-2,5-dihydrofuran-3-yl)-2,8-diazaspiro[4.5]decan-1-one, 6-fluoro-8-{(2S)-2-hydroxy-2-[6-(1H-tetrazol-1-yl)pyridin-3-yl]ethyl}-2-(4-methyl-5-oxo-2,5-dihydrofuran-3-yl)-2,8-diazaspiro[4.5]decan-1-one, 6-fluoro-8-{(2S)-2-hydroxy-2-[6-(1H-tetrazol-1-yl) pyridazin-3-yl]ethyl}-2-(4-methyl-5-oxo-2,5-dihydrofuran-3-yl)-2,8-diazaspiro[4.5]decan-1-one, 6-fluoro-8-{(2R)-2-hydroxy-2-[6-(1H-tetrazol-1-yl) pyridazin-3-yl]ethyl}-2-(4-methyl-5-oxo-2,5-dihydrofuran-3-yl)-2,8-diazaspiro[4.5]decan-1-one, 6-fluoro-8-{(2S)-2-hydroxy-2-[4-methyl-6-(1H-tetrazol-1-yl)pyridazin-3-yl]ethyl}-2-(4-methyl-5-oxo-2,5-dihydrofuran-3-yl)-2,8-diazaspiro[4.5]decan-1-one, 6-fluoro-8-{(2R)-2-hydroxy-2-[4-methyl-6-(1H-tetrazol-1-yl)pyridazin-3-yl]ethyl}-2-(4-methyl-5-oxo-2,5-dihydrofuran-3-yl)-2,8-diazaspiro[4.5]decan-1-one, 8-{(2S)-2-hydroxy-2-[5-(1H-tetrazol-1-yl)pyrazin-2-yl] ethyl}-2-[4-(methoxy methyl)-5-oxo-2,5-dihydrofuran-3-yl]-2,8-diazaspiro[4.5]decan-1-one, 8-{(2S)-2-hydroxy-2-[6-(1H-tetrazol-1-yl)pyridazin-3-yl]ethyl}-1-oxo-2-(5-oxo-2,5-dihydrofuran-3-yl)-2-aza-8-azoniaspiro [4.5]dec-3-ene, 6-Hydroxy-8-((R) -2-hydroxy-2-(2-methyl-6-(1H-tetrazol-1-yl)pyridin-3-yl)ethyl)-2-(4-methyl-5-oxo-2,5-dihydrofuran-3-yl)-2,8-diazaspiro[4.5]decan-1-one;

8-((S)-2-(5-(1H-tetrazol-1-yl)pyrazin-2-yl)-2-hydroxyethyl)-3-(fluoromethyl)-2-(5-oxo-2,5-dihydrofuran-3-yl)-2,8-diazaspiro[4.5]decan-1-one, 8-((R)-2-(6-(1H-tetrazol-1-yl)pyridin-3-yl)-2-hydroxyethy )-4-methoxy-2-(5-oxo-2,5-dihydrofuran-3-yl)-2,8-diazaspiro[4.5]decan-1-one, 3-cyclopropyl-8-{(2S)-2-hydroxy-2-[6-(1H-tetrazol-1-yl) pyridazin-3-yl]ethyl}-2-(5-oxo-2,5-dihydrofuran-3-yl)-2,8-diazaspiro[4.5]decan-1-one, 3-cyclopropyl-8-{(2S)-2-hydroxy-2-[5-(1H-tetrazol-1-yl) pyrazin-2-yl]ethyl}-2-(5-oxo-2,5-dihydrofuran-3-yl)-2,8-diazaspiro[4.5]decan-1-one, 3-cyclopropyl-8-{(2R)-2-hydroxy-2-[6-(1H-tetrazol-1-yl)pyridin-3-yl]ethyl}-2-(5-oxo-2,5-dihydrofuran-3-yl)-2,8-diazaspiro[4.5]decan-1-one, 3-ethyl-8-{(2R)-2-hydroxy-2-[6-(1H-tetrazol-1-yl)pyridin-3-yl]ethyl}-2-(5-oxo-2,5-dihydrofuran-3-yl)-2,8-diazaspiro[4.5]decan-1-one, 3-ethyl-8-{(2S)-2-hydroxy-2-[5-(1H-tetrazol-1-yl) pyrazin-2-yl]ethyl}-2-(5-oxo-2,5-dihydrofuran-3-yl)-2,8-diazaspiro[4.5]decan-1-one, 3-cyclopropyl-8-{(2S)-2-hydroxy-2-[5-(1H-tetrazol-1-yl) pyridin-2-yl]ethyl}-2-(5-oxo-2,5-dihydrofuran-3-yl)-2,8-diazaspiro[4.5]decan-1-one, 6-fluoro-8-{(2S)-2-hydroxy-2-[5-(1H-tetrazol-1-yl) pyrazin-2-yl]ethyl}-2-(4-methyl-5-oxo-2,5-dihydrofuran-3-yl)-1-oxo-2-aza-8-azoniaspiro[4.5]decane, 8-((R)-2-(6-(1H-tetrazol-1-yl)pyridin-3-yl)-2-hydroxyethyl)-2-(2-methyl-5-oxo-2,5-dihydrofuran-3-yl)-2,8-diazaspiro[4.5]decan-1-one, (3S)-8-((R)-2-(6-(1H-tetrazol-1-yl)pyridin-3-yl)-2-hydroxyethyl)-3-methyl-2-(2-methyl-5-oxo-2,5-dihydrofuran-3-yl)-2,8-diazaspiro[4.5]decan-1-one, (3R)-8-((R)-2-(6-(1H-tetrazol-1-yl)pyridin-3-yl)-2-hydroxyethyl)-3-methyl-2-(2-methyl-5-oxo-2,5-dihydrofuran-3-yl)-2,8-diazaspiro[4.5]decan-1-one, 8-(2-(6-(1H-Tetrazol-1-yl)pyridazin-3-yl)ethyl)-2-(4-methyl-5-oxo-2,5-dihydrofuran-3-yl)-2,8-diazaspiro [4.5]decan-1-one 8-(2-(6-(1H-Tetrazol-1-yl)pyridin-3-yl)ethyl)-2-(4-methyl-5-oxo-2,5-dihydrofuran-3-yl)-2,8-diazaspiro [4.5]decan-1-one 2-(4-methyl-5-oxo-2,5-dihydrofuran-3-yl)-1-oxo-8-{2-[5-(1H-tetrazol-1-yl)pyrazin-2-yl]ethyl}-2-aza-8-azoniaspiro[4.5]decane, (1S,5S)-1'-(4-methyl-5-oxo-2,5-dihydrofuran-3-yl)-2'-oxo-8-{2-[6-(1H-tetrazol-1-yl)pyridazin-3-yl]ethyl }spiro[8-azoniabicyclo[3.2.1]octane-3,3'-pyrrolidine], 2-(4-methyl-5-oxo-2,5-dihydrofuran-3-yl)-8-{2-[4-methyl-6-(1H-tetrazol-1-yl)pyridazin-3-yl]ethyl}-1-oxo-2-aza-8-azoniaspiro[4.5]decane, 2-(4-methyl-5-oxo-2,5-dihydrofuran-3-yl)-8-{2-[4-methyl-6-(1H-tetrazol-1-yl)pyridazin-3-yl]ethyl}-1-oxo-2-aza-8-azoniaspiro[4.5]decane, 2-(4-methyl-5-oxo-2,5-dihydrofuran-3-yl)-1-oxo-8-{2-[5-(1H-tetrazol-1-yl)pyridin-2-yl]ethyl}-2-aza-8-azoniaspiro[4.5]decane, (1R,5S,9r)-1'-(4-methyl-5-oxo-2,5-dihydrofuran-3-yl)-2'-oxo-9-{2-[6-(1H-tetrazol-1-yl)pyridazin-3-yl] ethyl}spiro[7-oxa-9-azoniabicyclo[3.3.1]nonane-3,3'-pyrrolidine], 3-methyl-2-(4-methyl-5-oxo-2,5-dihydrofuran-3-yl)-1-oxo-8-{2-[6-(1H-tetrazol-1-yl)pyridazin-3-yl]ethyl}-2-aza-8-azoniaspiro[4.5]decane, 3-methyl-2-(4-methyl-5-oxo-2,5-dihydrofuran-3-yl)-1-oxo-8-{2-[6-(1H-tetrazol-1-yl)pyridazin-3-yl]ethyl}-2-aza-8-azoniaspiro[4.5]decane, 3-methyl-1-oxo-2-(5-oxo-2,5-dihydrofuran-3-yl)-8-{2-[5-(1H-tetrazol-1-yl)pyrazin-2-yl]ethyl}-2-aza-8-azoniaspiro[4.5]decane, 4-hydroxy-2-(4-methyl-5-oxo-2,5-dihydrofuran-3-yl)-1-oxo-8-{2-[6-(1H-tetrazol-1-yl)pyridazin-3-yl]ethyl}-2-aza-8-azoniaspiro[4.5]decane, 4-hydroxy-2-(4-methyl-5-oxo-2,5-dihydrofuran-3-yl)-1-oxo-8-{2-[6-(1H-tetrazol-1-yl)pyridin-3-yl]ethyl}-2-aza-8-azoniaspiro[4.5]decane, 4-hydroxy-2-(4-methyl-5-oxo-2,5-dihydrofuran-3-yl)-1-oxo-8-{2-[6-(1H-tetrazol-1-yl)pyridin-3-yl]ethyl}-2-aza-8-azoniaspiro[4.5]decane, 3(S)-methyl-1-oxo-2-(5-oxo-2,5-dihydrofuran-3-yl)-8-{2-[5-(1H-tetrazol-1-yl)pyrazin-2-yl]ethyl}-2-aza-8-azoniaspiro[4.5]decane, 2-(4-methyl-5-oxo-2,5-dihydrofuran-3-yl)-1-oxo-8-{2-[6-(1H-tetrazol-1-yl)pyridazin-3-yl]ethyl}-2-aza-8-azoniaspiro[4.5]dec-3-ene, 2-(4-methyl-5-oxo-2,5-dihydrofuran-3-yl)-8-{2-[4-methyl-6-(1H-tetrazol-1-yl)pyridazin-3-yl]ethyl}-1-oxo-2-aza-8-azoniaspiro[4.5]dec-3-ene, 1-oxo-2-(5-oxo-2,5-dihydrofuran-3-yl)-8-{2-[6-(1H-tetrazol-1-yl)pyridazin-3-yl]ethyl}-2-aza-8-azoniaspiro [4.5]dec-3-ene, 8-{2-[4-(hydroxymethyl)-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane, 2-(4-methyl-5-oxo-2,5-dihydrofuran-3-yl)-1-oxo-8-{2-[5-(1H-tetrazol-1-yl)pyrazin-2-yl]ethyl}-2-aza-8-azoniaspiro[4.5]dec-3-ene, 2-(4-methyl-5-oxo-2,5-dihydrofuran-3-yl)-8-{2-[3-methyl-5-(1H-tetrazol-1-yl)pyrazin-2-yl]ethyl}-2,8-diazaspiro[4.5]decan-1-one, 4-methyl-2-(4-methyl-5-oxo-2,5-dihydrofuran-3-yl)-1-oxo-8-{2-[6-(1H-tetrazol-1-yl)pyridazin-3-yl]ethyl}-2-aza-8-azoniaspiro[4.5]dec-3-ene, methyl 5-(2-(2-(4-methyl-5-oxo-2,5-dihydrofuran-3-yl)-1-oxo-2,8-diazaspiro[4.5]decan-8-yl)ethyl)-2-(1H-tetrazol-1-yl)isonicotinate, 3-methyl-2-(5-oxo-2,5-dihydrofuran-3-yl)-8-{2-[6-(1H-tetrazol-1-yl)pyridazin-3-yl]ethyl}-2,8-diazaspiro[4.5]dec-3-en-1-one, 4-methyl-2-(4-methyl-5-oxo-2,5-dihydrofuran-3-yl)-8-{2-[4-methyl-6-(1H-tetrazol-1-yl)pyridazin-3-yl]ethyl}-1-oxo-2-aza-8-azoniaspiro[4.5]dec-3-ene, 6-methoxy-2-(4-methyl-5-oxo-2,5-dihydrofuran-3-yl)-8-{2-[6-(1H-tetrazol-1-yl)pyridazin-3-yl]ethyl}-2,8-diazaspiro[4.5]decan-1-one, 6-methoxy-2-(4-methyl-5-oxo-2,5-dihydrofuran-3-yl)-8-{2-[6-(1H-tetrazol-1-yl)pyridazin-3-yl]ethyl}-2,8-diazaspiro[4.5]decan-1-one, 6-methoxy-2-(4-methyl-5-oxo-2,5-dihydrofuran-3-yl)-8-{2-[4-methyl-6-(1H-tetrazol-1-yl)pyridazin-3-yl]ethyl}-2,8-diazaspiro[4.5]decan-1-one, 6-methoxy-2-(4-methyl-5-oxo-2,5-dihydrofuran-3-yl)-8-{2-[4-methyl-6-(1H-tetrazol-1-yl)pyridazin-3-yl]ethyl}-2,8-diazaspiro[4.5]decan-1-one, (3S)-3-methyl-8-{2-[3-methyl-5-(1H-tetrazol-1-yl)pyrazin-2-yl]ethyl}-2-(5-oxo-2,5-dihydrofuran-3-yl)-2,8-diazaspiro[4.5]decan-1-one, (3S)-3-methyl-8-{2-[4-methyl-6-(1H-tetrazol-1-yl)pyridazin-3-yl]ethyl}-2-(5-oxo-2,5-dihydrofuran-3-yl)-2,8-diazaspiro[4.5]decan-1-one, 2-(4-methyl-5-oxo-2,5-dihydrofuran-3-yl)-8-{2-[3-methyl-5-(1H-tetrazol-1-yl)pyrazin-2-yl]ethyl}-1-oxo-2-aza-8-azoniaspiro[4.5]dec-3-ene, (3S)-3-methyl-2-(5-oxo-2,5-dihydrofuran-3-yl)-8-{2[6-(1H-tetrazol-1-yl)pyridazin-3-yl]ethyl}-2,8-diazaspiro[4.5]decan-1-one, 6-fluoro-2-(4-methyl-5-oxo-2,5-dihydrofuran-3-yl)-8-{2-[6(1H-tetrazol-1-yl)pyridazin-3-yl]ethyl}-2,8-diazaspiro[4.5]decan-1-one, 6-fluoro-2-(4-methyl-5-oxo-2,5-dihydrofuran-3-yl)-8-{2-[6(1H-tetrazol-1-yl)pyridazin-3-yl]ethyl}-2,8-diazaspiro[4.5]decan-1-one, 6-fluoro-2-(4-methyl-5-oxo-2,5-dihydrofuran-3-yl)-8-{2-[4-methyl-6-(1H-tetrazol-1-yl)pyridazin-3-yl]ethyl}-2,8-diazaspiro[4.5]decan-1-one, 6-fluoro-2-(4-methyl-5-oxo-2,5-dihydrofuran-3-yl)-8-{2-[4-methyl-6-(1H-tetrazol-1-yl)pyridazin-3-yl]ethyl}-2,8-diazaspiro[4.5]decan-1-one, 8-{2-[3-methyl-5-(1H-tetrazol-1-yl)pyrazin-2-yl]ethyl}-2-(5-oxo-2,5-dihydrofuran-3-yl)-2,8-diazaspiro[4.5]decan-1-one, (S)-8-(2-(3-cyclopropyl-5-(1H-tetrazol-1-yl)pyrazin-2-yl)ethyl)-3-methyl-2-(5-oxo-2,5-dihydrofuran-3-yl)-2,8-diazaspiro[4.5]decan-1-one, (S)-8-(2-(3-ethyl-5-(1H-tetrazol-1-yl)pyrazin-2-yl)ethyl)-3-methyl-2-(5-oxo-2,5-dihydrofuran-3-yl)-2,8-diazaspiro[4.5]decan-1-one, (S)-8-(1-(6-(1H-tetrazol-1-yl)pyridazin-3-yl)propan-2-yl)-2-(4-methyl-5-oxo-2,5-dihydrofuran-3-yl)-2,8-diazaspiro[4.5]dec-3-en-1-one, (R)-8-(1-(6-(1H-tetrazol-1-yl)pyridazin-3-yl)propan-2-yl)-2-(4-methyl-5-oxo-2,5-dihydrofuran-3-yl)-2,8-diazaspiro[4.5]dec-3-en-1-one, (S)-2-(4-methyl-5-oxo-2,5-dihydrofuran-3-yl)-8-(1-(4-methyl-6-(1H-tetrazol-1-yl)pyridazin-3-yl)propan-2-yl)-2,8-diazaspiro[4.5]dec-3-en-1-one, (R)-2-(4-methyl-5-oxo-2,5-dihydrofuran-3-yl)-8-(1-(4-methyl-6-(1H-tetrazol-1-yl)pyridazin-3-yl)propan-2-yl)-2,8-diazaspiro[4.5]dec-3-en-1-one, (S)-8-(2-(5-(1H-Tetrazol-1-yl)pyrazin-2-yl)-2-fluoroethyl)-2-(4-methyl-5-oxo-2,5-dihydrofuran-3-yl)-2,8-diazaspiro[4.5]decan-1-one, 8-{(2R)-2-fluoro-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane, 8-{(2S)-2-fluoro-2-[6-(1H-tetrazol-1-yl)pyridazin-3-yl]ethyl}-2-(4-methyl-5-oxo-2,5-dihydrofuran-3-yl)-1-oxo-2-aza-8-azoniaspiro[4.5]decane, 8-{(2S)-2-fluoro-2-[5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2R)-2-fluoro-2-[5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2R)-2-methoxy-2-[5-(1H-tetrazol-1-yl)pyrazin-2-yl]ethyl}-2-(4-methyl-5-oxo-2,5-dihydrofuran-3-yl)-1-oxo-2-aza-8-azoniaspiro[4.5]decane, 8-{(2S)-2-methoxy-2-[5-(1H-tetrazol-1-yl)pyridin-2-yl]ethyl}-2-(4-methyl-5-oxo-2,5-dihydrofuran-3-yl)-1-oxo-2-aza-8-azoniaspiro[4.5]decane, 8-{(2S)-2-hydroxy-2-[2-methyl-6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane, 8-{(2R)-2-methoxy-2-[6-(1H-tetrazol-1-yl)pyridinium-3-yl]ethyl}-1-oxo-2-(5-oxo-2,5-dihydrofuran-3-yl)-2-aza-8-azoniaspiro[4.5]decane, 8-{(2R)-2-(1-methylethoxy)-2-[6-(1H-tetrazol-1-yl)pyridin-3-yl]ethyl}-2-(4-methyl-5-oxo-2,5-dihydrofuran-3-yl)-1-oxo-2-aza-8-azoniaspiro[4.5]decane, (3R)-8-{(2R)-2-methoxy-2-[5-(1H-tetrazol-1-yl)pyrazin-2-yl]ethyl}-3-methyl-1-oxo-2-(5-oxo-2,5-dihydrofuran-3-yl)-2-aza-8-azoniaspiro[4.5]decane, (3R)-8-{(2S)-2-methoxy-2-[6-(1H-tetrazol-1-yl)pyridin-3-yl]ethyl}-3-methyl-2-(4-methyl-5-oxo-2,5-dihydrofuran-3-yl)-1-oxo-2-aza-8-azoniaspiro[4.5]decane, (1R,3R,5S)-8-((R)-2-(6-(1H-tetrazol-1-yl)pyridin-3-yl)-2-methoxyethyl)-1'-(4-methyl-5-oxo-2,5-dihydrofuran-3-yl)-8-azaspiro[bicyclo[3.2.1]octane-3,3'-pyrrolidin]-2'-one, (R)-8-(2-(6-(1H-tetrazol-1-yl)pyridin-3-yl)-2-methoxyethyl)-2-(4-methyl-5-oxo-2,5-dihydrofuran-3-yl)-2,8-diazaspiro[4.5]decan-1-one, 2-(4-methyl-5-oxo-2,5-dihydrofuran-3-yl)-8-{(2S)-2-[6-(1H-tetrazol-1-yl)pyridazin-3-yl]propyl}-2,8-diazaspiro[4.5]decan-1-one, 2-(4-methyl-5-oxo-2,5-dihydrofuran-3-yl)-8-{(2R)-2-[6-(1H-tetrazol-1-yl)pyridazin-3-yl]propyl}-2,8-diazaspiro[4.5]decan-1-one, 2-(4-Methyl-5-oxo-2,5-dihydrofuran-3-yl)-8-{(1S)-1-methyl-2-[6-(1H-tetrazol-1-yl)pyridazin-3-yl]ethyl}-2,8-diazaspiro[4.5]decan-1-one, 2-(4-Methyl-5-oxo-2,5-dihydrofuran-3-yl)-8-{(1R)-1-methyl-2-[6-(1H-tetrazol-1-yl)pyridazin-3-yl]ethyl}-2,8-diazaspiro[4.5]decan-1-one, 8-[(1S)-2-hydroxy 1-{[6-(1H-tetrazol-1-yl)pyridin-3-yl]methyl}ethyl]-2-(4-methyl-5-oxo-2,5-dihydrofuran-3-yl)-2,8-diazaspiro[4.5]decan-1-one, 8-[(1R)-2-hydroxy-1-{[6-(1H-tetrazol-1-yl)pyridin-3-yl]methyl}ethyl]-2-(4-methyl-5-oxo-2,5-dihydrofuran-3-yl)-2,8-diazaspiro[4.5]decan-1-one, (S)-8-(1-(6-(1H-tetrazol-1-yl)pyridin-3-yl)-1-hydroxy-2-methylpropan-2-yl)-2-(4-methyl-5-oxo-2,5-dihydrofuran-3-yl)-2,8-diazaspiro[4.5]decan-1-one, (R)-8-(1-(6-(1H-tetrazol-1-yl)pyridin-3-yl)-1-hydroxy-2-methylpropan-2-yl)-2-(4-methyl-5-oxo-2,5-dihydrofuran-3-yl)-2,8-diazaspiro[4.5]decan-1-one, (S)-8-(1-(5-(1H-tetrazol-1-yl)pyridin-2-yl)-1-hydroxy-2-methylpropan-2-yl)-2-(4-methyl-5-oxo-2,5-dihydrofuran-3-yl)-2,8-diazaspiro[4.5]decan-1-one, 8-(1-(5-(1H-tetrazol-1-yl)pyrazin-2-yl)-1-hydroxy-2-methylpropan-2-yl)-3-methyl-2-(5-oxo-2,5-dihydrofuran-3-yl)-2,8-diazaspiro[4.5]decan-1-one, or a pharmaceutically acceptable salt thereof.

10. A pharmaceutical composition comprised of a compound of claim 1 or a pharmaceutically acceptable salt thereof and a pharmaceutically acceptable carrier.

11. The pharmaceutical composition of claim 10 further comprising an additional active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril, amiloride, spironolactone, epleranone or triamterene, or a pharmaceutically acceptable salt of any of the foregoing.

12. A method for inhibiting ROMK comprising administering a compound of claim 1 or a pharmaceutically acceptable salt thereof in a ROMK-inhibitory effective amount to a patient in need thereof.

13. A method for causing diueresis, natriuresis or both, comprising administering a compound of claim 1 or a pharmaceutically acceptable salt thereof in a therapeutically effective amount to a patient in need thereof.

14. A method for the treatment of hypertension comprising administering a compound of claim 1 or a pharmaceutically acceptable salt thereof in a therapeutically effective amount to a patient in need thereof.

* * * * *